US010729336B1

(12) United States Patent
Tran

(10) Patent No.: US 10,729,336 B1
(45) Date of Patent: *Aug. 4, 2020

(54) SMART WATCH

(71) Applicant: Bao Tran, Saratoga, CA (US)

(72) Inventor: Bao Tran, Saratoga, CA (US)

( * ) Notice: Subject to any disclaimer, the term of this patent is extended or adjusted under 35 U.S.C. 154(b) by 403 days.

This patent is subject to a terminal disclaimer.

(21) Appl. No.: 15/626,022

(22) Filed: Jun. 16, 2017

Related U.S. Application Data

(63) Continuation of application No. 11/512,630, filed on Aug. 30, 2006, now Pat. No. 9,820,658, which is a
(Continued)

(51) Int. Cl.
*A61B 5/0205* (2006.01)
*A61B 8/00* (2006.01)
(Continued)

(52) U.S. Cl.
CPC ........ *A61B 5/02055* (2013.01); *A61B 5/0006* (2013.01); *A61B 5/0022* (2013.01); *A61B 5/0404* (2013.01); *A61B 5/0492* (2013.01); *A61B 5/1112* (2013.01); *A61B 5/1117* (2013.01); *A61B 5/411* (2013.01); *A61B 5/4818* (2013.01); *A61B 5/4839* (2013.01); *A61B 5/681* (2013.01); *A61B 5/6804* (2013.01); *A61B 5/7225* (2013.01); *A61B 8/56* (2013.01); *A61B 8/565* (2013.01); *G06F 19/3418* (2013.01); *G06Q 50/22* (2013.01); *G16H 40/20* (2018.01);
(Continued)

(58) Field of Classification Search
CPC ... A61B 5/0022; A61B 5/0492; A61B 5/1112; A61B 5/6804; A61B 5/681; A61B 5/02438; A61B 5/021; A61B 5/02433; A61B 5/721; A61B 5/7275; A61B 5/024
See application file for complete search history.

(56) References Cited

U.S. PATENT DOCUMENTS 4,129,125 A 12/1978 Lester et al.
4,234,926 A 11/1980 Wallace et al.
(Continued)

FOREIGN PATENT DOCUMENTS

| WO | WO-0228123 A2 * | 4/2002 |
|---|---|---|
| WO | WO-2006025055 A2 * | 3/2006 |
| WO | 2006071892 | 7/2006 |

OTHER PUBLICATIONS

Urs Anliker, et al., "AMON: A Wearable Multiparameter Medical Monitoring and Alert System", IEEE Transactions on Information Technology in Biomedicine, vol. 8, No. 4, Dec. 2004 (Year: 2004).*
(Continued)

*Primary Examiner* — Evangeline Barr
(74) *Attorney, Agent, or Firm* — Patent Law Office, PC; Bao Tran

(57) ABSTRACT

Systems and methods include a cellular, WiFi, and Bluetooth transceiver coupled to a processor; an accelerometer or a motion sensor coupled to the processor; and a sensor coupled to the processor to sense mood or body vital sign; and a wearable device operating wirelessly with the processor, wherein the wearable device includes at least one sensor coupled to a back of the wearable device and wherein the wearable device recognizes and executes a speech command.

22 Claims, 25 Drawing Sheets

Related U.S. Application Data continuation of application No. 60/818,260, filed on Jun. 30, 2006.

(51) Int. Cl.

| | | |
|---|---|---|
| *G06Q 50/22* | (2018.01) | |
| *G06F 19/00* | (2018.01) | |
| *A61B 5/00* | (2006.01) | |
| *A61B 5/11* | (2006.01) | |
| *A61B 5/0492* | (2006.01) | |
| *A61B 5/0404* | (2006.01) | |
| *G16H 40/20* | (2018.01) | |
| *A61B 8/08* | (2006.01) | |
| *A61B 8/06* | (2006.01) | |
| *A61B 7/00* | (2006.01) | |
| *A61B 5/145* | (2006.01) | |
| *A61B 5/113* | (2006.01) | |
| *A61B 5/08* | (2006.01) | |
| *A61B 5/053* | (2006.01) | |
| *A61B 5/0496* | (2006.01) | |
| *A61B 5/0476* | (2006.01) | |
| *A61B 5/024* | (2006.01) | |
| *A61B 5/021* | (2006.01) | |

(52) U.S. Cl.
CPC ........... *A61B 5/021* (2013.01); *A61B 5/02438* (2013.01); *A61B 5/0476* (2013.01); *A61B 5/0496* (2013.01); *A61B 5/0537* (2013.01); *A61B 5/0816* (2013.01); *A61B 5/11* (2013.01); *A61B 5/1135* (2013.01); *A61B 5/145* (2013.01); *A61B 5/14532* (2013.01); *A61B 5/4023* (2013.01); *A61B 5/721* (2013.01); *A61B 5/726* (2013.01); *A61B 5/7214* (2013.01); *A61B 5/7232* (2013.01); *A61B 5/7257* (2013.01); *A61B 5/7267* (2013.01); *A61B 5/7275* (2013.01); *A61B 7/003* (2013.01); *A61B 8/06* (2013.01); *A61B 8/0808* (2013.01); *A61B 8/4472* (2013.01); *A61B 2503/08* (2013.01); *A61B 2560/0214* (2013.01)

(56) References Cited

U.S. PATENT DOCUMENTS

| | | | |
|---|---|---|---|
| 4,275,742 A | 7/1981 | Faisandier | |
| 4,320,767 A | 3/1982 | Villa-Real | |
| 4,412,545 A | 11/1983 | Okino et al. | |
| 4,420,000 A | 12/1983 | Bailey | |
| 4,537,202 A | 8/1985 | Mancini et al. | |
| 4,557,270 A | 12/1985 | John | |
| 4,566,461 A | 1/1986 | Lubell et al. | |
| 4,595,018 A | 7/1986 | Rantala | |
| 4,656,319 A | 4/1987 | Bially | |
| 4,679,144 A | 7/1987 | Cox et al. | |
| 4,778,449 A | 10/1988 | Weber et al. | |
| 4,807,642 A | 2/1989 | Brown | |
| 4,819,648 A | 4/1989 | Ko | |
| 4,862,359 A | 8/1989 | Trivedi et al. | |
| 4,869,261 A | 9/1989 | Penaz | |
| 4,880,013 A | 11/1989 | Chio | |
| 4,907,597 A | 3/1990 | Chamoun | |
| 4,922,229 A | 5/1990 | Guenst | |
| 4,928,690 A | 5/1990 | Heilman et al. | |
| 4,951,197 A | 8/1990 | Mellinger | |
| 4,964,411 A | 10/1990 | Johnson et al. | |
| 5,090,418 A | 2/1992 | Squires et al. | |
| RE34,015 E | 8/1992 | Duffy | |
| 5,140,990 A | 8/1992 | Jones et al. | |
| 5,161,529 A | 11/1992 | Stotts et al. | |
| 5,162,991 A | 11/1992 | Chio | |
| 5,271,411 A | 12/1993 | Ripley et al. | |
| 5,285,793 A | 2/1994 | Slovut et al. | |
| 5,287,859 A | 2/1994 | John | |
| 5,309,916 A | 5/1994 | Hatschek | |
| 5,331,969 A | 7/1994 | Silberstein | |
| 5,353,793 A | 10/1994 | Bornn | |
| 5,361,775 A | 11/1994 | Remes et al. | |
| 5,365,426 A | 11/1994 | Siegel et al. | |
| 5,368,039 A | 11/1994 | Moses | |
| 5,370,126 A | 12/1994 | Clifford, Jr. | |
| 5,375,610 A | 12/1994 | LaCourse et al. | |
| 5,410,471 A * | 4/1995 | Alyfuku | A61B 5/14507 600/300 |
| 5,434,419 A | 7/1995 | Decupper | |
| 5,435,316 A | 7/1995 | Kruse | |
| 5,438,607 A | 8/1995 | Przygoda, Jr. et al. | |
| 5,441,047 A | 8/1995 | David et al. | |
| 5,458,620 A | 10/1995 | Adams et al. | |
| 5,462,065 A | 10/1995 | Cusimano | |
| 5,497,781 A | 3/1996 | Chen et al. | |
| 5,505,208 A | 4/1996 | Toomim et al. | |
| 5,513,651 A | 5/1996 | Cusimano et al. | |
| 5,544,649 A | 8/1996 | David et al. | |
| 5,544,661 A | 8/1996 | Davis et al. | |
| 5,546,953 A | 8/1996 | Garfield | |
| 5,551,435 A | 9/1996 | Sramek | |
| 5,551,438 A | 9/1996 | Moses | |
| 5,579,001 A | 11/1996 | Dempsey et al. | |
| 5,579,775 A | 12/1996 | Dempsey et al. | |
| 5,584,298 A | 12/1996 | Kabal | |
| 5,623,939 A | 4/1997 | Garfield | |
| 5,633,910 A | 5/1997 | Cohen | |
| 5,652,570 A | 7/1997 | Lepkofker | |
| 5,662,118 A | 9/1997 | Skubick | |
| 5,671,741 A | 9/1997 | Lang et al. | |
| 5,683,425 A | 11/1997 | Hauptmann | |
| 5,685,316 A | 11/1997 | Schookin | |
| 5,692,215 A | 11/1997 | Kutzik et al. | |
| 5,694,940 A | 12/1997 | Unger et al. | |
| 5,708,417 A | 1/1998 | Tallman et al. | |
| 5,709,215 A | 1/1998 | Perttu et al. | |
| 5,710,551 A | 1/1998 | Ridgeway | |
| 5,720,771 A | 2/1998 | Snell | |
| 5,722,420 A | 3/1998 | Lee | |
| 5,733,230 A | 3/1998 | Sawchuck et al. | |
| 5,738,104 A | 4/1998 | Lo et al. | |
| 5,738,105 A | 4/1998 | Kroll | |
| 5,743,268 A | 4/1998 | Kabal | |
| 5,752,976 A | 5/1998 | Duffin et al. | |
| 5,772,603 A | 6/1998 | Ohlsson | |
| 5,775,330 A | 7/1998 | Kangas et al. | |
| 5,776,073 A | 7/1998 | Garfield et al. | |
| 5,785,960 A | 7/1998 | Rigg et al. | |
| 5,788,643 A | 8/1998 | Feldman | |
| 5,857,975 A | 1/1999 | Golub | |
| 5,865,755 A | 2/1999 | Golub | |
| 5,876,350 A | 3/1999 | Lo et al. | |
| 5,891,042 A | 4/1999 | Sham et al. | |
| 5,935,077 A | 8/1999 | Ogle | |
| 5,941,837 A | 8/1999 | Amano et al. | |
| 5,945,112 A | 8/1999 | Flynn et al. | |
| 5,960,366 A * | 9/1999 | Duwaer | H04M 1/72547 455/556.1 |
| 5,964,719 A | 10/1999 | Costello et al. | |
| 5,967,975 A | 10/1999 | Ridgeway | |
| 5,976,083 A | 11/1999 | Richardson et al. | |
| 5,987,519 A | 11/1999 | Peifer et al. | |
| 5,996,889 A | 12/1999 | Fuchs et al. | |
| 6,002,957 A | 12/1999 | Finneran | |
| 6,004,312 A | 12/1999 | Finneran et al. | |
| 6,010,454 A | 1/2000 | Arieff et al. | |
| 6,013,007 A | 1/2000 | Root et al. | |
| 6,014,626 A | 1/2000 | Cohen | |
| 6,032,035 A | 2/2000 | Webster et al. | |
| 6,038,469 A | 3/2000 | Karlsson et al. | |
| 6,047,202 A | 4/2000 | Finneran et al. | |
| 6,050,940 A | 4/2000 | Braun et al. | |
| 6,052,619 A | 4/2000 | John | |
| 6,056,671 A | 5/2000 | Marmer | |
| 6,063,051 A | 5/2000 | Stern | |

(56) References Cited

U.S. PATENT DOCUMENTS

| | | |
|---|---|---|
| 6,070,140 A | 5/2000 | Tran |
| 6,076,011 A | 6/2000 | Hoover |
| 6,108,685 A | 8/2000 | Kutzik et al. |
| 6,160,478 A | 12/2000 | Jacobsen et al. |
| 6,171,237 B1 | 1/2001 | Avitall |
| 6,175,308 B1 | 1/2001 | Tallman et al. |
| 6,176,831 B1 | 1/2001 | Voss et al. |
| 6,184,797 B1 | 2/2001 | Stark et al. |
| 6,206,829 B1 | 3/2001 | Iliff |
| 6,228,034 B1 | 5/2001 | Voss et al. |
| 6,230,056 B1 | 5/2001 | Kroll |
| 6,246,894 B1 | 6/2001 | Steuer et al. |
| 6,280,393 B1 | 8/2001 | Granger et al. |
| 6,287,252 B1 | 9/2001 | Lugo |
| 6,299,583 B1 | 10/2001 | Eggers et al. |
| 6,336,900 B1 | 1/2002 | Alleckson et al. |
| 6,364,834 B1 | 4/2002 | Reuss et al. |
| 6,364,842 B1 | 4/2002 | Amano et al. |
| 6,368,283 B1 | 4/2002 | Xu et al. |
| 6,374,614 B2 | 4/2002 | Prueitt |
| 6,375,614 B1 | 4/2002 | Braun et al. |
| 6,398,727 B1 | 6/2002 | Bui et al. |
| 6,406,426 B1 | 6/2002 | Reuss et al. |
| 6,413,223 B1 | 7/2002 | Yang et al. |
| 6,416,480 B1 | 7/2002 | Nenov |
| 6,424,251 B1 | 7/2002 | Byrne |
| 6,433,690 B2 | 8/2002 | Petelenz et al. |
| 6,440,067 B1 | 8/2002 | DeLuca et al. |
| 6,443,906 B1 | 9/2002 | Ting et al. |
| 6,445,299 B1 | 9/2002 | Rojas, Jr. |
| 6,450,953 B1 | 9/2002 | Place et al. |
| 6,466,816 B2 | 10/2002 | Granger et al. |
| 6,473,640 B1 | 10/2002 | Erlebacher |
| 6,475,146 B1 | 11/2002 | Frelburger et al. |
| 6,475,153 B1 | 11/2002 | Khair et al. |
| 6,475,161 B2 | 11/2002 | Teicher et al. |
| 6,487,442 B1 | 11/2002 | Wood |
| 6,514,211 B1 | 2/2003 | Baura |
| 6,515,593 B1 | 2/2003 | Stark et al. |
| 6,533,729 B1 | 3/2003 | Khair et al. |
| 6,544,173 B2 | 4/2003 | West et al. |
| 6,544,174 B2 | 4/2003 | West et al. |
| 6,546,269 B1 | 4/2003 | Kurnik |
| 6,554,774 B1 | 4/2003 | Miele |
| 6,556,860 B1 | 4/2003 | Groenewegen |
| 6,571,200 B1 | 5/2003 | Mault |
| 6,595,316 B2 | 7/2003 | Cybulski et al. |
| 6,595,929 B2 | 7/2003 | Stivoric et al. |
| 6,597,944 B1 | 7/2003 | Hadas |
| 6,602,191 B2 | 8/2003 | Quy |
| 6,605,038 B1 | 8/2003 | Teller et al. |
| 6,609,023 B1 | 8/2003 | Fischell et al. |
| 6,612,984 B1 | 9/2003 | Kerr, II |
| 6,615,074 B2 | 9/2003 | Mickle et al. |
| 6,615,075 B2 | 9/2003 | Mlynash et al. |
| 6,616,613 B1 | 9/2003 | Goodman |
| 6,660,042 B1 | 12/2003 | Curcie et al. |
| 6,661,161 B1 | 12/2003 | Lanzo et al. |
| 6,676,600 B1 | 1/2004 | Conero et al. |
| 6,678,549 B2 | 1/2004 | Cusimano |
| 6,678,551 B2 | 1/2004 | Maalouf et al. |
| 6,687,519 B2 | 2/2004 | Steuer et al. |
| 6,705,990 B1 | 3/2004 | Gallant et al. |
| 6,720,984 B1 | 4/2004 | Jorgensen et al. |
| 6,730,038 B2 | 5/2004 | Gallant et al. |
| 6,740,045 B2 | 5/2004 | Amano |
| 6,747,561 B1 | 7/2004 | Reeves |
| 6,760,620 B2 | 7/2004 | Sippens Groenewegen |
| 6,783,492 B2 | 8/2004 | Domiguez et al. |
| 6,804,656 B1 | 10/2004 | Rosenfeld et al. |
| 6,816,266 B2 | 11/2004 | Varshaneya et al. |
| 6,829,501 B2 | 12/2004 | Nielsen et al. |
| 6,832,251 B1 | 12/2004 | Gelvin et al. |
| 6,834,436 B2 | 12/2004 | Townsend et al. |
| 6,842,877 B2 | 1/2005 | Robarts et al. |
| 6,843,771 B2 | 1/2005 | Lo et al. |
| 6,856,291 B2 | 2/2005 | Mickle et al. |
| 6,865,409 B2 | 3/2005 | Getsla et al. |
| 6,871,211 B2 | 3/2005 | Labounty et al. |
| 6,882,128 B1 | 4/2005 | Rahmel et al. |
| 6,887,202 B2 | 5/2005 | Currie et al. |
| 6,898,460 B2 | 5/2005 | Hoctor et al. |
| 6,912,420 B2 | 6/2005 | Scheiner et al. |
| 6,907,288 B2 | 7/2005 | Daum |
| 6,942,615 B2 | 9/2005 | Suzuki |
| 6,944,496 B2 | 9/2005 | Jeong et al. |
| 6,957,107 B2 | 10/2005 | Rogers et al. |
| 6,961,285 B2 | 11/2005 | Niemiec et al. |
| 6,965,794 B2 | 11/2005 | Brody |
| 6,973,344 B2 | 12/2005 | Finneran et al. |
| 6,974,419 B1 | 12/2005 | Voss et al. |
| 6,975,206 B2 | 12/2005 | Reining |
| 6,980,852 B2 | 12/2005 | Jersey-Willuhn et al. |
| 6,982,930 B1 * | 1/2006 | Hung ............... A61B 5/02438 |
| | | 368/10 |
| 6,989,751 B2 | 1/2006 | Richards |
| 7,004,907 B2 | 2/2006 | Banet et al. |
| 7,011,629 B2 | 3/2006 | Bulat |
| 7,035,679 B2 | 4/2006 | Addison et al. |
| 7,043,293 B1 | 5/2006 | Baura |
| 7,126,467 B2 | 10/2006 | Albert et al. |
| 7,141,026 B2 | 11/2006 | Aminian |
| 7,161,484 B2 | 1/2007 | Tsoukalis |
| 7,263,379 B1 | 8/2007 | Parkulo et al. |
| 7,264,590 B2 | 9/2007 | Casey et al. |
| 7,271,704 B2 | 9/2007 | McSheffrey et al. |
| 7,277,745 B2 | 10/2007 | Natarajan |
| 7,278,966 B2 | 10/2007 | Hjelt et al. |
| 7,285,090 B2 | 10/2007 | Stivoric et al. |
| 7,298,327 B2 | 11/2007 | Dupray |
| 7,315,767 B2 | 1/2008 | Caduff et al. |
| 7,356,343 B2 | 4/2008 | Feher |
| 7,377,835 B2 | 5/2008 | Parkulo et al. |
| 7,382,247 B2 | 6/2008 | Welch et al. |
| 7,477,890 B1 * | 1/2009 | Narayanaswami ... H04L 69/329 |
| | | 455/414.1 |
| 7,508,840 B2 | 3/2009 | Delaney |
| 7,534,206 B1 | 5/2009 | Lovitt et al. |
| 7,539,487 B2 | 5/2009 | Sinclair et al. |
| 7,539,532 B2 | 5/2009 | Tran |
| 7,539,533 B2 | 5/2009 | Tran |
| 7,689,167 B2 | 3/2010 | Sengupta et al. |
| 7,733,224 B2 | 6/2010 | Tran |
| 8,103,333 B2 | 1/2012 | Tran |
| 8,108,036 B2 | 1/2012 | Tran |
| 8,121,673 B2 | 2/2012 | Tran |
| 8,204,786 B2 | 6/2012 | LeBoeuf |
| 8,303,500 B2 | 11/2012 | Raheman |
| 8,323,188 B2 | 12/2012 | Tran |
| 8,325,030 B2 | 12/2012 | Townsend et al. |
| 8,562,489 B2 | 10/2013 | Burton et al. |
| 8,708,903 B2 | 4/2014 | Tran |
| 8,764,651 B2 | 7/2014 | Tran |
| 9,028,405 B2 | 5/2015 | Tran |
| 2001/0022558 A1 | 9/2001 | Karr |
| 2002/0027164 A1 | 3/2002 | Mault |
| 2002/0118121 A1 | 8/2002 | Lehrman |
| 2002/0120184 A1 | 8/2002 | Beck et al. |
| 2003/0004421 A1 | 1/2003 | Ting et al. |
| 2003/0028116 A1 | 2/2003 | Bimbaum |
| 2003/0125635 A1 | 7/2003 | Maalouf et al. |
| 2003/0135127 A1 | 7/2003 | Sackner et al. |
| 2003/0176798 A1 | 9/2003 | Simon |
| 2003/0216630 A1 | 11/2003 | Jersey-Willuhn et al. |
| 2003/0216662 A1 | 11/2003 | Jersey-Willuhn et al. |
| 2003/0216663 A1 | 11/2003 | Jersey-Willuhn et al. |
| 2003/0231115 A1 | 12/2003 | Stanners et al. |
| 2004/0044273 A1 | 3/2004 | Keith et al. |
| 2004/0102683 A1 | 5/2004 | Khanuja et al. |
| 2004/0122487 A1 | 6/2004 | Hatlestad et al. |
| 2004/0138568 A1 | 7/2004 | Lo et al. |
| 2004/0152961 A1 | 8/2004 | Carlson |
| 2004/0167409 A1 | 8/2004 | Lo et al. |
| 2004/0167417 A1 | 8/2004 | Schulhauser et al. |

(56) References Cited

U.S. PATENT DOCUMENTS

| | | |
|---|---|---|
| 2004/0220490 A1 | 11/2004 | Appel et al. |
| 2004/0254493 A1 | 12/2004 | Chervin et al. |
| 2004/0260188 A1 | 12/2004 | Syed et al. |
| 2004/0260577 A1* | 12/2004 | Dahlin ............... G06Q 50/22 705/2 |
| 2004/0267148 A1 | 12/2004 | Arand et al. |
| 2005/0010139 A1 | 1/2005 | Aminian |
| 2005/0038345 A1 | 2/2005 | Gorgenburg et al. |
| 2005/0061568 A1 | 3/2005 | Schondorf et al. |
| 2005/0068169 A1* | 3/2005 | Copley ............ G08B 21/0283 340/539.13 |
| 2005/0079871 A1 | 4/2005 | Kirk et al. |
| 2005/0099387 A1 | 5/2005 | Matsumoto |
| 2005/0113630 A1 | 5/2005 | Fox et al. |
| 2005/0113710 A1 | 5/2005 | Stahmann et al. |
| 2005/0115561 A1 | 6/2005 | Stahmann et al. |
| 2005/0116820 A1* | 6/2005 | Goldreich ........... A61B 5/0002 340/539.12 |
| 2005/0131639 A1* | 6/2005 | Broussard ............ G01C 21/20 701/533 |
| 2005/0143667 A1 | 6/2005 | Park et al. |
| 2005/0148882 A1 | 7/2005 | Banet |
| 2005/0194926 A1 | 9/2005 | Di Stefano et al. |
| 2005/0195079 A1 | 9/2005 | Cohen |
| 2005/0201585 A1 | 9/2005 | Jannard |
| 2005/0209521 A1 | 9/2005 | Kettunen |
| 2005/0222515 A1 | 10/2005 | Polyshchuk et al. |
| 2005/0228244 A1 | 10/2005 | Banet et al. |
| 2005/0228299 A1 | 10/2005 | Banet et al. |
| 2005/0228316 A1 | 10/2005 | Morgenstern et al. |
| 2005/0240086 A1 | 10/2005 | Akay et al. |
| 2005/0240523 A1 | 10/2005 | Richardson |
| 2005/0245831 A1 | 11/2005 | Banet et al. |
| 2005/0250440 A1* | 11/2005 | Zhou .................. G01S 5/0027 455/12.1 |
| 2005/0261559 A1 | 11/2005 | Mumford et al. |
| 2005/0261594 A1 | 11/2005 | Banet et al. |
| 2005/0261598 A1 | 11/2005 | Banet et al. |
| 2005/0278409 A1 | 12/2005 | Kutzik et al. |
| 2006/0009697 A1 | 1/2006 | Banet et al. |
| 2006/0009698 A1 | 1/2006 | Banet et al. |
| 2006/0047215 A1 | 3/2006 | Newman et al. |
| 2006/0056655 A1 | 3/2006 | Wen |
| 2006/0079801 A1 | 4/2006 | DeLuca et al. |
| 2006/0082727 A1 | 4/2006 | Bolger et al. |
| 2006/0084878 A1 | 4/2006 | Banet et al. |
| 2006/0094975 A1 | 5/2006 | Manto |
| 2006/0105357 A1 | 5/2006 | Benesch et al. |
| 2006/0122474 A1* | 6/2006 | Teller ............... A61B 5/02055 600/300 |
| 2006/0154642 A1 | 7/2006 | Scannell |
| 2006/0195020 A1* | 8/2006 | Martin ............... G06F 19/3475 600/301 |
| 2007/0004969 A1 | 1/2007 | Kong et al. |
| 2007/0112287 A1 | 5/2007 | Fancourt |
| 2007/0197881 A1 | 8/2007 | Wolf et al. |
| 2009/0069642 A1 | 3/2009 | Gao et al. |
| 2009/0069724 A1 | 3/2009 | Otto |
| 2009/0072955 A1 | 3/2009 | Cary |
| 2009/0131759 A1 | 5/2009 | Sims et al. |
| 2009/0322513 A1 | 12/2009 | Hwang |
| 2010/0081946 A1 | 4/2010 | Garudadri et al. |
| 2010/0111383 A1 | 5/2010 | Boushey |
| 2010/0246651 A1 | 9/2010 | Baheti et al. |
| 2011/0066381 A1 | 3/2011 | Garudadri et al. |
| 2011/0124978 A1 | 5/2011 | Williams |
| 2012/0063389 A1 | 3/2012 | Abedi |
| 2013/0120106 A1 | 5/2013 | Cauwels |

OTHER PUBLICATIONS

U.S. Appl. No. 10/938,783, Wen.
U.S. Appl. No. 10/938,783, filed Sep. 10, 2004, Wen.

\* cited by examiner

| |
|---|
| Place a calibration sheet with known dots at a known distance and perpendicular to a camera view |
| Take snap shot of the sheet, and correlate the position of the dots to the camera image |
| Place a different calibration sheet that contains known dots at another different known distance and perpendicular to camera view. |
| Take snap shot of the sheet and correlate the position of the dots to the camera image |
| Smooth the dots to the pixels to minimize digitization errors |
| For each pixel, draw a line from Dot1(x,y,z) to Dot2 (x, y, z) defining a cone center where the camera can view |

FIG. 2

| |
|---|
| Find floor space area |
| Define camera view background 3D scene |
| Calculate patient's key features |
| Detect fall |

FIG. 3

| |
|---|
| Find floor space area |
| Define camera view background 3D scene |
| Calculate patient's key features |
| Extract facial objects |
| Detect facial orientation |
| Detect facial expression |

FIG. 4

| |
|---|
| Set up mesh network appliances (1000) |
| Determine patient position using in-door positioning system (1002) |
| Determine patient movement using accelerometer output (1004) |
| Determine vital parameter including patient heart rate (1006) |
| Determine if patient needs assistance based on in-door position, fall detection and vital parameter (1008) |
| Confirm prior to calling third party (1010) |
| If confirmed or non-responsive, make connection with third party and send voice over mesh network to appliance worn by the patient (1012) |
| If needed, call emergency personnel to get medical care (1014) |

FIG. 5

Patient A    Patient B    Patient C    .....    Patient N
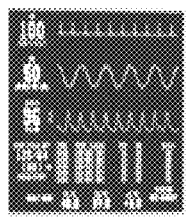 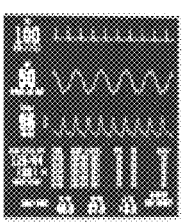 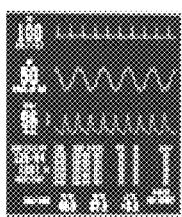 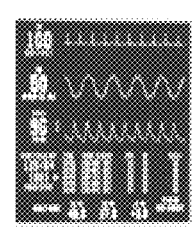
ALERT
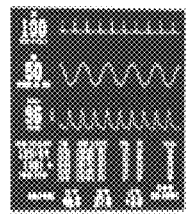 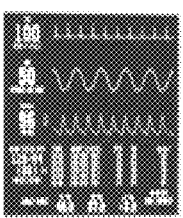 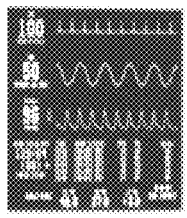 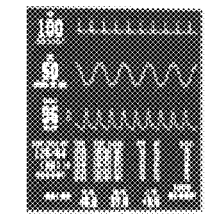
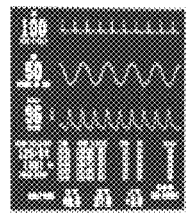 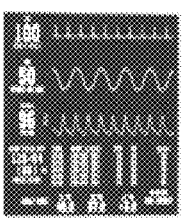 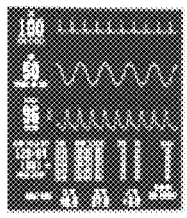 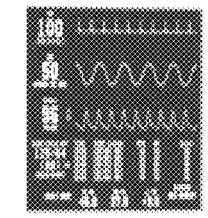
ALERT
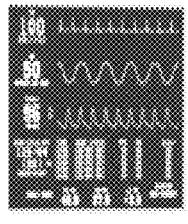 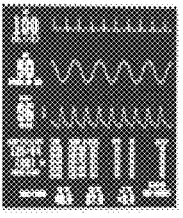 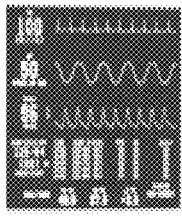 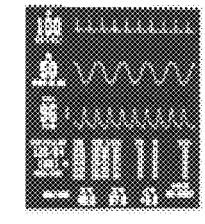
FIG. 15C

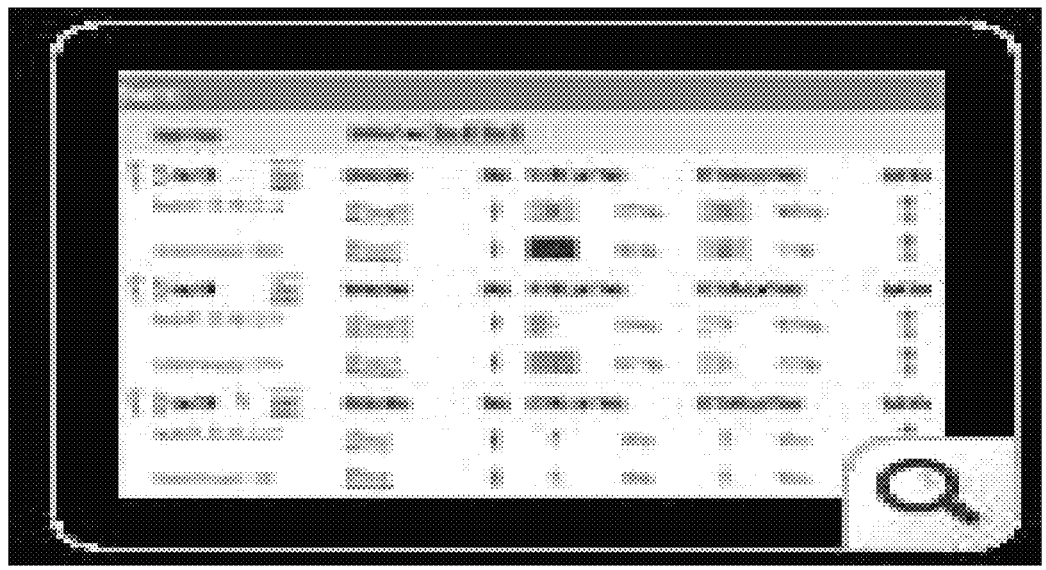
FIG. 15D
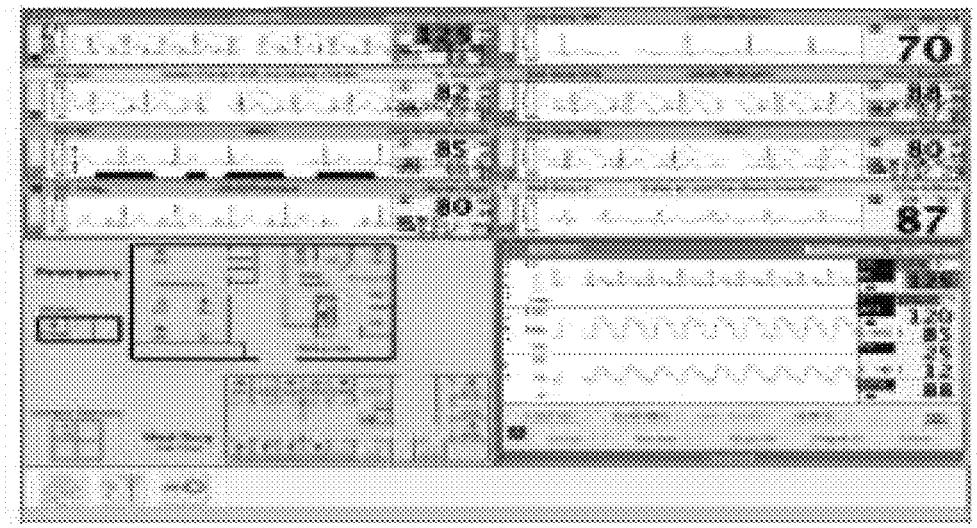
FIG. 15E
| |
|---|
| Generate a blood pressure model of a patient (2002) |
| Determine a blood flow velocity using a piezoelectric transducer (2004) |
| Provide the blood flow velocity to the blood pressure model to continuously estimate blood pressure (2006) |
FIG. 16A

| |
|---|
| Attach monitoring device and calibration device to patient (2010) |
| Determine blood flow velocity from the monitoring device and actual blood pressure from the calibration device (2012) |
| Generate a blood pressure model based on the blood flow velocity and the actual blood pressure (2014) |
| Remove calibration device (2016) |
| Determine blood flow velocity (2018) |
| Provide blood flow velocity to the blood pressure model to estimate blood pressure (2020) |

FIG. 16B

| |
|---|
| Detect weakness in left half and right half of patient body - arms, legs, face (3000) |
| Detect walking pattern for loss of balance or coordination (3002) |
| Ask user to move hands/feet in a predetermined pattern (3004) |
| Read accelerometer output in accordance with predetermined pattern movement (3006) |
| Provide accelerometer output to a pattern classifier (3008) |
| Check whether patient is experiencing dizziness or sudden, severe headache with no known cause (3010) |
| Display a text image and ask the patient to read back the text image, one eye at a time (3012) |
| Use speech recognizer to detect confusion, trouble speaking or understanding (3014) |
| Ask patient if they feel numbness in the body- arms, legs, face (3016) |
| Ask patient to squeeze gauge/force sensor to determine force applied during squeeze (3018) |

FIG. 16C

| |
|---|
| Compare historical left shoulder (LS) strength against current LS strength (3200) |
| Compare historical right shoulder (RS) strength against current RS strength (3202) |
| Compare historical left hip (LH) strength against current LH strength (3204) |
| Compare historical right hip (RH) strength against current RH strength (3206) |
| If variance between historical and current strength exceeds threshold, generate warning (3208) |

FIG. 16E

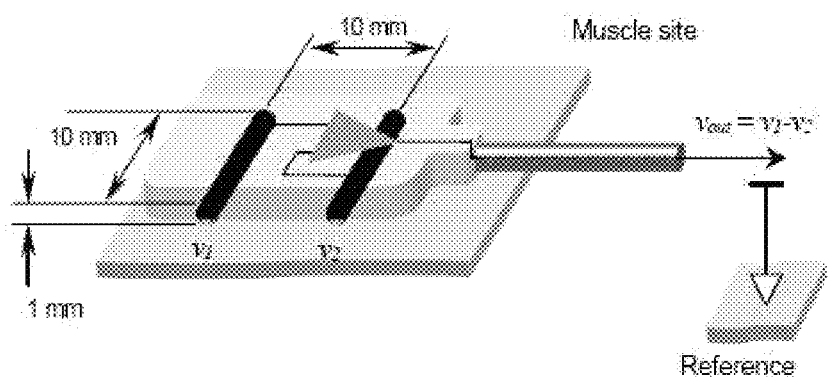
FIG. 17A
HISTORICAL MEASUREMENT
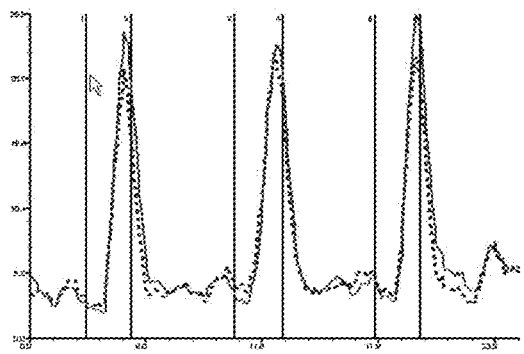
RECENT MEASUREMENT
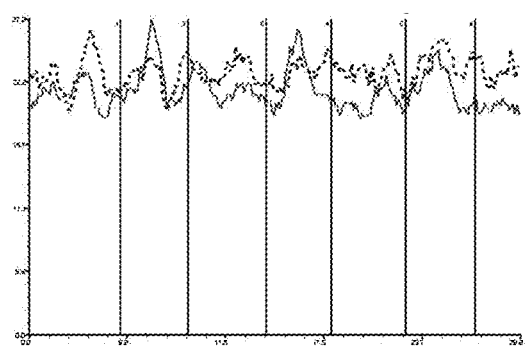
FIG. 17B
FIG. 17C

SMART WATCH

This application claims priority to Provisional Application Ser. No. 60/818,260 filed Jun. 30, 2006, the content of which is incorporated by reference.

BACKGROUND

This invention relates generally to a mobile device such as a watch.

SUMMARY

In one aspect, a system includes a cellular, WiFi, or and Bluetooth transceiver coupled to a processor; an accelerometer or a motion sensor coupled to the processor; and a sensor coupled to the processor to sense mood body vital sign, wherein text, image, sound, or video is rendered in response to a sensed mood or body vital sign; and a wearable device operating wirelessly with the processor, wherein the wearable device includes at least one sensor coupled to a back of the wearable device and wherein the wearable device recognizes and executes the speech command. In another aspect, a mobile system, comprising: a transceiver to communicate data via a personal area network (PAN); an accelerometer and a gyroscope; a processor coupled to the transceiver, the accelerometer and the gyroscope, the processor executing one or more applications to record user speech and to record data regarding movement detected by the accelerometer and the gyroscope; two or more sensors in communication with the processor to detect user vital sign data; and a health application executed by the processor to generate a health analysis using the vital sign data and the data regarding movement detected by the accelerometer and the gyroscope, wherein the transceiver communicates the analysis to another computer via the PAN.

In yet another aspect, a system includes a processor; a cellular, WiFi, or Bluetooth transceiver coupled to the processor; an accelerometer or a motion sensor coupled to the processor; and a sensor coupled to the processor to sense mood, wherein text, image, sound, or video is rendered in response to the sensed mood.

In another aspect, a system includes an accelerometer to detect movement or fitness; a sensor coupled to a wrist, hand or finger to detect blood-oxygen levels or heart rate or pulse rate and mounted on a wristwatch wearable device and a voice communication device having a wireless transceiver adapted to receive blood-oxygen level or heart rate or pulse rate from the sensor over a wireless personal area network (PAN).

In yet another aspect, a system includes a cellular telephone having a vital sign sensor thereon to detect heart rate, pulse rate or blood-oxygen levels; and a wristwatch wearable device in wireless communication with the cellular telephone, including: a sensor coupled to a wrist, hand or finger to detect blood-oxygen levels, heart rate or pulse rate; a wireless transceiver adapted to communicate with the cellular telephone over a wireless personal area network (PAN); and a processor coupled to the sensor and the transceiver to send pulse rate to the cellular telephone.

In a further aspect, a health care monitoring system for a person includes one or more wireless nodes forming a wireless network to communicate data over the wireless network to detect a health problem. Implementations can include watches that capture fitness data (activity, heart rate, blood pressure, walking rate, dietary or calorie consumption, among others) and sending the data to a hospital database where medical and fitness data is used to treat the patient. Other implementations include collecting data from different devices with different communication protocols such as blood pressure measurement devices, scales, glucose meters, among others, and upload the data to a computer which converts the data into an intermediate format that is compatible with different protocols for interoperability purposes.

In another aspect, a heart monitoring system for a person includes one or more wireless nodes forming a wireless network; a wearable sensor having a wireless transceiver adapted to communicate with the one or more wireless nodes; and a software module receiving data from the wireless nodes to detect changes in patient vital signs.

In another aspect, a monitoring system includes one or more wireless nodes forming a wireless network; a wearable blood pressure sensor having a wireless transceiver adapted to communicate with the one or more wireless nodes; and a software module receiving data from the wireless nodes to detect deteriorations in patient vital signs.

In another aspect, a health care monitoring system for a person includes one or more wireless nodes forming a wireless mesh network; a wearable appliance having a sound transducer coupled to the wireless transceiver; and a bio-electric impedance (BI) sensor coupled to the wireless mesh network to communicate BI data over the wireless mesh network.

In another aspect, a heart monitoring system for a person includes one or more wireless nodes forming a wireless mesh network and a wearable appliance having a sound transducer coupled to the wireless transceiver; and a heart disease recognizer coupled to the sound transducer to determine cardiovascular health and to transmit heart sound over the wireless mesh network to a remote listener if the recognizer identifies a cardiovascular problem. The heart sound being transmitted may be compressed to save transmission bandwidth.

In yet another aspect, a monitoring system for a person includes one or more wireless nodes; and a wristwatch having a wireless transceiver adapted to communicate with the one or more wireless nodes; and an accelerometer to detect a dangerous condition and to generate a warning when the dangerous condition is detected.

In yet another aspect, a monitoring system for a person includes one or more wireless nodes forming a wireless mesh network; and a wearable appliance having a wireless transceiver adapted to communicate with the one or more wireless nodes; and a heartbeat detector coupled to the wireless transceiver. The system may also include an accelerometer to detect a dangerous condition such as a falling condition and to generate a warning when the dangerous condition is detected.

In yet another aspect, a monitoring system for a person includes one or more wireless nodes forming a wireless network; and a wearable device including: a processor; a transceiver coupled to the processor to communicate with the one or more wireless nodes; a wearable sensor on a patch or bandage secured to the person's skin and coupled to the processor; an accelerometer coupled to the processor; and a thumb sensor coupled to the processor.

In another aspect, a health monitoring system for a person includes a mobile telephone case including a cellular transceiver to provide wireless data and voice communication; a sensor including one or more electrodes mounted on the mobile telephone case to contact the person's skin and capture bio-electrical signals therefrom; an amplifier coupled to the electrodes; a processor coupled to the amplifier; and a screen coupled to the processor to display medical data such as images of the bio-electrical signals.

Implementations of the above aspect may include one or more of the following. The wristwatch determines position based on triangulation. The wristwatch determines position based on RF signal strength and RF signal angle. A switch detects a confirmatory signal from the person. The confirmatory signal includes a head movement, a hand movement, or a mouth movement. The confirmatory signal includes the person's voice. A processor in the system executes computer readable code to transmit a help request to a remote computer. The code can encrypt or scramble data for privacy. The processor can execute voice over IP (VOIP) code to allow a user and a remote person to audibly communicate with each other. The voice communication system can include Zigbee VOIP or Bluetooth VOIP or 802.XX VOIP. The remote person can be a doctor, a nurse, a medical assistant, or a caregiver. The system includes code to store and analyze patient information. The patient information includes medicine taking habits, eating and drinking habits, sleeping habits, or excise habits. A patient interface is provided on a user computer for accessing information and the patient interface includes in one implementation a touch screen; voice-activated text reading; and one touch telephone dialing. The processor can execute code to store and analyze information relating to the person's ambulation. A global positioning system (GPS) receiver can be used to detect movement and where the person falls. The system can include code to map the person's location onto an area for viewing. The system can include one or more cameras positioned to capture three dimensional (3D) video of the patient; and a server coupled to the one or more cameras, the server executing code to detect a dangerous condition for the patient based on the 3D video and allow a remote third party to view images of the patient when the dangerous condition is detected.

In another aspect, a monitoring system for a person includes one or more wireless bases; and a cellular telephone having a wireless transceiver adapted to communicate with the one or more wireless bases; and an accelerometer to detect a dangerous condition and to generate a warning when the dangerous condition is detected.

In yet another aspect, a monitoring system includes one or more cameras to determine a three dimensional (3D) model of a person; means to detect a dangerous condition based on the 3D model; and means to generate a warning when the dangerous condition is detected.

In one aspect, systems and methods include one or more entities including a sensor configured to provide data in at least a first information standard from a first manufacturer and a second information standard from a second manufacturer; and an electronic health record database configured to: capture information from the one or more entities, normalize the captured information from first and second manufacturers in a common format, and add metadata for the captured information.

In another aspect, an interoperable health-care system includes a network; one or more medical data collection appliances coupled to the network, each appliance transmitting data conforming to an interoperable format; and a computer coupled to the network to store data for each individual in accordance with the interoperable format.

The user can take his/her weight, blood pressure, and cholesterol measurement daily, and the data is sent from a health base station to a monitoring service at his doctor's office. Periodically, the user gets an automated health summary generated by a service at his doctor's office as well as information to help him maintain a healthy lifestyle. The health information can be stored in an external HIPAA compliant health storage database so that the user and his doctor can access his health information over the web. The system extends health care system into the home and can record personal health data on a systematic periodic basis. Appointments can be automatically scheduled with providers. Long-term data for medical baseline can be collected. The system can also provide predictive alerts for high-risk conditions. The system can perform initial triage utilizing biosensors, images, e-mail/chat/video.

Advantages of the system may include one or more of the following. The system empowers people with the information they need to better manage their health and the health of their loved ones. The interoperability enables disparate industries to work together to combine their products and services through connectivity standards and provide millions of people with the tools they need to better manage their health and the health of their families. The system can perform chronic disease management, monitoring the health and healthcare needs of aging people and proactive health and fitness. The interoperable system can address the data storage requirements for health and wellness management, chronic disease management or patient recovery, medication management, and fitness and workout tracking. For example, using a blood pressure sensor, a weight scale or a cholesterol monitor, the user regularly collects health data that is then reviewed by the patient's caregiver for remote monitoring and health management of the patient. The system can provide remote monitoring of multiple patients, seamless device replacement and support for clinical trials. The Medical Device Profile will be compliant with the US Health Insurance Portability and Accountability Act (HIPAA) and other international data privacy requirements.

By enabling a network of readily connected health and medical devices, people with diabetes or other chronic diseases will be able to share vital sign information such as blood pressure and glucose level with their doctors. Adult children will be able to remotely watch over their aging parents and proactively help them manage safely in their own homes. Diet and fitness conscious individuals will also be able to seamlessly share their weight and exercise data with fitness consultants through the Internet.

The above system forms an interoperable health-care system with a network; a first medical appliance to capture a first vital information and coupled to the network, the first medical appliance transmitting the first vital information conforming to an interoperable format; and a second medical appliance to capture a second vital information and coupled to the network, the second medical appliance converting the first vital information in accordance with the interoperable format and processing the first and second vital information, the second medical appliance providing an output conforming to the interoperable format.

The appliances can communicate data conforming to the interoperable format over one of: cellular protocol, ZigBee protocol, Bluetooth protocol, WiFi protocol, WiMAX protocol, USB protocol, ultrawideband protocol. The appliances can communicate over two or more protocols. The first medical appliance can transmit the first vital information over a first protocol (such as Bluetooth protocol) to a computer, wherein the computer transmits the first vital information to the second medical appliance over a second protocol (such as ZigBee prototocol). The computer can then transmit to a hospital or physician office using broadband such as WiMAX protocol or cellular protocol. The computer can perform the interoperable format conversion for the appliances or devices, or alternatively each appliance or device can perform the format conversion. Regardless of which device performs the protocol conversion and format conversion, the user does not need to know about the underlying format or protocol in order to use the appliances. The user only needs to plug an appliance into the network, the data transfer is done automatically so that the electronic "plumbing" is not apparent to the user. In this way, the user is shielded from the complexity supporting interoperability.

In another aspect, a monitoring system for a person includes one or more wireless nodes and a stroke sensor coupled to the person and the wireless nodes to determine a medical problem, for example a stroke attack. The stroke monitoring system is interoperable with emergency vehicle and/or hospital systems and provides information to quickly treat stroke once the patient reaches the treatment center.

In one aspect, a monitoring system for a person includes one or more wireless nodes and an electromyography (EMG) sensor coupled to the person and the wireless nodes to determine a medical issue such as a stroke attack.

In another aspect, a health care monitoring system for a person includes one or more wireless nodes forming a wireless mesh network; a wearable appliance having a sound transducer coupled to the wireless transceiver; and a bio-electric impedance (BI) sensor coupled to the wireless mesh network to communicate BI data over the wireless mesh network.

In a further aspect, a heart monitoring system for a person includes one or more wireless nodes forming a wireless mesh network and a wearable appliance having a sound transducer coupled to the wireless transceiver; and a heart disease recognizer coupled to the sound transducer to determine cardiovascular health and to transmit heart sound over the wireless mesh network to a remote listener if the recognizer identifies a cardiovascular problem. The heart sound being transmitted may be compressed to save transmission bandwidth.

In yet another aspect, a monitoring system for a person includes one or more wireless nodes; and a wristwatch having a wireless transceiver adapted to communicate with the one or more wireless nodes; and an accelerometer to detect a dangerous condition and to generate a warning when the dangerous condition is detected.

In yet another aspect, a monitoring system for a person includes one or more wireless nodes forming a wireless mesh network; and a wearable appliance having a wireless transceiver adapted to communicate with the one or more wireless nodes; and a heartbeat detector coupled to the wireless transceiver. The system may also include an accelerometer to detect a dangerous condition such as a falling condition and to generate a warning when the dangerous condition is detected.

Implementations of the above aspect may include one or more of the following. The wristwatch determines position based on triangulation. The wristwatch determines position based on RF signal strength and RF signal angle. A switch detects a confirmatory signal from the person. The confirmatory signal includes a head movement, a hand movement, or a mouth movement. The confirmatory signal includes the person's voice. A processor in the system executes computer readable code to transmit a help request to a remote computer. The code can encrypt or scramble data for privacy. The processor can execute voice over IP (VOIP) code to allow a user and a remote person to audibly communicate with each other. The voice communication system can include Zigbee VOIP or Bluetooth VOIP or 802.XX VOIP. The remote person can be a doctor, a nurse, a medical assistant, or a caregiver. The system includes code to store and analyze patient information. The patient information includes medicine taking habits, eating and drinking habits, sleeping habits, or excise habits. A patient interface is provided on a user computer for accessing information and the patient interface includes in one implementation a touch screen; voice-activated text reading; and one touch telephone dialing. The processor can execute code to store and analyze information relating to the person's ambulation. A global positioning system (GPS) receiver can be used to detect movement and where the person falls. The system can include code to map the person's location onto an area for viewing. The system can include one or more cameras positioned to capture three dimensional (3D) video of the patient; and a server coupled to the one or more cameras, the server executing code to detect a dangerous condition for the patient based on the 3D video and allow a remote third party to view images of the patient when the dangerous condition is detected.

In another aspect, a monitoring system for a person includes one or more wireless bases; and a cellular telephone having a wireless transceiver adapted to communicate with the one or more wireless bases; and an accelerometer to detect a dangerous condition and to generate a warning when the dangerous condition is detected.

In yet another aspect, a monitoring system includes one or more cameras to determine a three dimensional (3D) model of a person; means to detect a dangerous condition based on the 3D model; and means to generate a warning when the dangerous condition is detected.

In another aspect, a method to detect a dangerous condition for an infant includes placing a pad with one or more sensors in the infant's diaper; collecting infant vital parameters; processing the vital parameter to detect SIDS onset; and generating a warning.

Advantages of the system may include one or more of the following. The system detects the warning signs of stroke and prompts the user to reach a health care provider within 2 hours of symptom onset. The system enables patent to properly manage acute stroke, and the resulting early treatment might reduce the degree of morbidity that is associated with first-ever strokes.

Other advantages of the invention may include one or more of the following. The system for non-invasively and continually monitors a subject's arterial blood pressure, with reduced susceptibility to noise and subject movement, and relative insensitivity to placement of the apparatus on the subject. The system does not need frequent recalibration of the system while in use on the subject.

In particular, it allows patients to conduct a low-cost, comprehensive, real-time monitoring of their vital parameters including blood pressure. Using the web services software interface, the invention then avails this information to hospitals, home-health care organizations, insurance companies, pharmaceutical agencies conducting clinical trials and other organizations. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

The wearable appliance is small, easily worn by the patient during periods of exercise or day-to-day activities, and non-invasively measures blood pressure can be done in a matter of seconds without affecting the patient. An onboard or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure at isolated times.

The wearable appliance provides an in-depth, cost-effective mechanism to evaluate a patient's cardiac condition. Certain cardiac conditions can be controlled, and in some cases predicted, before they actually occur. Moreover, data from the patient can be collected and analyzed while the patient participates in their normal, day-to-day activities.

In cases where the device has fall detection in addition to blood pressure measurement, other advantages of the invention may include one or more of the following. The system provides timely assistance and enables elderly and disabled individuals to live relatively independent lives. The system monitors physical activity patterns, detects the occurrence of falls, and recognizes body motion patterns leading to falls. Continuous monitoring of patients is done in an accurate, convenient, unobtrusive, private and socially acceptable manner since a computer monitors the images and human involvement is allowed only under pre-designated events. The patient's privacy is preserved since human access to videos of the patient is restricted: the system only allows human viewing under emergency or other highly controlled conditions designated in advance by the user. When the patient is healthy, people cannot view the patient's video without the patient's consent. Only when the patient's safety is threatened would the system provide patient information to authorized medical providers to assist the patient. When an emergency occurs, images of the patient and related medical data can be compiled and sent to paramedics or hospital for proper preparation for pick up and check into emergency room.

The system allows certain designated people such as a family member, a friend, or a neighbor to informally check on the well-being of the patient. The system is also effective in containing the spiraling cost of healthcare and outpatient care as a treatment modality by providing remote diagnostic capability so that a remote healthcare provider (such as a doctor, nurse, therapist or caregiver) can visually communicate with the patient in performing remote diagnosis. The system allows skilled doctors, nurses, physical therapists, and other scarce resources to assist patients in a highly efficient manner since they can do the majority of their functions remotely.

Additionally, a sudden change of activity (or inactivity) can indicate a problem. The remote healthcare provider may receive alerts over the Internet or urgent notifications over the phone in case of such sudden accident indicating changes. Reports of health/activity indicators and the overall well being of the individual can be compiled for the remote healthcare provider. Feedback reports can be sent to monitored subjects, their designated informal caregiver and their remote healthcare provider. Feedback to the individual can encourage the individual to remain active. The content of the report may be tailored to the target recipient's needs, and can present the information in a format understandable by an elder person unfamiliar with computers, via an appealing patient interface. The remote healthcare provider will have access to the health and well-being status of their patients without being intrusive, having to call or visit to get such information interrogatively. Additionally, remote healthcare provider can receive a report on the health of the monitored subjects that will help them evaluate these individuals better during the short routine check up visits. For example, the system can perform patient behavior analysis such as eating/drinking/smoke habits and medication compliance, among others.

The patient's home equipment is simple to use and modular to allow for the accommodation of the monitoring device to the specific needs of each patient. Moreover, the system is simple to install. Regular monitoring of the basic wellness parameters provides significant benefits in helping to capture adverse events sooner, reduce hospital admissions, and improve the effectiveness of medications, hence, lowering patient care costs and improving the overall quality of care. Suitable users for such systems are disease management companies, health insurance companies, self-insured employers, medical device manufacturers and pharmaceutical firms.

The system reduces costs by automating data collection and compliance monitoring, and hence reduce the cost of nurses for hospital and nursing home applications. At-home vital signs monitoring enables reduced hospital admissions and lower emergency room visits of chronic patients. Operators in the call centers or emergency response units get high quality information to identify patients that need urgent care so that they can be treated quickly, safely, and cost effectively. The Web based tools allow easy access to patient information for authorized parties such as family members, neighbors, physicians, nurses, pharmacists, caregivers, and other affiliated parties to improved the Quality of Care for the patient.

In an on-line pharmacy aspect, a method for providing patient access to medication includes collecting patient medical information from a patient computer; securing the patient medical information and sending the secured patient medical information from the patient computer to a remote computer; remotely examining the patient and reviewing the patient medical information; generating a prescription for the patient and sending the prescription to a pharmacy; and performing a drug interaction analysis on the prescription.

Implementations of the on-line pharmacy aspect may include one or more of the following. The medical information can include temperature, EKG, blood pressure, weight, sugar level, image of the patient, or sound of the patient. Responses from the patient to a patient medical questionnaire can be captured. The doctor can listen to the patient's organ with a digital stethoscope, scanning a video of the patient, running a diagnostic test on the patient, verbally communicating with the patient. The digital stethoscope can be a microphone or piezoelectric transducer coupled to the Zigbee network to relay the sound. A plurality of medical rules can be applied to the medical information to arrive at a diagnosis. Genetic tests or pharmacogenetic tests can be run on the patient to check compatibility with the prescription. Approval for the prescription can come from one of: a doctor, a physician, a physician assistant, a nurse. The system can monitor drug compliance, and can automatically ordering a medication refill from the pharmacy.

For pharmacy applications, advantages of the pharmacy system may include one or more of the following. The system shares the patient's medical history and can be updated by a remote physician and the remote dispensing pharmacy. As the doctor and the pharmacy have the same access to the patient medical history database, patient data is updated in real time, and is as current and complete as possible. The patient, doctor, pharmacy, and third party testing entities benefit from a uniform pricing structure that is based on the diagnosis and treatment. The patient only pays for standard medical treatments for his or her illness. The physician is paid a standard fee which covers the average work spent with a patient with the specific type of medical situation. The dispensing pharmacy is able to provide the highest level of service, since it is able to double check all medications dispensed to each patient along with the optimal way to detect anticipated negative drug interactions. The pricing structure is competitive as physicians do not need to be distributed physically, and those with specialty areas may remain centrally located and yet be able to interact electronically with patients. The system still provides physical access to specialists since the patients which are evaluated can be directed to visit a specialists physically, when remote review and contact is ineffectual. The on-line pharmacy tracks the specific needs and medical history of each patient and can provide an expert system to advise the patient on proper drug usage and potential drug interactions. The system automates the purchasing of drugs, pricing the prescription or submission of the claims to a third party for pricing, entering the complete prescription in their computer system, and auditing from third parties which provide payment. The on-line pharmacy provides detailed multimedia guidance or assistance to the patient regarding the filled prescription. The patient can freely search for answers regarding the use of the filled prescription, its possible side effects, possible interactions with other drugs, possible alternative treatments, etc. The patient can communicate using video or VOIP with a remote pharmacist regarding any number of questions, and be counseled by the local pharmacist on the use of the filled prescription. Thus, the system minimizes the danger from harmful side effects or drug interactions by providing patients with full access to information. The system allows a patient to enjoy the selection and price of a mail-order pharmacy without subjecting the patient to dangerous interactions or side effects which may occur in unsupervised prescription purchases. The on-line pharmacy offers the selection and benefits of a "central fill" pharmacy method without requiring the local pharmacy to purchase drugs to fill each prescription, price each prescription, or be subjected to audits from third parties who provide payment.

In yet another embodiment, a wireless housing provides one or more bioelectric contacts conveniently positioned to collect bioelectric patient data. The housing can be a patch, a wristwatch, a band, a wristband, a chest band, a leg band, a sock, a glove, a foot pad, a head-band, an ear-clip, an ear phone, a shower-cap, an armband, an ear-ring, eye-glasses, sun-glasses, a belt, a sock, a shirt, a garment, a jewelry, a bed spread, a pillow cover, a pillow, a mattress, a blanket or a sleeping garment such as a pajama. The bed spread, pillow cover, pillow, mattress, blanket or pajama can have bioelectrically conductive contacts in an array so that the patient can enjoy his/her sleep while vital parameters can be captured. In one embodiment, an array of parallel conductive lines can be formed on the housing side that faces the patient and the electrical signal can be picked up. The data captured by the contacts are transmitted over the mesh network such as ZigBee to a base station.

In the above embodiments, the base station can perform the bioelectric signal processing to extract patient parameters from data captured by the contacts. In this case, the base station may need a DSP or powerful CPU to perform the calculations. Alternatively, in an ASP model, the base station can simply compress the data and upload the data to a central server or server farm for processing and the result of the signal processing are sent back to the base station for relay to the patient interface which can be a wrist-watch, a pad, or a band, among others, for notification of any warning signs.

BRIEF DESCRIPTION OF THE DRAWINGS

FIG. 2 illustrates a process for determining three dimensional (3D) detection.

FIG. 3 illustrates a process for detecting falls.

FIG. 4 illustrates a process for detecting facial expressions.

FIG. 5 illustrates an exemplary process for determining and getting assistance for a patient or user.

FIGS. 8-14A and 14B show various exemplary wearable appliances to monitor a patient.

FIG. 15C shows an exemplary interface to monitor a plurality of persons.

FIG. 15D shows an exemplary dash-board that provides summary information on the status of a plurality of persons.

FIG. 15E shows an exemplary multi-station vital parameter user interface for a professional embodiment.

FIGS. 16A-16B show exemplary blood pressure determination processes.

FIGS. 16C-E shows exemplary stroke determination processes.

FIG. 17A shows an exemplary EMG sensor.

FIGS. 17B-C show exemplary EMG graphs of a patient.

DESCRIPTION

Figure 1A:
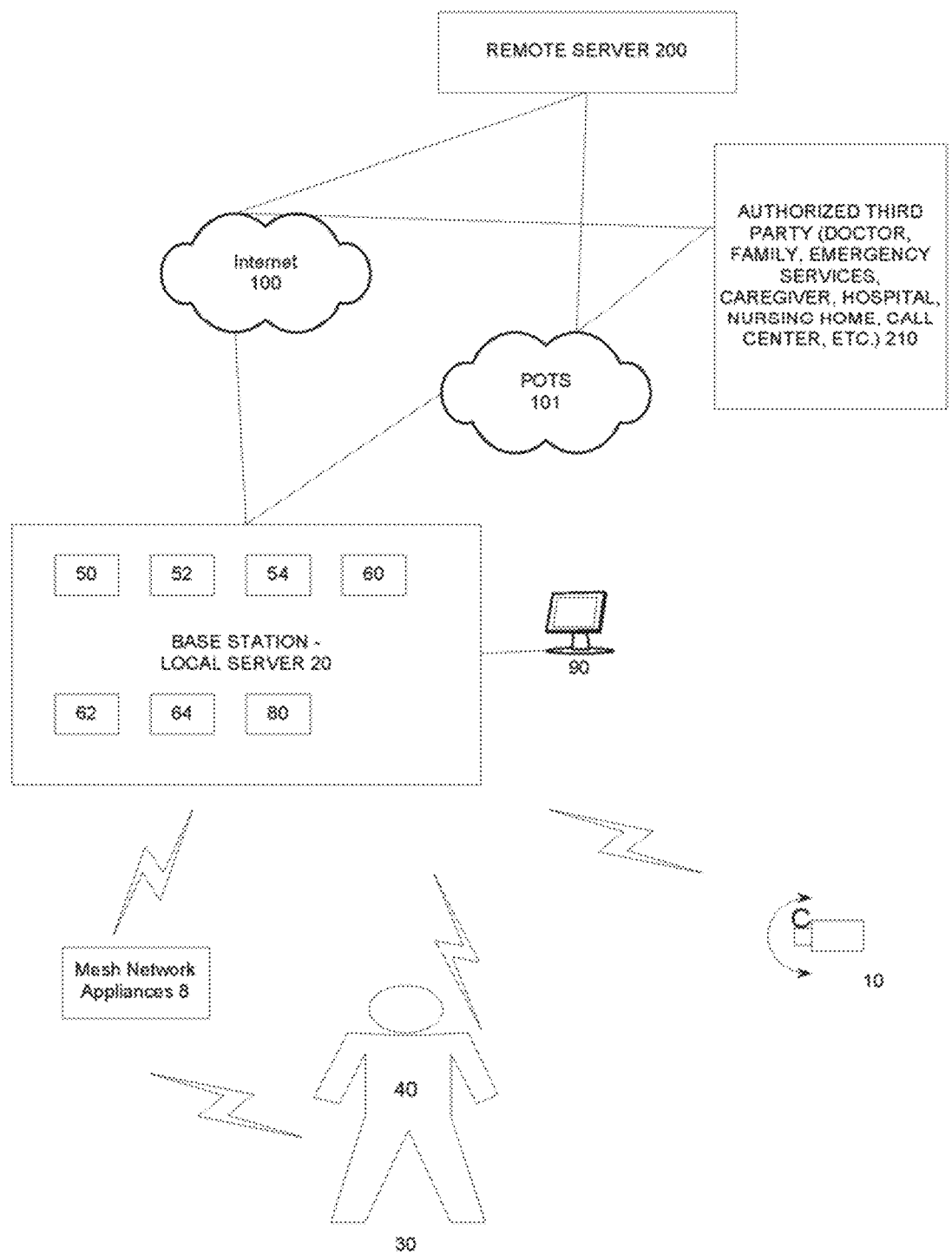
FIG. 1A illustrates an exemplary system for monitoring a person.
Figure 7:
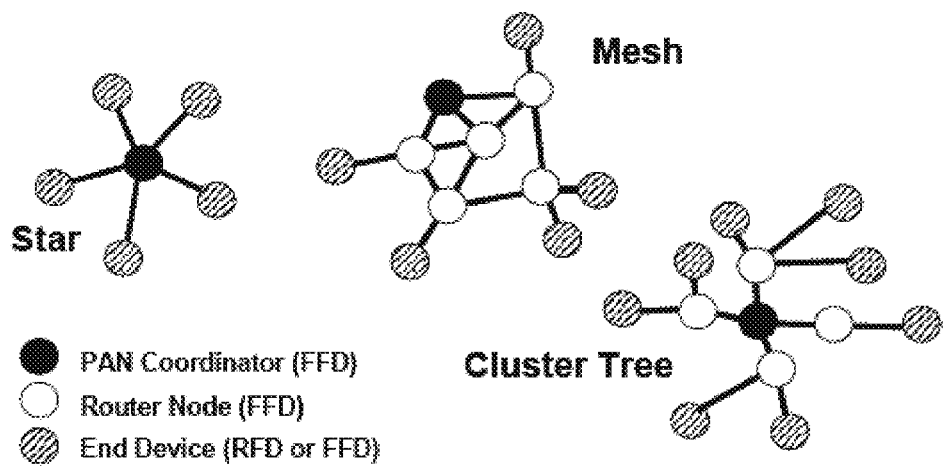
FIG. 7 shows an exemplary mesh network in communication with the wrist-watch device of FIG. 6.

FIG. 1A shows an exemplary patient monitoring system. The system can operate in a home, a care facility, a nursing home, or a hospital. In this system, one or more mesh network appliances 8 are provided to enable wireless communication in the home monitoring system. Appliances 8 in the mesh network can include home security monitoring devices, door alarm, window alarm, home temperature control devices, fire alarm devices, among others. Appliances 8 in the mesh network can be one of multiple portable physiological transducer, such as a blood pressure monitor, heart rate monitor, weight scale, thermometer, spirometer, single or multiple lead electrocardiograph (ECG), a pulse oxymeter, a body fat monitor, a cholesterol monitor, a signal from a medicine cabinet, a signal from a drug container, a signal from a commonly used appliance such as a refrigerator/stove/oven/washer, or a signal from an exercise machine, such as a heart rate. As will be discussed in more detail below, one appliance is a patient monitoring device that can be worn by the patient and includes a single or bi-directional wireless communication link, generally identified by the bolt symbol in FIG. 1, for transmitting data from the appliances 8 to the local hub or receiving station or server 20 by way of a wireless radio frequency (RF) link using a proprietary or non-proprietary protocol. For example, within a house, a user may have mesh network appliances that detect window and door contacts, smoke detectors and motion sensors, video cameras, key chain control, temperature monitors, CO and other gas detectors, vibration sensors, and others. A user may have flood sensors and other detectors on a boat. An individual, such as an ill or elderly grandparent, may have access to a panic transmitter or other alarm transmitter. Other sensors and/or detectors may also be included. The user may register these appliances on a central security network by entering the identification code for each registered appliance/device and/or system. The mesh network can be Zigbee network or 802.15 network. More details of the mesh network is shown in FIG. 7 and discussed in more detail below. An interoperability protocol supports the automatic configuration of an appliance with the base station. When the user operates a new appliance, the appliance announces its presence and the base station detects the presence and queries the device for its identity. If the device is not recognized, the base station determines where to find the needed software, retrieves the software, install the support software for the appliance, and then ran the device's default startup protocol that came in the downloaded installation package. The protocol allows remotely located systems or users to authenticate the identity (and possibly credentials) of the persons or organizations with whom they are interacting and ensures the privacy and authenticity of all data and command flowing between the appliances and any internal or external data storage devices. A public key infrastructure or cryptographic mechanism for facilitating these trusted interactions is used to support a global e-medicine system infrastructure. The protocol allows independently designed and implemented systems to locate each other, explore each other's capabilities (subject to each station's access control rules), to negotiate with each other and with the networks that they will use to determine how a given session will be run (for example, what Quality of Service requirements will be levied and what resources will be leased from each other), and to then conduct collaborative operations. The protocol contains instructions regarding the kinds of components that are needed to support the protocol's operation, the ways in which these components need to be interconnected, and events that are to be monitored during the time that the protocol is active.

A plurality of monitoring camera 10 may be placed in various predetermined positions in a home of a patient 30. The camera 10 can be wired or wireless. For example, the cameras can communicate over infrared links or over radio links conforming to the 802X (e.g. 802.11A, 802.11B, 802.11G, 802.15) standard or the Bluetooth standard to a base station server 20 may communicate over various communication links, such as a direct connection, such a serial connection, USB connection, Firewire connection or may be optically based, such as infrared or wireless based, for example, home RF, IEEE standard 802.11a/b, Bluetooth or the like. In one embodiment, appliances 8 monitor the patient and activates the camera 10 to capture and transmit video to an authorized third party for providing assistance should the appliances 8 detect that the user needs assistance or that an emergency had occurred.

The server 20 stores the patient's ambulation pattern and vital parameters and can be accessed by the patient's family members (sons/daughters), physicians, caretakers, nurses, hospitals, and elderly community. The server 20 may communicate with the remote server 200 by DSL, T-1 connection over a private communication network or a public information network, such as the Internet 100, among others.

The patient 30 may wear one or more wearable patient monitoring appliances such as wrist-watches or clip on devices or electronic jewelry to monitor the patient. One wearable appliance such as a wrist-watch includes sensors, for example devices for sensing ECG, EKG, blood pressure, sugar level, among others. In one embodiment, the sensors are mounted on the patient's wrist (such as a wristwatch sensor) and other convenient anatomical locations. Exemplary sensors include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors can individually transmit data to the server 20 using wired or wireless transmission. Alternatively, all sensors can be fed through a common bus into a single transceiver for wired or wireless transmission. The transmission can be done using a magnetic medium such as a floppy disk or a flash memory card, or can be done using infrared or radio network link, among others. The sensor can also include an indoor positioning system or alternatively a global position system (GPS) receiver that relays the position and ambulatory patterns of the patient to the server 20 for mobility tracking.

In one embodiment, the sensors for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch.

In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

The case may be of a number of variations of shape but can be conveniently made a rectangular, approaching a box-like configuration. The wrist-band can be an expansion band or a wristwatch strap of plastic, leather or woven material. The wrist-band further contains an antenna for transmitting or receiving radio frequency signals. The wrist-band and the antenna inside the band are mechanically coupled to the top and bottom sides of the wrist-watch housing. Further, the antenna is electrically coupled to a radio frequency transmitter and receiver for wireless communications with another computer or another user. Although a wrist-band is disclosed, a number of substitutes may be used, including a belt, a ring holder, a brace, or a bracelet, among other suitable substitutes known to one skilled in the art. The housing contains the processor and associated peripherals to provide the human-machine interface. A display is located on the front section of the housing. A speaker, a microphone, and a plurality of push-button switches and are also located on the front section of housing. An infrared LED transmitter and an infrared LED receiver are positioned on the right side of housing to enable the watch to communicate with another computer using infrared transmission.

In another embodiment, the sensors are mounted on the patient's clothing. For example, sensors can be woven into a single-piece garment (an undershirt) on a weaving machine. A plastic optical fiber can be integrated into the structure during the fabric production process without any discontinuities at the armhole or the seams. An interconnection technology transmits information from (and to) sensors mounted at any location on the body thus creating a flexible "bus" structure. T-Connectors—similar to "button clips" used in clothing—are attached to the fibers that serve as a data bus to carry the information from the sensors (e.g., EKG sensors) on the body. The sensors will plug into these connectors and at the other end similar T-Connectors will be used to transmit the information to monitoring equipment or personal status monitor. Since shapes and sizes of humans will be different, sensors can be positioned on the right locations for all patients and without any constraints being imposed by the clothing. Moreover, the clothing can be laundered without any damage to the sensors themselves. In addition to the fiber optic and specialty fibers that serve as sensors and data bus to carry sensory information from the wearer to the monitoring devices, sensors for monitoring the respiration rate can be integrated into the structure.

In another embodiment, instead of being mounted on the patient, the sensors can be mounted on fixed surfaces such as walls or tables, for example. One such sensor is a motion detector. Another sensor is a proximity sensor. The fixed sensors can operate alone or in conjunction with the camera 10. In one embodiment where the motion detector operates with the camera 10, the motion detector can be used to trigger camera recording. Thus, as long as motion is sensed, images from the camera 10 are not saved. However, when motion is not detected, the images are stored and an alarm may be generated. In another embodiment where the motion detector operates stand alone, when no motion is sensed, the system generates an alarm.

The server 20 also executes one or more software modules to analyze data from the patient. A module 50 monitors the patient's vital signs such as ECG/EKG and generates warnings should problems occur. In this module, vital signs can be collected and communicated to the server 20 using wired or wireless transmitters. In one embodiment, the server 20 feeds the data to a statistical analyzer such as a neural network which has been trained to flag potentially dangerous conditions. The neural network can be a back-propagation neural network, for example. In this embodiment, the statistical analyzer is trained with training data where certain signals are determined to be undesirable for the patient, given his age, weight, and physical limitations, among others. For example, the patient's glucose level should be within a well established range, and any value outside of this range is flagged by the statistical analyzer as a dangerous condition. As used herein, the dangerous condition can be specified as an event or a pattern that can cause physiological or psychological damage to the patient. Moreover, interactions between different vital signals can be accounted for so that the statistical analyzer can take into consideration instances where individually the vital signs are acceptable, but in certain combinations, the vital signs can indicate potentially dangerous conditions. Once trained, the data received by the server 20 can be appropriately scaled and processed by the statistical analyzer. In addition to statistical analyzers, the server 20 can process vital signs using rule-based inference engines, fuzzy logic, as well as conventional if-then logic. Additionally, the server can process vital signs using Hidden Markov Models (HMMs), dynamic time warping, or template matching, among others.

Through various software modules, the system reads video sequence and generates a 3D anatomy file out of the sequence. The proper bone and muscle scene structure are created for head and face. A based profile stock phase shape will be created by this scene structure. Every scene will then be normalized to a standardized viewport.

A module monitors the patient ambulatory pattern and generates warnings should the patient's patterns indicate that the patient has fallen or is likely to fall. 3D detection is used to monitor the patient's ambulation. In the 3D detection process, by putting 3 or more known coordinate objects in a scene, camera origin, view direction and up vector can be calculated and the 3D space that each camera views can be defined.

In one embodiment with two or more cameras, camera parameters (e.g. field of view) are preset to fixed numbers. Each pixel from each camera maps to a cone space. The system identifies one or more 3D feature points (such as a birthmark or an identifiable body landmark) on the patient. The 3D feature point can be detected by identifying the same point from two or more different angles. By determining the intersection for the two or more cones, the system determines the position of the feature point. The above process can be extended to certain feature curves and surfaces, e.g. straight lines, arcs; flat surfaces, cylindrical surfaces. Thus, the system can detect curves if a feature curve is known as a straight line or arc. Additionally, the system can detect surfaces if a feature surface is known as a flat or cylindrical surface. The further the patient is from the camera, the lower the accuracy of the feature point determination. Also, the presence of more cameras would lead to more correlation data for increased accuracy in feature point determination. When correlated feature points, curves and surfaces are detected, the remaining surfaces are detected by texture matching and shading changes. Predetermined constraints are applied based on silhouette curves from different views. A different constraint can be applied when one part of the patient is occluded by another object. Further, as the system knows what basic organic shape it is detecting, the basic profile can be applied and adjusted in the process.

In a single camera embodiment, the 3D feature point (e.g. a birth mark) can be detected if the system can identify the same point from two frames. The relative motion from the two frames should be small but detectable. Other features curves and surfaces will be detected correspondingly, but can be tessellated or sampled to generate more feature points. A transformation matrix is calculated between a set of feature points from the first frame to a set of feature points from the second frame. When correlated feature points, curves and surfaces are detected, the rest of the surfaces will be detected by texture matching and shading changes.

Each camera exists in a sphere coordinate system where the sphere origin (0,0,0) is defined as the position of the camera. The system detects theta and phi for each observed object, but not the radius or size of the object. The radius is approximated by detecting the size of known objects and scaling the size of known objects to the object whose size is to be determined. For example, to detect the position of a ball that is 10 cm in radius, the system detects the ball and scales other features based on the known ball size. For human, features that are known in advance include head size and leg length, among others. Surface texture can also be detected, but the light and shade information from different camera views is removed. In either single or multiple camera embodiments, depending on frame rate and picture resolution, certain undetected areas such as holes can exist. For example, if the patient yawns, the patient's mouth can appear as a hole in an image. For 3D modeling purposes, the hole can be filled by blending neighborhood surfaces. The blended surfaces are behind the visible line.

In FIG. 1, the exemplary devices 40 include a layer of device-specific software (application interface) which supports a common language (such as, for example, the Extension Markup Language (XML)) to interface with the server 20. The server 20 acts as a gateway or moderator to coordinate the devices 40 in a local network neighborhood. The server 20 supports multiple communication protocols and connectivity standards so that it may talk to other devices in one language (e.g., XML) but using different protocols and/or connectivity standards (such as, for example, Hypertext Transfer Protocol (HTTP), File Transfer Protocol (FTP), Simple Network Management Protocol (SNMP), Internet Inter-Orb Protocol (HOP) in Common Object Request Broken Architecture (CORBA), Simple Object Access Protocol (SOAP) with Extension Markup Language (XML), Ethernet, Bluetooth, IEEE 802.11 a/b/g (WiFi), 802.16 (WiMAX), ZigBee, Infrared Detection and Acquisition (IrDA), General Packet Radio Service (GPRS), Code Division Multiplexed Access (CDMA), and Global System for Mobile Communication (GSM), or any other appropriate communications protocol or connectivity standard). The server 20 performs device registration, synchronization, and user authentication and authorization. The application interface provides a simplified way of communicating with the server 20 which provides a seamless integration and synchronization among the devices 40 for example. Hence, instead of connecting individual devices directly (point-to-point) to a network, such as, for example, the Internet, to obtain services, the server 20 runs a "middleware" software that hides protocol and connectivity details from the device. Consequently, services from the Internet, for example, may be provided without being concerned about future development of new protocols, services, and connectivity.

To obtain services from external sources, the server 20 makes a request based on the information collected from the multiple devices and issues the request to the remote server 200. The remote server 200 acts as a proxy/gateway to request, consume, and/or distribute web services from a variety of content sources. In this regard, the communications between the server 20 and the server 200 are encrypted to protect patient identifiable information and other private details of the person. Also, a variety of services may be aggregated and cached, thus providing a faster response time and better use of network bandwidth. The server 200 may store information regarding the devices and/or service providers. In this regard, the server 200 may include a user profile database that maintains an updated copy of the user profile and application data so that intelligent content services and synchronization among different devices may be provided. In a wireless network environment, availability may not always be guaranteed so that another mechanism, such as, for example, a queue structure, may be required to save the data, profiles, and results for later retrieval.

The devices 9, 11, and 40 register with the server 20 and provide information regarding the capabilities of the device, including, for example, device type (EKG, EMG, blood pressure sensor, etc.) memory size, processing capacity, and supported protocols and connectivity. The server 20 processes service requests from the devices and may enhance the service requests and/or combine them collectively before issuing the requests in response to queries from a requester such as a doctor who polls the server 200 on the status of the patient. Upon receiving the request from the doctor through the server 200, the server 20 "tailors" the request to suit the proper device capability before relaying it the appropriate device. Hence, the devices 9, 11, and 40, issue requests on behalf of themselves and receive responses individually according to their particular capabilities while the server 20 customizes and combines requests/responses to simplify and/or improve communication efficiency. Data is automatically synchronized to maintain a consistent state of the devices, regardless, for example, of network availability and/or unreliable networks.

Next, an exemplary process for providing interoperability between two devices within the base station network (such as devices 9, 11, and 40) is described. Pseudo-code for the device interoperability process is as follows:

Device requests registration with base station (S2)
Base station registers devices with remote server on their behalf (S4)
Device requests application data from base station (S6)
Base station searches for a responsive device from its registration list and forwards request to responsive device over preferred communication channel (S8)

Responsive device replies to base station with data (S10)
Base station reformats data to match requesting data's preference (S12)
Base station forwards formatted data to requesting device on requesting device's communication channel (S14)

In the next example, an exemplary process for providing interoperability between a device within the base station network (such as one of devices 9, 11, and 40) and an external device (such as a cell phone) is described. Pseudo-code for the device interoperability process is as follows:

Cell phone and In-Network Devices requests registration with base station (S22)
Base station registers devices with remote server on their behalf (S24)
Cell phone requests application data from base station (S26)
Base station searches for a responsive device from its registration list and forwards request to responsive device over preferred communication channel (S28)
Responsive device replies to base station with data (S30)
Base station reformats data to match cell phone's preference, in this example SMS (S32)
Base station forwards SMS formatted data to cell phone over cellular channel (S34)

In S24, the base station registers the devices, including their connectivity and protocol capabilities. During the registration, the base station determines, for example, that the EKG monitor device supports IEEE 802.15.4 connectivity standard (ZigBee) and the cellular telephone supports Bluetooth and SMS messaging. In S26, the cell phone may trigger an application supported by the EKG device. In S28, the base station receives the request and searches for a registered device that supports that application. For example, base station searches a device table and finds that the cellular telephone is able to process SMS messages and the EKG monitoring device can communicate over ZigBee and stores data in the OpenEKG format. In step S28, the base station relays the application request to the EKG monitoring device. The monitoring device captures EKG data from the patient and sends the data to the base station. In S32, the base station reformats data to SMS message format and to send the SMS message to the requesting cell phone. In this regard, the exemplary system may provide a transparent SMS service to the cell phone from a Zigbee device. Hence, from a receiving device perspective, the cell phone thinks that the EKG monitoring device is sending and receiving SMS messages, but the EKG monitoring device is not able to perform SMS messaging by itself. The translation is transparently and automatically done by the base station.

In the following example, an exemplary process for providing interoperability between a device within the base station network (such as one of devices 9, 11, and 40) and an external device at a clinic or hospital is described. Pseudo-code for the device interoperability process is as follows:

Hospital/Clinic devices and In-Network devices requests registration with remote server (S42)
Remote server forwards registration request to all base stations, which in turn register hospital/clinic device (S44)
Hospital device requests application data from server, which in turn forwards request to base station (S46)
Base station searches for a responsive device from its registration list and forwards request to responsive device over preferred communication channel (S48)
Responsive device replies to base station with data (S50)
Base station reformats data to match requestor's preference (S52)
Base station forwards formatted data to hospital/clinic device through the remote server (S54)

In this example, a doctor at a hospital, clinic or doctor office registers and authenticates with the remote server 200. In a thin-client application, the server 200 maintains all patient information in its database. Upon authentication, the server 200 polls the base station for the latest information and displays the patient screens for the doctor. In this case, the server 200 uses secure HTTP (SHTTP) protocol for communication with the server 20 and the base station performs auto-translation among devices. For example, a hospital EKG device can store time series EKG data in XML format, while a home based EKG device can store compressed EKG data. The base station can translate the Open EKG format to the uncompressed XML data.

In one uncompressed XML embodiment, the EKG recordings for a single sitting are described in a SESSION. An EPOCH describes a continuous (evenly-sampled) data from a set of channels. Each SESSION contains a HEADER identifying the person from whom the recording was obtained, what equipment was used, and when recording began. Each EPOCH identifies data collection characteristics, the characteristics of the CHANNELS, and ANNOTATIONS that apply across all channels. Parameters captured in clued a BASELINE date and time, a SAMPLERATE (Hz), SYNCHRONOUS/NON-SYNCHRONOUS sampling, BITS, ZEROOFFSET, UNITS, and the SCALE factor, FILTER type (HIGHPASS and LOWPASS), BANDpass (Hz). The DATA would be uncompressed hexadecimal, packed to the nearest nibble, ordered as acquired. Data may be inserted in-line with the BINHEX or UUENCODE attribute, or may use a DREF reference to an external XML file (containing a DATA element with a BINHEX or UUENCODE attribute). IN an exemplary standard 12-lead ECG, standard lead names (<CHANNEL NAME=" ">) are "I", "II", "III", "AVL", "AVR", "AVF", "V1", "V2", "V3", "V4", "V5", and "V6", the standard UNIT for the data is "UV" (microvolts), a set of standard POINT or INTERVAL TYPE names can be used: "PSTART" (POINT), "QSTART" (POINT), "RSTART" (POINT), "RPEAK" (POINT), "SPEAK" (POINT), "JPOINT" (POINT), "TEND" (POINT), and "UWAVE" (INTERVAL). An example of 12-lead ECG data is as follows:

```
<TIMESERIES>
 <SESSION>
  <HEADER>
   <SUBJECT ID="xxxxxxxxxxxxxxxxx">
   <SOURCE TYPE="ECG"
      MFR="Sentinel System, Inc."
      MODEL="Sentinel One">
   <BASELINE DATE="2007-07-19"
      TIME="07:48:00">
  </HEADER>
  <ANNOTATIONS>
   <POINT TYPE="STUDY DRUG"
      OFFSET="-900">
  </ANNOTATIONS>
  <EPOCHS>
   <EPOCH OFFSET="00:00:00"
      SAMPLERATE=500
      SYNCHRONOUS="T">
    <ANNOTATIONS>
     <INTERVAL TYPE="PVC"
        TIME="819-1302">
    </ANNOTATIONS>
    <CHANNELS COUNT=2
```

```
            BITS=12
            ZEROOFFSET=0
            UNITS="UV"
            SCALE=0.023132>
        <FILTER BAND="5-250"
            HIGHPASS="FFT-IFFT"
            LOWPASS="BUTTERWORTH"
            BASELINEADJUSTED>
        <CHANNEL NAME="I">
          <DATA BINHEX="15A119AD827D9C72C012312341...">
          <ANNOTATIONS>
            <POINT TYPE="P"
               TIME="127,192,318,455">
            <INTERVAL TYPE="QRS"
                  TIME="137-145,218-223,462-518">
          </ANNOTATIONS>
        </CHANNEL>
        <CHANNEL NAME="II">
          <DATA BINHEX="15A119AD827D9C72C012312341...">
        </CHANNEL>
        <CHANNEL NAME="III">
          <DATA BINHEX="15A119AD827D9C72C012312341...">
        </CHANNEL>
        <CHANNEL NAME="AVL"
            CALCULATED
            ZEROOFFSET=2048>
          <DATA BINHEX="15A119AD827D9C72C012312341...">
        </CHANNEL>
        <CHANNEL NAME="AVR"
            CALCULATED
            ZEROOFFSET=2048>
          <DATA BINHEX="15A119AD827D9C72C012312341...">
        </CHANNEL>
        <CHANNEL NAME="AVF"
            CALCULATED
            ZEROOFFSET=2048>
          <DATA BINHEX="15A119AD827D9C72C012312341...">
        </CHANNEL>
       </CHANNELS>
     </EPOCH>
     <EPOCH OFFSET="00:00:06"
         SAMPLERATE=500
         SYNCHRONOUS="T">
       <CHANNELS COUNT=6
            BITS=12
            ZEROOFFSET=0
            UNITS="mV"
            SCALE=0.023132>
         <CHANNEL NAME="V1">
          <DATA BINHEX="15A119AD827D9C72C012312341...">
         </CHANNEL>
         <CHANNEL NAME="V2">
          <DATA BINHEX="15A119AD827D9C72C012312341...">
         </CHANNEL>
         <CHANNEL NAME="V3">
          <DATA BINHEX="15A119AD827D9C72C012312341...">
         </CHANNEL>
         <CHANNEL NAME="V4">
          <DATA BINHEX="15A119AD827D9C72C012312341...">
         </CHANNEL>
         <CHANNEL NAME="V5">
          <DATA BINHEX="15A119AD827D9C72C012312341...">
         </CHANNEL>
         <CHANNEL NAME="V6">
          <DATA BINHEX="15A119AD827D9C72C012312341...">
         </CHANNEL>
       </CHANNELS>
      </EPOCH>
      <EPOCH ...> ... </EPOCH>
     </EPOCHS>
    </SESSION>
    <SESSION> ... </SESSION>
   </TIMESERIES>
Draft TIMESERIES DTD
<!-- timeseries.dtd -->
<!ELEMENT timeseries (session)+>
  <!ELEMENT session (header, annotations, epochs)?>
    <!ELEMENT header (subject, source, baseline)>
      <!ELEMENT subject (EMPTY)>
        <!ATTLIST subject id CDATA#REQUIRED>
      <!ELEMENT source (EMPTY)>
        <!ATTLIST source type CDATA#REQUIRED
                mfr CDATA#IMPLIED
                model CDATA#IMPLIED>
      <!ELEMENT baseline (EMPTY)>
        <!ATTLIST baseline date CDATA#REQUIRED
                  time CDATA#REQUIRED>
    <!ELEMENT epochs (epoch)+>
      <!ELEMENT epoch (annotations, channels)?>
        <!ATTLIST epoch offset CDATA#IMPLIED
                samplerate CDATA#IMPLIED
                synchronous CDATA#IMPLIED>
        <!ELEMENT channels (filter, channel)+>
          <!ATTLIST channels count CDATA#IMPLIED
                  bits CDATA#IMPLIED
                  zerooffset CDATA#IMPLIED
                  units CDATA#IMPLIED
                  scale CDATA#IMPLIED>
          <!ELEMENT filter (EMPTY)>
            <!ATTLIST filter band CDATA#IMPLIED
                  highpass CDATA#IMPLIED
                  lowpass CDATA#IMPLIED
                  baselineadjusted CDATA#IMPLIED>
          <!ELEMENT channel (filter, data, annotations)+>
            <!ATTLIST channel name CDATA#IMPLIED
                  bits CDATA#IMPLIED
                  zerooffset CDATA#IMPLIED
                  units CDATA#IMPLIED
                  scale CDATA#IMPLIED>
            <!ELEMENT data (EMPTY)>
              <!ATTLIST data type CDATA#IMPLIED
                    binhex CDATA#IMPLIED
                    uuencode CDATA#IMPLIED
                    dref CDATA#IMPLIED>
            <!ELEMENT annotations (point, interval)*>
              <!ELEMENT point (EMPTY)>
                <!ATTLIST point type CDATA#REQUIRED
                      time CDATA#IMPLIED
                      offset CDATA#IMPLIED>
              <!ELEMENT interval (EMPTY)>
                <!ATTLIST interval type CDATA#REQUIRED
                      time CDATA#IMPLIED
                      offset CDATA#IMPLI
```

In this example, the doctor at the hospital accesses data stored in the XML format wishes to view an ECG monitoring device at home that stores data in accordance with the openEKG group's Standard Communication Protocol for Computer-assisted Electrocardiography (SCP-ECG). OpenECG was launched by the European Commission on July 2002 to support the Implementation and Dissemination of the SCP-ECG Standard. The protocol stores ECG data as compressed or raw data with a checksum such as CRC checksum, record size, pointers to data areas in the record, header, and ECG data, among others. The server 200, based on its stored profiles, automatically performs the data format decompression and conversion and transmits the data to the doctor's station. The action is done automatically so that the doctor's computer needs not be aware of the underlying data format and thus the devices are "interoperable." Moreover, the server 200 can automatically synchronize data so that only one set of consistent data is saved.

In another embodiment, instead of having the doctor using a thin-client, a remote user such as a patient representative (attorney in fact), family member, or a doctor can be miming his/her own computer system that is registered with the server 200 as an authorized user. The server 200 forwards such registration to the server 20 and the server 20 registers the doctor's computer as an authorized doctor base station in the network. The doctor base station in turn communicates with devices in the doctor's office such as digital scales, blood pressure measurement devices, digital X-ray machines, glucose measurement devices, digital scanners such as computer aided tomography (CAT) scanners and nuclear magnetic resonance (NMR) scanners, among others. These devices capture patient information through a unique patient identifier and the data is stored in the doctor base station and can also be uploaded to the remote server 200 to store data. Since numerous base stations can exist that provide medical information on a patient (different doctors/specialists, different hospitals and care centers), the server 200 performs data synchronization to ensure that all base stations have access to the latest information.

To allow the remote person such as a physician or a family member to monitor a patient, a plurality of user interface modules enable the remote person to control each appliance and to display the data generated by the appliance. In one example scenario, an EKG sensor wirelessly communicates with the server 20 and outputs a continuous EKG waveform. A pattern recognizer or analyzer positioned at the doctor's station accepts waveform data and generates a variety of statistics that characterize the waveform and can generate alarms or messages to the doctor if certain predefined conditions are met. While it is operating, the EKG sends its waveform data to its subscribing components or modules at the doctor's office and the analyzer processes the data and sends summaries or recommendations to the doctor for viewing. If, during the operation of this network of components, any of these components experience an event that compromises its ability to support the protocol (e.g., the EKG unit is disconnected or deactivated from the base station), then the affected components notify the remote base station of a disconnected appliance. When finished with the EKG data sampling, the user may "deselect" the device on the user interface framework, which results in the EKG user interface module being disabled and terminating data collection by the EKG device. In turn, the protocol instructs each of the leased components to terminate its subscriptions. The protocol then notifies the registry that it is vacating its lease on these components and tells the user interface event handler that it is ending.

The system can support procedure-centric workflow management such as those described in Application Serial No. 20060122865. In one example, the system manages a workflow involving a specialist, an electronic medial record (EMR) or other external patient information system, a referring provider, a rural health care facility, and appropriate appliances (e.g., modalities) corresponding to the particular procedure of interest. In one example, the specialist's workflow includes capturing/reviewing patient history, which itself entails reviewing prior procedures, reviewing prior data and/or digital images, reviewing problem lists in communication with the EMR, capturing/reviewing patient physical and history information in communication with EMR, and reviewing lab results in communication with EMR. The workflow further includes capturing follow-up orders in communication with EMR. In addition, the workflow also involves capturing procedure results and corresponding data obtained during the procedure, and distributing such data in communication with a referring provider and rural facility. Finally, in communication with external devices or appliances, the specialist receives the captured data from the procedure and reviews/interprets the data or digital images. Workflow management as described here includes recognition of various roles of people involved in workflows, whether they are different types of caregivers or different types of patients.

In one embodiment, the authentication source is a trusted key distribution center (KDC) and the authentication type is user IDs with passwords. The initial authentication can also be based on public key. The public key infrastructure (PKI) system can be used where the authentication source is a certificate authority (CA) and the authentication type is challenge/response. Another authentication system called the secure remote password (SRP) protocol authenticates clients to servers securely, in cases where the client must memorize a small secret (like a password) and carries no other secret information, and where the server carries a verifier which allows it to authenticate the client but which, if compromised, would not allow someone to impersonate the client.

The system may be based on a peer-to-peer (P2P) architecture rather than a client-server approach. In this exemplary architecture, each participating device, that is, each peer, belongs to a peer group, such as, for example, a local area impromptu network neighborhood formed by nearby devices through authentication and authorization. Each device communicates to a router, residing, for example, on another device. The router may also function as a device except that it may be additionally responsible for device synchronization, device registration, authentication, authorization, and obtaining services from service providers. The device router may aggregate the service requests from each device to form a single query and may be required to have a suitable connectivity/bandwidth to the service provider to obtain responses. To accommodate unreliable networks, the router may also store or cache the requests and results so that if the devices become disconnected a reconnection and resend of the request may be performed. According to an exemplary embodiment, at least one device router should exist in the peer group. As devices join and leave the network, their roles may change. For example, a more capable (e.g., faster connectivity or higher computation power) device may become the router. Hence, a flexible and dynamic network topology may be provided.

Interprocess communication in a heterogeneous distributed environment may require support for different language bindings (e.g., C, C++, Java, etc.), different protocols (e.g., HTTP, IIOP, RMI, HTTPS, SOAP, XML, XML-RPC, etc.) and different frameworks (e.g., CORBA, OS sockets, JMS, Java object serialization, etc). A Message Oriented Middleware (MoM) may be provided which runs continuously (e.g., acting as a server middleware) to regulate and facilitate the exchange of messages between publishers (those who "announce") and subscribers (those who "listen"). The message may be described with XML-encoded Meta information. Message data may include simple ASCII text, GIF images, XML data, Java objects, or any binary-encoded data. Other protocols, such as, for example, E-mail or SOAP may be plugged in later without making any changes in the client code. The MoM may hide much of the networking protocol and operating system issues, which should alleviate the burden of maintaining socket communication and session management from programmers.

In one embodiment, a device first appears on a network. The device searches the local cache for information regarding the base station. If base station information is found, the device attempts to contact the base station and setup a connection. Otherwise if the information is not found, then a discovery request is sent. The discovery request may be sent via a broadcast or a multicast. In this regard, the device sends out a discovery request and all the devices in the network neighborhood should receive the message and respond appropriately. The device agent examines the responses to determine and/or confirm the base station. If the device does not discover the base station, the system assumes that there is no base station in the network neighborhood at present and repeats the discovery request process until a base station is found. Otherwise, if the device discovers the base station, the connection token is saved (an XML message that tells where the device communicator is located and how to contact it) in the cache for later usage. The cache may allow for faster discovery but it may also expire due to the feature that devices may join and leave the network. Therefore a time-to-live (TTL) may be attached so that after a certain period the cached data may be considered expired. A check may also be preformed to ensure that the device exists before a network connection is initiated. To provide a generalized format, XML may be used to provide an easily expandable and hierarchical representation. XML may also be used to aggregate information from other agents and send back results from service providers to device through the base station.

Figure 1B:
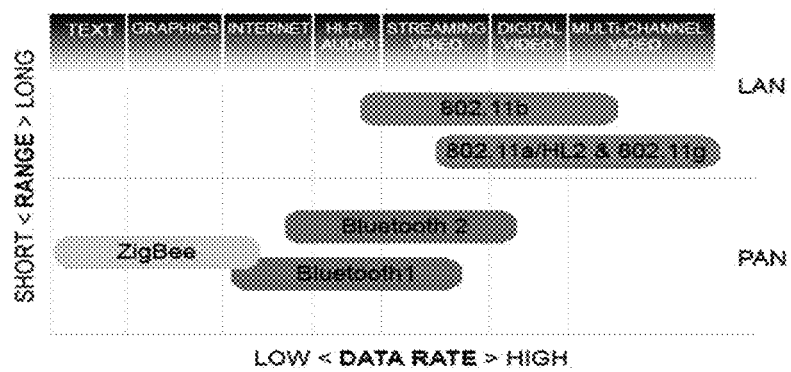
FIG. 1B shows a multitude of standards that address mid to high data rates for voice, PC LANs, video, among others.

FIG. 1B shows a multitude of standards that address mid to high data rates for voice, PC LANs, video, among others. ZigBee provides good bandwidth with low latency and very low energy consumption for long battery lives and for large device arrays. Bluetooth provides higher speed (and higher power consumption) for cell phone headset applications, among others. Variants of the 802.11 standard (802.11b, 802.11g, 802.11a) provide yet faster data transmission capability with correspondingly high power consumption. Other devices include WiMAX (802.16) and ultrawideband devices that are very high in power consumption and provide long range and/or video capable transmission.

Device discovery and service discovery are provided for each class of devices (Zigbee or Bluetooth, for example). For interoperability, a local discovery mapper running on the personal server or a remote discovery mapper running on a remote server is provided to enable Zigbee services to be advertised to Bluetooth devices and vice versa, for example. In other implementations, the services of ZigBee devices can be advertised to body PAN devices (PAN devices that are attached to a biological being such as humans or pets), Bluetooth devices, cellular devices, UWB devices, WiFi, and WiMAX devices, among others.

In one implementation, a Bluetooth device discovery can be done by having one device initiating queries that are broadcast or unicast addressed. Service discovery is the process whereby services available on endpoints at the receiving device are discovered by external devices. Service means the interfaces described by means of Device Descriptors set. Service discovery can be accomplished by issuing a query for each endpoint on a given device, by using a match service feature (either broadcast or unicast) or by having devices announce themselves when they join the network. Service discovery utilizes the complex, user, node or power descriptors plus the simple descriptor further addressed by the endpoint (for the connected application object). The service discovery process enables devices to be interfaced and interoperable within the network. Through specific requests for descriptors on specified nodes, broadcast requests for service matching and the ability to ask a device which endpoints support application objects, a range of options are available for commissioning universal healthcare applications that interact with each other and are compatible.

Figure 1C:
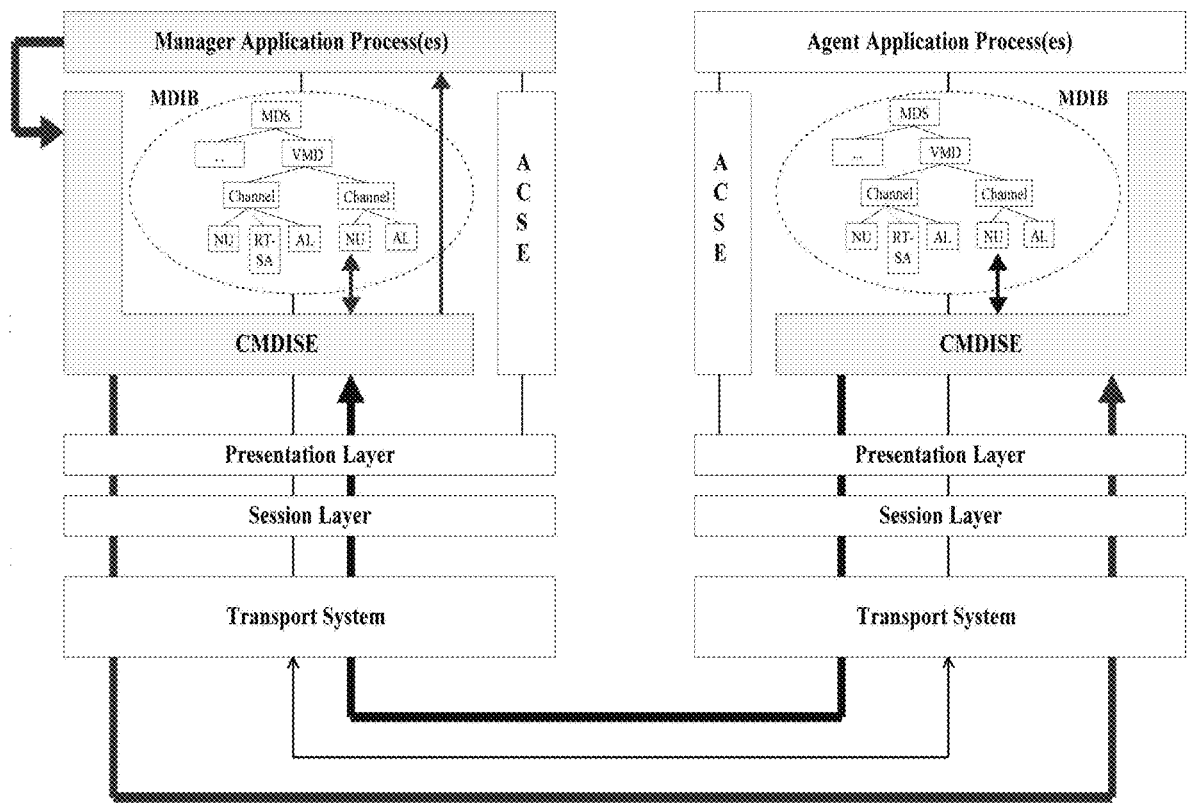
FIG. 1C shows a logical interface between two connected systems.

FIG. 1C shows a logical interface between two connected systems, a Manager (typically a host/BCC) and an Agent (typically a device/DCC). The interface is generally patterned after the International Organization for Standardization's Open Systems Interconnection (OSI-ISO) seven-layer communications model. That model was created to foster interoperability between communicating systems by isolating functional layers and defining their abstract capabilities and the services relating adjacent levels. The four so-called "lower" OSI layers are the (1) physical, (2) data link, (3) network, and (4) transport layers. Layers 5, 6, and 7—the session, presentation, and application layers—are known as "upper" layers. Layers 1-4, the "lower" layers, constitute the transport system, which provides reliable transport of data across different media. The session layer includes services for connection and data transfer (e.g., session connect, session accept, and session data transfer). The Presentation Layer holds services for negotiating abstract syntax, such as Medical Device Data Language (MDDL) over CMDISE ASN., and transfer syntax, which are basic encoding rules (BER) or optimized medical device encoding rules (MDER). MDERs are abstract message definitions that include primitive data types such as FLOAT (floating-point numeric) or 32-bit integer, and the way they are encoded as bits and bytes for communication over the transport. The association control service element or ACSE (ISO/IEC 8650) provides services used initially to establish an association between two communicating entities, including association request and response, association release, association abort, and others. The ROSE or remote operation service element (ISO/IEC 9072-2) provides basic services for performing operations across a connection, including remote operation invoke, result, error, and reject. The CMDISE or common medical device information service element, is based on CMIP (the common management information protocol; ISO/IEC 9596-1) and provides basic services for managed objects, including the performance of GET, SET, CREATE, DELETE, ACTION, and EVENT REPORT functions. These services, invoked using ROSE primitives, represent the basic means for interacting with the medical data information base (MDIB). The medical data information base supplies an abstract object-oriented data model representing the information and services provided by the medical device. The data originate in the device agent (the right side in FIG. 1) and are replicated during connection on the Manager side of the system. Objects include the medical device system (MDS), virtual medical device (VMD), channels, numerics, real-time sample arrays, alerts, and others. Application Processes. This layer represents the core software on both the host (BCC) and device (DCC) sides of the connection that either creates or consumes the information that is sent across the link.

To provide orderly system behavior, a finite-state-machine model for the life cycle of a BCC-DCC interaction is used. After a connection is made at the transport level, the DCC proceeds to associate with the managing BCC system and configure the link. Once configuration has been completed, the communication enters the normal operating state in which, in accordance with the profile that is active, data may be exchanged between the two systems. If the device is reconfigured—for example, if a new plug-in module is added—it can transition through the reconfiguration state, in which the Manager is notified of the changes in the Agent's MDIB data model, and then cycle back to the operating state. The interactions between an Agent (DCC) system and a Manager (BCC) system begins once the Manager transport layer indicates that a connection has been made, the Manager application, using ACSE PDUs, initiates the association-establishment process, which results on the Agent side in the association-request event being generated. Association being accomplished, the Agent notifies the Manager that the MDS object has been created. This MDS-create-notification event report includes static information about the device's manufacturer, its serial number, and other configuration data. At this point, the Manager can create a context scanner within the device's MDIB. A scanner is a tool that collects information of various kinds from the device's MDIB and sends it to the Manager in event-report messages. A periodic scanner will examine a set list of data items in the MDIB (for example, in an infusion pump, this list might include the parameters "volume infused" and "volume to be infused"), and send an update at regular intervals of every few seconds.

In one example with an infusion-pump, a context scanner is used to report the object-model containment tree to the Manager system. This way, the Manager can "discover" the data that are supported by a given device. Because the MDIB contains a finite set of object types (MDS, VMD, channel, numeric, alert, battery, etc.), a Manager does not need to know what an infusion device looks like, it can simply process the containment tree retrieved from the context scanner and configure itself accordingly.

Once the containment tree has been sent to the Manager system and the Agent has received a confirmation reply, the MDS object indicates that it has entered the configured state and automatically passes to the operating state, ready to begin regular data communications. A set of base station-to-device interfaces are provided and include those that enable appliances, medical instruments, patient record cards, and user interface components, among others, to be added to and removed from the station in a plug-and-play fashion.

The above system forms an interoperable health-care system with a network; a first medical appliance to capture a first vital information and coupled to the network, the first medical appliance transmitting the first vital information conforming to an interoperable format; and a second medical appliance to capture a second vital information and coupled to the network, the second medical appliance converting the first vital information in accordance with the interoperable format and processing the first and second vital information, the second medical appliance providing an output conforming to the interoperable format.

The appliances can communicate data conforming to the interoperable format over one of: cellular protocol, ZigBee protocol, Bluetooth protocol, WiFi protocol, WiMAX protocol, USB protocol, ultrawideband protocol. The appliances can communicate over two or more protocols. The first medical appliance can transmit the first vital information over a first protocol (such as Bluetooth protocol) to a computer, wherein the computer transmits the first vital information to the second medical appliance over a second protocol (such as ZigBee prototocol). The computer can then transmit to a hospital or physician office using broadband such as WiMAX protocol or cellular protocol. The computer can perform the interoperable format conversion for the appliances or devices, or alternatively each appliance or device can perform the format conversion. Regardless of which device performs the protocol conversion and format conversion, the user does not need to know about the underlying format or protocol in order to use the appliances. The user only needs to plug an appliance into the network, the data transfer is done automatically so that the electronic "plumbing" is not apparent to the user. In this way, the user is shielded from the complexity supporting interoperability.

In one embodiment shown in FIG. 2, each camera is calibrated before 3D detection is done. Pseudo-code for one implementation of a camera calibration process is as follows:

Place a calibration sheet with known dots at a known distance (e.g. 1 meter), and perpendicular to a camera view.
Take snap shot of the sheet, and correlate the position of the dots to the camera image:
Dot1 (x,y,1)←→pixel (x,y)
Place a different calibration sheet that contains known dots at another different known distance (e.g. 2 meters), and perpendicular to camera view.
Take another snapshot of the sheet, and correlate the position of the dots to the camera image:
Dot2 (x,y,2)←→pixel (x,y)
Smooth the dots and pixels to minimize digitization errors. By smoothing the map using a global map function, step errors will be eliminated and each pixel will be mapped to a cone space.
For each pixel, draw a line from Dot1(x,y,z) to Dot2(x, y, z) defining a cone center where the camera can view.
One smoothing method is to apply a weighted filter for Dot1 and Dot2. A weight filter can be used. In one example, the following exemplary filter is applied.
1 2 1
2 4 2
1 2 1
Assuming Dot1_Left refers to the value of the dot on the left side of Dot1 and Dot1_Right refers to the value of the dot to the right of Dot1 and Dot1_Upper refers to the dot above Dot1, for example, the resulting smoothed Dot1 value is as follows:
$1/16$*(Dot1*4+Dot1_Left*2+Dot1_Right*2+
Dot1_Upper*2+Dot1_Down*2+Dot1_UpperLeft+
Dot1_UpperRight+Dot1_LowerLeft+
Dot1_LowerRight)
Similarly, the resulting smoothed Dot2 value is as follows:
$1/16$*(Dot2*4+Dot2_Left*2+Dot2_Right*2+
Dot2_Upper*2+Dot2_Down*2+Dot2_UpperLeft+
Dot2_UpperRight+Dot2_LowerLeft+
Dot2_LowerRight)
In another smoothing method, features from Dot1 sheet are mapped to a sub pixel level and features of Dot2 sheet are mapped to a sub pixel level and smooth them. To illustrate, Dot1 dot center (5, 5, 1) are mapped to pixel (1.05, 2.86), and Dot2 dot center (10, 10, 2) are mapped to pixel (1.15, 2.76). A predetermined correlation function is then applied.

A module 54 monitors patient activity and generates a warning if the patient has fallen. In one implementation, the system detects the speed of center of mass movement. If the center of mass movement is zero for a predetermined period, the patient is either sleeping or unconscious. The system then attempts to signal the patient and receive confirmatory signals indicating that the patient is conscious. If patient does not confirm, then the system generates an alarm. For example, if the patient has fallen, the system would generate an alarm signal that can be sent to friends, relatives or neighbors of the patient. Alternatively, a third party such as a call center can monitor the alarm signal. Besides monitoring for falls, the system performs video analysis of the patient. For example, during a particular day, the system can determine the amount of time for exercise, sleep, and entertainment, among others. The network of sensors in a patient's home can recognize ordinary patterns—such as eating, sleeping, and greeting visitors—and to alert caretakers to out-of-the-ordinary ones—such as prolonged inactivity or absence. For instance, if the patient goes into the bathroom then disappears off the sensor for 13 minutes and don't show up anywhere else in the house, the system infers that patient had taken a bath or a shower. However, if a person falls and remains motionless for a predetermined period, the system would record the event and notify a designated person to get assistance.

A fall detection process (shown in FIG. 3) performs the following operations:

Find floor space area
Define camera view background 3D scene
Calculate patient's key features
Detect fall In one implementation, pseudo-code for determining the floor space area is as follows:
1. Sample the camera view space by M by N, e.g. M=1000, N=500.
2. Calculate all sample points the 3D coordinates in room coordinate system; where Z axis is pointing up. Refer to the 3D detection for how to calculate 3D positions.
3. Find the lowest Z value point (Zmin)
4. Find all points whose Z values are less than Zmin+Ztol; where Ztol is a user adjustable value, e.g. 2 inches.
5. If rooms have different elevation levels, then excluding the lowest Z floor points, repeat steps 2, 3 and 4 while keeping the lowest Z is within Ztol2 of previous Z. In this example Ztol2=2 feet, which means the floor level difference should be within 2 feet.
6. Detect stairs by finding approximate same flat area but within equal Z differences between them.
7. Optionally, additional information from the user can be used to define floor space more accurately, especially in single camera system where the coordinates are less accurate, e.g.:
    a. Import the CAD file from constructors' blue prints.
    b. Pick regions from the camera space to define the floor, then use software to calculate its room coordinates.
    c. User software to find all flat surfaces, e.g. floors, counter tops, then user pick the ones, which are actually floors and/or stairs.

In the implementation, pseudo-code for determining the camera view background 3D scene is as follows:
1. With the same sample points, calculate x, y coordinates and the Z depth and calculate 3D positions.
2. Determine background scene using one the following methods, among others:
    a. When there is nobody in the room.
    b. Retrieve and update the previous calculated background scene.
    c. Continuous updating every sample point when the furthest Z value was found, that is the background value.

In the implementation, pseudo-code for determining key features of the patient is as follows:
1. Foreground objects can be extracted by comparing each sample point's Z value to the background scene point's Z value, if it is smaller, then it is on the foreground.
2. In normal condition, the feet/shoe can be detected by finding the lowest Z point clouds close the floor in room space, its color will be extracted.
3. In normal condition, the hair/hat can be detected by finding the highest Z point clouds close the floor in room space, its color will be extracted.
4. The rest of the features can be determined by searching from either head or toe. E.g, hat, hair, face, eye, mouth, ear, earring, neck, lipstick, moustache, jacket, limbs, belt, ring, hand, etc.
5. The key dimension of features will be determined by retrieving the historic stored data or recalculated, e.g., head size, mouth width, arm length, leg length, waist, etc.
6. In abnormal conditions, features can be detected by detect individual features then correlated them to different body parts. E.g, if patient's skin is black, we can hardly get a yellow or white face, by detecting eye and nose, we know which part is the face, then we can detect other characteristics.

To detect fall, the pseudo-code for the embodiment is as follows:
1. The fall has to be detected in almost real time by tracking movements of key features very quickly. E.g. if patient has black hair/face, track the center of the black blob will know roughly where his head move to.
2. Then the center of mass will be tracked, center of mass is usually around belly button area, so the belt or borderline between upper and lower body closed will be good indications.
3. Patient's fall always coupled with rapid deceleration of center of mass. Software can adjust this threshold based on patient age, height and physical conditions.
4. Then if the fall is accidental and patient has difficult to get up, one or more of following will happen:
    a. Patient will move very slowly to find support object to get up.
    b. Patient will wave hand to camera ask for help. To detect this condition, the patient hand has to be detected first by finding a blob of points with his skin color. Hand motion can be tracked by calculate the motion of the center of the points, if it swings left and right, it means patient is waving to camera.
    c. Patient is unconscious, motionless. To detect this condition, extract the foreground object, calculate its motion vectors, if it is within certain tolerance, it means patient is not moving. In the mean time, test how long it last, if it past a user defined time threshold, it means patient is in great danger.

In one embodiment for fall detection, the system determines a patient fall-down as when the patient's knee, butt or hand is on the floor. The fall action is defined a quick deceleration of center of mass, which is around belly button area. An accidental fall action is defined when the patient falls down with limited movement for a predetermined period.

The system monitors the patients' fall relative to a floor. In one embodiment, the plan of the floor is specified in advance by the patient. Alternatively, the system can automatically determine the floor layout by examining the movement of the patient's feet and estimated the surfaces touched by the feet as the floor.

In one embodiment with in door positioning, the user can create a facsimile of the floor plan during initialization by walking around the perimeter of each room and recording his/her movement through the in-door positioning system and when complete, press a button to indicate to the system the type of room such as living room, bed room, bath room, among others. Also, the user can calibrate the floor level by sitting down and then standing up (or vice versa) and allowing the accelerometer to sense the floor through the user motion. Periodically, the user can recalibrate the floor plan and/or the floor level.

The system detects a patient fall by detecting a center of mass of an exemplary feature. Thus, the software can monitor the center of one or more objects, for example the head and toe, the patient's belt, the bottom line of the shirt, or the top line of the pants.

The detection of the fall can be adjusted based on two thresholds:
 a. Speed of deceleration of the center of mass.
 b. The amount of time that the patient lies motionless on the floor after the fall.

In one example, once a stroke occurs, the system detects a slow motion of patient as the patient rests or a quick motion as the patient collapses. By adjust the sensitivity threshold, the system detects whether a patient is uncomfortable and ready to rest or collapse.

If the center of mass movement ceases to move for a predetermined period, the system can generate the warning. In another embodiment, before generating the warning, the system can request the patient to confirm that he or she does not need assistance. The confirmation can be in the form of a button that the user can press to override the warning. Alternatively, the confirmation can be in the form of a single utterance that is then detected by a speech recognizer.

In another embodiment, the confirmatory signal is a patient gesture. The patient can nod his or her head to request help and can shake the head to cancel the help request. Alternatively, the patient can use a plurality of hand gestures to signal to the server 20 the actions that the patient desires.

By adding other detecting mechanism such as sweat detection, the system can know whether patient is uncomfortable or not. Other items that can be monitored include chest movement (frequency and amplitude) and rest length when the patient sits still in one area, among others.

Besides monitoring for falls, the system performs video analysis of the patient. For example, during a particular day, the system can determine the amount of time for exercise, sleep, entertainment, among others. The network of sensors in a patient's home can recognize ordinary patterns—such as eating, sleeping, and greeting visitors—and to alert caretakers to out-of-the-ordinary ones—such as prolonged inactivity or absence. For instance, if the patient goes into the bathroom then disappears off the camera 10 view for a predetermined period and does not show up anywhere else in the house, the system infers that patient had taken a bath or a shower. However, if a person falls and remains motionless for a predetermined period, the system would record the event and notify a designated person to get assistance.

In one embodiment, changes in the patient's skin color can be detected by measuring the current light environment, properly calibrating color space between two photos, and then determining global color change between two states. Thus, when the patient's face turn red, based on the redness, a severity level warning is generated.

In another embodiment, changes in the patient's face are detected by analyzing a texture distortion in the images. If the patient perspires heavily, the texture will show small glisters, make-up smudges, or sweat/tear drippings. Another example is, when long stretched face will be detected as texture distortion. Agony will show certain wrinkle texture patterns, among others.

The system can also utilize high light changes. Thus, when the patient sweats or changes facial appearance, different high light areas are shown, glisters reflect light and pop up geometry generates more high light areas.

A module 62 analyzes facial changes such as facial asymmetries. The change will be detected by superimpose a newly acquired 3D anatomy structure to a historical (normal) 3D anatomy structure to detect face/eye sagging or excess stretch of facial muscles.

In one embodiment, the system determines a set of base 3D shapes, which are a set of shapes which can represent extremes of certain facial effects, e.g. frown, open mouth, smiling, among others. The rest of the 3D face shape can be generated by blending/interpolating these base shapes by applied different weight to each base shapes.

The base 3D shape can be captured using 1) a 3D camera such as cameras from Steinbichler, Genex Technology, Minolta 3D, Olympus 3D or 2) one or more 2D camera with preset camera field of view (FOV) parameters. To make it more accurate, one or more special markers can be placed on patient's face. For example, a known dimension square stick can be placed on the forehead for camera calibration purposes.

Using the above 3D detection method, facial shapes are then extracted. The proper features (e.g. a wrinkle) will be detected and attached to each base shape. These features can be animated or blended by changing the weight of different shape(s). The proper features change can be detected and determine what type of facial shape it will be.

Next, the system super-imposes two 3D facial shapes (historical or normal facial shapes and current facial shapes). By matching features and geometry of changing areas on the face, closely blended shapes can be matched and facial shape change detection can be performed. By overlaying the two shapes, the abnormal facial change such as sagging eyes or mouth can be detected.

The above processes are used to determine paralysis of specific regions of the face or disorders in the peripheral or central nervous system (trigeminal paralysis; CVA, among others). The software also detects eyelid positions for evidence of ptosis (incomplete opening of one or both eyelids) as a sign of innervation problems (CVA; Horner syndrome, for example). The software also checks eye movements for pathological conditions, mainly of neurological origin are reflected in aberrations in eye movement. Pupil reaction is also checked for abnormal reaction of the pupil to light (pupil gets smaller the stronger the light) may indicate various pathological conditions mainly of the nervous system. In patients treated for glaucoma pupillary status and motion pattern may be important to the follow-up of adequate treatment. The software also checks for asymmetry in tongue movement, which is usually indicative of neurological problems. Another check is neck veins: Engorgement of the neck veins may be an indication of heart failure or obstruction of normal blood flow from the head and upper extremities to the heart. The software also analyzes the face, which is usually a mirror of the emotional state of the observed subject. Fear, joy, anger, apathy are only some of the emotions that can be readily detected, facial expressions of emotions are relatively uniform regardless of age, sex, race, etc. This relative uniformity allows for the creation of computer programs attempting to automatically diagnose people's emotional states.

Speech recognition is performed to determine a change in the form of speech (slurred speech, difficulties in the formation of words, for example) may indicated neurological problems, such an observation can also indicate some outward effects of various drugs or toxic agents.

In one embodiment shown in FIG. 4, a facial expression analysis process performs the following operations:
 Find floor space area
 Define camera view background 3D scene
 Calculate patient's key features
 Extract facial objects Detect facial orientation Detect facial expression The first three steps are already discussed above. The patient's key features provide information on the location of the face, and once the face area has been determined, other features can be detected by detecting relative position to each other and special characteristics of the features:

Eye: pupil can be detected by applying Chamfer matching algorithm, by using stock pupil objects.

Hair: located on the top of the head, using previous stored hair color to locate the hair point clouds.

Birthmarks, wrinkles and tattoos: pre store all these features then use Chamfer matching to locate them.

Nose: nose bridge and nose holes usually show special characteristics for detection, sometime depend on the view angle, is side view, special silhouette will be shown.

Eye browse, Lips and Moustache: All these features have special colors, e.g. red lipstick; and base shape, e.g. patient has no expression with mouth closed. Software will locate these features by color matching, then try to deform the base shape based on expression, and match shape with expression, we can detect objects and expression at the same time.

Teeth, earring, necklace: All these features can be detected by color and style, which will give extra information.

In one implementation, pseudo-code for detecting facial orientation is as follows:

Detect forehead area

Use the previously determined features and superimpose them on the base face model to detect a patient face orientation.

Depending on where patient is facing, for a side facing view, silhouette edges will provide unique view information because there is a one to one correspondent between the view and silhouette shape.

Once the patient's face has been aligned to the right view, exemplary pseudo code to detect facial expression is as follows:

1. Detect shape change. The shape can be match by superimpose different expression shapes to current shape, and judge by minimum discrepancy. E.g. wide mouth open.
2. Detect occlusion. Sometime the expression can be detected by occlusal of another objects, e.g., teeth show up means mouth is open.
3. Detect texture map change. The expression can relate to certain texture changes, if patient smile, certain wrinkles patents will show up.
4. Detect highlight change. The expression can relate to certain high light changes, if patient sweats or cries, different highlight area will show up.

Speech recognition can be performed in one embodiment to determine a change in the form of speech (slurred speech, difficulties in the formation of words, for example) may indicated neurological problems, such an observation can also indicate some outward effects of various drugs or toxic agents.

A module 80 communicates with a third party such as the police department, a security monitoring center, or a call center. The module 80 operates with a POTS telephone and can use a broadband medium such as DSL or cable network if available. The module 80 requires that at least the telephone is available as a lifeline support. In this embodiment, duplex sound transmission is done using the POTS telephone network. The broadband network, if available, is optional for high resolution video and other advanced services transmission.

During operation, the module checks whether broadband network is available. If broadband network is available, the module 80 allows high resolution video, among others, to be broadcasted directly from the server 20 to the third party or indirectly from the server 20 to the remote server 200 to the third party. In parallel, the module 80 allows sound to be transmitted using the telephone circuit. In this manner, high resolution video can be transmitted since sound data is separately sent through the POTS network.

If broadband network is not available, the system relies on the POTS telephone network for transmission of voice and images. In this system, one or more images are compressed for burst transmission, and at the request of the third party or the remote server 200, the telephone's sound system is placed on hold for a brief period to allow transmission of images over the POTS network. In this manner, existing POTS lifeline telephone can be used to monitor patients. The resolution and quantity of images are selectable by the third party. Thus, using only the lifeline as a communication medium, the person monitoring the patient can elect to only listen, to view one high resolution image with duplex telephone voice transmission, to view a few low resolution images, to view a compressed stream of low resolution video with digitized voice, among others. During installation or while no live person in the scene, each camera will capture its own environment objects and store it as background images, the software then detect the live person in the scene, changes of the live person, so only the portion of live person will be send to the local server, other compression techniques will be applied, e.g. send changing file, balanced video streaming based on change.

The local server will control and schedule how the video/picture will be send, e.g. when the camera is view an empty room, no pictures will be sent, the local server will also determine which camera is at the right view, and request only the corresponding video be sent. The local server will determine which feature it is interested in looking at, e.g. face and request only that portion be sent.

With predetermined background images and local server controlled streaming, the system will enable higher resolution and more camera system by using narrower bandwidth.

Through this module, a police officer, a security agent, or a healthcare agent such as a physician at a remote location can engage, in interactive visual communication with the patient. The patient's health data or audio-visual signal can be remotely accessed. The patient also has access to a video transmission of the third party. Should the patient experience health symptoms requiring intervention and immediate care, the health care practitioner at the central station may summon help from an emergency services provider. The emergency services provider may send an ambulance, fire department personnel, family member, or other emergency personnel to the patient's remote location. The emergency services provider may, perhaps, be an ambulance facility, a police station, the local fire department, or any suitable support facility.

Communication between the patient's remote location and the central station can be initiated by a variety of techniques. One method is by manually or automatically placing a call on the telephone to the patient's home or from the patient's home to the central station.

Alternatively, the system can ask a confirmatory question to the patient through text to speech software. The patient can be orally instructed by the health practitioner to conduct specific physical activities such as specific arm movements, walking, bending, among others. The examination begins during the initial conversation with the monitored subject. Any changes in the spontaneous gestures of the body, arms and hands during speech as well as the fulfillment of nonspecific tasks are important signs of possible pathological events. The monitoring person can instruct the monitored subject to perform a series of simple tasks which can be used for diagnosis of neurological abnormalities. These observations may yield early indicators of the onset of a disease.

A network such as the Internet receives images from the server 20 and passes the data to one or more remote servers 200. The images are transmitted from the server 20 over a secure communication link such as virtual private network (VPN) to the remote server(s) 200.

In one embodiment where cameras are deployed, the server 20 collects data from a plurality of cameras and uses the 3D images technology to determine if the patient needs help. The system can transmit video (live or archived) to the friend, relative, neighbor, or call center for human review. At each viewer site, after a viewer specifies the correct URL to the client browser computer, a connection with the server 200 is established and user identity authenticated using suitable password or other security mechanisms. The server 200 then retrieves the document from its local disk or cache memory storage and transmits the content over the network. In the typical scenario, the user of a Web browser requests that a media stream file be downloaded, such as sending, in particular, the URL of a media redirection file from a Web server. The media redirection file (MRF) is a type of specialized Hypertext Markup Language (HTML) file that contains instructions for how to locate the multimedia file and in what format the multimedia file is in. The Web server returns the MRF file to the user's browser program. The browser program then reads the MRF file to determine the location of the media server containing one or more multimedia content files. The browser then launches the associated media player application program and passes the MRF file to it. The media player reads the MRF file to obtain the information needed to open a connection to a media server, such as a URL, and the required protocol information, depending upon the type of medial content is in the file. The streaming media content file is then routed from the media server down to the user.

In the camera embodiment, the transactions between the server 20 and one of the remote servers 200 are detailed. The server 200 compares one image frame to the next image frame. If no difference exists, the duplicate frame is deleted to minimize storage space. If a difference exists, only the difference information is stored as described in the JPEG standard. This operation effectively compresses video information so that the camera images can be transmitted even at telephone modem speed of 64$k$ or less. More aggressive compression techniques can be used. For example, patient movements can be clusterized into a group of known motion vectors, and patient movements can be described using a set of vectors. Only the vector data is saved. During view back, each vector is translated into a picture object which is suitably rasterized. The information can also be compressed as motion information.

Next, the server 20 transmits the compressed video to the remote server 200. The server 200 stores and caches the video data so that multiple viewers can view the images at once since the server 200 is connected to a network link such as telephone line modem, cable modem, DSL modem, and ATM transceiver, among others.

In one implementation, the servers 200 use RAID-5 striping and parity techniques to organize data in a fault tolerant and efficient manner. The RAID (Redundant Array of Inexpensive Disks) approach is well described in the literature and has various levels of operation, including RAID-5, and the data organization can achieve data storage in a fault tolerant and load balanced manner. RAID-5 provides that the stored data is spread among three or more disk drives, in a redundant manner, so that even if one of the disk drives fails, the data stored on the drive can be recovered in an efficient and error free manner from the other storage locations. This method also advantageously makes use of each of the disk drives in relatively equal and substantially parallel operations. Accordingly, if one has a six gigabyte cluster volume which spans three disk drives, each disk drive would be responsible for servicing two gigabytes of the cluster volume. Each two gigabyte drive would be comprised of one-third redundant information, to provide the redundant, and thus fault tolerant, operation required for the RAID-5 approach. For additional physical security, the server can be stored in a Fire Safe or other secured box, so there is no chance to erase the recorded data, this is very important for forensic analysis.

The system can also monitor the patient's gait pattern and generate warnings should the patient's gait patterns indicate that the patient is likely to fall. The system will detect patient skeleton structure, stride and frequency; and based on this information to judge whether patient has joint problem, asymmetrical bone structure, among others. The system can store historical gait information, and by overlaying current structure to the historical (normal) gait information, gait changes can be detected. In the camera embodiment, an estimate of the gait pattern is done using the camera. In a camera-less embodiment, the gait can be sensed by providing a sensor on the floor and a sensor near the head and the variance in the two sensor positions are used to estimate gait characteristics.

The system also provides a patient interface 90 to assist the patient in easily accessing information. In one embodiment, the patient interface includes a touch screen; voice-activated text reading; one touch telephone dialing; and video conferencing. The touch screen has large icons that are pre-selected to the patient's needs, such as his or her favorite web sites or application programs. The voice activated text reading allows a user with poor eye-sight to get information from the patient interface 90. Buttons with pre-designated dialing numbers, or video conferencing contact information allow the user to call a friend or a healthcare provider quickly.

In one embodiment, medicine for the patient is tracked using radio frequency identification (RFID) tags. In this embodiment, each drug container is tracked through an RFID tag that is also a drug label. The RF tag is an integrated circuit that is coupled with a mini-antenna to transmit data. The circuit contains memory that stores the identification Code and other pertinent data to be transmitted when the chip is activated or interrogated using radio energy from a reader. A reader consists of an RF antenna, transceiver and a micro-processor. The transceiver sends activation signals to and receives identification data from the tag. The antenna may be enclosed with the reader or located outside the reader as a separate piece. RFID readers communicate directly with the RFID tags and send encrypted usage data over the patient's network to the server 200 and eventually over the Internet 100. The readers can be built directly into the walls or the cabinet doors.

In one embodiment, capacitively coupled RFID tags are used. The capacitive RFID tag includes a silicon microprocessor that can store 96 bits of information, including the pharmaceutical manufacturer, drug name, usage instruction and a 40-bit serial number. A conductive carbon ink acts as the tag's antenna and is applied to a paper substrate through conventional printing means. The silicon chip is attached to printed carbon-ink electrodes on the back of a paper label, creating a low-cost, disposable tag that can be integrated on the drug label. The information stored on the drug labels is written in a Medicine Markup Language (MML), which is based on the eXtensible Markup Language (XML). MML would allow all computers to communicate with any computer system in a similar way that Web servers read Hyper Text Markup Language (HTML), the common language used to create Web pages.

After receiving the medicine container, the patient places the medicine in a medicine cabinet, which is also equipped with a tag reader. This smart cabinet then tracks all medicine stored in it. It can track the medicine taken, how often the medicine is restocked and can let the patient know when a particular medication is about to expire. At this point, the server 200 can order these items automatically. The server 200 also monitors drug compliance, and if the patient does not remove the bottle to dispense medication as prescribed, the server 200 sends a warning to the healthcare provider.

The database tracks typical arm and leg movements to determine whether the user is experiencing muscle weakness reflective of a stroke. If muscle weakness is detected, the system presents the user with additional tests to confirm the likelihood of a stroke attack. If the information indicates a stroke had occurred, the system stores the time of the stroke detection and calls for emergency assistance to get timely treatment for the stroke. The user's habits and movements can be determined by the system for stroke detection. This is done by tracking location, ambulatory travel vectors and time in a database. If the user typically sleeps between 10 pm to 6 am, the location would reflect that the user's location maps to the bedroom between 10 pm and 6 am. In one exemplary system, the system builds a schedule of the user's activity as follows:

| Location | Time Start | Time End | Heart Rate |
| --- | --- | --- | --- |
| Bed room | 10 pm | 6 am | 60-80 |
| Gym room | 6 am | 7 am | 90-120 |
| Bath room | 7 am | 7:30 am | 85-120 |
| Dining room | 7:30 am | 8:45 am | 80-90 |
| Home Office | 8:45 am | 11:30 am | 85-100 |
| ... | | | |
| ... | | | |

The habit tracking is adaptive in that it gradually adjusts to the user's new habits. If there are sudden changes, the system flags these sudden changes for follow up. For instance, if the user spends three hours in the bathroom, the system prompts the third party (such as a call center) to follow up with the patient to make sure he or she does not need help.

In one embodiment, data driven analyzers may be used to track the patient's habits. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient's habits or ambulation patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In general, multiple dimensions of a user's daily activities such as start and stop times of interactions of different interactions are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences.

Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's habits. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

Substantially any type of learning system or process may be employed to determine the user's ambulatory and living patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible points within the permitted domain for each value of i. Because the best path from the current point to the next point is independent of what happens beyond that point. Thus, the total cost of [i(k), j(k)] is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of user habit information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations $O(1), O(2), \ldots O(t), \ldots, O(T)$, where each observation $O(t)$ may be either a discrete symbol under the VQ approach or a continuous vector. The sequence of observations may be modeled as a probabilistic function of an underlying Markov chain having state transitions that are not directly observable. In one embodiment, the Markov network is used to model a number of user habits and activities. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B=[b(j) (O(t)]$, where the $b(j) (O(t)$ term of the output symbol matrix is the probability of outputting observation $O(t)$, given that the model is in state j. The first state is always constrained to be the initial state for the first time frame of the utterance, as only a prescribed set of left to right state transitions are possible. A predetermined final state is defined from which transitions to other states cannot occur. Transitions are restricted to reentry of a state or entry to one of the next two states. Such transitions are defined in the model as transition probabilities. Although the preferred embodiment restricts the flow graphs to the present state or to the next two states, one skilled in the art can build an HMM model without any transition restrictions, although the sum of all the probabilities of transitioning from any state must still add up to one. In each state of the model, the current feature frame may be identified with one of a set of predefined output symbols or may be labeled probabilistically. In this case, the output symbol probability $b(j) O(t)$ corresponds to the probability assigned by the model that the feature frame symbol is $O(t)$. The model arrangement is a matrix $A=[a(i,j)]$ of transition probabilities and a technique of computing $B=b(j) O(t)$, the feature frame symbol probability in state j. The Markov model is formed for a reference pattern from a plurality of sequences of training patterns and the output symbol probabilities are multivariate Gaussian function probability densities. The patient habit information is processed by a feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator. The HMM template has a number of states, each having a discrete value. However, because treatment pattern features may have a dynamic pattern in contrast to a single value. The addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output states, which normally would be the output layer of the neuron. However, each output has transition probabilities to itself or to the next outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

The system allows patients to conduct a low-cost, comprehensive, real-time monitoring of their vital parameters such as ambulation and falls. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

The wearable appliance is small, easily worn by the patient during periods of exercise or day-to-day activities, and non-invasively measures blood pressure can be done in a matter of seconds without affecting the patient. An onboard or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure at isolated times.

The wearable appliance provides an in-depth, cost-effective mechanism to evaluate a patient's health condition. Certain cardiac conditions can be controlled, and in some cases predicted, before they actually occur. Moreover, data from the patient can be collected and analyzed while the patient participates in their normal, day-to-day activities.

Software programs associated with the Internet-accessible website, secondary software system, and the personal computer analyze the blood pressure, and heart rate, and pulse oximetry values to characterize the patient's cardiac condition. These programs, for example, may provide a report that features statistical analysis of these data to determine averages, data displayed in a graphical format, trends, and comparisons to doctor-recommended values.

When the appliance cannot communicate with the mesh network, the appliance simply stores information in memory and continues to make measurements. The watch component automatically transmits all the stored information (along with a time/date stamp) when it comes in proximity to the wireless mesh network, which then transmits the information through the wireless network.

In one embodiment, the server provides a web services that communicate with third party software through an interface. To generate vital parameters such as blood pressure information for the web services software interface, the patient continuously wears the blood-pressure monitor for a short period of time, e.g. one to two weeks after visiting a medical professional during a typical 'check up' or after signing up for a short-term monitoring program through the website. In this case, the wearable device such as the watch measures mobility through the accelerometer and blood pressure in a near-continuous, periodic manner such as every fifteen minutes. This information is then transmitted over the mesh network to a base station that communicates over the Internet to the server.

To view information sent from the blood-pressure monitor and fall detector on the wearable appliance, the patient or an authorized third party such as family members, emergency personnel, or medical professional accesses a patient user interface hosted on the server 200 through the Internet 100 from a remote computer system. The patient interface displays vital information such as ambulation, blood pressure and related data measured from a single patient. The system may also include a call center, typically staffed with medical professionals such as doctors, nurses, or nurse practioners, whom access a care-provider interface hosted on the same website on the server 200. The care-provider interface displays vital data from multiple patients.

The wearable appliance has an indoor positioning system and processes these signals to determine a location (e.g., latitude, longitude, and altitude) of the monitor and, presumably, the patient. This location could be plotted on a map by the server, and used to locate a patient during an emergency, e.g. to dispatch an ambulance.

In one embodiment, the web page hosted by the server 200 includes a header field that lists general information about the patient (e.g. name, age, and ID number, general location, and information concerning recent measurements); a table that lists recently measured blood pressure data and suggested (i.e. doctor-recommended) values of these data; and graphs that plot the systolic and diastolic blood pressure data in a time-dependent manner. The header field additionally includes a series of tabs that each link to separate web pages that include, e.g., tables and graphs corresponding to a different data measured by the wearable device such as calorie consumption/dissipation, ambulation pattern, sleeping pattern, heart rate, pulse oximetry, and temperature. The table lists a series of data fields that show running average values of the patient's daily, monthly, and yearly vital parameters. The levels are compared to a series of corresponding ' suggested' values of vital parameters that are extracted from a database associated with the web site. The suggested values depend on, among other things, the patient's age, sex, and weight. The table then calculates the difference between the running average and suggested values to give the patient an idea of how their data compares to that of a healthy patient. The web software interface may also include security measures such as authentication, authorization, encryption, credential presentation, and digital signature resolution. The interface may also be modified to conform to industry-mandated, XML schema definitions, while being 'backwards compatible' with any existing XML schema definitions.

The system provides for self-registration of appliances by the user. Data can be synchronized between the Repository and appliance(s) via the server 20. The user can preview the readings received from the appliance(s) and reject erroneous readings. The user or treating professional can set up the system to generate alerts against received data, based on pre-defined parameters. The system can determine trends in received data, based on user defined parameters.

Appliance registration is the process by which a patient monitoring appliance is associated with one or more users of the system. This mechanism is also used when provisioning appliances for a user by a third party, such as a clinician (or their respective delegate). In one implementation, the user (or delegate) logs into the portal to select one or more appliances and available for registration. In turn, the server 20 broadcasts a query to all nodes in the mesh network to retrieve identification information for the appliance such as manufacturer information, appliance model information, appliance serial number and optionally a hub number (available on hub packaging). The user may register more than one appliance at this point. The system optionally sets up a service subscription for appliance(s) usage. This includes selecting service plans and providing payment information. The appliance(s) are then associated with this user's account and a control file with appliance identification information is synchronized between the server 200 and the server 20 and each appliance on initialization. In one embodiment, each of the appliances 8 transmits data to the server 20 in an XML format for ease of interfacing and is either kept encrypted or in a non-readable format on the server 20 for security reasons.

The server 20 frequently collects and synchronizes data from the appliances 8. The server 20 may use one of various transportation methods to connect to the repository on the server 200 using a PC as conduit or through a connection established using an embedded modem (connected to a phone line), a wireless router (DSL or cable wireless router), a cellular modem, or another network-connected appliance (such as, but not limited to, a web-phone, video-phone, embedded computer, PDA or handheld computer).

In one embodiment, users may set up alerts or reminders that are triggered when one or more reading meet a certain set of conditions, depending on parameters defined by the user. The user chooses the condition that they would like to be alerted to and by providing the parameters (e.g. threshold value for the reading) for alert generation. Each alert may have an interval which may be either the number of data points or a time duration in units such as hours, days, weeks or months. The user chooses the destination where the alert may be sent. This destination may include the user's portal, e-mail, pager, voice-mail or any combination of the above.

Trends are determined by applying mathematical and statistical rules (e.g. moving average and deviation) over a set of reading values. Each rule is configurable by parameters that are either automatically calculated or are set by the user.

The user may give permission to others as needed to read or edit their personal data or receive alerts. The user or clinician could have a list of people that they want to monitor and have it show on their "My Account" page, which serves as a local central monitoring station in one embodiment. Each person may be assigned different access rights which may be more or less than the access rights that the patient has. For example, a doctor or clinician could be allowed to edit data for example to annotate it, while the patient would have read-only privileges for certain pages. An authorized person could set the reminders and alerts parameters with limited access to others. In one embodiment, the server 20 serves a web page customized by the user or the user's representative as the monitoring center that third parties such as family, physicians, or caregivers can log in and access information. In another embodiment, the server 20 communicates with the server 200 at a call center so that the call center provides all services. In yet another embodiment, a hybrid solution where authorized representatives can log in to the server 20 server access patient information while the call center logs into both the server 200 and the server 20 server to provide complete care services to the patient.

The server 200 may communicate with a business process outsourcing (BPO) company or a call center to provide central monitoring in an environment where a small number of monitoring agents can cost effectively monitor multiple people 24 hours a day. A call center agent, a clinician or a nursing home manager may monitor a group or a number of users via a summary "dashboard" of their readings data, with ability to drill-down into details for the collected data. A clinician administrator may monitor the data for and otherwise administer a number of users of the system. A summary "dashboard" of readings from all Patients assigned to the Administrator is displayed upon log in to the Portal by the Administrator. Readings may be color coded to visually distinguish normal vs. readings that have generated an alert, along with description of the alert generated. The Administrator may drill down into the details for each Patient to further examine the readings data, view charts etc. in a manner similar to the Patient's own use of the system. The Administrator may also view a summary of all the appliances registered to all assigned Patients, including but not limited to all appliance identification information. The Administrator has access only to information about Patients that have been assigned to the Administrator by a Super Administrator. This allows for segmenting the entire population of monitored Patients amongst multiple Administrators. The Super Administrator may assign, remove and/or reassign Patients amongst a number of Administrators.

In one embodiment, a patient using an Internet-accessible computer and web browser, directs the browser to an appropriate URL and signs up for a service for a short-term (e.g., 1 month) period of time. The company providing the service completes an accompanying financial transaction (e.g. processes a credit card), registers the patient, and ships the patient a wearable appliance for the short period of time. The registration process involves recording the patient's name and contact information, a number associated with the monitor (e.g. a serial number), and setting up a personalized website. The patient then uses the monitor throughout the monitoring period, e.g. while working, sleeping, and exercising. During this time the monitor measures data from the patient and wirelessly transmits it through the channel to a data center. There, the data are analyzed using software running on computer servers to generate a statistical report. The computer servers then automatically send the report to the patient using email, regular mail, or a facsimile machine at different times during the monitoring period. When the monitoring period is expired, the patient ships the wearable appliance back to the monitoring company.

Different web pages may be designed and accessed depending on the end-user. As described above, individual users have access to web pages that only their ambulation and blood pressure data (i.e., the patient interface), while organizations that support a large number of patients (nursing homes or hospitals) have access to web pages that contain data from a group of patients using a care-provider interface. Other interfaces can also be used with the web site, such as interfaces used for: insurance companies, members of a particular company, clinical trials for pharmaceutical companies, and e-commerce purposes. Vital patient data displayed on these web pages, for example, can be sorted and analyzed depending on the patient's medical history, age, sex, medical condition, and geographic location. The web pages also support a wide range of algorithms that can be used to analyze data once they are extracted from the data packets. For example, an instant message or email can be sent out as an 'alert' in response to blood pressure indicating a medical condition that requires immediate attention. Alternatively, the message could be sent out when a data parameter (e.g. systolic blood pressure) exceeds a predetermined value. In some cases, multiple parameters (e.g., fall detection, positioning data, and blood pressure) can be analyzed simultaneously to generate an alert message. In general, an alert message can be sent out after analyzing one or more data parameters using any type of algorithm. These algorithms range from the relatively simple (e.g., comparing blood pressure to a recommended value) to the complex (e.g., predictive medical diagnoses using 'data mining' techniques). In some cases data may be 'fit' using algorithms such as a linear or non-linear least-squares fitting algorithm.

In one embodiment, a physician, other health care practitioner, or emergency personnel is provided with access to patient medical information through the server 200. In one embodiment, if the wearable appliance detects that the patient needs help, or if the patient decides help is needed, the system can call his or her primary care physician. If the patient is unable to access his or her primary care physician (or another practicing physician providing care to the patient) a call from the patient is received, by an answering service or a call center associated with the patient or with the practicing physician. The call center determines whether the patient is exhibiting symptoms of an emergency condition by polling vital patient information generated by the wearable device, and if so, the answering service contacts 911 emergency service or some other emergency service. The call center can review falls information, blood pressure information, and other vital information to determine if the patient is in need of emergency assistance. If it is determined that the patient in not exhibiting symptoms of an emergent condition, the answering service may then determine if the patient is exhibiting symptoms of a non-urgent condition. If the patient is exhibiting symptoms of a non-urgent condition, the answering service will inform the patient that he or she may log into the server 200 for immediate information on treatment of the condition. If the answering service determines that the patient is exhibiting symptoms that are not related to a non-urgent condition, the answering service may refer the patient to an emergency room, a clinic, the practicing physician (when the practicing physician is available) for treatment.

In another embodiment, the wearable appliance permits direct access to the call center when the user pushes a switch or button on the appliance, for instance. In one implementation, telephones and switching systems in call centers are integrated with the home mesh network to provide for, among other things, better routing of telephone calls, faster delivery of telephone calls and associated information, and improved service with regard to client satisfaction through computer-telephony integration (CTI). CTI implementations of various design and purpose are implemented both within individual call-centers and, in some cases, at the telephone network level. For example, processors miming CTI software applications may be linked to telephone switches, service control points (SCPs), and network entry points within a public or private telephone network. At the call-center level, CTI-enhanced processors, data servers, transaction servers, and the like, are linked to telephone switches and, in some cases, to similar CTI hardware at the network level, often by a dedicated digital link. CTI processors and other hardware within a call-center is commonly referred to as customer premises equipment (CPE). It is the CTI processor and application software is such centers that provides computer enhancement to a call center. In a CTI-enhanced call center, telephones at agent stations are connected to a central telephony switching apparatus, such as an automatic call distributor (ACD) switch or a private branch exchange (PBX). The agent stations may also be equipped with computer terminals such as personal computer/video display unit's (PC/VDU's) so that agents manning such stations may have access to stored data as well as being linked to incoming callers by telephone equipment. Such stations may be interconnected through the PC/VDUs by a local area network (LAN). One or more data or transaction servers may also be connected to the LAN that interconnects agent stations. The LAN is, in turn, typically connected to the CTI processor, which is connected to the call switching apparatus of the call center.

When a call from a patient arrives at a call center, whether or not the call has been pre-processed at an SCP, the telephone number of the calling line and the medical record are made available to the receiving switch at the call center by the network provider. This service is available by most networks as caller-ID information in one of several formats such as Automatic Number Identification (ANI). Typically the number called is also available through a service such as Dialed Number Identification Service (DNIS). If the call center is computer-enhanced (CTI), the phone number of the calling party may be used as a key to access additional medical and/or historical information from a customer information system (CIS) database at a server on the network that connects the agent workstations. In this manner information pertinent to a call may be provided to an agent, often as a screen pop on the agent's PC/VDU.

The call center enables any of a first plurality of physician or health care practitioner terminals to be in audio communication over the network with any of a second plurality of patient wearable appliances. The call center will route the call to a physician or other health care practitioner at a physician or health care practitioner terminal and information related to the patient (such as an electronic medical record) will be received at the physician or health care practitioner terminal via the network. The information may be forwarded via a computer or database in the practicing physician's office or by a computer or database associated with the practicing physician, a health care management system or other health care facility or an insurance provider. The physician or health care practitioner is then permitted to assess the patient, to treat the patient accordingly, and to forward updated information related to the patient (such as examination, treatment and prescription details related to the patient's visit to the patient terminal) to the practicing physician via the network.

In one embodiment, the system informs a patient of a practicing physician of the availability of the web services and referring the patient to the web site upon agreement of the patient. A call from the patient is received at a call center. The call center enables physicians to be in audio communication over the network with any patient wearable appliances, and the call is routed to an available physician at one of the physician so that the available physician may carry on a two-way conversation with the patient. The available physician is permitted to make an assessment of the patient and to treat the patient. The system can forward information related to the patient to a health care management system associated with the physician. The health care management system may be a healthcare management organization, a point of service health care system, or a preferred provider organization. The health care practitioner may be a nurse practitioner or an internist.

The available health care practitioner can make an assessment of the patient and to conduct an examination of the patient over the network, including optionally by a visual study of the patient. The system can make an assessment in accordance with a protocol. The assessment can be made in accordance with a protocol stored in a database and/or making an assessment in accordance with the protocol may include displaying in real time a relevant segment of the protocol to the available physician. Similarly, permitting the physician to prescribe a treatment may include permitting the physician to refer the patient to a third party for treatment and/or referring the patient to a third party for treatment may include referring the patient to one or more of a primary care physician, specialist, hospital, emergency room, ambulance service or clinic. Referring the patient to a third party may additionally include communicating with the third party via an electronic link included in a relevant segment of a protocol stored in a protocol database resident on a digital storage medium and the electronic link may be a hypertext link. When a treatment is being prescribed by a physician, the system can communicate a prescription over the network to a pharmacy and/or communicating the prescription over the network to the pharmacy may include communicating to the pharmacy instructions to be given to the patient pertaining to the treatment of the patient. Communicating the prescription over the network to the pharmacy may also include communicating the prescription to the pharmacy via a hypertext link included in a relevant segment of a protocol stored in a database resident on a digital storage medium. In accordance with another related embodiment, permitting the physician to conduct the examination may be accomplished under conditions such that the examination is conducted without medical instruments at the patient terminal where the patient is located.

In another embodiment, a system for delivering medical examination, diagnosis, and treatment services from a physician to a patient over a network includes a first plurality of health care practitioners at a plurality of terminals, each of the first plurality of health care practitioner terminals including a display device that shows information collected by the wearable appliances and a second plurality of patient terminals or wearable appliances in audiovisual communication over a network with any of the first plurality of health care practitioner terminals. A call center is in communication with the patient wearable appliances and the health care practitioner terminals, the call center routing a call from a patient at one of the patient terminals to an available health care practitioner at one of the health care practitioner terminals, so that the available health care practitioner may carry on a two-way conversation with the patient. A protocol database resident on a digital storage medium is accessible to each of the health care practitioner terminals. The protocol database contains a plurality of protocol segments such that a relevant segment of the protocol may be displayed in real time on the display device of the health care practitioner terminal of the available health care practitioner for use by the available health care practitioner in making an assessment of the patient. The relevant segment of the protocol displayed in real time on the display device of the health care practitioner terminal may include an electronic link that establishes communication between the available health care practitioner and a third party and the third party may be one or more of a primary care physician, specialist, hospital, emergency room, ambulance service, clinic or pharmacy.

In accordance with other related embodiment, the patient wearable appliance may include establish a direct connection to the call center by pushing a button on the appliance. Further, the protocol database may be resident on a server that is in communication with each of the health care practitioner terminals and each of the health care practitioner terminals may include a local storage device and the protocol database is replicated on the local storage device of one or more of the physician terminals.

In another embodiment, a system for delivering medical examination, diagnosis, and treatment services from a physician to a patient over a network includes a first plurality of health care practitioner terminals, each of the first plurality of health care practitioner terminals including a display device and a second plurality of patient terminals in audiovisual communication over a network with any of the first plurality of health care practitioner terminals. Each of the second plurality of patient terminals includes a camera having pan, tilt and zoom modes, such modes being controlled from the first plurality of health care practitioner terminals. A call center is in communication with the patient terminals and the health care practitioner terminals and the call center routes a call from a patient at one of the patient terminals to an available health care practitioner at one of the health care practitioner terminals, so that the available health care practitioner may carry on a two-way conversation with the patient and visually observe the patient.

In one embodiment, the information is store in a secure environment, with security levels equal to those of online banking, social security number input, and other confidential information. Conforming to Health Insurance Portability and Accountability Act (HIPAA) requirements, the system creates audit trails, requires logins and passwords, and provides data encryption to ensure the patient information is private and secure. The HIPAA privacy regulations ensure a national floor of privacy protections for patients by limiting the ways that health plans, pharmacies, hospitals and other covered entities can use patients' personal medical information. The regulations protect medical records and other individually identifiable health information, whether it is on paper, in computers or communicated orally.

Due to its awareness of the patient's position, the server 200 can optionally control a mobility assistance device such as a smart cane or robot. The robotic smart cane sends video from its camera to the server 200, which in turn coordinates the position of the robot, as determined by the camera 10 mounted in the home as well as the robot camera. The robot position, as determined by the server 200, is then transmitted to the robot for navigation. The robot has a frame with an extended handle. The handle includes handle sensors mounted thereon to detect the force places on each handle to receive as input the movement desired by the patient. In one embodiment, the robot has a control navigation system that accepts patient command as well as robot self-guidance command. The mobility is a result of give-and-take between the patient's self-propulsion and the walker's automated reactions. Thus, when the patient moves the handle to the right, the robot determines that the patient is interested in turning and actuates the drive systems appropriately. However, if the patient is turning into an obstacle, as determined by the cameras and the server 200, the drive system provides gentle resistance that tells the patient of an impending collision.

If, for example, a patient does not see a coffee table ahead, the walker will detect it, override the patient's steering to avoid it, and thereby prevent a possible fall. Onboard software processes the data from 180 degrees of approaching terrain and steers the front wheel toward openings and away from obstacles.

The control module executes software that enables the robot to move around its environment safely. The software performs localization, mapping, path planning and obstacle avoidance. In one embodiment, images from a plurality of wall-mounted camera 10 are transmitted to the server 200. The server 200 collects images of the robot and triangulates the robot position by cross-referencing the images. The information is then correlated with the image from the robot-mounted camera and optical encoders that count the wheel rotations to calculate traveled distance for range measurement. In this process, a visual map of unique "landmarks" created as the robot moves along its path is annotated with the robot's position to indicate the position estimate of the landmark. The current image, seen from the robot, is compared with the images in the database to find matching landmarks. Such matches are used to update the position of the robot according to the relative position of the matching landmark. By repeatedly updating the position of landmarks based on new data, the software incrementally improves the map by calculating more accurate estimates for the position of the landmarks. An improved map results in more accurate robot position estimates. Better position estimates contribute to better estimates for the landmark positions and so on. If the environment changes so much that the robot no longer recognizes previous landmarks, the robot automatically updates the map with new landmarks. Outdated landmarks that are no longer recognized can easily be deleted from the map by simply determining if they were seen or matched when expected.

Using the obstacle avoidance algorithm, the robot generates corrective movements to avoid obstacles not represented in the path planner such as open/closed doors, furniture, people, and more. The robot rapidly detects obstacles using its sensors and controls its speed and heading to avoid obstacles.

The hazard avoidance mechanisms provide a reflexive response to hazardous situations to insure the robot's safety and guarantee that it does not damage itself or the environment. Mechanisms for hazard avoidance include collision detection using not one but a complementary set of sensors and techniques. For instance, collision avoidance can be provided using contact sensing, motor load sensing, and vision. The combination of multiple sources for collision detection guarantees safe collision avoidance. Collision detection provides a last resort for negotiating obstacles in case obstacle avoidance fails to do so in the first place, which can be caused by moving objects or software and hardware failures.

If the walker is in motion (as determined by the wheel encoder), the force applied to the brake pads is inversely proportional to the distance to obstacles. If the walker is stopped, the brakes should be fully applied to provide a stable base on which the patient can rest. When the walker is stopped and the patient wishes to move again, the brakes should come off slowly to prevent the walker from lurching forward The walker should mostly follow the patient's commands, as this is crucial for patient acceptance. For the safety braking and the safety braking and steering control systems, the control system only influences the motion when obstacles or cliffs are near the patient. In other words, the walker is, typically, fully patient controlled. For all other situations, the control system submits to the patient's desire. This does not mean that the control system shuts down, or does not provide the usual safety features. In fact, all of the control systems fall back on their emergency braking to keep the patient safe. When the control system has had to brake to avoid an obstacle or has given up trying to lead the patient on a particular path, the patient must disengage the brakes (via a pushbutton) or re-engage the path following (again via a pushbutton) to regain control or allow collaboration again. This lets the patient select the walker's mode manually when they disagree with the control system's choices.

FIG. 5 shows an exemplary process to monitor patient. First, the process sets up mesh network appliances at step 1000. Next, the process determines patient position using in-door positioning system at step 1002. The process then determines patient movement using accelerometer output at step 1004. Sharp accelerations may be used to indicate fall. Further, the z axis accelerometer changes can indicate the height of the appliance from the floor and if the height is near zero, the system infers that the patient had fallen. The system can also determine vital parameter including patient heart rate at step 1006. The system determines if patient needs assistance based on in-door position, fall detection and vital parameter at step 1008. If a fall is suspected, the system confirms the fall by communicating with the patient prior to calling a third party such as the patient's physician, nurse, family member, or a paid call center to get assistance for the patient at step 1010. If confirmed or if the patient is non-responsive, the system contacts the third party and sends voice over mesh network to appliance on the patient to allow one or more third parties to talk with the patient at step 1012. If needed, the system calls and/or conferences emergency personnel into the call at step 1016.

In one embodiment, if the patient is outside of the mesh network range such as when the user is traveling away from his/her home, the system continuously records information into memory until the home mesh network is reached or until the monitoring appliance reaches an internet access point. While the wearable appliance is outside of the mesh network range, the device searches for a cell phone with an expansion card plugged into a cell phone expansion slot such as the SDIO slot. If the wearable appliance detects a cell phone that is mesh network compatible, the wearable appliance communicates with the cell phone and provides information to the server 200 using the cellular connection. In one embodiment, a Zigbee SDIO card from C-guys, Inc., enables device-to-device communications for PDAs and smart phones. C-guys' ZigBee SDIO card includes the company's CG-100 SDIO application interface controller, which is designed to convert an application signal to an SD signal (or vice versa). The ZigBee card can provide signal ranges of up to 10 m in the 2.4 GHz band and data rates of up to 200 kbps. The card has peer-to-peer communications mode and supports direct application to PDAs or any SD supported hand-held cell phones. In this embodiment, the PDA or cell phone can provide a GPS position information instead of the indoor position information generated by the mesh network appliances 8. The cell phone GPS position information, accelerometer information and vital information such as heart rate information is transmitted using the cellular channel to the server 200 for processing as is normal. In another embodiment where the phone works through WiFi (802.11) or WiMAX (802.16) or ultra-wideband protocol instead of the cellular protocol, the wearable appliance can communicate over these protocols using a suitable mesh network interface to the phone. In instances where the wearable appliance is outside of its home base and a dangerous condition such as a fall is detected, the wearable appliance can initiate a distress call to the authorized third party using cellular, WiFi, WiMAX, or UWB protocols as is available.

Figure 6A:
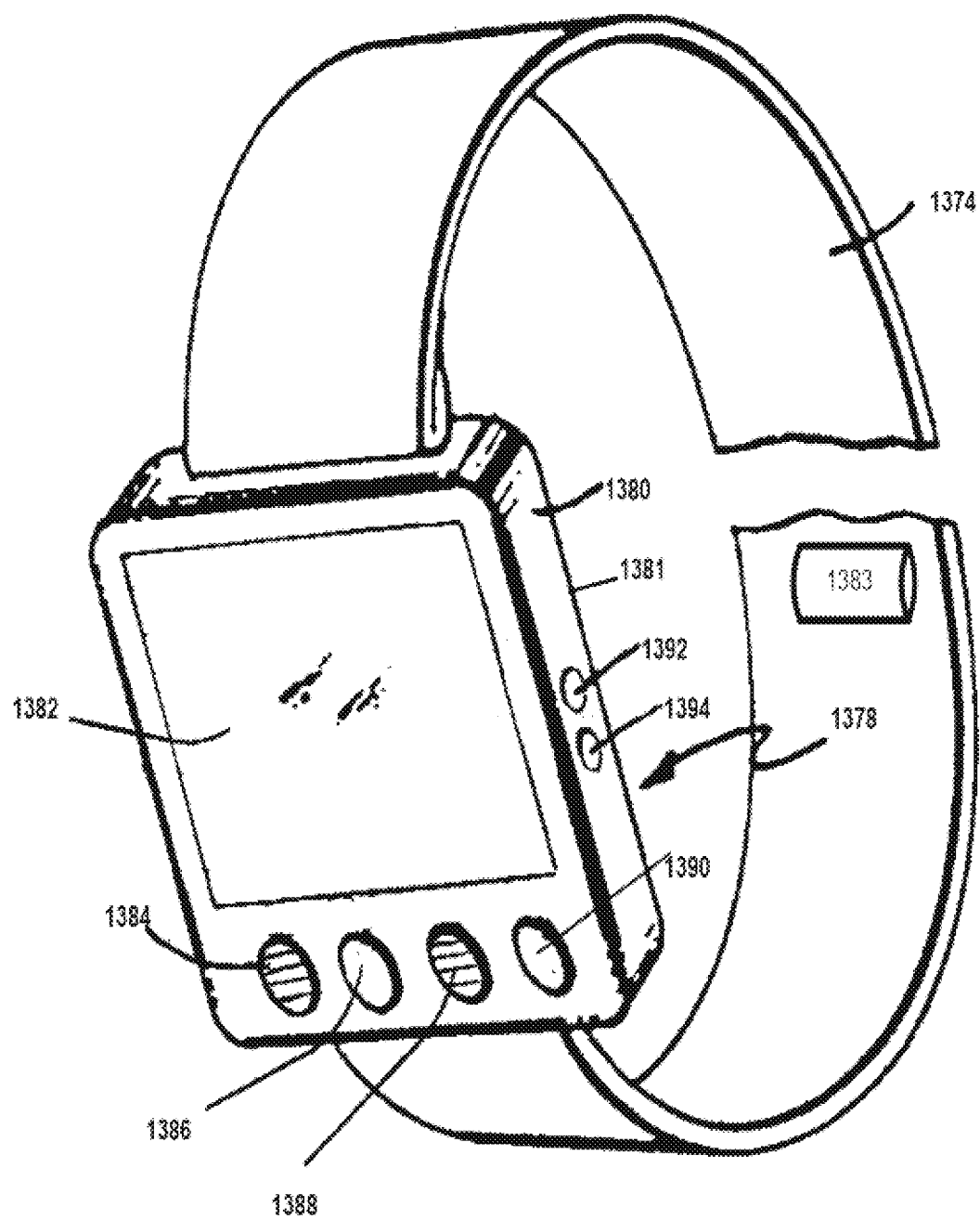
FIG. 6A shows an exemplary wrist-watch based assistance device.

FIG. 6A shows a portable embodiment of the present invention where the voice recognizer is housed in a wristwatch. As shown in FIG. 6, the device includes a wristwatch sized housing 1380 supported on a wrist band 1374. The housing 1380 may be of a number of variations of shape but can be conveniently made a rectangular, approaching a box-like configuration. The wrist band 1374 can be an expansion band or a wristwatch strap of plastic, leather or woven material. The processor or CPU of the wearable appliance is connected to a radio frequency (RF) transmitter/receiver (such as a Bluetooth device, a Zigbee device, a WiFi device, a WiMAX device, or an 802.X transceiver, among others.

In one embodiment, the back of the device is a conductive metal electrode 1381 that in conjunction with a second electrode 1383 mounted on the wrist band 1374, enables differential EKG or ECG to be measured. The electrical signal derived from the electrodes is typically 1 mV peak-peak. In one embodiment where only one electrode 1381 or 1383 is available, an amplification of about 1000 is necessary to render this signal usable for heart rate detection. In the embodiment with electrodes 1381 and 1383 available, a differential amplifier is used to take advantage of the identical common mode signals from the EKG contact points, the common mode noise is automatically cancelled out using a matched differential amplifier. In one embodiment, the differential amplifier is a Texas Instruments INA321 instrumentation amplifier that has matched and balanced integrated gain resistors. This device is specified to operate with a minimum of 2.7V single rail power supply. The INA321 provides a fixed amplification of 5× for the EKG signal. With its CMRR specification of 94 dB extended up to 3 KHz the INA321 rejects the common mode noise signals including the line frequency and its harmonics. The quiescent current of the INA321 is 40 mA and the shut down mode current is less than 1 mA. The amplified EKG signal is internally fed to the on chip analog to digital converter. The ADC samples the EKG signal with a sampling frequency of 512 Hz. Precise sampling period is achieved by triggering the ADC conversions with a timer that is clocked from a 32.768 kHz low frequency crystal oscillator. The sampled EKG waveform contains some amount of super imposed line frequency content. This line frequency noise is removed by digitally filtering the samples. In one implementation, a 17-tap low pass FIR filter with pass band upper frequency of 6 Hz and stop band lower frequency of 30 Hz is implemented in this application. The filter coefficients are scaled to compensate the filter attenuation and provide additional gain for the EKG signal at the filter output. This adds up to a total amplification factor of greater than 1000× for the EKG signal.

The wrist band 1374 can also contain other electrical devices such as ultrasound transducer, optical transducer or electromagnetic sensors, among others. In one embodiment, the transducer is an ultrasonic transducer that generates and transmits an acoustic wave upon command from the CPU during one period and listens to the echo returns during a subsequent period. In use, the transmitted bursts of sonic energy are scattered by red blood cells flowing through the subject's radial artery, and a portion of the scattered energy is directed back toward the ultrasonic transducer. The time required for the return energy to reach the ultrasonic transducer varies according to the speed of sound in the tissue and according to the depth of the artery. Typical transit times are in the range of 6 to 7 microseconds. The ultrasonic transducer is used to receive the reflected ultrasound energy during the dead times between the successive transmitted bursts. The frequency of the ultrasonic transducer's transmit signal will differ from that of the return signal, because the scattering red blood cells within the radial artery are moving. Thus, the return signal, effectively, is frequency modulated by the blood flow velocity.

A driving and receiving circuit generates electrical pulses which, when applied to the transducer, produce acoustic energy having a frequency on the order of 8 MHz, a pulse width or duration of approximately 8 microseconds, and a pulse repetition interval (PRI) of approximately 16 µs, although other values of frequency, pulse width, and PRI may be used. In one embodiment, the transducer emits an 8 microsecond pulse, which is followed by an 8 microsecond "listen" period, every 16 microseconds. The echoes from these pulses are received by the ultrasonic transducer during the listen period. The ultrasonic transducer can be a ceramic piezoelectric device of the type well known in the art, although other types may be substituted.

An analog signal representative of the Doppler frequency of the echo is received by the transducer and converted to a digital representation by the ADC, and supplied to the CPU for signal processing. Within the CPU, the digitized Doppler frequency is scaled to compute the blood flow velocity within the artery based on the Doppler frequency. Based on the real time the blood flow velocity, the CPU applies the vital model to the corresponding blood flow velocity to produce the estimated blood pressure value.

Prior to operation, calibration is done using a calibration device and the monitoring device to simultaneously collect blood pressure values (systolic, diastolic pressures) and a corresponding blood flow velocity generated by the monitoring device. The calibration device is attached to the base station and measures systolic and diastolic blood pressure using a cuff-based blood pressure monitoring device that includes a motor-controlled pump and data-processing electronics. While the cuff-based blood pressure monitoring device collects patient data, the transducer collects patient data in parallel and through the watch's radio transmitter, blood flow velocity is sent to the base station for generating a computer model that converts the blood flow velocity information into systolic and diastolic blood pressure values and this information is sent wirelessly from the base station to the watch for display and to a remote server if needed.

This process is repeated at a later time (e.g., 15 minutes later) to collect a second set of calibration parameters. In one embodiment, the computer model fits the blood flow velocity to the systolic/diastolic values. In another embodiment, the computer trains a neural network or HMM to recognize the systolic and diastolic blood pressure values.

After the computer model has been generated, the system is ready for real-time blood pressure monitoring. In an acoustic embodiment, the transducer directs ultrasound at the patient's artery and subsequently listens to the echos therefrom. The echoes are used to determine blood flow, which is fed to the computer model to generate the systolic and diastolic pressure values as well as heart rate value. The CPU's output signal is then converted to a form useful to the user such as a digital or analog display, computer data file, or audible indicator. The output signal can drive a speaker to enable an operator to hear a representation of the Doppler signals and thereby to determine when the transducer is located approximately over the radial artery. The output signal can also be wirelessly sent to a base station for subsequent analysis by a physician, nurse, caregiver, or treating professional. The output signal can also be analyzed for medical attention and medical treatment.

It is noted that while the above embodiment utilizes a preselected pulse duration of 8 microseconds and pulse repetition interval of 16 microseconds, other acoustic sampling techniques may be used in conjunction with the invention. For example, in a second embodiment of the ultrasonic driver and receiver circuit (not shown), the acoustic pulses are range-gated with a more complex implementation of the gate logic. As is well known in the signal processing arts, range-gating is a technique by which the pulse-to-pulse interval is varied based on the receipt of range information from earlier emitted and reflected pulses. Using this technique, the system may be "tuned" to receive echoes falling within a specific temporal window which is chosen based on the range of the echo-producing entity in relation to the acoustic source. The delay time before the gate is turned on determines the depth of the sample volume. The amount of time the gate is activated establishes the axial length of the sample volume. Thus, as the acoustic source (in this case the ultrasonic transducer) is tuned to the echo-producing entity (red blood cells, or arterial walls), the pulse repetition interval is shortened such that the system may obtain more samples per unit time, thereby increasing its resolution. It will be recognized that other acoustic processing techniques may also be used, all of which are considered to be equivalent.

In one optical embodiment, the transducer can be an optical transducer. The optical transducer can be a light source and a photo-detector embedded in the wrist band 1374 portions. The light source can be light-emitting diodes that generate red ($\lambda$~630 nm) and infrared ($\lambda$~900 nm) radiation, for example. The light source and the photo-detector are slidably adjustable and can be moved along the wrist band to optimize beam transmission and pick up. As the heart pumps blood through the patient's finger, blood cells absorb and transmit varying amounts of the red and infrared radiation depending on how much oxygen binds to the cells' hemoglobin. The photo-detector detects transmission at the predetermined wavelengths, for example red and infrared wavelengths, and provides the detected transmission to a pulse-oximetry circuit embedded within the wristwatch. The output of the pulse-oximetry circuit is digitized into a time-dependent optical waveform, which is then sent back to the pulse-oximetry circuit and analyzed to determine the user's vital signs.

In the electromagnetic sensor embodiment, the wrist band 1374 is a flexible plastic material incorporated with a flexible magnet. The magnet provides a magnetic field, and one or more electrodes similar to electrode 1383 are positioned on the wrist band to measure voltage drops which are proportional to the blood velocity. The electromagnetic embodiment may be mounted on the upper arm of the patient, on the ankle or on the neck where peripheral blood vessels pass through and their blood velocity may be measured with minimal interruptions. The flexible magnet produces a pseudo-uniform (non-gradient) magnetic field. The magnetic field can be normal to the blood flow direction when wrist band 1374 is mounted on the user's wrist or may be a rotative pseudo-uniform magnetic field so that the magnetic field is in a transversal direction in respect to the blood flow direction. The electrode output signals are processed to obtain a differential measurement enhancing the signal to noise ratio. The flow information is derived based on the periodicity of the signals. The decoded signal is filtered over several periods and then analyzed for changes used to estimate artery and vein blood flow. Systemic stroke volume and cardiac output may be calculated from the peripheral SV index value.

The wrist band 1374 further contains an antenna for transmitting or receiving radio frequency signals. The wrist band 1374 and the antenna inside the band are mechanically coupled to the top and bottom sides of the housing 1380. Further, the antenna is electrically coupled to a radio frequency transmitter and receiver for wireless communications with another computer or another user. Although the wrist band is disclosed, a number of substitutes may be used, including a belt, a ring holder, a brace, or a bracelet, among other suitable substitutes known to one skilled in the art. The housing 1380 contains the processor and associated peripherals to provide the human-machine interface. A display 1382 is located on the front section of the housing 1380. A speaker 1384, a microphone 1388, and a plurality of push-button switches 1386 and 1393 are also located on the front section of housing 1380.

The electronic circuitry housed in the housing 1380 detects adverse conditions such as falls or seizures. In one implementation, the circuitry can recognize speech, namely utterances of spoken words by the user, and converting the utterances into digital signals. The circuitry for detecting and processing speech to be sent from the wristwatch to the server 20 over the mesh network includes a central processing unit (CPU) connected to a ROM/RAM memory via a bus. The CPU is a preferably low power 16-bit or 32-bit microprocessor and the memory is preferably a high density, low-power RAM. The CPU is coupled via the bus to processor wake-up logic, one or more accelerometers to detect sudden movement in a patient, an ADC which receives speech input from the microphone. The ADC converts the analog signal produced by the microphone into a sequence of digital values representing the amplitude of the signal produced by the microphone at a sequence of evenly spaced times. The CPU is also coupled to a digital to analog (D/A) converter, which drives the speaker to communicate with the user. Speech signals from the microphone are first amplified, pass through an antialiasing filter before being sampled. The front-end processing includes an amplifier, a bandpass filter to avoid antialiasing, and an analog-to-digital (A/D) converter or a CODEC. To minimize space, the ADC, the DAC and the interface for wireless transceiver and switches may be integrated into one integrated circuit to save space. In one embodiment, the wrist watch acts as a walkie-talkie so that voice is received over the mesh network by the server 20 and then delivered to a call center over the POTS or PSTN network. In another embodiment, voice is provided to the call center using the Internet through suitable VOIP techniques. In one embodiment, speech recognition such as a speech recognizer is discussed in U.S. Pat. No. 6,070,140 by the inventor of the instant invention, the content of which is incorporated by reference.

In one embodiment, the wireless nodes convert freely available energy inherent in most operating environments into conditioned electrical power. Energy harvesting is defined as the conversion of ambient energy into usable electrical energy. When compared with the energy stored in common storage elements, like batteries and the like, the environment represents a relatively inexhaustible source of energy. Energy harvesters can be based on piezoelectric devices, solar cells or electromagnetic devices that convert mechanical vibrations.

Power generation with piezoelectrics can be done with body vibrations or by physical compression (impacting the material and using a rapid deceleration using foot action, for example). The vibration energy harvester consists of three main parts. A piezoelectric transducer (PZT) serves as the energy conversion device, a specialized power converter rectifies the resulting voltage, and a capacitor or battery stores the power. The PZT takes the form of an aluminum cantilever with a piezoelectric patch. The vibration-induced strain in the PZT produces an ac voltage. The system repeatedly charges a battery or capacitor, which then operates the EKG/EMG sensors or other sensors at a relatively low duty cycle. In one embodiment, a vest made of piezoelectric materials can be wrapped around a person's chest to generate power when strained through breathing as breathing increases the circumference of the chest for an average human by about 2.5 to 5 cm. Energy can be constantly harvested because breathing is a constant activity, even when a person is sedate. In another embodiment, piezoelectric materials are placed in between the sole and the insole; therefore as the shoe bends from walking, the materials bend along with it. When the stave is bent, the piezoelectric sheets on the outside surface are pulled into expansion, while those on the inside surface are pushed into contraction due to their differing radii of curvature, producing voltages across the electrodes. In another embodiment, PZT materials from Advanced Cerametrics, Inc., Lambertville, N.J. can be incorporated into flexible, motion sensitive (vibration, compression or flexure), active fiber composite shapes that can be placed in shoes, boots, and clothing or any location where there is a source of waste energy or mechanical force. These flexible composites generate power from the scavenged energy and harness it using microprocessor controls developed specifically for this purpose. Advanced Cerametric's viscose suspension spinning process (VSSP) can produce fibers ranging in diameter from 10 μm (⅟₅₀ of a human hair) to 250 μm and mechanical to electrical transduction efficiency can reach 70 percent compared with the 16-18 percent common to solar energy conversion. The composite fibers can be molded into user-defined shapes and is flexible and motion-sensitive. In one implementation, energy is harvested by the body motion such as the foot action or vibration of the PZT composites. The energy is converted and stored in a low-leakage charge circuit until a predetermined threshold voltage is reached. Once the threshold is reached, the regulated power is allowed to flow for a sufficient period to power the wireless node such as the Zigbee CPU/transceiver. The transmission is detected by nearby wireless nodes that are AC-powered and forwarded to the base station for signal processing. Power comes from the vibration of the system being monitored and the unit requires no maintenance, thus reducing life-cycle costs. In one embodiment, the housing of the unit can be PZT composite, thus reducing the weight.

In another embodiment, body energy generation systems include electro active polymers (EAPs) and dielectric elastomers. EAPs are a class of active materials that have a mechanical response to electrical stimulation and produce an electric potential in response to mechanical stimulation. EAPs are divided into two categories, electronic, driven by electric field, and ionic, driven by diffusion of ions. In one embodiment, ionic polymers are used as biological actuators that assist muscles for organs such as the heart and eyes. Since the ionic polymers require a solvent, the hydrated human body provides a natural environment. Polymers are actuated to contract, assisting the heart to pump, or correcting the shape of the eye to improve vision. Another use is as miniature surgical tools that can be inserted inside the body. EAPs can also be used as artificial smooth muscles, one of the original ideas for EAPs. These muscles could be placed in exoskeletal suits for soldiers or prosthetic devices for disabled persons. Along with the energy generation device, ionic polymers can be the energy storage vessel for harvesting energy. The capacitive characteristics of the EAP allow the polymers to be used in place of a standard capacitor bank. With EAP based jacket, when a person moves his/her arms, it will put the electro active material around the elbow in tension to generate power. Dielectric elastomers can support 50-100% area strain and generate power when compressed. Although the material could again be used in a bending arm type application, a shoe type electric generator can be deployed by placing the dielectric elastomers in the sole of a shoe. The constant compressive force provided by the feet while walking would ensure adequate power generation.

For wireless nodes that require more power, electromagnetics, including coils, magnets, and a resonant beam, and micro-generators can be used to produce electricity from readily available foot movement. Typically, a transmitter needs about 30 mW, but the device transmits for only tens of milliseconds, and a capacitor in the circuit can be charged using harvested energy and the capacitor energy drives the wireless transmission, which is the heaviest power requirement. Electromagnetic energy harvesting uses a magnetic field to convert mechanical energy to electrical. A coil attached to the oscillating mass traverses through a magnetic field that is established by a stationary magnet. The coil travels through a varying amount of magnetic flux, inducing a voltage according to Faraday's law. The induced voltage is inherently small and must therefore be increased to viably source energy. Methods to increase the induced voltage include using a transformer, increasing the number of turns of the coil, and/or increasing the permanent magnetic field. Electromagnetic devices use the motion of a magnet relative to a wire coil to generate an electric voltage. A permanent magnet is placed inside a wound coil. As the magnet is moved through the coil it causes a changing magnetic flux. This flux is responsible for generating the voltage which collects on the coil terminals. This voltage can then be supplied to an electrical load. Because an electromagnetic device needs a magnet to be sliding through the coil to produce voltage, energy harvesting through vibrations is an ideal application. In one embodiment, electromagnetic devices are placed inside the heel of a shoe. One implementation uses a sliding magnet-coil design, the other, opposing magnets with one fixed and one free to move inside the coil. If the length of the coil is increased, which increases the turns, the device is able to produce more power.

In an electrostatic (capacitive) embodiment, energy harvesting relies on the changing capacitance of vibration-dependant varactors. A varactor, or variable capacitor, is initially charged and, as its plates separate because of vibrations, mechanical energy is transformed into electrical energy. MEMS variable capacitors are fabricated through relatively mature silicon micro-machining techniques.

In another embodiment, the wireless node can be powered from thermal and/or kinetic energy. Temperature differentials between opposite segments of a conducting material result in heat flow and consequently charge flow, since mobile, high-energy carriers diffuse from high to low concentration regions. Thermopiles consisting of n- and p-type materials electrically joined at the high-temperature junction are therefore constructed, allowing heat flow to carry the dominant charge carriers of each material to the low temperature end, establishing in the process a voltage difference across the base electrodes. The generated voltage and power is proportional to the temperature differential and the Seebeck coefficient of the thermoelectric materials. Body heat from a user's wrist is captured by a thermoelectric element whose output is boosted and used to charge the a lithium ion rechargeable battery. The unit utilizes the Seeback Effect which describes the voltage created when a temperature difference exists across two different metals. The thermoelectric generator takes body heat and dissipates it to the ambient air, creating electricity in the process.

In another embodiment, the kinetic energy of a person's movement is converted into energy. As a person moves their weight, a small weight inside the wireless node moves like a pendulum and turns a magnet to produce electricity which can be stored in a super-capacitor or a rechargeable lithium battery. Similarly, in a vibration energy embodiment, energy extraction from vibrations is based on the movement of a "spring-mounted" mass relative to its support frame. Mechanical acceleration is produced by vibrations that in turn cause the mass component to move and oscillate (kinetic energy). This relative displacement causes opposing frictional and damping forces to be exerted against the mass, thereby reducing and eventually extinguishing the oscillations. The damping forces literally absorb the kinetic energy of the initial vibration. This energy can be converted into electrical energy via an electric field (electrostatic), magnetic field (electromagnetic), or strain on a piezoelectric material.

Another embodiment extracts energy from the surrounding environment using a small rectenna (microwave-power receivers or ultrasound power receivers) placed in patches or membranes on the skin or alternatively injected underneath the skin.

The rectenna converts the received emitted power back to usable low frequency/dc power. A basic rectenna consists of an antenna, a low pass filter, an ac/dc converter and a dc bypass filter. The rectenna can capture renewable electromagnetic energy available in the radio frequency (RF) bands such as AM radio, FM radio, TV, very high frequency (VHF), ultra high frequency (UHF), global system for mobile communications (GSM), digital cellular systems (DCS) and especially the personal communication system (PCS) bands, and unlicensed ISM bands such as 2.4 GHz and 5.8 GHz bands, among others. The system captures the ubiquitous electromagnetic energy (ambient RF noise and signals) opportunistically present in the environment and transforming that energy into useful electrical power. The energy-harvesting antenna is preferably designed to be a wideband, omnidirectional antenna or antenna array that has maximum efficiency at selected bands of frequencies containing the highest energy levels. In a system with an array of antennas, each antenna in the array can be designed to have maximum efficiency at the same or different bands of frequency from one another. The collected RF energy is then converted into usable DC power using a diode-type or other suitable rectifier. This power may be used to drive, for example, an amplifier/filter module connected to a second antenna system that is optimized for a particular frequency and application. One antenna system can act as an energy harvester while the other antenna acts as a signal transmitter/receiver. The antenna circuit elements are formed using standard wafer manufacturing techniques. The antenna output is stepped up and rectified before presented to a trickle charger. The charger can recharge a complete battery by providing a larger potential difference between terminals and more power for charging during a period of time. If battery includes individual micro-battery cells, the trickle charger provides smaller amounts of power to each individual battery cell, with the charging proceeding on a cell by cell basis. Charging of the battery cells continues whenever ambient power is available. As the load depletes cells, depleted cells are switched out with charged cells. The rotation of depleted cells and charged cells continues as required. Energy is banked and managed on a micro-cell basis.

In a solar cell embodiment, photovoltaic cells convert incident light into electrical energy. Each cell consists of a reverse biased pn+ junction, where light interfaces with the heavily doped and narrow n+ region. Photons are absorbed within the depletion region, generating electron-hole pairs. The built-in electric field of the junction immediately separates each pair, accumulating electrons and holes in the n+ and p-regions, respectively, and establishing in the process an open circuit voltage. With a load connected, accumulated electrons travel through the load and recombine with holes at the p-side, generating a photocurrent that is directly proportional to light intensity and independent of cell voltage.

As the energy-harvesting sources supply energy in irregular, random "bursts," an intermittent charger waits until sufficient energy is accumulated in a specially designed transitional storage such as a capacitor before attempting to transfer it to the storage device, lithium-ion battery, in this case. Moreover, the system must partition its functions into time slices (time-division multiplex), ensuring enough energy is harvested and stored in the battery before engaging in power-sensitive tasks. Energy can be stored using a secondary (rechargeable) battery and/or a supercapacitor. The different characteristics of batteries and supercapacitors make them suitable for different functions of energy storage. Supercapacitors provide the most volumetrically efficient approach to meeting high power pulsed loads. If the energy must be stored for a long time, and released slowly, for example as back up, a battery would be the preferred energy storage device. If the energy must be delivered quickly, as in a pulse for RF communications, but long term storage is not critical, a supercapacitor would be sufficient. The system can employ i) a battery (or several batteries), ii) a supercapacitor (or supercapacitors), or iii) a combination of batteries and supercapacitors appropriate for the application of interest. In one embodiment, a microbattery and a microsupercapacitor can be used to store energy. Like batteries, supercapacitors are electrochemical devices; however, rather than generating a voltage from a chemical reaction, supercapacitors store energy by separating charged species in an electrolyte. In one embodiment, a flexible, thin-film, rechargeable battery from Cymbet Corp. of Elk River, Minn. provides 3.6V and can be recharged by a reader. The battery cells can be from 5 to 25 microns thick. The batteries can be recharged with solar energy, or can be recharged by inductive coupling. The tag is put within range of a coil attached to an energy source. The coil "couples" with the antenna on the RFID tag, enabling the tag to draw energy from the magnetic field created by the two coils.

Figure 6B:
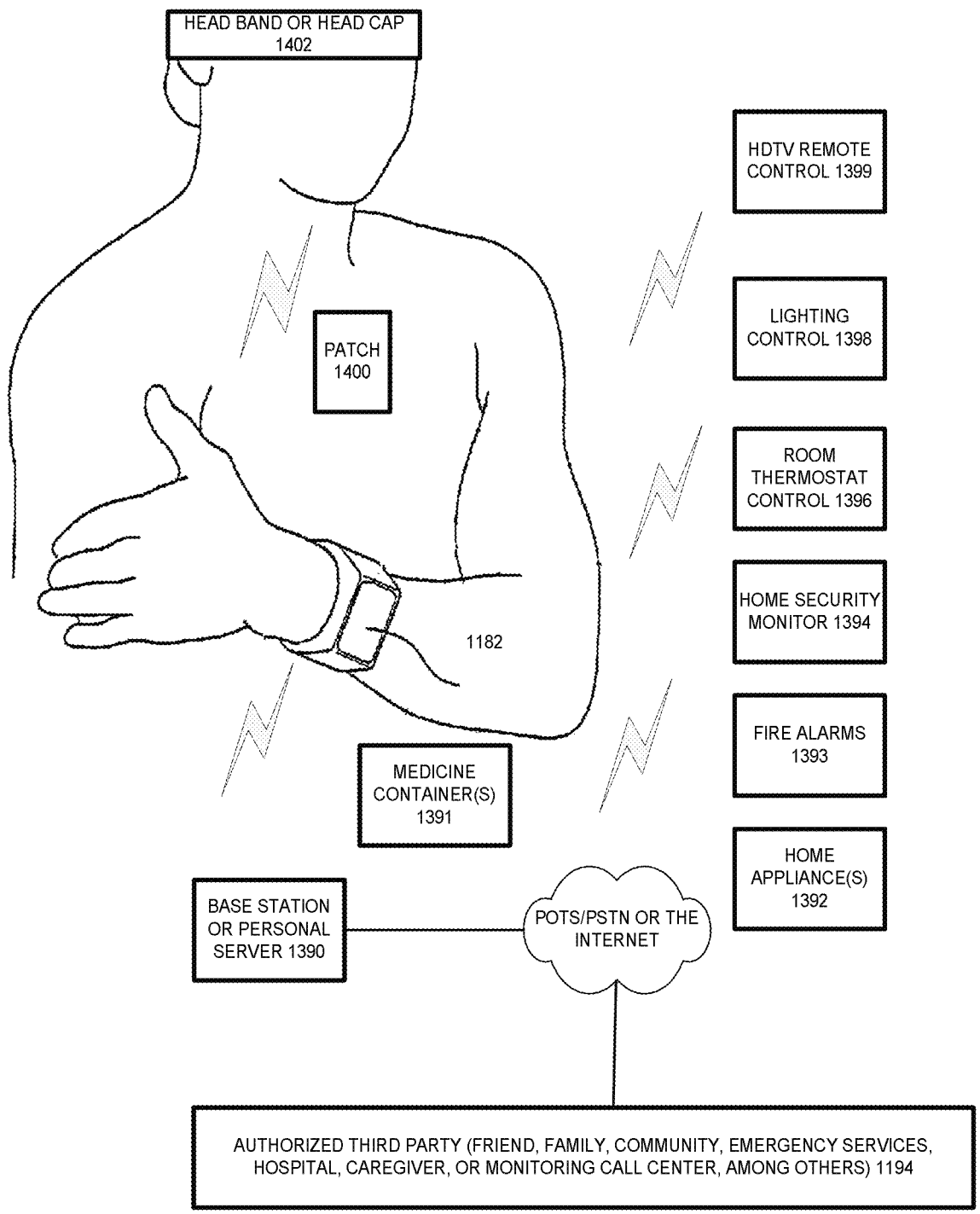
FIG. 6B shows an exemplary mesh network working with the wearable appliance of FIG. 6A.

FIG. 6B shows an exemplary mesh network working with the wearable appliance of FIG. 6A. Data collected and communicated on the display 1382 of the watch as well as voice is transmitted to a base station 1390 for communicating over a network to an authorized party 1394. The watch and the base station 1390 is part of a mesh network that may communicate with a medicine cabinet to detect opening or to each medicine container 1391 to detect medication compliance. Other devices include mesh network thermometers, scales, or exercise devices. The mesh network also includes a plurality of home/room appliances 1392-1399. The ability to transmit voice is useful in the case the patient has fallen down and cannot walk to the base station 1390 to request help. Hence, in one embodiment, the watch captures voice from the user and transmits the voice over the Zigbee mesh network to the base station 1390. The base station 1390 in turn dials out to an authorized third party to allow voice communication and at the same time transmits the collected patient vital parameter data and identifying information so that help can be dispatched quickly, efficiently and error-free. In one embodiment, the base station 1390 is a POTS telephone base station connected to the wired phone network. In a second embodiment, the base station 1390 can be a cellular telephone connected to a cellular network for voice and data transmission. In a third embodiment, the base station 1390 can be a WiMAX or 802.16 standard base station that can communicate VOIP and data over a wide area network. In one implementation, Zigbee or 802.15 appliances communicate locally and then transmits to the wide area network (WAN) such as the Internet over WiFi or WiMAX. Alternatively, the base station 1390 can communicate with the WAN over POTS and a wireless network such as cellular or WiMAX or both.

One embodiment of FIG. 6B includes bioelectrical impedance (BI) spectroscopy sensors in addition to or as alternates to EKG sensors and heart sound transducer sensors. BI spectroscopy is based on Ohm's Law: current in a circuit is directly proportional to voltage and inversely proportional to resistance in a DC circuit or impedance in an alternating current (AC) circuit. Bioelectric impedance exchanges electrical energy with the patient body or body segment. The exchanged electrical energy can include alternating current and/or voltage and direct current and/or voltage. The exchanged electrical energy can include alternating currents and/or voltages at one or more frequencies. For example, the alternating currents and/or voltages can be provided at one or more frequencies between 100 Hz and 1 MHz, preferably at one or more frequencies between 5 KHz and 250 KHz. A BI instrument operating at the single frequency of 50 KHz reflects primarily the extra cellular water compartment as a very small current passes through the cell. Because low frequency (<1 KHz) current does not penetrate the cells and that complete penetration occurs only at a very high frequency (>1 MHz), multi-frequency BI or bioelectrical impedance spectroscopy devices can be used to scan a wide range of frequencies.

In a tetrapolar implementation, two electrodes on the wrist watch or wrist band are used to apply AC or DC constant current into the body or body segment. The voltage signal from the surface of the body is measured in terms of impedance using the same or an additional two electrodes on the watch or wrist band. In a bipolar implementation, one electrode on the wrist watch or wrist band is used to apply AC or DC constant current into the body or body segment. The voltage signal from the surface of the body is measured in terms of impedance using the same or an alternative electrode on the watch or wrist band. The system of FIG. 6B may include a BI patch 1400 that wirelessly communicates BI information with the wrist watch. Other patches 1400 can be used to collect other medical information or vital parameter and communicate with the wrist watch or base station or the information could be relayed through each wireless node or appliance to reach a destination appliance such as the base station, for example. The system of FIG. 6B can also include a head-cap 1402 that allows a number of EEG probes access to the brain electrical activities, EKG probes to measure cranial EKG activity, as well as BI probes to determine cranial fluid presence indicative of a stroke. As will be discussed below, the EEG probes allow the system to determine cognitive status of the patient to determine whether a stroke had just occurred, the EKG and the BI probes provide information on the stroke to enable timely treatment to minimize loss of functionality to the patient if treatment is delayed.

Bipolar or tetrapolar electrode systems can be used in the BI instruments. Of these, the tetrapolar system provides a uniform current density distribution in the body segment and measures impedance with less electrode interface artifact and impedance errors. In the tetrapolar system, a pair of surface electrodes (I1, I2) is used as current electrodes to introduce a low intensity constant current at high frequency into the body. A pair of electrodes (E1, E2) measures changes accompanying physiological events. Voltage measured across E1-E2 is directly proportional to the segment electrical impedance of the human subject. Circular flat electrodes as well as band type electrodes can be used. In one embodiment, the electrodes are in direct contact with the skin surface. In other embodiments, the voltage measurements may employ one or more contactless, voltage sensitive electrodes such as inductively or capacitively coupled electrodes. The current application and the voltage measurement electrodes in these embodiments can be the same, adjacent to one another, or at significantly different locations. The electrode(s) can apply current levels from 20 uA to 10 mA rms at a frequency range of 20-100 KHz. A constant current source and high input impedance circuit is used in conjunction with the tetrapolar electrode configuration to avoid the contact pressure effects at the electrode-skin interface.

The BI sensor can be a Series Model which assumes that there is one conductive path and that the body consists of a series of resistors. An electrical current, injected at a single frequency, is used to measure whole body impedance (i.e., wrist to ankle) for the purpose of estimating total body water and fat free mass. Alternatively, the BI instrument can be a Parallel BI Model. In this model of impedance, the resistors and capacitors are oriented both in series and in parallel in the human body. Whole body BI can be used to estimate TBW and FFM in healthy subjects or to estimate intracellular water (ICW) and body cell mass (BCM). High-low BI can be used to estimate extracellular water (ECW) and total body water (TBW). Multi-frequency BI can be used to estimate ECW, ICW, and TBW; to monitor changes in the ECW/BCM and ECW/TBW ratios in clinical populations. The instrument can also be a Segmental BI Model and can be used in the evaluation of regional fluid changes and in monitoring extra cellular water in patients with abnormal fluid distribution, such as those undergoing hemodialysis. Segmental BI can be used to measure fluid distribution or regional fluid accumulation in clinical populations. Upper-body and Lower-body BI can be used to estimate percentage BF in healthy subjects with normal hydration status and fluid distribution. The BI sensor can be used to detect acute dehydration, pulmonary edema (caused by mitral stenosis or left ventricular failure or congestive heart failure, among others), or hyperhydration cause by kidney dialysis, for example. In one embodiment, the system determines the impedance of skin and subcutaneous adipose tissue using tetrapolar and bipolar impedance measurements. In the bipolar arrangement the inner electrodes act both as the electrodes that send the current (outer electrodes in the tetrapolar arrangement) and as receiving electrodes. If the outer two electrodes (electrodes sending current) are superimposed onto the inner electrodes (receiving electrodes) then a bipolar BIA arrangement exists with the same electrodes acting as receiving and sending electrodes. The difference in impedance measurements between the tetrapolar and bipolar arrangement reflects the impedance of skin and subcutaneous fat. The difference between the two impedance measurements represents the combined impedance of skin and subcutaneous tissue at one or more sites. The system determines the resistivities of skin and subcutaneous adipose tissue, and then calculates the skinfold thickness (mainly due to adipose tissue).

Various BI analysis methods can be used in a variety of clinical applications such as to estimate body composition, to determine total body water, to assess compartmentalization of body fluids, to provide cardiac monitoring, measure blood flow, dehydration, blood loss, wound monitoring, ulcer detection and deep vein thrombosis. Other uses for the BI sensor includes detecting and/or monitoring hypovolemia, hemorrhage or blood loss. The impedance measurements can be made sequentially over a period of in time; and the system can determine whether the subject is externally or internally bleeding based on a change in measured impedance. The watch can also report temperature, heat flux, vasodilation and blood pressure along with the BI information.

In one embodiment, the BI system monitors cardiac function using impedance cardiography (ICG) technique. ICG provides a single impedance tracing, from which parameters related to the pump function of the heart, such as cardiac output (CO), are estimated. ICG measures the beat-to-beat changes of thoracic bioimpedance via four dual sensors applied on the neck and thorax in order to calculate stroke volume (SV). By using the resistivity p of blood and the length L of the chest, the impedance change ΔZ and base impedance (Zo) to the volume change ΔV of the tissue under measurement can be derived as follows:

$$\Delta V = \rho \frac{L^2}{Z_0^2} \Delta Z$$

In one embodiment, SV is determined as a function of the first derivative of the impedance waveform (dZ/dtmax) and the left ventricular ejection time (LVET)

$$SV = \rho \frac{L^2}{Z_0^2} \left(\frac{dZ}{dt}\right)_{max} LVET$$

In one embodiment, L is approximated to be 17% of the patient's height (H) to yield the following:

$$SV = \left(\frac{(0.17\,H)^3}{4.2}\right)\frac{\left(\frac{dZ}{dt}\right)_{max}}{Z_0} LVET$$

In another embodiment, δ or the actual weight divided by the ideal weight is used:

$$SV = \delta \times \left(\frac{(0.17\,H)^3}{4.2}\right)\frac{\left(\frac{dZ}{dt}\right)_{max}}{Z_0} LVET$$

The impedance cardiographic embodiment allows hemodynamic assessment to be regularly monitored to avoid the occurrence of an acute cardiac episode. The system provides an accurate, noninvasive measurement of cardiac output (CO) monitoring so that ill and surgical patients undergoing major operations such as coronary artery bypass graft (CABG) would benefit. In addition, many patients with chronic and comorbid diseases that ultimately lead to the need for major operations and other costly interventions might benefit from more routine monitoring of CO and its dependent parameters such as systemic vascular resistance (SVR).

Once SV has been determined, CO can be determined according to the following expression:

CO=SV*HR, where HR=heart rate

CO can be determined for every heart-beat. Thus, the system can determine SV and CO on a beat-to-beat basis.

In one embodiment to monitor heart failure, an array of BI sensors are place in proximity to the heart. The array of BI sensors detect the presence or absence, or rate of change, or body fluids proximal to the heart. The BI sensors can be supplemented by the EKG sensors. A normal, healthy, heart beats at a regular rate. Irregular heart beats, known as cardiac arrhythmia, on the other hand, may characterize an unhealthy condition. Another unhealthy condition is known as congestive heart failure ("CHF"). CHF, also known as heart failure, is a condition where the heart has inadequate capacity to pump sufficient blood to meet metabolic demand. CHF may be caused by a variety of sources, including, coronary artery disease, myocardial infarction, high blood pressure, heart valve disease, cardiomyopathy, congenital heart disease, endocarditis, myocarditis, and others. Unhealthy heart conditions may be treated using a cardiac rhythm management (CRM) system. Examples of CRM systems, or pulse generator systems, include defibrillators (including implantable cardioverter defibrillator), pacemakers and other cardiac resynchronization devices.

In one implementation, BIA measurements can be made using an array of bipolar or tetrapolar electrodes that deliver a constant alternating current at 50 KHz frequency. Whole body measurements can be done using standard right-sided. The ability of any biological tissue to resist a constant electric current depends on the relative proportions of water and electrolytes it contains, and is called resistivity (in Ohms/cm 3). The measuring of bioimpedance to assess congestive heart failure employs the different bio-electric properties of blood and lung tissue to permit separate assessment of: (a) systemic venous congestion via a low frequency or direct current resistance measurement of the current path through the right ventricle, right atrium, superior vena cava, and subclavian vein, or by computing the real component of impedance at a high frequency, and (b) pulmonary congestion via a high frequency measurement of capacitive impedance of the lung. The resistance is impedance measured using direct current or alternating current (AC) which can flow through capacitors.

In one embodiment, a belt is worn by the patient with a plurality of BI probes positioned around the belt perimeter. The output of the tetrapolar probes is processed using a second-order Newton-Raphson method to estimate the left and right-lung resistivity values in the thoracic geometry. The locations of the electrodes are marked. During the measurements procedure, the belt is worn around the patient's thorax while sitting, and the reference electrode is attached to his waist. The data is collected during tidal respiration to minimize lung resistivity changes due to breathing, and lasts approximately one minute. The process is repeated periodically and the impedance trend is analyzed to detect CHF. Upon detection, the system provides vital parameters to a call center and the call center can refer to a physician for consultation or can call 911 for assistance.

In one embodiment, an array of noninvasive thoracic electrical bioimpedance monitoring probes can be used alone or in conjunction with other techniques such as impedance cardiography (ICG) for early comprehensive cardiovascular assessment and trending of acute trauma victims. This embodiment provides early, continuous cardiovascular assessment to help identify patients whose injuries were so severe that they were not likely to survive. This included severe blood and/or fluid volume deficits induced by trauma, which did not respond readily to expeditious volume resuscitation and vasopressor therapy. One exemplary system monitors cardiorespiratory variables that served as statistically significant measures of treatment outcomes: Qt, BP, pulse oximetry, and transcutaneous Po2 (Ptco2). A high Qt may not be sustainable in the presence of hypovolemia, acute anemia, pre-existing impaired cardiac function, acute myocardial injury, or coronary ischemia. Thus a fall in Ptco2 could also be interpreted as too high a metabolic demand for a patient's cardiovascular reserve. Too high a metabolic demand may compromise other critical organs. Acute lung injury from hypotension, blunt trauma, and massive fluid resuscitation can drastically reduce respiratory reserve.

One embodiment that measures thoracic impedance (a resistive or reactive impedance associated with at least a portion of a thorax of a living organism). The thoracic impedance signal is influenced by the patient's thoracic intravascular fluid tension, heart beat, and breathing (also referred to as "respiration" or "ventilation"). A "de" or "baseline" or "low frequency" component of the thoracic impedance signal (e.g., less than a cutoff value that is approximately between 0.1 Hz and 0.5 Hz, inclusive, such as, for example, a cutoff value of approximately 0.1 Hz) provides information about the subject patient's thoracic fluid tension, and is therefore influenced by intravascular fluid shifts to and away from the thorax. Higher frequency components of the thoracic impedance signal are influenced by the patient's breathing (e.g., approximately between 0.05 Hz and 2.0 Hz inclusive) and heartbeat (e.g., approximately between 0.5 Hz and 10 Hz inclusive). A low intravascular fluid tension in the thorax ("thoracic hypotension") may result from changes in posture. For example, in a person who has been in a recumbent position for some time, approximately ⅓ of the blood volume is in the thorax. When that person then sits upright, approximately ⅓ of the blood that was in the thorax migrates to the lower body. This increases thoracic impedance. Approximately 90% of this fluid shift takes place within 2 to 3 minutes after the person sits upright.

The accelerometer can be used to provide reproducible measurements. Body activity will increase cardiac output and also change the amount of blood in the systemic venous system or lungs. Measurements of congestion may be most reproducible when body activity is at a minimum and the patient is at rest. The use of an accelerometer allows one to sense both body position and body activity. Comparative measurements over time may best be taken under reproducible conditions of body position and activity. Ideally, measurements for the upright position should be compared as among themselves. Likewise measurements in the supine, prone, left lateral decubitus and right lateral decubitus should be compared as among themselves. Other variables can be used to permit reproducible measurements, i.e. variations of the cardiac cycle and variations in the respiratory cycle. The ventricles are at their most compliant during diastole. The end of the diastolic period is marked by the QRS on the electrocardiographic means (EKG) for monitoring the cardiac cycle. The second variable is respiratory variation in impedance, which is used to monitor respiratory rate and volume. As the lungs fill with air during inspiration, impedance increases, and during expiration, impedance decreases. Impedance can be measured during expiration to minimize the effect of breathing on central systemic venous volume. While respiration and CHF both cause variations in impedance, the rates and magnitudes of the impedance variation are different enough to separate out the respiratory variations which have a frequency of about 8 to 60 cycles per minute and congestion changes which take at least several minutes to hours or even days to occur. Also, the magnitude of impedance change is likely to be much greater for congestive changes than for normal respiratory variation. Thus, the system can detect congestive heart failure (CHF) in early stages and alert a patient to prevent disabling and even lethal episodes of CHF. Early treatment can avert progression of the disorder to a dangerous stage.

In an embodiment to monitor wounds such as diabetic related wounds, the conductivity of a region of the patient with a wound or is susceptible to wound formation is monitored by the system. The system determines healing wounds if the impedance and reactance of the wound region increases as the skin region becomes dry. The system detects infected, open, interrupted healing, or draining wounds through lower regional electric impedances. In yet another embodiment, the bioimpedance sensor can be used to determine body fat. In one embodiment, the BI system determines Total Body Water (TBW) which is an estimate of total hydration level, including intracellular and extracellular water; Intracellular Water (ICW) which is an estimate of the water in active tissue and as a percent of a normal range (near 60% of TBW); Extracellular Water (ECW) which is water in tissues and plasma and as a percent of a normal range (near 40% of TBW); Body Cell Mass (BCM) which is an estimate of total pounds/kg of all active cells; Extracellular Tissue (ECT)/Extracellular Mass (ECM) which is an estimate of the mass of all other non-muscle inactive tissues including ligaments, bone and ECW; Fat Free Mass (FFM)/ Lean Body Mass (LBM) which is an estimate of the entire mass that is not fat. It should be available in pounds/kg and may be presented as a percent with a normal range; Fat Mass (FM) which is an estimate of pounds/kg of body fat and percentage body fat; and Phase Angle (PA) which is associated with both nutrition and physical fitness.

Additional sensors such as thermocouples or thermisters and/or heat flux sensors can also be provided to provide measured values useful in analysis. In general, skin surface temperature will change with changes in blood flow in the vicinity of the skin surface of an organism. Such changes in blood flow can occur for a number of reasons, including thermal regulation, conservation of blood volume, and hormonal changes. In one implementation, skin surface measurements of temperature or heat flux are made in conjunction with hydration monitoring so that such changes in blood flow can be detected and appropriately treated.

In one embodiment, the patch includes a sound transducer such as a microphone or a piezoelectric transducer to pick up sound produced by bones or joints during movement. If bone surfaces are rough and poorly lubricated, as in an arthritic knee, they will move unevenly against each other, producing a high-frequency, scratching sound. The high-frequency sound from joints is picked up by wide-band acoustic sensor(s) or microphone(s) on a patient's body such as the knee. As the patient flexes and extends their knee, the sensors measure the sound frequency emitted by the knee and correlate the sound to monitor osteoarthritis, for example.

In another embodiment, the patch includes a Galvanic Skin Response (GSR) sensor. In this sensor, a small current is passed through one of the electrodes into the user's body such as the fingers and the CPU calculates how long it takes for a capacitor to fill up. The length of time the capacitor takes to fill up allows us to calculate the skin resistance: a short time means low resistance while a long time means high resistance. The GSR reflects sweat gland activity and changes in the sympathetic nervous system and measurement variables. Measured from the palm or fingertips, there are changes in the relative conductance of a small electrical current between the electrodes. The activity of the sweat glands in response to sympathetic nervous stimulation (Increased sympathetic activation) results in an increase in the level of conductance. Fear, anger, startle response, orienting response and sexual feelings are all among the emotions which may produce similar GSR responses.

In yet another embodiment, measurement of lung function such as peak expiratory flow readings is done though a sensor such as Wright's peak flow meter. In another embodiment, a respiratory estimator is provided that avoids the inconvenience of having the patient breathing through the flow sensor. In the respiratory estimator embodiment, heart period data from EKG/ECG is used to extract respiratory detection features. The heart period data is transformed into time-frequency distribution by applying a time-frequency transformation such as short-term Fourier transformation (STFT). Other possible methods are, for example, complex demodulation and wavelet transformation. Next, one or more respiratory detection features may be determined by setting up amplitude modulation of time-frequency plane, among others. The respiratory recognizer first generates a math model that correlates the respiratory detection features with the actual flow readings. The math model can be adaptive based on pre-determined data and on the combination of different features to provide a single estimate of the respiration. The estimator can be based on different mathematical functions, such as a curve fitting approach with linear or polynomial equations, and other types of neural network implementations, non-linear models, fuzzy systems, time series models, and other types of multivariate models capable of transferring and combining the information from several inputs into one estimate. Once the math model has been generated, the respirator estimator provides a real-time flow estimate by receiving EKG/ECG information and applying the information to the math model to compute the respiratory rate. Next, the computation of ventilation uses information on the tidal volume. An estimate of the tidal volume may be derived by utilizing different forms of information on the basis of the heart period signal. For example, the functional organization of the respiratory system has an impact in both respiratory period and tidal volume. Therefore, given the known relationships between the respiratory period and tidal volume during and transitions to different states, the information inherent in the heart period derived respiratory frequency may be used in providing values of tidal volume. In specific, the tidal volume contains inherent dynamics which may be, after modeling, applied to capture more closely the behavioral dynamics of the tidal volume. Moreover, it appears that the heart period signal, itself, is closely associated with tidal volume and may be therefore used to increase the reliability of deriving information on tidal volume. The accuracy of the tidal volume estimation may be further enhanced by using information on the subjects vital capacity (i.e., the maximal quantity of air that can be contained in the lungs during one breath). The information on vital capacity, as based on physiological measurement or on estimates derived from body measures such as height and weight, may be helpful in estimating tidal volume, since it is likely to reduce the effects of individual differences on the estimated tidal volume. Using information on the vital capacity, the mathematical model may first give values on the percentage of lung capacity in use, which may be then transformed to liters per breath. The optimizing of tidal volume estimation can based on, for example, least squares or other type of fit between the features and actual tidal volume. The minute ventilation may be derived by multiplying respiratory rate (breaths/min) with tidal volume (liters/breath).

In another embodiment, inductive plethysmography can be used to measure a cross-sectional area of the body by determining the self-inductance of a flexible conductor closely encircling the area to be measured. Since the inductance of a substantially planar conductive loop is well known to vary as, inter alia, the cross-sectional area of the loop, a inductance measurement may be converted into a plethysmographic area determination. Varying loop inductance may be measured by techniques known in the art, such as, e.g., by connecting the loop as the inductance in a variable frequency LC oscillator, the frequency of the oscillator then varying with the cross-sectional area of the loop inductance varies. Oscillator frequency is converted into a digital value, which is then further processed to yield the physiological parameters of interest. Specifically, a flexible conductor measuring a cross-sectional area of the body is closely looped around the area of the body so that the inductance, and the changes in inductance, being measured results from magnetic flux through the cross-sectional area being measured. The inductance thus depends directly on the cross-sectional area being measured, and not indirectly on an area which changes as a result of the factors changing the measured cross-sectional area. Various physiological parameters of medical and research interest may be extracted from repetitive measurements of the areas of various cross-sections of the body. For example, pulmonary function parameters, such as respiration volumes and rates and apneas and their types, may be determined from measurements of, at least, a chest transverse cross-sectional area and also an abdominal transverse cross-sectional area. Cardiac parameters, such central venous pressure, left and right ventricular volumes waveforms, and aortic and carotid artery pressure waveforms, may be extracted from repetitive measurements of transverse cross-sectional areas of the neck and of the chest passing through the heart. Timing measurements can be obtained from concurrent ECG measurements, and less preferably from the carotid pulse signal present in the neck. From the cardiac-related signals, indications of ischemia may be obtained independently of any ECG changes. Ventricular wall ischemia is known to result in paradoxical wall motion during ventricular contraction (the ischemic segment paradoxically "balloons" outward instead of normally contracting inward). Such paradoxical wall motion, and thus indications of cardiac ischemia, may be extracted from chest transverse cross-section area measurements. Left or right ventricular ischemia may be distinguished where paradoxical motion is seen predominantly in left or right ventricular waveforms, respectively. For another example, observations of the onset of contraction in the left and right ventricles separately may be of use in providing feedback to bi-ventricular cardiac pacing devices. For a further example, pulse oximetry determines hemoglobin saturation by measuring the changing infrared optical properties of a finger. This signal may be disambiguated and combined with pulmonary data to yield improved information concerning lung function.

In one embodiment to monitor and predict stroke attack, a cranial bioimpedance sensor is applied to detect fluids in the brain. The brain tissue can be modeled as an electrical circuit where cells with the lipid bilayer act as capacitors and the intra and extra cellular fluids act as resistors. The opposition to the flow of the electrical current through the cellular fluids is resistance. The system takes 50-kHz single-frequency bioimpedance measurements reflecting the electrical conductivity of brain tissue. The opposition to the flow of the current by the capacitance of lipid bilayer is reactance. In this embodiment, microamps of current at 50 kHz are applied to the electrode system. In one implementation, the electrode system consists of a pair of coaxial electrodes each of which has a current electrode and a voltage sensing electrode. For the measurement of cerebral bioimpedance, one pair of gel current electrodes is placed on closed eyelids and the second pair of voltage electrodes is placed in the suboccipital region projecting towards the foramen magnum. The electrical current passes through the orbital fissures and brain tissue. The drop in voltage is detected by the suboccipital electrodes and then calculated by the processor to bioimpedance values. The bioimpedance value is used to detect brain edema, which is defined as an increase in the water content of cerebral tissue which then leads to an increase in overall brain mass. Two types of brain edema are vasogenic or cytotoxic. Vasogenic edema is a result of increased capillary permeability. Cytotoxic edema reflects the increase of brain water due to an osmotic imbalance between plasma and the brain extracellular fluid. Cerebral edema in brain swelling contributes to the increase in intracranial pressure and an early detection leads to timely stroke intervention.

In another example, a cranial bioimpedance tomography system contructs brain impedance maps from surface measurements using nonlinear optimization. A nonlinear optimization technique utilizing known and stored constraint values permits reconstruction of a wide range of conductivity values in the tissue. In the nonlinear system, a Jacobian Matrix is renewed for a plurality of iterations. The Jacobian Matrix describes changes in surface voltage that result from changes in conductivity. The Jacobian Matrix stores information relating to the pattern and position of measuring electrodes, and the geometry and conductivity distributions of measurements resulting in a normal case and in an abnormal case. The nonlinear estimation determines the maximum voltage difference in the normal and abnormal cases.

In one embodiment, an electrode array sensor can include impedance, bio-potential, or electromagnetic field tomography imaging of cranial tissue. The electrode array sensor can be a geometric array of discrete electrodes having an equally-spaced geometry of multiple nodes that are capable of functioning as sense and reference electrodes. In a typical tomography application the electrodes are equally-spaced in a circular configuration. Alternatively, the electrodes can have non-equal spacing and/or can be in rectangular or other configurations in one circuit or multiple circuits. Electrodes can be configured in concentric layers too. Points of extension form multiple nodes that are capable of functioning as an electrical reference. Data from the multiple reference points can be collected to generate a spectrographic composite for monitoring over time.

The patient's brain cell generates an electromagnetic field of positive or negative polarity, typically in the millivolt range. The sensor measures the electromagnetic field by detecting the difference in potential between one or more test electrodes and a reference electrode. The bio-potential sensor uses signal conditioners or processors to condition the potential signal. In one example, the test electrode and reference electrode are coupled to a signal conditioner/processor that includes a lowpass filter to remove undesired high frequency signal components. The electromagnetic field signal is typically a slowly varying DC voltage signal. The lowpass filter removes undesired alternating current components arising from static discharge, electromagnetic interference, and other sources.

In one embodiment, the impedance sensor has an electrode structure with annular concentric circles including a central electrode, an intermediate electrode and an outer electrode, all of which are connected to the skin. One electrode is a common electrode and supplies a low frequency signal between this common electrode and another of the three electrodes. An amplifier converts the resulting current into a voltage between the common electrode and another of the three electrodes. A switch switches between a first circuit using the intermediate electrode as the common electrode and a second circuit that uses the outer electrode as a common electrode. The sensor selects depth by controlling the extension of the electric field in the vicinity of the measuring electrodes using the control electrode between the measuring electrodes. The control electrode is actively driven with the same frequency as the measuring electrodes to a signal level taken from one of the measuring electrodes but multiplied by a complex number with real and imaginary parts controlled to attain a desired depth penetration. The controlling field functions in the manner of a field effect transistor in which ionic and polarization effects act upon tissue in the manner of a semiconductor material.

With multiple groups of electrodes and a capability to measure at a plurality of depths, the system can perform tomographic imaging or measurement, and/or object recognition. In one embodiment, a fast reconstruction technique is used to reduce computation load by utilizing prior information of normal and abnormal tissue conductivity characteristics to estimate tissue condition without requiring full computation of a non-linear inverse solution.

In another embodiment, the bioimpedance system can be used with electro-encephalograph (EEG) or ERP. Since this embodiment collects signals related to blood flow in the brain, collection can be concentrated in those regions of the brain surface corresponding to blood vessels of interest. A headcap with additional electrodes placed in proximity to regions of the brain surface fed by a blood vessel of interest, such as the medial cerebral artery enables targeted information from the regions of interest to be collected. The headcap can cover the region of the brain surface that is fed by the medial cerebral artery. Other embodiments of the headcap can concentrate electrodes on other regions of the brain surface, such as the region associated with the somatosensory motor cortex. In alternative embodiments, the headcap can cover the skull more completely. Further, such a headcap can include electrodes thoughout the cap while concentrating electrodes in a region of interest. Depending upon the particular application, arrays of 1-16 head electrodes may be used, as compared to the International 10/20 system of 19-21 head electrodes generally used in an EEG instrument.

In one implementation, each amplifier for each EEG channel is a high quality analog amplifier device. Full bandwidth and ultra-low noise amplification are obtained for each electrode. Low pass, high pass, hum notch filters, gain, un-block, calibration and electrode impedance check facilities are included in each amplifier. All 8 channels in one EEG amplifier unit have the same filter, gain, etc. settings. Noise figures of less than 0.1 uV r.m.s. are achieved at the input and optical coupling stages. These figures, coupled with good isolation/common mode rejection result in signal clarity. Nine high pass filter ranges include 0.01 Hz for readiness potential measurement, and 30 Hz for EMG measurement.

In one embodiment, stimulations to elicit EEG signals are used in two different modes, i.e., auditory clicks and electric pulses to the skin. The stimuli, although concurrent, are at different prime number frequencies to permit separation of different evoked potentials (EPs) and avoid interference. Such concurrent stimulations for EP permit a more rapid, and less costly, examination and provide the patient's responses more quickly. Power spectra of spontaneous EEG, waveshapes of Averaged Evoked Potentials, and extracted measures, such as frequency specific power ratios, can be transmitted to a remote receiver. The latencies of successive EP peaks of the patient may be compared to those of a normal group by use of a normative template. To test for ischemic stroke or intracerebral or subarachnoid hemorrhage, the system provides a blood oxygen saturation monitor, using an infra-red or laser source, to alert the user if the patient's blood in the brain or some brain region is deoxygenated.

A stimulus device may optionally be placed on each subject, such as an audio generator in the form of an ear plug, which produces a series of "click" sounds. The subject's brain waves are detected and converted into audio tones. The device may have an array of LED (Light Emitting Diodes) which blink depending on the power and frequency composition of the brain wave signal. Power ratios in the frequencies of audio or somatosensory stimuli are similarly encoded. The EEG can be transmitted to a remote physician or medical aide who is properly trained to determine whether the patient's brain function is abnormal and may evaluate the functional state of various levels of the patient's nervous system.

In another embodiment, three pairs of electrodes are attached to the head of the subject under examination via tape or by wearing a cap with electrodes embedded. In one embodiment, the electrode pairs are as follows:
1) top of head to anterior throat
2) inion-nasion
3) left to right mastoid (behind ear).

A ground electrode is located at an inactive site of the upper part of the vertebral column. The electrodes are connected to differential amplification devices as disclosed below. Because the electrical charges of the brain are so small (on the order of microvolts), amplification is needed. The three amplified analog signals are converted to digital signals and averaged over a certain number of successive digital values to eliminate erroneous values originated by noise on the analog signal.

All steps defined above are linked to a timing signal which is also responsible for generating stimuli to the subject. The responses are processed in a timed relation to the stimuli and averaged as the brain responds to these stimuli. Of special interest are the responses within certain time periods and time instances after the occurrence of a stimulus of interest. These time periods and instances and their references can be:

25 to 60 milliseconds: P1-N1
180 to 250 milliseconds: N2
100 milliseconds: N100
200 milliseconds: P2
300 milliseconds: P300.

In an examination two stimuli sets may be used in a manner that the brain has to respond to the two stimuli differently, one stimulus has a high probability of occurrence, and the other stimulus is a rare occurring phenomena. The rare response is the response of importance. Three response signals are sensed and joined into a three dimensional cartesian system by a mapping program. The assignments can be nasion-inion=X,
left-right mastoid=Y, and
top of head to anterior throat=Z.

The assignment of the probes to the axes and the simultaneous sampling of the three response signals at the same rate and time relative to the stimuli allows to real-time map the electrical signal in a three dimensional space. The signal can be displayed in a perspective representation of the three dimensional space, or the three components of the vector are displayed by projecting the vector onto the three planes X-Y, Y-Z, and X-Z, and the three planes are inspected together or separately. Spatial information is preserved for reconstruction as a map. The Vector Amplitude (VA) measure provides information about how far from the center of the head the observed event is occurring; the center of the head being the center (0,0,0) of the coordinate system.

The cranial bioimpedance sensor can be applied singly or in combination with a cranial blood flow sensor, which can be optical, ultrasound, electromagnetic sensor(s) as described in more details below. In an ultrasound imaging implementation, the carotid artery is checked for plaque build-up. Atherosclerosis is systemic—meaning that if the carotid artery has plaque buildup, other important arteries, such as coronary and leg arteries, might also be atherosclerotic.

In another embodiment, an epicardial array monopolar ECG system converts signals into the multichannel spectrum domain and identifies decision variables from the autospectra. The system detects and localizes the epicardial projections of ischemic myocardial ECGs during the cardiac activation phase. This is done by transforming ECG signals from an epicardial or torso sensor array into the multichannel spectral domain and identifying any one or more of a plurality of decision variables. The ECG array data can be used to detect, localize and quantify reversible myocardial ischemia.

In yet another embodiment, a trans-cranial Doppler velocimetry sensor provides a non-invasive technique for measuring blood flow in the brain. An ultrasound beam from a transducer is directed through one of three natural acoustical windows in the skull to produce a waveform of blood flow in the arteries using Doppler sonography. The data collected to determine the blood flow may include values such as the pulse cycle, blood flow velocity, end diastolic velocity, peak systolic velocity, mean flow velocity, total volume of cerebral blood flow, flow acceleration, the mean blood pressure in an artery, and the pulsatility index, or impedance to flow through a vessel. From this data, the condition of an artery may be derived, those conditions including stenosis, vasoconstriction, irreversible stenosis, vasodilation, compensatory vasodilation, hyperemic vasodilation, vascular failure, compliance, breakthrough, and pseudo-normalization.

In addition to the above techniques to detect stroke attack, the system can detect numbness or weakness of the face, arm or leg, especially on one side of the body. The system detects sudden confusion, trouble speaking or understanding, sudden trouble seeing in one or both eyes, sudden trouble walking, dizziness, loss of balance or coordination, or sudden, severe headache with no known cause.

In one embodiment to detect heart attack, the system detects discomfort in the center of the chest that lasts more than a few minutes, or that goes away and comes back. Symptoms can include pain or discomfort in one or both arms, the back, neck, jaw or stomach. The system can also monitor for shortness of breath which may occur with or without chest discomfort. Other signs may include breaking out in a cold sweat, nausea or lightheadedness.

In order to best analyze a patient's risk of stroke, additional patient data is utilized by a stroke risk analyzer. This data may include personal data, such as date of birth, ethnic group, sex, physical activity level, and address. The data may further include clinical data such as a visit identification, height, weight, date of visit, age, blood pressure, pulse rate, respiration rate, and so forth. The data may further include data collected from blood work, such as the antinuclear antibody panel, B-vitamin deficiency, C-reactive protein value, calcium level, cholesterol levels, entidal $CO_2$, fibromogin, amount of folic acid, glucose level, hematocrit percentage, *H-pylori* antibodies, hemocysteine level, hypercapnia, magnesium level, methyl maloric acid level, platelets count, potassium level, sedrate (ESR), serum osmolality, sodium level, zinc level, and so forth. The data may further include the health history data of the patient, including alcohol intake, autoimmune diseases, caffeine intake, carbohydrate intake, carotid artery disease, coronary disease, diabetes, drug abuse, fainting, glaucoma, head injury, hypertension, lupus, medications, smoking, stroke, family history of stroke, surgery history, for example.

In one embodiment, data driven analyzers may be used to track the patient's risk of stroke or heart attack. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient stoke patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In general, multiple dimensions of a user's EEG, EKG, BI, ultrasound, optical, acoustic, electromagnetic, or electrical parameters are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences. Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's stroke risks or heart attack risks. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

Substantially any type of learning system or process may be employed to determine the stroke or heart attack patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible points within the permitted domain for each value of i. Because the best path from the current point to the next point is independent of what happens beyond that point. Thus, the total cost of [i(k), j(k)] is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of user habit information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations O(1), O(2), . . . O(t), . . . , O(T), where each observation O(t) may be either a discrete symbol under the VQ approach or a continuous vector. The sequence of observations may be modeled as a probabilistic function of an underlying Markov chain having state transitions that are not directly observable. In one embodiment, the Markov network is used to model a number of user habits and activities. The transitions between states are represented by a transition matrix A=[a(i,j)]. Each a(i,j) term of the transition matrix is the probability of making a transition to state j given that the model is in state i. The output symbol probability of the model is represented by a set of functions B=[b(j) (O(t)], where the b(j) (O(t) term of the output symbol matrix is the probability of outputting observation O(t), given that the model is in state j. The first state is always constrained to be the initial state for the first time frame of the utterance, as only a prescribed set of left to right state transitions are possible. A predetermined final state is defined from which transitions to other states cannot occur. Transitions are restricted to reentry of a state or entry to one of the next two states. Such transitions are defined in the model as transition probabilities. Although the preferred embodiment restricts the flow graphs to the present state or to the next two states, one skilled in the art can build an HMM model without any transition restrictions, although the sum of all the probabilities of transitioning from any state must still add up to one. In each state of the model, the current feature frame may be identified with one of a set of predefined output symbols or may be labeled probabilistically. In this case, the output symbol probability b(j) O(t) corresponds to the probability assigned by the model that the feature frame symbol is O(t). The model arrangement is a matrix A=[a(i,j)] of transition probabilities and a technique of computing B=b(j) O(t), the feature frame symbol probability in state j. The Markov model is formed for a reference pattern from a plurality of sequences of training patterns and the output symbol probabilities are multivariate Gaussian function probability densities. The patient habit information is processed by a feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator. The HMM template has a number of states, each having a discrete value. However, because treatment pattern features may have a dynamic pattern in contrast to a single value. The addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output states, which normally would be the output layer of the neuron. However, each output has transition probabilities to itself or to the next outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

The automated analyzer can also consider related pathologies in analyzing a patient's risk of stroke, including but not limited to gastritis, increased intracranial pressure, sleep disorders, small vessel disease, and vasculitis.

In one embodiment, the processor and transceiver on the watch, the patch(es) and the base station conform to the Zigbee protocol. ZigBee is a cost-effective, standards-based wireless networking solution that supports low data-rates, low-power consumption, security, and reliability. Single chip Zigbee controllers with wireless transceivers built-in include the Chipcon/Ember CC2420: Single-chip 802.15.4 radio transceiver and the FreeScale single chip Zigbee and microcontroller. In various embodiments, the processor communicates with a Z axis accelerometer measures the patient's up and down motion and/or an X and Y axis accelerometer measures the patient's forward and side movements. In one embodiment, EKG and/or blood pressure parameters can be captured by the processor. The controllers upload the captured data when the memory is full or while in wireless contact with other Zigbee nodes.

The wristwatch device can also be used to control home automation. The user can have flexible management of lighting, heating and cooling systems from anywhere in the home. The watch automates control of multiple home systems to improve conservation, convenience and safety. The watch can capture highly detailed electric, water and gas utility usage data and embed intelligence to optimize consumption of natural resources. The system is convenient in that it can be installed, upgraded and networked without wires. The patient can receive automatic notification upon detection of unusual events in his or her home. For example, if smoke or carbon monoxide detectors detect a problem, the wrist-watch can buzz or vibrate to alert the user and the central hub triggers selected lights to illuminate the safest exit route.

In another embodiment, the watch serves a key fob allowing the user to wirelessly unlock doors controlled by Zigbee wireless receiver. In this embodiment, when the user is within range, the door Zigbee transceiver receives a request to unlock the door, and the Zigbee transceiver on the door transmits an authentication request using suitable security mechanism. Upon entry, the Zigbee doorlock device sends access signals to the lighting, air-conditioning and entertainment systems, among others. The lights and temperature are automatically set to pre-programmed preferences when the user's presence is detected.

Although Zigbee is mentioned as an exemplary protocol, other protocols such as UWB, Bluetooth, WiFi and WiMAX can be used as well.

While the foregoing addresses the needs of the elderly, the system can assist infants as well. Much attention has been given to ways to reduce a risk of dying from Sudden Infant Death Syndrome (SIDS), an affliction which threatens infants who have died in their sleep for heretofore unknown reasons. Many different explanations for this syndrome and ways to prevent the syndrome are found in the literature. It is thought that infants which sleep on their backs may be at risk of death because of the danger of formula regurgitation and liquid aspiration into the lungs. It has been thought that infants of six (6) months or less do not have the motor skills or body muscular development to regulate movements responsive to correcting breathing problems that may occur during sleep.

In an exemplary system to detect and minimize SIDS problem in an infant patient, a diaper pad is used to hold an array of integrated sensors and the pad can be placed over a diaper, clothing, or blanket. The integrated sensors can provide data for measuring position, temperature, sound, vibration, movement, and optionally other physical properties through additional sensors. Each pad can have sensors that provide one or more of the above data. The sensors can be added or removed as necessary depending on the type of data being collected.

The sensor can be water proof and disposable. The sensor can be switch on/off locally or remotely. The sensor can be removable or clip on easily. The sensor can store or beam out information for analysis purpose, e.g. store body temperature every 5 seconds. The sensor can be turn-on for other purposed, e.g. diaper wet, it will beep and allow a baby care provider to take care of the business in time. The array of sensors can be self selective, e.g., when one sensor can detect strong heart beat, it will turn off others to do so.

The sensor can be used for drug delivery system, e.g. when patient has abdomen pain, soothing drug can be applied, based on the level of pain the sensor detects, different dose of drugs will be applied.

The array of sensors may allow the selection and analysis of zones of sensors in the areas of interest such as the abdomen area. Each sensor array has a low spatial resolution: approximately 10 cm between each sensor. In addition to lower cost due to the low number of sensors, it is also possible to modify the data collection rate from certain sensors that are providing high-quality data. Other sensors may include those worn on the body, such as in watch bands, finger rings, or adhesive sensors, but telemetry, not wires, would be used to communicate with the controller.

The sensor can be passive device such as a reader, which mounted near the crib can active it from time to time. In any emergency situation, the sensor automatically signals a different state which the reader can detect.

The sensor can be active and powered by body motion or body heat. The sensor can detect low battery situation and warn the user to provide a replacement battery.

In one embodiment, a plurality of sensors attached to the infant collects the vital parameters. For example, the sensors can be attached to the infant's clothing (shirt or pant), diaper, undergarment or bed sheet, bed linen, or bed spread.

The patient may wear one or more sensors, for example devices for sensing EMG, EKG, blood pressure, sugar level, weight, temperature and pressure, among others. In one embodiment, an optical temperature sensor can be used. In another embodiment, a temperature thermistor can be used to sense patient temperature. In another embodiment, a fat scale sensor can be used to detect the patient's fat content. In yet another embodiment, a pressure sensor such as a MEMS sensor can be used to sense pressure on the patient.

In one embodiment, the sensors are mounted on the patient's wrist (such as a wristwatch sensor) and other convenient anatomical locations. Exemplary sensors include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors can individually transmit data to the server 20 using wired or wireless transmission. Alternatively, all sensors can be fed through a common bus into a single transceiver for wired or wireless transmission. The transmission can be done using a magnetic medium such as a floppy disk or a flash memory card, or can be done using infrared or radio network link, among others.

In one embodiment, the sensors for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch.

In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

The heartbeat detector can be one of: EKG detector, ECG detector, optical detector, ultrasonic detector, or microphone/digital stethoscope for picking up heart sound. In one embodiment, one EKG/ECG contact point is provided on the back of the wrist watch case and one or more EKG/ECG contact points are provided on the surface of the watch so that when a user's finger or skin touches the contact points, an electrical signal indicative of heartbeat activity is generated. An electrocardiogram (ECG) or EKG is a graphic tracing of the voltage generated by the cardiac or heart muscle during a heartbeat. It provides very accurate evaluation of the performance of the heart. The heart generates an electrochemical impulse that spreads out in the heart in such a fashion as to cause the cells to contract and relax in a timely order and thus give the heart a pumping characteristic. This sequence is initiated by a group of nerve cells called the sinoatrial (SA) node resulting in a polarization and depolarization of the cells of the heart. Because this action is electrical in nature and because the body is conductive with its fluid content, this electrochemical action can be measured at the surface of the body. An actual voltage potential of approximately 1 mV develops between various body points. This can be measured by placing electrode contacts on the body. The four extremities and the chest wall have become standard sites for applying the electrodes. Standardizing electrocardiograms makes it possible to compare them as taken from person to person and from time to time from the same person. The normal electrocardiogram shows typical upward and downward deflections that reflect the alternate contraction of the atria (the two upper chambers) and of the ventricles (the two lower chambers) of the heart. The voltages produced represent pressures exerted by the heart muscles in one pumping cycle. The first upward deflection, P, is due to atria contraction and is known as the atrial complex. The other deflections, Q, R, S, and T, are all due to the action of the ventricles and are known as the ventricular complexes. Any deviation from the norm in a particular electrocardiogram is indicative of a possible heart disorder.

The CPU measures the time duration between the sequential pulses and converts each such measurement into a corresponding timing measurement indicative of heart rate. The CPU also processes a predetermined number of most recently occurring timing measurements in a prescribed fashion, to produce an estimate of heartbeat rate for display on a display device on the watch and/or for transmission over the wireless network. This estimate is updated with the occurrence of each successive pulse.

In one embodiment, the CPU produces the estimate of heartbeat rate by first averaging a plurality of measurements, then adjusting the particular one of the measurements that differs most from the average to be equal to that average, and finally computing an adjusted average based on the adjusted set of measurements. The process may repeat the foregoing operations a number of times so that the estimate of heartbeat rate is substantially unaffected by the occurrence of heartbeat artifacts.

In one EKG or ECG detector, the heartbeat detection circuitry includes a differential amplifier for amplifying the signal transmitted from the EKG/ECG electrodes and for converting it into single-ended form, and a bandpass filter and a 60 Hz notch filter for removing background noise. The CPU measures the time durations between the successive pulses and estimates the heartbeat rate. The time durations between the successive pulses of the pulse sequence signal provides an estimate of heartbeat rate. Each time duration measurement is first converted to a corresponding rate, preferably expressed in beats per minute (bpm), and then stored in a file, taking the place of the earliest measurement previously stored. After a new measurement is entered into the file, the stored measurements are averaged, to produce an average rate measurement. The CPU optionally determines which of the stored measurements differs most from the average, and replaces that measurement with the average.

Upon initiation, the CPU increments a period timer used in measuring the time duration between successive pulses. This timer is incremented in steps of about two milliseconds in one embodiment. It is then determined whether or not a pulse has occurred during the previous two milliseconds. If it has not, the CPU returns to the initial step of incrementing the period timer. If a heartbeat has occurred, on the other hand, the CPU converts the time duration measurement currently stored in the period timer to a corresponding heartbeat rate, preferably expressed in bpm. After the heartbeat rate measurement is computed, the CPU determines whether or not the computed rate is intermediate prescribed thresholds of 20 bpm and 240 bpm. If it is not, it is assumed that the detected pulse was not in fact a heartbeat and the period timer is cleared.

In an optical heartbeat detector embodiment, an optical transducer is positioned on a finger, wrist, or ear lobe. The ear, wrist or finger pulse oximeter waveform is then analyzed to extract the beat-to-beat amplitude, area, and width (half height) measurements. The oximeter waveform is used to generate heartbeat rate in this embodiment. In one implementation, a reflective sensor such as the Honeywell HLC1395 can be used. The device emits lights from a window in the infrared spectrum and receives reflected light in a second window. When the heart beats, blood flow increases temporarily and more red blood cells flow through the windows, which increases the light reflected back to the detector. The light can be reflected, refracted, scattered, and absorbed by one or more detectors. Suitable noise reduction is done, and the resulting optical waveform is captured by the CPU.

In another optical embodiment, blood pressure is estimated from the optical reading using a mathematical model such as a linear correlation with a known blood pressure reading. In this embodiment, the pulse oximeter readings are compared to the blood-pressure readings from a known working blood pressure measurement device during calibration. Using these measurements the linear equation is developed relating oximeter output waveform such as width to blood-pressure (systolic, mean and pulse pressure). In one embodiment, a transform (such as a Fourier analysis or a Wavelet transform) of the oximeter output can be used to generate a model to relate the oximeter output waveform to the blood pressure. Other non-linear math model or relationship can be determined to relate the oximeter waveform to the blood pressure.

In one implementation, the pulse oximeter probe and a blood pressure cuff are placed on the corresponding contralateral limb to the oscillometric (Dinamap 8100; Critikon, Inc, Tampa, Fla., USA) cuff site. The pulse oximeter captures data on plethysmographic waveform, heart rate, and oxygen saturation. Simultaneous blood pressure measurements were obtained from the oscillometric device, and the pulse oximeter. Systolic, diastolic, and mean blood pressures are recorded from the oscillometric device. This information is used derive calibration parameters relating the pulse oximeter output to the expected blood pressure. During real time operation, the calibration parameters are applied to the oximeter output to predict blood pressure in a continuous or in a periodic fashion. In yet another embodiment, the device includes an accelerometer or alternative motion-detecting device to determine when the patient' hand is at rest, thereby reducing motion-related artifacts introduced to the measurement during calibration and/or operation. The accelerometer can also function as a falls detection device.

In an ultrasonic embodiment, a piezo film sensor element is placed on the wristwatch band. The sensor can be the SDT1-028K made by Measurement Specialties, Inc. The sensor should have features such as: (a) it is sensitive to low level mechanical movements, (b) it has an electrostatic shield located on both sides of the element (to minimize 50/60 Hz AC line interference), (c) it is responsive to low frequency movements in the 0.7-12 Hz range of interest. A filter/amplifier circuit has a three-pole low pass filter with a lower (−3 dB) cutoff frequency at about 12-13 Hz. The low-pass filter prevents unwanted 50/60 Hz AC line interference from entering the sensor. However, the piezo film element has a wide band frequency response so the filter also attenuates any extraneous sound waves or vibrations that get into the piezo element. The DC gain is about +30 dB.

Waveform averaging can be used to reduce noise. It reinforces the waveform of interest by minimizing the effect of any random noise. These pulses were obtained when the arm was motionless. If the arm was moved while capturing the data the waveform did not look nearly as clean. That's because motion of the arm causes the sonic vibrations to enter the piezo film through the arm or by way of the cable. An accelerometer is used to detect arm movement and used to remove inappropriate data capture.

In one embodiment that can determine blood pressure, two piezo film sensors and filter/amplifier circuits can be configured as a non-invasive velocity type blood pressure monitor. One sensor can be on the wrist and the other can be located on the inner left elbow at the same location where Korotkoff sounds are monitored during traditional blood pressure measurements with a spygmometer. The correlation between pulse delay and blood pressure is well known in the art of non-invasive blood pressure monitors.

In yet another embodiment, an ultrasonic transducer generates and transmits an acoustic wave into the user's body such as the wrist or finger. The transducer subsequently receives pressure waves in the form of echoes resulting from the transmitted acoustic waves. In one embodiment, an ultrasonic driving and receiving circuit generates electrical pulses which, when applied to the transducer produce acoustic energy having a frequency on the order of 8 MHz, a pulse width or duration of approximately 8 microseconds, and a pulse repetition interval (PRI) of approximately 16 microseconds, although other values of frequency, pulse width, and PRI may be used. Hence, the transducer emits an 8 microsecond ultrasonic pulse, which is followed by an 8 microsecond "listen" period, every 16 microseconds. The echoes from these pulses are received by the ultrasonic transducer during the listen period. The ultrasonic transducer can be a ceramic piezoelectric device of the type well known in the art, although other types may be substituted. The transducer converts the received acoustic signal to an electrical signal, which is then supplied to the receiving section of the ultrasonic driver and receiver circuit, which contains two receiver circuits. The output of the first receiver circuit is an analog signal representative of the Doppler frequency of the echo received by the transducer which is digitized and supplied to the CPU. Within the CPU, the digitized Doppler frequency is scaled to compute the blood velocity within the artery based on the Doppler frequency.

The time-frequency distribution of the blood velocity is then computed. Finally, the CPU maps in time the peak of the time-frequency distribution to the corresponding pressure waveform to produce the estimated mean arterial pressure (MAP). The output of the ultrasonic receiver circuit is an analog echo signal proportional to absorption of the transmitted frequencies by blood or tissue. This analog signal is digitized and process so that each group of echoes, generated for a different transversal position, is integrated to determine a mean value. The mean echo values are compared to determine the minimum value, which is caused by direct positioning over the artery. In one embodiment, the device includes an accelerometer or alternative motion-detecting device to determine when the patient' hand is at rest, thereby reducing motion-related artifacts introduced to the measurement.

In yet another ultrasonic embodiment, a transducer includes a first and a second piezoelectric crystal, wherein the crystals are positioned at an angle to each other, and wherein the angle is determined based on the distance of the transducer to the living subject. The first piezoelectric crystal is energized by an original ultrasonic frequency signal, wherein the original ultrasonic frequency signal is reflected off the living subject and received by the second piezoelectric crystal. More specifically, the system includes a pair of piezoelectric crystals at an angle to each other, wherein the angle is determined by the depth of the object being monitored. If the object is the radial artery of a human subject (e.g., adult, infant), the angle of the two crystals with respect to the direction of the blood flow would be about 5 to about 20 degrees. One of the crystals is energized at an ultrasonic frequency. The signal is then reflected back by the user's wrist and picked up by the second crystal. The frequency received is either higher or lower than the original frequency depending upon the direction and the speed of the fluidic mass flow. For example, when blood flow is monitored, the direction of flow is fixed. Thus, the Doppler frequency which is the difference between the original and the reflected frequency depends only upon the speed of the blood flow. Ultrasonic energy is delivered to one of the two piezoelectric elements in the module by the power amplifier. The other element picks up the reflected ultrasonic signal as Doppler frequencies.

In a digital stethoscope embodiment, a microphone or a piezoelectric transducer is placed near the wrist artery to pick up heart rate information. In one embodiment, the microphone sensor and optionally the EKG sensor are place on the wrist band 1374 of the watch to analyze the acoustic signal or signals emanating from the cardiovascular system and, optionally can combine the sound with an electric signal (EKG) emanating from the cardiovascular system and/or an acoustic signal emanating from the respiratory system. The system can perform automated auscultation of the cardiovascular system, the respiratory system, or both. For example, the system can differentiate pathological from benign heart murmurs, detect cardiovascular diseases or conditions that might otherwise escape attention, recommend that the patient go through for a diagnostic study such as an echocardiography or to a specialist, monitor the course of a disease and the effects of therapy, decide when additional therapy or intervention is necessary, and providing a more objective basis for the decision(s) made. In one embodiment, the analysis includes selecting one or more beats for analysis, wherein each beat comprises an acoustic signal emanating from the cardiovascular system; performing a time-frequency analysis of beats selected for analysis so as to provide information regarding the distribution of energy, the relative distribution of energy, or both, over different frequency ranges at one or more points in the cardiac cycle; and processing the information to reach a clinically relevant conclusion or recommendation. In another implementation, the system selects one or more beats for analysis, wherein each beat comprises an acoustic signal emanating from the cardiovascular system; performs a time-frequency analysis of beats selected for analysis so as to provide information regarding the distribution of energy, the relative distribution of energy, or both, over different frequency ranges at one or more points in the cardiac cycle; and present information derived at least in part from the acoustic signal, wherein the information comprises one or more items selected from the group consisting of: a visual or audio presentation of a prototypical beat, a display of the time-frequency decomposition of one or more beats or prototypical beats, and a playback of the acoustic signal at a reduced rate with preservation of frequency content.

In an electromagnetic embodiment where the wrist band incorporates a flexible magnet to provide a magnetic field and one or more electrodes positioned on the wrist band to measure voltage drops which are proportional to the blood velocity, instantaneously variation of the flow can be detected but not artery flow by itself. To estimate the flow of blood in the artery, the user or an actuator such as motorized cuff temporarily stops the blood flow in the vein by applying external pressure or by any other method. During the period of time in which the vein flow is occluded, the decay of the artery flow is measured. This measurement may be used for zeroing the sensor and may be used in a model for estimating the steady artery flow. The decay in artery flow due to occlusion of veins is measured to arrive at a model the rate of artery decay. The system then estimates an average artery flow before occlusion. The blood flow can then be related to the blood pressure.

In another embodiment, an ionic flow sensor is used with a driving electrode that produces a pulsatile current. The pulsatile current causes a separation of positive and negative charges that flows in the blood of the arteries and veins passing in the wrist area. Using electrophoresis principle, the resistance of the volume surrounded by the source first decreases and then increases. The difference in resistance in the blood acts as a mark that moves according to the flow of blood so that marks are flowing in opposite directions by arteries and veins.

In the above embodiments, accelerometer information is used to detect that the patient is at rest prior to making a blood pressure measurement and estimation. Further, a temperature sensor may be incorporated so that the temperature is known at any minute. The processor correlates the temperature measurement to the blood flow measurement for calibration purposes.

In another embodiment, the automatic identification of the first, second, third and fourth heart sounds (S1, S2, S3, S4) is done. In yet another embodiment, based on the heart sound, the system analyzes the patient for mitral valve prolapse. The system performs a time-frequency analysis of an acoustic signal emanating from the subject's cardiovascular system and examines the energy content of the signal in one or more frequency bands, particularly higher frequency bands, in order to determine whether a subject suffers from mitral valve prolapse.

FIG. 7 shows an exemplary mesh network that includes the wrist-watch of FIG. 6 in communication with a mesh network including a telephone such as a wired telephone as well as a cordless telephone. In one embodiment, the mesh network is an IEEE 802.15.4 (ZigBee) network. IEEE 802.15.4 defines two device types; the reduced function device (RFD) and the full function device (FFD). In ZigBee these are referred to as the ZigBee Physical Device types. In a ZigBee network a node can have three roles: ZigBee Coordinator, ZigBee Router, and ZigBee End Device. These are the ZigBee Logical Device types. The main responsibility of a ZigBee Coordinator is to establish a network and to define its main parameters (e.g. choosing a radio-frequency channel and defining a unique network identifier). One can extend the communication range of a network by using ZigBee Routers. These can act as relays between devices that are too far apart to communicate directly. ZigBee End Devices do not participate in routing. An FFD can talk to RFDs or other FFDs, while an RFD can talk only to an FFD. An RFD is intended for applications that are extremely simple, such as a light switch or a passive infrared sensor; they do not have the need to send large amounts of data and may only associate with a single FFD at a time. Consequently, the RFD can be implemented using minimal resources and memory capacity and have lower cost than an FFD. An FFD can be used to implement all three ZigBee Logical Device types, while an RFD can take the role as an End Device.

One embodiment supports a multicluster-multihop network assembly to enable communication among every node in a distribution of nodes. The algorithm should ensure total connectivity, given a network distribution that will allow total connectivity. One such algorithm of an embodiment is described in U.S. Pat. No. 6,832,251, the content of which is incorporated by referenced. The '251 algorithm runs on each node independently. Consequently, the algorithm does not have global knowledge of network topology, only local knowledge of its immediate neighborhood. This makes it well suited to a wide variety of applications in which the topology may be time-varying, and the number of nodes may be unknown. Initially, all nodes consider themselves remotes on cluster zero. The assembly algorithm floods one packet (called an assembly packet) throughout the network. As the packet is flooded, each node modifies it slightly to indicate what the next node should do. The assembly packet tells a node whether it is a base or a remote, and to what cluster it belongs. If a node has seen an assembly packet before, it will ignore all further assembly packets.

The algorithm starts by selecting (manually or automatically) a start node. For example, this could be the first node to wake up. This start node becomes a base on cluster 1, and floods an assembly packet to all of its neighbors, telling them to be remotes on cluster 1. These remotes in turn tell all their neighbors to be bases on cluster 2. Only nodes that have not seen an assembly packet before will respond to this request, so nodes that already have decided what to be will not change their status. The packet continues on, oscillating back and forth between "become base/become remote", and increasing the cluster number each time. Since the packet is flooded to all neighbors at every step, it will reach every node in the network. Because of the oscillating nature of the "become base/become remote" instructions, no two bases will be adjacent. The basic algorithm establishes a multicluster network with all gateways between clusters, but self-assembly time is proportional with the size of the network. Further, it includes only single hop clusters. Many generalizations are possible, however. If many nodes can begin the network nucleation, all that is required to harmonize the clusters is a mechanism that recognizes precedence (e.g., time of nucleation, size of subnetwork), so that conflicts in boundary clusters are resolved. Multiple-hop clusters can be enabled by means of establishing new clusters from nodes that are N hops distant from the master.

Having established a network in this fashion, the masters can be optimized either based on number of neighbors, or other criteria such as minimum energy per neighbor communication. Thus, the basic algorithm is at the heart of a number of variations that lead to a scalable multi-cluster network that establishes itself in time, and that is nearly independent of the number of nodes, with clusters arranged according to any of a wide range of optimality criteria. Network synchronism is established at the same time as the network connections, since the assembly packet(s) convey timing information outwards from connected nodes.

The network nodes can be mesh network appliances to provide voice communications, home security, door access control, lighting control, power outlet control, dimmer control, switch control, temperature control, humidity control, carbon monoxide control, fire alarm control, blind control, shade control, window control, oven control, cooking range control, personal computer control, entertainment console control, television control, projector control, garage door control, car control, pool temperature control, water pump control, furnace control, heater control, thermostat control, electricity meter monitor, water meter monitor, gas meter monitor, or remote diagnostics. The telephone can be connected to a cellular telephone to answer calls directed at the cellular telephone. The connection can be wired or wireless using Bluetooth or ZigBee. The telephone synchronizes calendar, contact, emails, blogs, or instant messaging with the cellular telephone. Similarly, the telephone synchronizes calendar, contact, emails, blogs, or instant messaging with a personal computer. A web server can communicate with the Internet through the POTS to provide information to an authorized remote user who logs into the server. A wireless router such as 802.11 router, 802.16 router, WiFi router, WiMAX router, Bluetooth router, X10 router can be connected to the mesh network.

A mesh network appliance can be connected to a power line to communicate X10 data to and from the mesh network. X10 is a communication protocol that allows up to 256 X10 products to talk to each other using the existing electrical wiring in the home. Typically, the installation is simple, a transmitter plugs (or wires) in at one location in the home and sends its control signal (on, off, dim, bright, etc.) to a receiver which plugs (or wires) into another location in the home. The mesh network appliance translates messages intended for X10 device to be relayed over the ZigBee wireless network, and then transmitted over the power line using a ZigBee to X10 converter appliance.

An in-door positioning system links one or more mesh network appliances to provide location information. Inside the home or office, the radio frequency signals have negligible multipath delay spread (for timing purposes) over short distances. Hence, radio strength can be used as a basis for determining position. Alternatively, time of arrival can be used to determine position, or a combination of radio signal strength and time of arrival can be used. Position estimates can also be achieved in an embodiment by beamforming, a method that exchanges time-stamped raw data among the nodes. While the processing is relatively more costly, it yields processed data with a higher signal to noise ratio (SNR) for subsequent classification decisions, and enables estimates of angles of arrival for targets that are outside the convex hull of the participating sensors. Two such clusters of ZigBee nodes can then provide for triangulation of distant targets. Further, beamforming enables suppression of interfering sources, by placing nulls in the synthetic beam pattern in their directions. Another use of beamforming is in self-location of nodes when the positions of only a very small number of nodes or appliances are known such as those sensors nearest the wireless stations. In one implementation where each node knows the distances to its neighbors due to their positions, and some small fraction of the nodes (such as those nearest a PC with GPS) of the network know their true locations. As part of the network-building procedure, estimates of the locations of the nodes that lie within or near the convex hull of the nodes with known position can be quickly generated. To start, the shortest distance (multihop) paths are determined between each reference node. All nodes on this path are assigned a location that is the simple linear average of the two reference locations, as if the path were a straight line. A node which lies on the intersection of two such paths is assigned the average of the two indicated locations. All nodes that have been assigned locations now serve as references. The shortest paths among these new reference nodes are computed, assigning locations to all intermediate nodes as before, and continuing these iterations until no further nodes get assigned locations. This will not assign initial position estimates to all sensors. The remainder can be assigned locations based on pairwise averages of distances to the nearest four original reference nodes. Some consistency checks on location can be made using trigonometry and one further reference node to determine whether or not the node likely lies within the convex hull of the original four reference sensors.

In two dimensions, if two nodes have known locations, and the distances to a third node are known from the two nodes, then trigonometry can be used to precisely determine the location of the third node. Distances from another node can resolve any ambiguity. Similarly, simple geometry produces precise calculations in three dimensions given four reference nodes. But since the references may also have uncertainty, an alternative procedure is to perform a series of iterations where successive trigonometric calculations result only in a delta of movement in the position of the node. This process can determine locations of nodes outside the convex hull of the reference sensors. It is also amenable to averaging over the positions of all neighbors, since there will often be more neighbors than are strictly required to determine location. This will reduce the effects of distance measurement errors. Alternatively, the network can solve the complete set of equations of intersections of hyperbola as a least squares optimization problem.

In yet another embodiment, any or all of the nodes may include transducers for acoustic, infrared (IR), and radio frequency (RF) ranging. Therefore, the nodes have heterogeneous capabilities for ranging. The heterogeneous capabilities further include different margins of ranging error. Furthermore, the ranging system is re-used for sensing and communication functions. For example, wideband acoustic functionality is available for use in communicating, bistatic sensing, and ranging. Such heterogeneous capability of the sensors can provide for ranging functionality in addition to communications functions. As one example, repeated use of the communications function improves position determination accuracy over time. Also, when the ranging and the timing are conducted together, they can be integrated in a self-organization protocol in order to reduce energy consumption. Moreover, information from several ranging sources is capable of being fused to provide improved accuracy and resistance to environmental variability. Each ranging means is exploited as a communication means, thereby providing improved robustness in the presence of noise and interference. Those skilled in the art will realize that there are many architectural possibilities, but allowing for heterogeneity from the outset is a component in many of the architectures.

Figure 8:
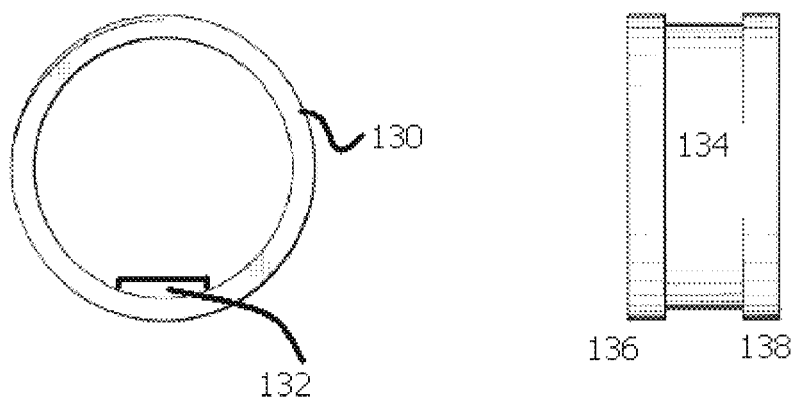

Turning now to FIGS. 8-13, various exemplary monitoring devices are shown. In FIG. 8, a ring 130 has an opening 132 for transmitting and receiving acoustic energy to and from the sensor in an acoustic implementation. In an optical implementation, a second opening (not shown) is provided to emit an optical signal from an LED, for example, and an optical detector can be located at the opening 132 to receive the optical signal passing through the finger wearing the ring 130. In another implementation, the ring has an electrically movable portion 134 and rigid portions 136-138 connected thereto. The electrically movable portion 134 can squeeze the finger as directed by the CPU during an applanation sweep to determine the arterial blood pressure.

Figure 9:
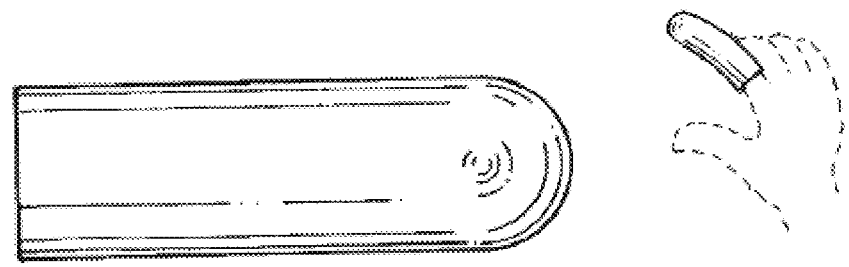

FIG. 9 shows an alternate finger cover embodiment where a finger-mounted module housing the photo-detector and light source. The finger mounted module can be used to measure information that is processed to determine the user's blood pressure by measuring blood flow in the user's finger and sending the information through a wireless connection to the base station. In one implementation, the housing is made from a flexible polymer material.

Figure 10:
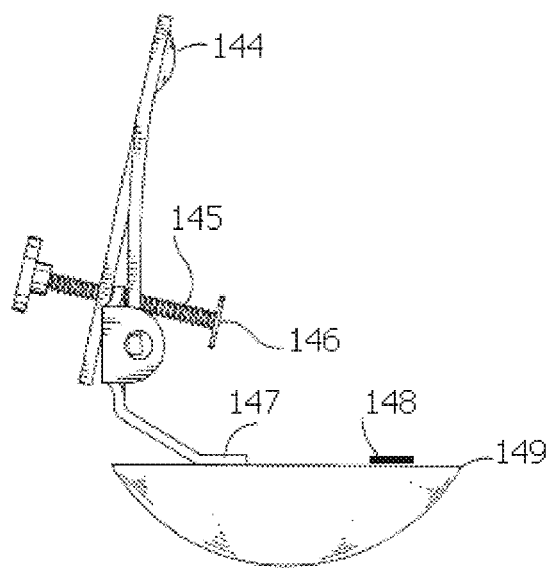

In an embodiment to be worn on the patient's ear lobe, the monitoring device can be part of an earring jewelry clipped to the ear lobe. In the implementation of FIG. 10, the monitoring device has a jewelry body 149 that contains the monitoring electronics and power source. The surface of the body 149 is an ornamental surface such as jade, ivory, pearl, silver, or gold, among others. The body 149 has an opening 148 that transmits energy such as optical or acoustic energy through the ear lobe to be detected by a sensor 144 mounted on a clamp portion that is secured to the body 149 at a base 147. The energy detected through the sensor 144 is communicated through an electrical connector to the electronics in the body 149 for processing the received energy and for performing wireless communication with a base station. In FIG. 10, a bolt 145 having a stop end 146 allows the user to adjust the pressure of the clamp against the ear lobe. In other implementations, a spring biased clip is employed to retain the clip on the wearer's ear lobe. A pair of members, which snap together under pressure, are commonly used and the spring pressure employed should be strong enough to suit different thicknesses of the ear lobe.

Figure 11:
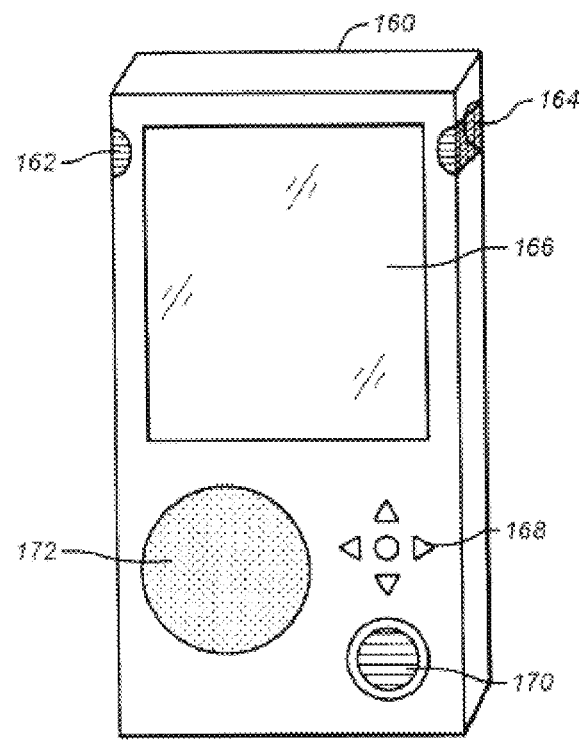
Figure 12:
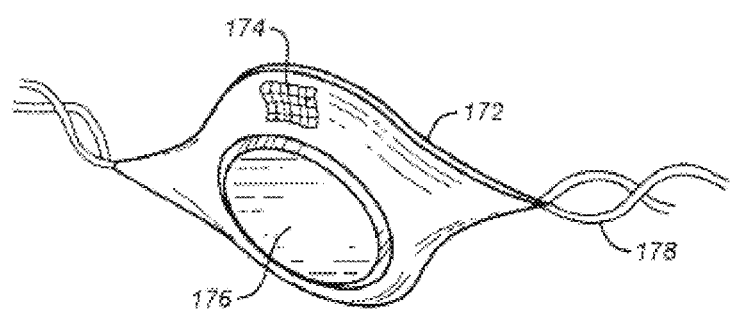

FIGS. 11 and 12 show two additional embodiments of the monitoring device. In FIG. 11, a wearable monitoring device is shown. The monitoring device has a body 160 comprising microphone ports 162, 164 and 170 arranged in a first order noise cancelling microphone arrangement. The microphone ports 162 and 164 are configured to optimally receive distant noises, while the microphone port 170 is optimized for capturing the user's speech. A touch sensitive display 166 and a plurality of keys 168 are provided to capture hand inputs. Further, a speaker 173 is provided to generate a verbal feedback to the user.

Turning now to FIG. 12, a jewelry-sized monitoring device is illustrated. In this embodiment, a body 172 houses a microphone port 174 and a speaker port 176. The body 172 is coupled to the user via the necklace 178 so as to provide a personal, highly accessible personal computer. Due to space limitations, voice input/output is an important user interface of the jewelry-sized computer. Although a necklace is disclosed, one skilled in the art can use a number of other substitutes such as a belt, a brace, a ring, or a band to secure the jewelry-sized computer to the user.

Figure 13:
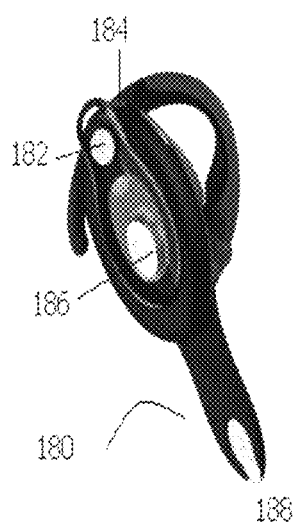

FIG. 13 shows an exemplary ear phone embodiment 180. The ear phone 180 has an optical transmitter 182 which emits LED wavelengths that are received by the optical receiver 184. The blood oximetry information is generated and used to determine blood pulse or blood pressure. Additionally, a module 186 contains mesh network communication electronics, accelerometer, and physiological sensors such as EKG/ECG sensors or temperature sensors or ultrasonic sensors. In addition, a speaker (not shown) is provided to enable voice communication over the mesh network, and a microphone 188 is provided to pick up voice during verbal communication and pick up heart sound when the user is not using the microphone for voice communication. The ear phone optionally has an ear canal temperature sensor for sensing temperature in a human.

Figure 14B:
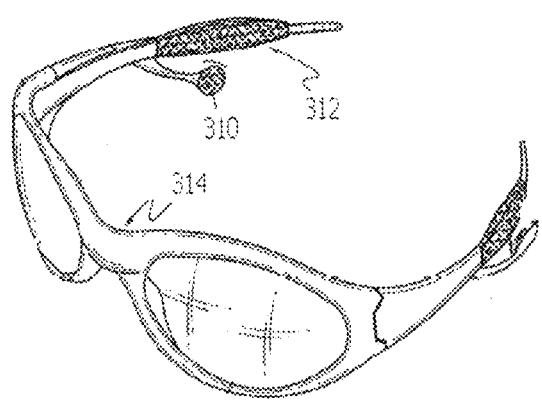
Figure 14A:
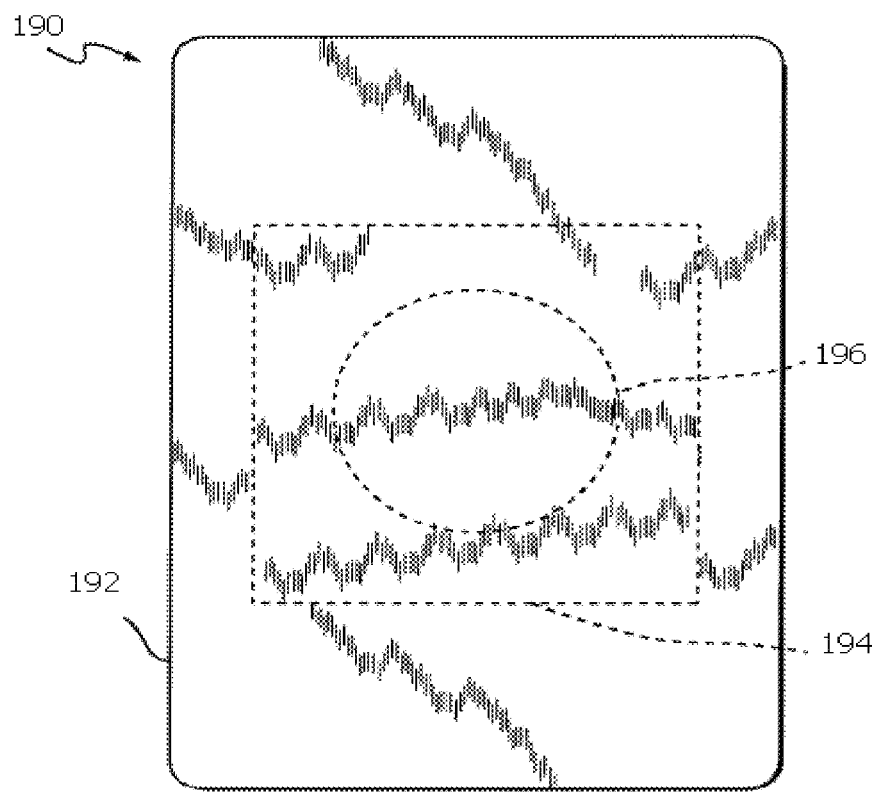

FIG. 14A shows an exemplary adhesive patch embodiment. The patch may be applied to a persons skin by anyone including the person themselves or an authorized person such as a family member or physician. The adhesive patch is shown generally at 190 having a gauze pad 194 attached to one side of a backing 192, preferably of plastic, and wherein the pad can have an impermeable side 194 coating with backing 192 and a module 196 which contains electronics for communicating with the mesh network and for sensing acceleration and bioimpedance, EKG/ECG, heart sound, microphone, optical sensor, or ultrasonic sensor in contacts with a wearer's skin. In one embodiment, the module 196 has a skin side that may be coated with a conductive electrode lotion or gel to improve the contact. The entire patch described above may be covered with a plastic or foil strip to retain moisture and retard evaporation by a conductive electrode lotion or gel provided improve the electrode contact. In one embodiment, an acoustic sensor (microphone or piezoelectric sensor) and an electrical sensor such as EKG sensor contact the patient with a conductive gel material. The conductive gel material provides transmission characteristics so as to provide an effective acoustic impedance match to the skin in addition to providing electrical conductivity for the electrical sensor. The acoustic transducer can be directed mounted on the conductive gel material substantially with or without an intermediate air buffer. The entire patch is then packaged as sterile as are other over-the-counter adhesive bandages. When the patch is worn out, the module 196 may be removed and the backing 192 may be used in place of the old patch. One or more patches may be applied to the patient's body and these patches may communicate wirelessly using the mesh network or alternatively they may communicate through a personal area network using the patient's body as a communication medium.

The term "positional measurement," as that term is used herein, is not limited to longitude and latitude measurements, or to metes and bounds, but includes information in any form from which geophysical positions can be derived. These include, but are not limited to, the distance and direction from a known benchmark, measurements of the time required for certain signals to travel from a known source to the geophysical location where the signals may be electromagnetic or other forms, or measured in terms of phase, range, Doppler or other units.

FIG. 14B shows a sunglass or eyeglass embodiment which contains electronics for communicating with the mesh network and for sensing acceleration and bioimpedance, EKG/ECG, EMG, heart sound, microphone, optical sensor, or ultrasonic sensor in contacts with a wearer's skin. In one embodiment, the ear module 310 contains optical sensors to detect temperature, blood flow and blood oxygen level as well as a speaker to provide wireless communication or hearing aid. The blood flow or velocity information can be used to estimate blood pressure. The side module 312 can contain an array of bioimpedance sensors such as bipolar or tetrapolar bioimpedance probes to sense fluids in the brain. Additional bioimpedance electrodes can be positioned around the rim of the glasses as well as the glass handle or in any spots on the eyewear that contacts the user. The side module 312 or 314 can also contain one or more EKG electrodes to detect heart beat parameters and to detect heart problems. The side module 312 or 314 can also contain piezoelectric transducers or microphones to detect heart activities near the brain. The side module 312 or 314 can also contain ultrasound transmitter and receiver to create an ultrasound model of brain fluids. In one embodiment, an acoustic sensor (microphone or piezoelectric sensor) and an electrical sensor such as EKG sensor contact the patient with a conductive gel material. The conductive gel material provides transmission characteristics so as to provide an effective acoustic impedance match to the skin in addition to providing electrical conductivity for the electrical sensor. The acoustic transducer can be directed mounted on the conductive gel material substantially with or without an intermediate air buffer. In another embodiment, electronics components are distributed between first and second ear stems. In yet another embodiment, the method further comprises providing a nose bridge, wherein digital signals generated by the electronics circuit are transmitted across the nose bridge. The eyewear device may communicate wirelessly using the mesh network or alternatively they may communicate through a personal area network using the patient's body as a communication medium. Voice can be transmitted over the mesh wireless network. The speaker can play digital audio file, which can be compressed according to a compression format. The compression format may be selected from the group consisting of: PCM, DPCM, ADPCM, AAC, RAW, DM, RIFF, WAV, BWF, AIFF, AU, SND, CDA, MPEG, MPEG-1, MPEG-2, MPEG-2.5, MPEG-4, MPEG-J, MPEG 2-ACC, MP3, MP3Pro, ACE, MACE, MACE-3, MACE-6, AC-3, ATRAC, ATRAC3, EPAC, Twin VQ, VQF, WMA, WMA with DRM, DTS, DVD Audio, SACD, TAC, SHN, OGG, Ogg Vorbis, Ogg Tarkin, Ogg Theora, ASF, LQT, QDMC, A2b, .ra, .rm, and Real Audio G2, RMX formats, Fairplay, Quicktime, SWF, and PCA, among others.

In one embodiment, the eye wear device of FIG. 14B can provide a data port, wherein the data port is carried by the ear stem. The data port may be a mini-USB connector, a FIREWIRE connector, an IEEE 1394 cable connector, an RS232 connector, a JTAB connector, an antenna, a wireless receiver, a radio, an RF receiver, or a Bluetooth receiver. In another embodiment, the wearable device is removably connectable to a computing device. The wearable wireless audio device may be removably connectable to a computing device with a data port, wherein said data port is mounted to said wearable wireless audio device. In another embodiment, projectors can project images on the glasses to provide head-mounted display on the eye wear device. The processor can display fact, figure, to do list, and reminders need in front of the user's eyes.

Figure 15B:
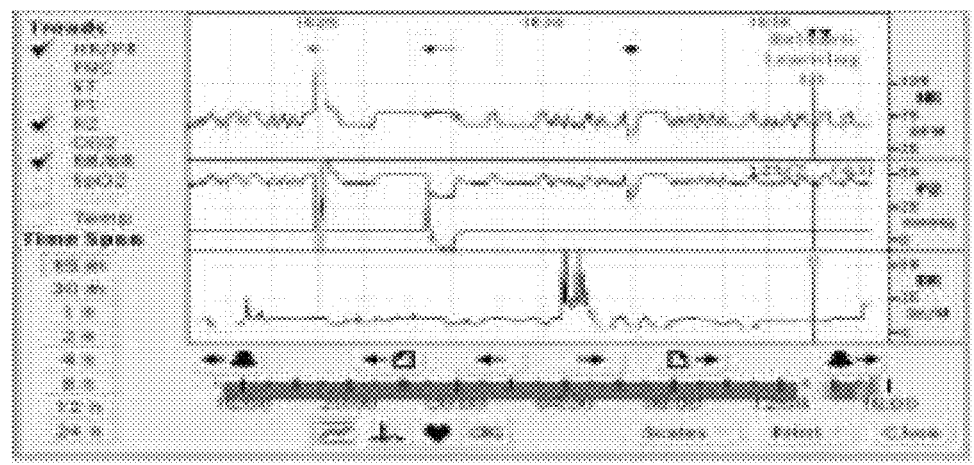
FIGS. 15A and 15B shows exemplary systems for performing patient monitoring.
Figure 15A:
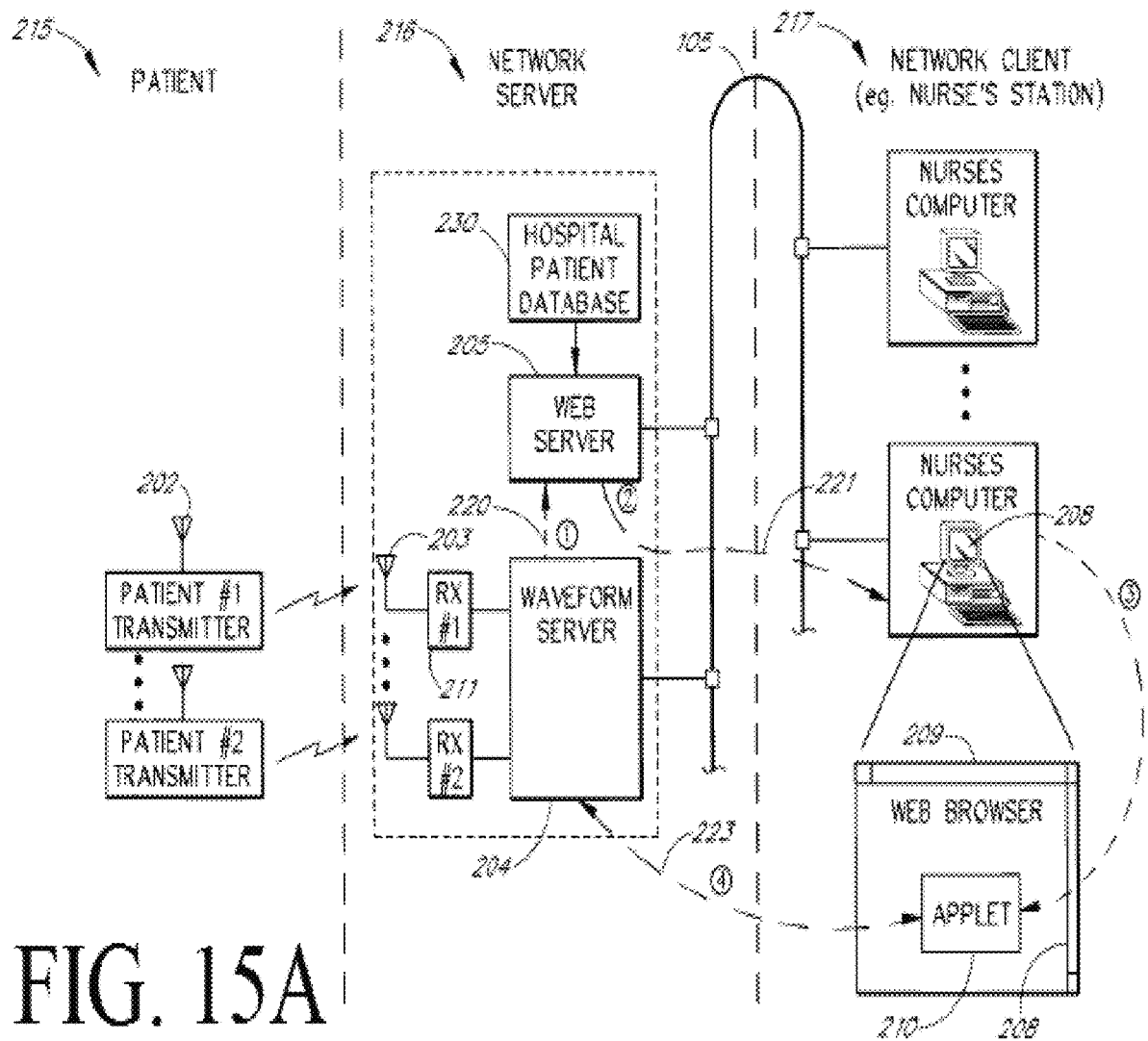

FIG. 15 shows a system block diagram of the network-based patient monitoring system in a hospital or nursing home setting. The system has a patient component 215, a server component 216, and a client component 217. The patient component 215 has one or more mesh network patient transmitters 202 for transmitting data to the central station. The central server comprises one or more Web servers 205, one or more waveform servers 206 and one or more mesh network receivers 211. The output of each mesh network receiver 211 is connected to at least one of the waveform servers 206. The waveform servers 206 and the Web servers 205 are connected to the network. The Web servers 205 are also connected to a hospital database 230. The hospital database 230 contains patient records. In the embodiment of FIG. 15A, a plurality of nurse stations provide a plurality of nurse computer user interface 212. The user interface 212 receives data from an applet 210 that communicates with the waveform servers 206 and updates the display of the nurse computers for treating patients.

The network client component 217 comprises a series of workstations connected to the network. Each of the workstations runs a World Wide Web (WWW or Web) browser application 209. Each Web browser can open a page that includes one or more media player applets 210. The waveform servers 206 use the network to send a series of messages 220 to the Web servers 205. The Web servers 205 use the network to communicate messages, shown as a path 221, to the workstations. The media player applets running on the workstations use the network to send messages over a path 223 directly to the waveform servers 206.

In another embodiment, the patient appliances 204 wirelessly communicate to home base stations (not shown) which are connected to the POTS or PSTN network for voice as well as data transmission. The data is captured by the waveform servers 206 and the voice is passed through to the call center agent computer where the agent can communicate by voice with the patient. The call center agent can forward the call to a professional such as a nurse or doctor or emergency service personnel if necessary. Hence, the system can include a patient monitoring appliance coupled to the POTS or PSTN through the mesh network. The patient monitoring appliance monitors drug usage and patient falls. The patient monitoring appliance monitors patient movement. A call center can call to the telephone to provide a human response.

In one exemplary monitoring service providing system, such as an emergency service providing system, the system includes a communication network (e.g., the Public Switch Telephone Network or PSTN or POTS), a wide area communication network (e.g., TCP/IP network) in call centers. The communication network receives calls destined for one of the call centers. In this regard, each call destined for one of the call centers is preferably associated with a particular patient, a call identifier or a call identifier of a particular set of identifiers. A call identifier associated with an incoming call may be an identifier dialed or otherwise input by the caller. For example, the call centers may be locations for receiving calls from a particular hospital or nursing home.

To network may analyze the automatic number information (ANI) and/or automatic location information (ALI) associated with the call. In this regard, well known techniques exist for analyzing the ANI and ALI of an incoming call to identify the call as originating from a particular calling device or a particular calling area. Such techniques may be employed by the network to determine whether an incoming call originated from a calling device within an area serviced by the call centers. Moreover, if an incoming call originated from such an area and if the incoming call is associated with the particular call identifier referred to above, then the network preferably routes the call to a designated facility.

When a call is routed to the facility, a central data manager, which may be implemented in software, hardware, or a combination thereof, processes the call according to techniques that will be described in more detail hereafter and routes the call, over the wide area network, to one of the call centers depending on the ANI and/or ALI associated with the call. In processing the call, the central data manager may convert the call from one communication protocol to another communication protocol, such as voice over internet protocol (VoIP), for example, in order to increase the performance and/or efficiency of the system. The central data manager may also gather information to help the call centers in processing the call. There are various techniques that may be employed by the central data manager to enhance the performance and/or efficiency of the system, and examples of such techniques will be described in more detail hereafter.

Various benefits may be realized by utilizing a central facility to intercept or otherwise receive a call from the network and to then route the call to one of the call centers via WAN. For example, serving multiple call centers with a central data manager, may help to reduce total equipment costs. In this regard, it is not generally necessary to duplicate the processing performed by the central data manager at each of the call centers. Thus, equipment at each of the call centers may be reduced. As more call centers are added, the equipment savings enabled by implementing equipment at the central data manager instead of the call centers generally increases. Furthermore, the system is not dependent on any telephone company's switch for controlling the manner in which data is communicated to the call centers. In this regard, the central data manager may receive a call from the network and communicate the call to the destination call centers via any desirable communication technique, such as VoIP, for example. Data security is another possible benefit of the exemplary system 14 as the central data manager is able to store the data for different network providers associated with network on different partitions.

In one embodiment for professional users such as hospitals and nursing homes, a Central Monitoring Station provides alarm and vital sign oversight for a plurality of patients from a single computer workstation. The clinician interface uses simple point and click actions with a computer mouse or trackball. The clinician can initiate or change monitoring functions from either the Central Station or the bedside monitor. One skilled in the art will recognize that patient data such as EKG/EMG/EEG/BP data can be shown either by a scrolling waveform that moves along the screen display, or by a moving bar where the waveform is essentially stationary and the bar moves across the screen.

In one embodiment, software for the professional monitoring system provides a login screen to enter user name and password, together with database credentials. In Select Record function, the user can select a person, based on either entered or pre-selected criteria. From here navigate to their demographics, medical record, etc. The system can show a persons demographics, includes aliases, people involved in their care, friends and family, previous addresses, home and work locations, alternative numbers and custom fields. The system can show all data elements of a person's medical record. These data elements are not 'hard wired', but may be configured in the data dictionary to suit particular user requirements. It is possible to create views of the record that filter it to show (for instance) just the medications or diagnosis, etc. Any data element can be designated 'plan able' in the data dictionary and then scheduled. A Summary Report can be done. Example of a report displayed in simple format, selecting particular elements and dates. As many of these reports as required can be created, going across all data in the system based on some criteria, with a particular selection of fields and sorting, grouping and totaling criteria. Reports can be created that can format and analyze any data stored on the server. The system supports OLE controls and can include graphs, bar codes, etc. These can be previewed on screen, printed out or exported in a wide variety of formats. The system also maintains a directory of all organizations the administrator wishes to record as well as your own. These locations are then used to record the location for elements of the medical record (where applicable), work addresses for people involved in the care and for residential addresses for people in residential care. The data elements that form the medical record are not 'hard wired' (ie pre-defined) but may be customized by the users to suit current and future requirements.

In one embodiment, the wearable appliance can store patient data in its data storage device such as flash memory. The data can include Immunizations and dates; medications (prescriptions and supplements); physician names, addresses, phone numbers, email addresses; location and details of advance directives; insurance company, billing address, phone number, policy number; emergency contacts, addresses, home/business/pager phone numbers, email addresses. The data can include color or black and white photo of the wearer of the device; a thumb print, iris print of other distinguishing physical characteristic; dental records; sample ECG or Cardiac Echo Scan; blood type; present medication being taken; drug interaction precautions; drug and/or allergic reaction precautions; a description of serious preexisting medical conditions; Emergency Medical Instructions, which could include: administering of certain suggested drugs or physical treatments; calling emergency physician numbers listed; bringing the patient to a certain type of clinic or facility based on religious beliefs; and living will instructions in the case of seriously ill patients; Organ Donor instructions; Living Will instructions which could include: instructions for life support or termination of treatment; notification of next of kin and/or friends including addresses and telephone numbers; ECG trace; Cardiac Echo Scan; EEG trace; diabetes test results; x-ray scans, among others. The wearable appliance stores the wearer's medical records and ID information. In one embodiment, to start the process new/original medical information is organized and edited to fit into the BWD page format either in physicians office or by a third party with access to a patient's medical records using the base unit storage and encrypting software which can be stored in a normal pc or other compatible computer device. The system can encrypt the records so as to be secure and confidential and only accessible to authorized individuals with compatible de-encrypting software. In the event the wearer is stricken with an emergency illness a Paramedic, EMT or Emergency Room Technician can use a wireless interrogator to rapidly retrieve and display the stored medical records in the wearable appliance and send the medical records via wireless telemetry to a remote emergency room or physicians office for rapid and life saving medical intervention in a crisis situation. In a Non-emergency Situation, the personal health information service is also helpful as it eliminates the hassle of repeatedly filling out forms when changing health plans or seeing a new physician; stores vaccination records to schools or organizations without calling the pediatrician; or enlists the doctor's or pharmacist's advice about multiple medications without carrying all the bottles to a personal visit. The system can store 48 hrs. of EKG, EEG, EMG, or blood pressure data.

In one embodiment, a plurality of body worn sensors with in-door positioning can be used as an Emergency Department and Urgent Care Center Tracking System. The system tracks time from triage to MD assessment, identifies patients that have not yet been registered, records room usage, average wait time, and average length of stay. The system allows user defined "activities" so that hospitals can track times and assist in improving patient flow and satisfaction. The system can set custom alerts and send email/pager notifications to better identify long patient wait times and record the number of these alert occurrences. The system can manage room usage by identifying those rooms which are under/over utilized. The hospital administrator can set manual or automatic alerts and generate custom reports for analysis of patient flow. The system maximizes revenue by streamlining processes and improving throughput; improves charge capture by ensuring compliance with regulatory standards; increases accountability by collecting clear, meaningful data; enhances risk management and QA; and decreases liability.

FIG. 16A shows an exemplary process to continuously determine blood pressure of a patient. The process generates a blood pressure model of a patient at step 2002; determines a blood flow velocity using a piezoelectric transducer at step 2004; and provides the blood flow velocity to the blood pressure model to continuously estimate blood pressure at step 2006.

FIG. 16B shows another exemplary process to continuously determine blood pressure of a patient. First, during an initialization mode, a monitoring device and calibration device are attached to patient at step 2010. The monitoring device generates patient blood flow velocity, while actual blood pressure is measured by a calibration device at step 2012. Next, the process generates a blood pressure model based on the blood flow velocity and the actual blood pressure at step 2014. Once this is done, the calibration device can be removed at step 2016. Next, during an operation mode, the process periodically samples blood flow velocity from the monitoring device on a real-time basis and provides the blood flow velocity as input information to the blood pressure model to estimate blood pressure 22. This process can be done in continuously or periodically as specified by a user.

In one embodiment, to determine blood flow velocity, acoustic pulses are generated and transmitted into the artery using an ultrasonic transducer positioned near a wrist artery. These pulses are reflected by various structures or entities within the artery (such as the artery walls, and the red blood cells within the subject's blood), and subsequently received as frequency shifts by the ultrasonic transducer. Next, the blood flow velocity is determined. In this process, the frequencies of those echoes reflected by blood cells within the blood flowing in the artery differ from that of the transmitted acoustic pulses due to the motion of the blood cells. This well known "Doppler shift" in frequency is used to calculate the blood flow velocity. In one embodiment for determining blood flow velocity, the Doppler frequency is used to determine mean blood velocity. For example, U.S. Pat. No. 6,514,211, the content of which is incorporated by reference, discusses blood flow velocity using a time-frequency representation.

In one implementation, the system can obtain one or more numerical calibration curves describing the patient's vital signs such as blood pressure. The system can then direct energy such as infrared or ultrasound at the patient's artery and detecting reflections thereof to determine blood flow velocity from the detected reflections. The system can numerically fit or map the blood flow velocity to one or more calibration parameters describing a vital-sign value. The calibration parameters can then be compared with one or more numerical calibration curves to determine the blood pressure.

Additionally, the system can analyze blood pressure, and heart rate, and pulse oximetry values to characterize the user's cardiac condition. These programs, for example, may provide a report that features statistical analysis of these data to determine averages, data displayed in a graphical format, trends, and comparisons to doctor-recommended values.

In one embodiment, feed forward artificial neural networks (NNs) are used to classify valve-related heart disorders. The heart sounds are captured using the microphone or piezoelectric transducer. Relevant features were extracted using several signal processing tools, discrete wavelet transfer, fast fourier transform, and linear prediction coding. The heart beat sounds are processed to extract the necessary features by: a) denoising using wavelet analysis, b) separating one beat out of each record c) identifying each of the first heart sound (FHS) and the second heart sound (SHS). Valve problems are classified according to the time separation between the FHS and the SHS relative to cardiac cycle time, namely whether it is greater or smaller than 20% of cardiac cycle time. In one embodiment, the NN comprises 6 nodes at both ends, with one hidden layer containing 10 nodes. In another embodiment, linear predictive code (LPC) coefficients for each event were fed to two separate neural networks containing hidden neurons.

In another embodiment, a normalized energy spectrum of the sound data is obtained by applying a Fast Fourier Transform. The various spectral resolutions and frequency ranges were used as inputs into the NN to optimize these parameters to obtain the most favorable results.

In another embodiment, the heart sounds are denoised using six-stage wavelet decomposition, thresholding, and then reconstruction. Three feature extraction techniques were used: the Decimation method, and the wavelet method. Classification of the heart diseases is done using Hidden Markov Models (HMMs).

In yet another embodiment, a wavelet transform is applied to a window of two periods of heart sounds. Two analyses are realized for the signals in the window: segmentation of first and second heart sounds, and the extraction of the features. After segmentation, feature vectors are formed by using the wavelet detail coefficients at the sixth decomposition level. The best feature elements are analyzed by using dynamic programming.

In another embodiment, the wavelet decomposition and reconstruction method extract features from the heart sound recordings. An artificial neural network classification method classifies the heart sound signals into physiological and pathological murmurs. The heart sounds are segmented into four parts: the first heart sound, the systolic period, the second heart sound, and the diastolic period. The following features can be extracted and used in the classification algorithm: a) Peak intensity, peak timing, and the duration of the first heart sound b) the duration of the second heart sound c) peak intensity of the aortic component of S2(A2) and the pulmonic component of S2 (P2), the splitting interval and the reverse flag of A2 and P2, and the timing of A2 d) the duration, the three largest frequency components of the systolic signal and the shape of the envelope of systolic murmur e) the duration the three largest frequency components of the diastolic signal and the shape of the envelope of the diastolic murmur.

In one embodiment, the time intervals between the ECG R-waves are detected using an envelope detection process. The intervals between R and T waves are also determined.

The Fourier transform is applied to the sound to detect S1 and S2. To expedite processing, the system applies Fourier transform to detect S1 in the interval 0.1-0.5 R-R. The system looks for S2 the intervals R-T and 0.6 R-R. S2 has an aortic component A2 and a pulmonary component P2. The interval between these two components and its changes with respiration has clinical significance. A2 sound occurs before P2, and the intensity of each component depends on the closing pressure and hence A2 is louder than P2. The third heard sound S3 results from the sudden halt in the movement of the ventricle in response to filling in early diastole after the AV valves and is normally observed in children and young adults. The fourth heart sound S4 is caused by the sudden halt of the ventricle in response to filling in presystole due to atrial contraction.

In yet another embodiment, the S2 is identified and a normalized splitting interval between A2 and P2 is determined. If there is no overlap, A2 and P2 are determined from the heart sound. When overlap exists between A2 and P2, the sound is dechirped for identification and extraction of A2 and P2 from S2. The A2-P2 splitting interval (SI) is calculated by computing the cross-correlation function between A2 and P2 and measuring the time of occurrence of its maximum amplitude. SI is then normalized (NSI) for heart rate as follows: NSI=SI/cardiac cycle time. The duration of the cardiac cycle can be the average interval of QRS waves of the ECG. It could also be estimated by computing the mean interval between a series of consecutive S1 and S2 from the heart sound data. A non linear regressive analysis maps the relationship between the normalized NSI and PAP. A mapping process such as a curve-fitting procedure determines the curve that provides the best fit with the patient data. Once the mathematical relationship is determined, NSI can be used to provide an accurate quantitative estimate of the systolic and mean PAP relatively independent of heart rate and systemic arterial pressure.

In another embodiment, the first heart sound (S1) is detected using a time-delayed neural network (TDNN). The network consists of a single hidden layer, with time-delayed links connecting the hidden units to the time-frequency energy coefficients of a Morlet wavelet decomposition of the input phonocardiogram (PCG) signal. The neural network operates on a 200 msec sliding window with each time-delay hidden unit spanning 100 msec of wavelet data.

In yet another embodiment, a local signal analysis is used with a classifier to detect, characterize, and interpret sounds corresponding to symptoms important for cardiac diagnosis. The system detects a plurality of different heart conditions. Heart sounds are automatically segmented into a segment of a single heart beat cycle. Each segment are then transformed using 7 level wavelet decomposition, based on Coifman 4th order wavelet kernel. The resulting vectors 4096 values, are reduced to 256 element feature vectors, this simplified the neural network and reduced noise.

In another embodiment, feature vectors are formed by using the wavelet detail and approximation coefficients at the second and sixth decomposition levels. The classification (decision making) is performed in 4 steps: segmentation of the first and second heart sounds, normalization process, feature extraction, and classification by the artificial neural network.

In another embodiment using decision trees, the system distinguishes (1) the Aortic Stenosis (AS) from the Mitral Regurgitation (MR) and (2) the Opening Snap (OS), the Second Heart Sound Split (A2_P2) and the Third Heart Sound (S3). The heart sound signals are processed to detect the first and second heart sounds in the following steps: a)

wavelet decomposition, b) calculation of normalized average Shannon Energy, c) a morphological transform action that amplifies the sharp peaks and attenuates the broad ones d) a method that selects and recovers the peaks corresponding to S1 and S2 and rejects others e) algorithm that determines the boundaries of S1 and S2 in each heart cycle f) a method that distinguishes S1 from S2.

In one embodiment, once the heart sound signal has been digitized and captured into the memory, the digitized heart sound signal is parameterized into acoustic features by a feature extractor. The output of the feature extractor is delivered to a sound recognizer. The feature extractor can include the short time energy, the zero crossing rates, the level crossing rates, the filter-bank spectrum, the linear predictive coding (LPC), and the fractal method of analysis. In addition, vector quantization may be utilized in combination with any representation techniques. Further, one skilled in the art may use an auditory signal-processing model in place of the spectral models to enhance the system's robustness to noise and reverberation.

In one embodiment of the feature extractor, the digitized heart sound signal series s(n) is put through a low-order filter, typically a first-order finite impulse response filter, to spectrally flatten the signal and to make the signal less susceptible to finite precision effects encountered later in the signal processing. The signal is pre-emphasized preferably using a fixed pre-emphasis network, or preemphasizer. The signal can also be passed through a slowly adaptive pre-emphasizer. The preemphasized heart sound signal is next presented to a frame blocker to be blocked into frames of N samples with adjacent frames being separated by M samples. In one implementation, frame 1 contains the first 400 samples. The frame 2 also contains 400 samples, but begins at the 300th sample and continues until the 700th sample. Because the adjacent frames overlap, the resulting LPC spectral analysis will be correlated from frame to frame. Each frame is windowed to minimize signal discontinuities at the beginning and end of each frame. The windower tapers the signal to zero at the beginning and end of each frame. Preferably, the window used for the autocorrelation method of LPC is the Hamming window. A noise canceller operates in conjunction with the autocorrelator to minimize noise. Noise in the heart sound pattern is estimated during quiet periods, and the temporally stationary noise sources are damped by means of spectral subtraction, where the autocorrelation of a clean heart sound signal is obtained by subtracting the autocorrelation of noise from that of corrupted heart sound. In the noise cancellation unit, if the energy of the current frame exceeds a reference threshold level, the heart is generating sound and the autocorrelation of coefficients representing noise is not updated. However, if the energy of the current frame is below the reference threshold level, the effect of noise on the correlation coefficients is subtracted off in the spectral domain. The result is half-wave rectified with proper threshold setting and then converted to the desired autocorrelation coefficients. The output of the autocorrelator and the noise canceller are presented to one or more parameterization units, including an LPC parameter unit, an FFT parameter unit, an auditory model parameter unit, a fractal parameter unit, or a wavelet parameter unit, among others. The LPC parameter is then converted into cepstral coefficients. The cepstral coefficients are the coefficients of the Fourier transform representation of the log magnitude spectrum. A filter bank spectral analysis, which uses the short-time Fourier transformation (STFT) may also be used alone or in conjunction with other parameter blocks. FFT is well known in the art of digital signal processing. Such a transform converts a time domain signal, measured as amplitude over time, into a frequency domain spectrum, which expresses the frequency content of the time domain signal as a number of different frequency bands. The FFT thus produces a vector of values corresponding to the energy amplitude in each of the frequency bands. The FFT converts the energy amplitude values into a logarithmic value which reduces subsequent computation since the logarithmic values are more simple to perform calculations on than the longer linear energy amplitude values produced by the FFT, while representing the same dynamic range. Ways for improving logarithmic conversions are well known in the art, one of the simplest being use of a look-up table. In addition, the FFT modifies its output to simplify computations based on the amplitude of a given frame. This modification is made by deriving an average value of the logarithms of the amplitudes for all bands. This average value is then subtracted from each of a predetermined group of logarithms, representative of a predetermined group of frequencies. The predetermined group consists of the logarithmic values, representing each of the frequency bands. Thus, utterances are converted from acoustic data to a sequence of vectors of k dimensions, each sequence of vectors identified as an acoustic frame, each frame represents a portion of the utterance. Alternatively, auditory modeling parameter unit can be used alone or in conjunction with others to improve the parameterization of heart sound signals in noisy and reverberant environments. In this approach, the filtering section may be represented by a plurality of filters equally spaced on a log-frequency scale from 0 Hz to about 3000 Hz and having a prescribed response corresponding to the cochlea. The nerve fiber firing mechanism is simulated by a multilevel crossing detector at the output of each cochlear filter. The ensemble of the multilevel crossing intervals corresponds to the firing activity at the auditory nerve fiber-array. The interval between each successive pair of same direction, either positive or negative going, crossings of each predetermined sound intensity level is determined and a count of the inverse of these interspike intervals of the multilevel detectors for each spectral portion is stored as a function of frequency. The resulting histogram of the ensemble of inverse interspike intervals forms a spectral pattern that is representative of the spectral distribution of the auditory neural response to the input sound and is relatively insensitive to noise. The use of a plurality of logarithmically related sound intensity levels accounts for the intensity of the input signal in a particular frequency range. Thus, a signal of a particular frequency having high intensity peaks results in a much larger count for that frequency than a low intensity signal of the same frequency. The multiple level histograms of the type described herein readily indicate the intensity levels of the nerve firing spectral distribution and cancel noise effects in the individual intensity level histograms. Alternatively, the fractal parameter block can further be used alone or in conjunction with others to represent spectral information. Fractals have the property of self similarity as the spatial scale is changed over many orders of magnitude. A fractal function includes both the basic form inherent in a shape and the statistical or random properties of the replacement of that shape in space. As is known in the art, a fractal generator employs mathematical operations known as local affine transformations. These transformations are employed in the process of encoding digital data representing spectral data. The encoded output constitutes a "fractal transform" of the spectral data and consists of coefficients of the affine transformations. Different fractal transforms correspond to different images or sounds.

Alternatively, a wavelet parameterization block can be used alone or in conjunction with others to generate the parameters. Like the FFT, the discrete wavelet transform (DWT) can be viewed as a rotation in function space, from the input space, or time domain, to a different domain. The DWT consists of applying a wavelet coefficient matrix hierarchically, first to the full data vector of length N, then to a smooth vector of length N/2, then to the smooth-smooth vector of length N/4, and so on. Most of the usefulness of wavelets rests on the fact that wavelet transforms can usefully be severely truncated, or turned into sparse expansions. In the DWT parameterization block, the wavelet transform of the heart sound signal is performed. The wavelet coefficients are allocated in a non-uniform, optimized manner. In general, large wavelet coefficients are quantized accurately, while small coefficients are quantized coarsely or even truncated completely to achieve the parameterization. Due to the sensitivity of the low-order cepstral coefficients to the overall spectral slope and the sensitivity of the high-order cepstral coefficients to noise variations, the parameters generated may be weighted by a parameter weighing block, which is a tapered window, so as to minimize these sensitivities. Next, a temporal derivator measures the dynamic changes in the spectra. Power features are also generated to enable the system to distinguish heart sound from silence.

After the feature extraction has been performed, the heart sound parameters are next assembled into a multidimensional vector and a large collection of such feature signal vectors can be used to generate a much smaller set of vector quantized (VQ) feature signals by a vector quantizer that cover the range of the larger collection. In addition to reducing the storage space, the VQ representation simplifies the computation for determining the similarity of spectral analysis vectors and reduces the similarity computation to a look-up table of similarities between pairs of codebook vectors. To reduce the quantization error and to increase the dynamic range and the precision of the vector quantizer, the preferred embodiment partitions the feature parameters into separate codebooks, preferably three. In the preferred embodiment, the first, second and third codebooks correspond to the cepstral coefficients, the differenced cepstral coefficients, and the differenced power coefficients.

With conventional vector quantization, an input vector is represented by the codeword closest to the input vector in terms of distortion. In conventional set theory, an object either belongs to or does not belong to a set. This is in contrast to fuzzy sets where the membership of an object to a set is not so clearly defined so that the object can be a part member of a set. Data are assigned to fuzzy sets based upon the degree of membership therein, which ranges from 0 (no membership) to 1.0 (full membership). A fuzzy set theory uses membership functions to determine the fuzzy set or sets to which a particular data value belongs and its degree of membership therein.

To handle the variance of heart sound patterns of individuals over time and to perform speaker adaptation in an automatic, self-organizing manner, an adaptive clustering technique called hierarchical spectral clustering is used. Such speaker changes can result from temporary or permanent changes in vocal tract characteristics or from environmental effects. Thus, the codebook performance is improved by collecting heart sound patterns over a long period of time to account for natural variations in speaker behavior. In one embodiment, data from the vector quantizer is presented to one or more recognition models, including an HMM model, a dynamic time warping model, a neural network, a fuzzy logic, or a template matcher, among others. These models may be used singly or in combination.

In dynamic processing, at the time of recognition, dynamic programming slides, or expands and contracts, an operating region, or window, relative to the frames of heart sound so as to align those frames with the node models of each S1-S4 pattern to find a relatively optimal time alignment between those frames and those nodes. The dynamic processing in effect calculates the probability that a given sequence of frames matches a given word model as a function of how well each such frame matches the node model with which it has been time-aligned. The word model which has the highest probability score is selected as corresponding to the heart sound. Dynamic programming obtains a relatively optimal time alignment between the heart sound to be recognized and the nodes of each word model, which compensates for the unavoidable differences in speaking rates which occur in different utterances of the same word. In addition, since dynamic programming scores words as a function of the fit between word models and the heart sound over many frames, it usually gives the correct word the best score, even if the word has been slightly misspoken or obscured by background sound. This is important, because humans often mispronounce words either by deleting or mispronouncing proper sounds, or by inserting sounds which do not belong.

In dynamic time warping (DTW), the input heart sound A, defined as the sampled time values $A=a(1) \ldots a(n)$, and the vocabulary candidate B, defined as the sampled time values $B=b(1) \ldots b(n)$, are matched up to minimize the discrepancy in each matched pair of samples. Computing the warping function can be viewed as the process of finding the minimum cost path from the beginning to the end of the words, where the cost is a function of the discrepancy between the corresponding points of the two words to be compared. Dynamic programming considers all possible points within the permitted domain for each value of i. Because the best path from the current point to the next point is independent of what happens beyond that point. Thus, the total cost of $[i(k), j(k)]$ is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the heart sound recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of heart sound against a given word model if the partial probability score for that comparison drops below a given threshold. This greatly reduces computation, since the dynamic programming of a given portion of heart sound against most words produces poor dynamic programming scores rather quickly, enabling most words to be pruned after only a small percent of their comparison has been performed. To reduce the computations involved, one embodiment limits the search to that within a legal path of the warping.

A Hidden Markov model can be used in one embodiment to evaluate the probability of occurrence of a sequence of observations $O(1), O(2), \ldots O(t), \ldots, O(T)$, where each observation O(t) may be either a discrete symbol under the VQ approach or a continuous vector. The sequence of observations may be modeled as a probabilistic function of an underlying Markov chain having state transitions that are not directly observable. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B=[b(j)(O(t)]$, where the $b(j)(O(t)$ term of the output symbol matrix is the probability of outputting observation O(t), given that the model is in state j. The first state is always constrained to be the initial state for the first time frame of the utterance, as only a prescribed set of left-to-right state transitions are possible. A predetermined final state is defined from which transitions to other states cannot occur. Transitions are restricted to reentry of a state or entry to one of the next two states. Such transitions are defined in the model as transition probabilities. For example, a heart sound pattern currently having a frame of feature signals in state 2 has a probability of reentering state 2 of $a(2,2)$, a probability $a(2,3)$ of entering state 3 and a probability of $a(2,4)=1-a(2,1)-a(2,2)$ of entering state 4. The probability $a(2,1)$ of entering state 1 or the probability $a(2,5)$ of entering state 5 is zero and the sum of the probabilities $a(2,1)$ through $a(2,5)$ is one. Although the preferred embodiment restricts the flow graphs to the present state or to the next two states, one skilled in the art can build an HMM model without any transition restrictions.

The Markov model is formed for a reference pattern from a plurality of sequences of training patterns and the output symbol probabilities are multivariate Gaussian function probability densities. The heart sound traverses through the feature extractor. During learning, the resulting feature vector series is processed by a parameter estimator, whose output is provided to the hidden Markov model. The hidden Markov model is used to derive a set of reference pattern templates, each template representative of an identified S1-S4 pattern in a vocabulary set of reference patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator.

In one embodiment, a heart sound analyzer detects Normal S1, Split S1, Normal S2, Normal split S2, Wide split S2, Paradoxical split S2, Fixed split S2, S3 right ventricle origin, S3 left ventricle origin, opening snap, S4 right ventricle origin, S4 left ventricle origin, aortic ejection sound, and pulmonic ejection sound, among others. The sound analyzer can be an HMM type analyzer, a neural network type analyzer, a fuzzy logic type analyzer, a genetic algorithm type analyzer, a rule-based analyzer, or any suitable classifier. The heart sound data is captured, filtered, and the major features of the heart sound are determined and then operated by a classifier such as HMM or neural network, among others.

The analyzer can detect S1, whose major audible components are related to mitral and tricuspid valve closure. Mitral (MI) closure is the first audible component of the first sound. It normally occurs before tricuspid (T1) closure, and is of slightly higher intensity than T1. A split of the first sound occurs when both components that make up the sound are separately distinguishable. In a normally split first sound, the mitral and tricuspid components are 20 to 30 milliseconds apart. Under certain conditions a wide or abnormally split first sound can be heard. An abnormally wide split first sound can be due to either electrical or mechanical causes, which create asynchrony of the two ventricles. Some of the electrical causes may be right bundle branch block, premature ventricular beats and ventricular tachycardia. An apparently wide split can be caused by another sound around the time of the first. The closure of the aortic and pulmonic valves contributes to second sound production. In the normal sequence, the aortic valve closes before the pulmonic valve. The left sided mechanical events normally precede right sided events.

The system can analyze the second sound S2. The aortic (A2) component of the second sound is the loudest of the two components and is discernible at all auscultation sites, but especially well at the base. The pulmonic (P2) component of the second sound is the softer of the two components and is usually audible at base left. A physiological split occurs when both components of the second sound are separately distinguishable. Normally this split sound is heard on inspiration and becomes single on expiration. The A2 and P2 components of the physiological split usually coincide, or are less than 30 milliseconds apart during expiration and often moved to around 50 to 60 milliseconds apart by the end of inspiration. The physiological split is heard during inspiration because it is during that respiratory cycle that intrathoracic pressure drops. This drop permits more blood to return to the right heart. The increased blood volume in the right ventricle results in a delayed pulmonic valve closure. At the same time, the capacity of the pulmonary vessels in the lung is increased, which results in a slight decrease in the blood volume returning to the left heart. With less blood in the left ventricle, its ejection takes less time, resulting in earlier closing of the aortic valve. Therefore, the net effect of inspiration is to cause aortic closure to occur earlier, and pulmonary closure to occur later. Thus, a split second is heard during inspiration, and a single second sound is heard during expiration. A reversed (paradoxical) split of the second sound occurs when there is a reversal of the normal closure sequence with pulmonic closure occurring before aortic. During inspiration the second sound is single, and during expiration the second sound splits. This paradoxical splitting of the second sound may be heard when aortic closure is delayed, as in marked volume or pressure loads on the left ventricle (i.e., aortic stenosis) or with conduction defects which delay left ventricular depolarization (i.e., left bundle branch block). The normal physiological split second sound can be accentuated by conditions that cause an abnormal delay in pulmonic valve-1 closure. Such a delay may be due to an increased volume in the right ventricle as o compared with the left (atrial septal defect, or ventricular septal defect); chronic right ventricular outflow obstruction (pulmonic stenosis); acute or chronic dilatation of the right ventricle due to sudden rise in pulmonary artery pressure (pulmonary embolism); electrical delay or activation of AA the right ventricle (right bundle branch block); decreased elastic recoil of the pulmonary artery (idiopathic dilatation of the pulmonary artery). The wide split has a duration of 40 to 50 milliseconds, compared to the normal physiologic split of 30 milliseconds. Fixed splitting of the second sound refers to split sound which displays little or no respiratory variation. The two components making up the sound occur in their normal sequence, but the ventricles are unable to change their volumes with respiration. This finding is typical in atrial septal defect, but is occasionally heard in congestive heart failure. The fixed split is heard best at base left with the diaphragm.

The third heart sound is also of low frequency, but it is heard just after the second heart sound. It occurs in early diastole, during the time of rapid ventricular filling. This sound occurs about 140 to 160 milliseconds after the second sound. The S3 is often heard in normal children or young adults but when heard in individuals over the age of 40 it usually reflects cardiac disease characterized by ventricular dilatation, decreased systolic function, and elevated ventricular diastolic filling pressure. The nomenclature includes the term ventricular gallop, protodiastolic gallop, S3 gallop, or the more common, S3. When normal it is referred to as a physiological third heart sound, and is usually not heard past the age of forty. The abnormal, or pathological third heart sound, may be heard in individuals with coronary artery disease, cardiomyopathies, incompetent valves, left to right shunts, Ventricular Septal Defect (VSD), or Patent Ductus Arteriosus (PDA). The pathological S3 may be the first clinical sign of congestive heart failure. The fourth heart sound is a low frequency sound heard just before the first heart sound, usually preceding this sound by a longer interval than that separating the two components of the normal first sound. It has also been known as an "atrial gallop", a "presystolic gallop", and an "S4 gallop". It is most commonly known as an "S4".

The S4 is a diastolic sound, which occurs during the late diastolic filling phase at the time when the atria contract. When the ventricles have a decreased compliance, or are receiving an increased diastolic volume, they generate a low frequency vibration, the S4. Some authorities believe the S4 may be normal in youth, but is seldom considered normal after the age of 20. The abnormal or pathological S4 is heard in primary myocardial disease, coronary artery disease, hypertension, and aortic and pulmonic stenosis. The S4 may have its origin in either the left or right heart. The S4 of left ventricular origin is best heard at the apex, with the patient supine, or in the left lateral recumbent position. Its causes include severe hypertension, aortic stenosis, cardiomyopathies, and left ventricular myocardial infarctions. In association with ischemic heart disease the S4 is often loudest during episodes of angina pectoris or may occur early after an acute myocardial infarction, often becoming fainter as the patient improves. The S4 of right ventricular origin is best heard at the left lateral sternal border. It is usually accentuated with inspiration, and may be due to pulmonary stenosis, pulmonary hypertension, or right ventricular myocardial infarction. When both the third heart sound and a fourth heart sound are present, with a normal heart rate, 60-100 heart beats per minute, the four sound cadence of a quadruple rhythm may be heard.

Ejection sounds are high frequency clicky sounds occurring shortly after the first sound with the onset of ventricular ejection. They are produced by the opening of the semilunar valves, aortic or pulmonic, either when one of these valves is diseased, or when ejection is rapid through a normal valve. They are heard best at the base, and may be of either aortic or pulmonic origin. Ejection sounds of aortic origin often radiate widely and may be heard anywhere on a straight line from the base right to the apex. Aortic ejection sounds are most typically heard in patients with valvular aortic stenosis, but are occasionally heard in various other conditions, such as aortic insufficiency, coarctation of the aorta, or aneurysm of the ascending aorta. Ejection sounds of pulmonic origin are heard anywhere on a straight line from base left, where they are usually best heard, to the epigastrium. Pulmonic ejection sounds are typically heard in pulmonic stenosis, but may be encountered in pulmonary hypertension, atrial septal defects (ASD) or in conditions causing enlargement of the pulmonary artery. Clicks are high frequency sounds which occur in systole, either mid, early, or late. The click generally occurs at least 100 milliseconds after the first sound. The most common cause of the click is mitral valve prolapse. The clicks of mitral origin are best heard at the apex, or toward the left lateral sternal border. The click will move closer to the first sound when volume to the ventricle is reduced, as occurs in standing or the Valsalva maneuver. The opening snap is a short high frequency sound, which occurs after the second heart sound in early diastole. It usually follows the second sound by about 60 to 100 milliseconds. It is most frequently the result of the sudden arrest of the opening of the mitral valve, occurring in mitral stenosis, but may also be encountered in conditions producing increased flow through this valve (i.e., VSD or PDA). In tricuspid stenosis or in association with increased flow across the tricuspid valve, as in ASD, a tricuspid opening snap may be heard. The tricuspid opening snap is loudest at the left lateral sternal border, and becomes louder with inspiration.

Murmurs are sustained noises that are audible during the time periods of systole, diastole, or both. They are basically produced by these factors: 1) Backward regurgitation through a leaking valve or septal defect; 2) Forward flow through a narrowed or deformed valve or conduit or through an arterial venous connection; 3) High rate of blood flow through a normal or abnormal valve; 4) Vibration of loose structures within the heart (i.e., chordae tendineae or valvular tissue). Murmurs that occur when the ventricles are contracting, that is, during systole, are referred to as systolic murmurs. Murmurs occurring when the ventricles are relaxed and filling, that is during diastole, are referred to as diastolic murmurs. There are six characteristics useful in murmur identification and differentiation:

1) Location or the valve area over which the murmur is best heard. This is one clue to the origin of the murmur. Murmurs of mitral origin are usually best heard at the apex. Tricuspid murmurs at the lower left lateral sternal border, and pulmonic murmurs at base left. Aortic systolic murmurs are best heard at base right, and aortic diastolic murmurs at Erb's point, the third intercostal space to the left of the sternum.
2) Frequency (pitch). Low, medium, or high.
3) Intensity.
4) Quality.
5) Timing. (Occurring during systole, diastole, or both).
6) Areas where the sound is audible in addition to the area over which it is heard best.

Systolic murmurs are sustained noises that are audible during the time period of systole, or the period between S1 and S2. Forward flow across the aortic or pulmonic valves, or regurgitant flow from the mitral or tricuspid valve may produce a systolic murmur. Systolic murmurs may be normal, and can represent normal blood flow, i.e., thin chest, babies and children, or increased blood flow, i.e., pregnant women. Early systolic murmurs begin with or shortly after the first sound and peak in the first third of systole. Early murmurs have the greatest intensity in the early part of the cycle. The commonest cause is the innocent murmur of childhood (to be discussed later). A small ventricular septal defect (VSD) occasionally causes an early systolic murmur. The early systolic murmur of a small VSD begins with S1 and stops in mid systole, because as ejection continues and the ventricular size decreases, the small defect is sealed shut, causing the murmur to soften or cease. This murmur is characteristic of the type of children's VSD located in the muscular portion of the ventricular septum. This defect may disappear with age. A mid-systolic murmur begins shortly after the first sound, peaks in the middle of systole, and does not quite extend to the second sound. It is the crescendo decrescendo murmur which builds up and decrease symmetrically. It is also known as an ejection murmur. It most commonly is due to forward blood flow through a normal, narrow or irregular valve, i.e., aortic or pulmonic stenosis. The murmur begins when the pressure in the respective ventricle exceeds the aortic or pulmonary arterial pressure. The most characteristic feature of this murmur is its cessation before the second sound, thus leaving this latter sound identifiable as a discrete entity. This type of murmur is commonly heard in normal individuals, particularly in the young, who usually have increased blood volumes flowing over normal valves. In this setting the murmur is usually short, with its peak intensity early in systole, and is soft, seldom over 2 over 6 in intensity. It is then designated as an innocent murmur. In order for a murmur to be classified as innocent (i.e. normal), the following are present:

1) Normal splitting of the second sound together with absence of abnormal sounds or murmurs, such as ejection sounds, diastolic murmurs, etc.
2) Normal jugular venus and carotid pulses
3) Normal precordial pulsations or palpation, and
4) Normal chest x-ray and ECG Obstruction or stenosis across the aortic or pulmonic valves also may give rise to a murmur of this type. These murmurs are usually longer and louder than the innocent murmur, and reach a peak intensity in mid-systole. The murmur of aortic stenosis is harsh in quality and is heard equally well with either the bell or the diaphragm. It is heard best at base right, and radiates to the apex and to the neck bilaterally.

An early diastolic murmur begins with a second sound, and peaks in the first third of diastole. Common causes are aortic regurgitation and pulmonic regurgitation. The early diastolic murmur of aortic regurgitation usually has a high frequency blowing quality, is heard best with a diaphragm at Erb's point, and radiates downward along the left sternal border. Aortic regurgitation tends to be of short duration, and heard best on inspiration. This respiratory variation is helpful in differentiating pulmonic regurgitation from aortic regurgitation. A mid-diastolic murmur begins after the second sound and peaks in mid-diastole. Common causes are mitral stenosis, and tricuspid stenosis. The murmur of mitral stenosis is a low frequency, crescendo de crescendo rumble, heard at the apex with the bell lightly held. If it radiates, it does so minimally to the axilla. Mitral stenosis normally produces three distinct abnormalities which can be heard: 1) A loud first sound, 2) An opening snap, and 3) A mid-diastolic rumble with a late diastolic accentuation.

A late diastolic murmur occurs in the latter half of diastole, synchronous with atrial contraction, and extends to the first sound. Although occasionally occurring alone, it is usually a component of the longer diastolic murmur of mitral stenosis or tricuspid stenosis. This murmur is low in frequency, and rumbling in quality. A continuous murmur usually begins during systole and extends through the second sound and throughout the diastolic period. It is usually produced as a result of one of four mechanisms: 1) An abnormal communication between an artery and vein; 2) An abnormal communication between the aorta and the right side of the heart or with the left atrium; 3) An abnormal increase in flow, or constriction in an artery; and 4) Increased or turbulent blood flow through veins. Patent Ductus Arteriosus (PDA) is the classical example of this murmur. This condition is usually corrected in childhood. It is heard best at base left, and is usually easily audible with the bell or diaphragm. Another example of a continuous murmur is the so-called venous hum, but in this instance one hears a constant roaring sound which changes little with the cardiac cycle. A late systolic murmur begins in the latter half of systole, peaks in the later third of systole, and extends to the second sound. It is a modified regurgitant murmur with a backward flow through an incompetent valve, usually the mitral valve. It is commonly heard in mitral valve prolapse, and is usually high in frequency (blowing in quality), and heard best with a diaphragm at the apex. It may radiate to the axilla or left sternal border. A pansystolic or holosystolic murmur is heard continuously throughout systole. It begins with the first heart sound, and ends with the second heart sound. It is commonly heard in mitral regurgitation, tricuspid regurgitation, and ventricular septal defect. This type of murmur is caused by backward blood flow. Since the pressure remains higher throughout systole in the ejecting chamber than in the receiving chamber, the murmur is continuous throughout systole. Diastolic murmurs are sustained noises that are audible between S2 and the next S. Unlike systolic murmurs, diastolic murmurs should usually be considered pathological, and not normal. Typical abnormalities causing diastolic murmurs are aortic regurgitation, pulmonic regurgitation, mitral stenosis, and tricuspid stenosis. The timing of diastolic murmurs is the primary concern of this program. These murmurs can be early, mid, late and pan in nature. In a pericardial friction rub, there are three sounds, one systolic, and two diastolic. The systolic sound may occur anywhere in systole, and the two diastolic sounds occur at the times the ventricles are stretched. This stretching occurs in early diastole, and at the end of diastole. The pericardial friction rub has a scratching, grating, or squeaking leathery quality. It tends to be high in frequency and best heard with a diaphragm. A pericardial friction rub is a sign of pericardial inflammation and may be heard in infective pericarditis, in myocardial infarction, following cardiac surgery, trauma, and in autoimmune problems such as rheumatic fever.

In addition to heart sound analysis, the timing between the onset and offset of particular features of the ECG (referred to as an interval) provides a measure of the state of the heart and can indicate the presence of certain cardiological conditions. An EKG analyzer is provided to interpret EKG/ECG data and generate warnings if needed. The analyzer examines intervals in the ECG waveform such as the QT interval and the PR interval. The QT interval is defined as the time from the start of the QRS complex to the end of the T wave and corresponds to the total duration of electrical activity (both depolarization and repolarization) in the ventricles. Similarly, the PR interval is defined as the time from the start of the P wave to the start of the QRS complex and corresponds to the time from the onset of atrial depolarization to the onset of ventricular depolarization. In one embodiment, hidden Markov and hidden semi-Markov models are used for automatically segmenting an electrocardiogram waveform into its constituent waveform features. An undecimated wavelet transform is used to generate an overcomplete representation of the signal that is more appropriate for subsequent modelling. By examining the ECG signal in detail it is possible to derive a number of informative measurements from the characteristic ECG waveform. These can then be used to assess the medical well-being of the patient. The wavelet methods such as the undecimated wavelet transform, can be used instead of raw time series data to generate an encoding of the ECG which is tuned to the unique spectral characteristics of the ECG waveform features. The segmentation process can use explicit state duration modelling with hidden semi-Markov models. Using a labelled data set of ECG waveforms, a hidden Markov model is trained in a supervised manner. The model was comprised of the following states: P wave, QRS complex, T wave, U wave, and Baseline. The parameters of the transition matrix aij were computed using the maximum likelihood estimates. The ECG data is encoded with wavelets from the Daubechies, Symlet, Coiflet or Biorthogonal wavelet families, among others. In the frequency domain, a wavelet at a given scale is associated with a bandpass filter of a particular centre frequency. Thus the optimal wavelet basis will correspond to the set of bandpass filters that are tuned to the unique spectral characteristics of the ECG. In another implementation, a hidden semi-Markov model (HSMM) is used. HSMM differs from a standard HMM in that each of the self-transition coefficients ail are set to zero, and an explicit probability density is specified for the duration of each state. In this way, the individual state duration densities govern the amount of time the model spends in a given state, and the transition matrix governs the probability of the next state once this time has elapsed. Thus the underlying stochastic process is now a "semi-Markov" process. To model the durations of the various waveform features of the ECG, a Gamma density is used since this is a positive distribution which is able to capture the skewness of the ECG state durations. For each state i, maximum likelihood estimates of the shape and scale parameters were computed directly from the set of labelled ECG signals.

In addition to providing beat-to-beat timing information for other sensors to use, the patterns of the constituent waveform features determined by the HMM or neural networks, among other classifiers, can be used for detecting heart attacks or stroke attacks, among others. For example, the detection and classification of ventricular complexes from the ECG data is can be used for rhythm and various types of arrhythmia to be recognized. The system analyzes pattern recognition parameters for classification of normal QRS complexes and premature ventricular contractions (PVC). Exemplary parameters include the width of the QRS complex, vectorcardiogram parameters, amplitudes of positive and negative peaks, area of positive and negative waves, various time-interval durations, amplitude and angle of the QRS vector, among others. The EKG analyzer can analyze EKG/ECG patterns for Hypertrophy, Enlargement of the Heart, Atrial Enlargement, Ventricular Hypertrophy, Arrhythmias, Ectopic Supraventricular Arrhythmias, Ventricular Tachycardia (VT), Paroxysmal Supraventricular Tachycardia (PSVT), Conduction Blocks, AV Block, Bundle Branch Block, Hemiblocks, Bifascicular Block, Preexcitation Syndromes, Wolff-Parkinson-White Syndrome, Lown-Ganong-Levine Syndrome, Myocardial Ischemia, Infarction, Non-Q Wave Myocardial Infarction, Angina, Electrolyte Disturbances, Heart Attack, Stroke Attack, Hypothermia, Pulmonary Disorder, Central Nervous System Disease, or Athlete's Heart, for example.

FIG. 16C shows an exemplary process to detect stroke attack. In this embodiment, 3D accelerometer sensing is used. First, the process looks for weakness (hemiparesis) in either the left half or the right half of the body, for example the left/right arms, legs, or face at step 3000. Next, the system analyzes walking pattern to see if the patient has a loss of balance or coordination at step 3002. The system then asks the user to move hands/feet in a predetermined pattern at step 3004 and reads accelerometer output in accordance with predetermined pattern movement 3006. For example, the system can ask the user to point his/her right or left hand to the nose. The accelerometer outputs are tested to check if the correct hand did reach the nose. In another example, the user can be prompted to extend his or her hands on both side and wiggle the hands or to kick the legs. Again, the outputs of the accelerometers are used to confirm that the user is able to follow direction. The accelerometer outputs are provided to a pattern classifier, which can be an HMM, a neural network, a Bayesian network, fuzzy logic, or any suitable classifiers at step 3008. The system also checks whether patient is experiencing dizziness or sudden, severe headache with no known cause 3010. Next, the system displays a text image and asks the patient to read back the text image, one eye at a time at step 3012. Using a speech recognizer module, the user speech is converted into text to compare against the text image. The speech recognizer also detects if the user exhibits signs of confusion, trouble speaking or understanding at step 3014. The system also asks the patient if they feel numbness in the body-arms, legs, face at step 3016. Next the system asks the patient to squeeze gauge/force sensor to determine force applied during squeeze at step 3018. If any of the above tests indicate a possible stroke, the system displays a warning to the patient and also connects the patient to the appropriate emergency response authority, family member, or physician.

Figure 16D:
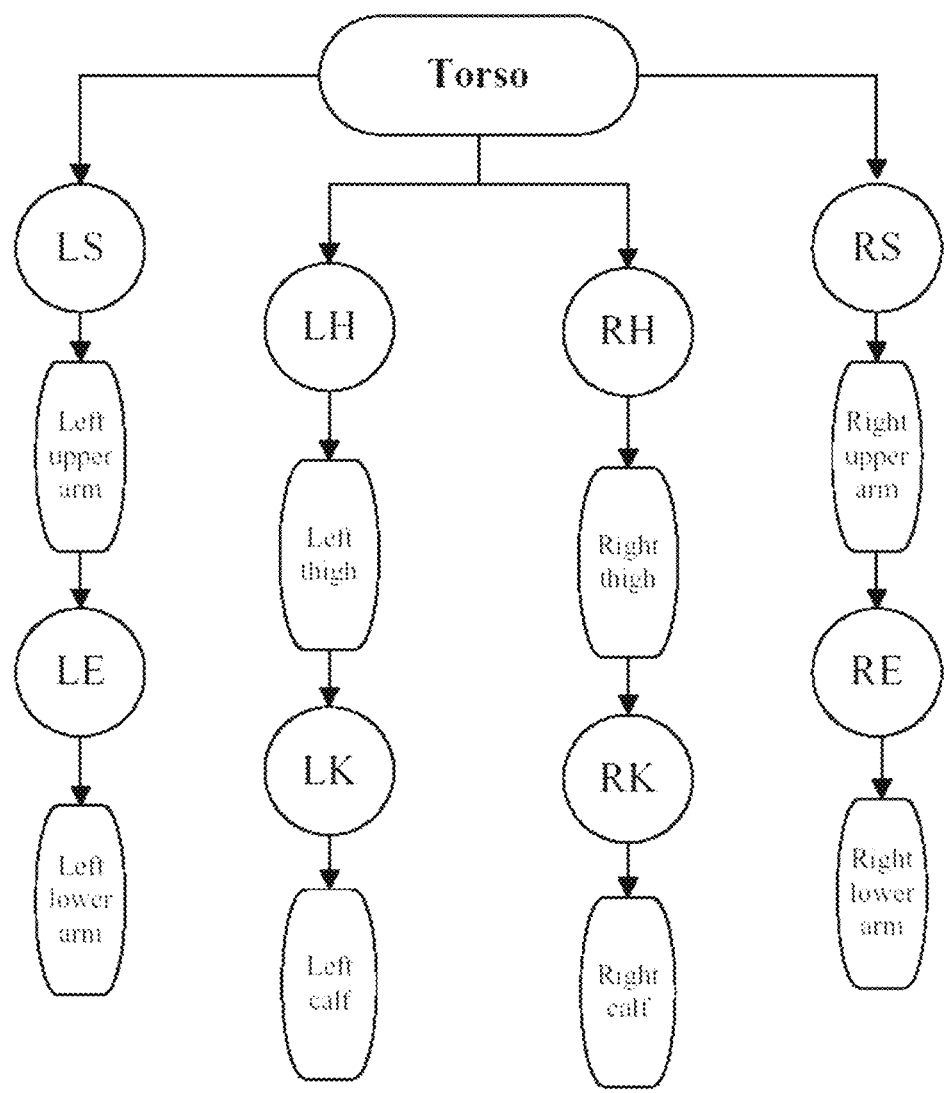

In one implementation, an HMM is used to track patient motor skills or patient movement patterns. Human movement involves a periodic motion of the legs. Regular walking involves the coordination of motion at the hip, knee and ankle, which consist of complex joints. The muscular groups attached at various locations along the skeletal structure often have multiple functions. The majority of energy expended during walking is for vertical motion of the body. When a body is in contact with the ground, the downward force due to gravity is reflected back to the body as a reaction to the force. When a person stands still, this ground reaction force is equal to the person's weight multiplied by gravitational acceleration. Forces can act in other directions. For example, when we walk, we also produce friction forces on the ground. When the foot hits the ground at a heel strike, the friction between the heel and the ground causes a friction force in the horizontal plane to act backwards against the foot. This force therefore causes a breaking action on the body and slows it down. Not only do people accelerate and brake while walking, they also climb and dive. Since reaction force is mass times acceleration, any such acceleration of the body will be reflected in a reaction when at least one foot is on the ground. An upwards acceleration will be reflected in an increase in the vertical load recorded, while a downwards acceleration will be reduce the effective body weight. Zigbee wireless sensors with tri-axial accelerometers are mounted to the patient on different body locations for recording, for example the tree structure as shown in FIG. 16D. As shown therein, sensors can be placed on the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others.

The sequence of human motions can be classified into several groups of similar postures and represented by mathematical models called model-states. A model-state contains the extracted features of body signatures and other associated characteristics of body signatures. Moreover, a posture graph is used to depict the inter-relationships among all the model-states, defined as PG(ND,LK), where ND is a finite set of nodes and LK is a set of directional connections between every two nodes. The directional connection links are called posture links. Each node represents one model-state, and each link indicates a transition between two model-states. In the posture graph, each node may have posture links pointing to itself or the other nodes.

In the pre-processing phase, the system obtains the human body profile and the body signatures to produce feature vectors. In the model construction phase, the system generates a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and if differences for the motion parameters and curves over time is detected, the system then runs the patient through additional tests to confirm a stroke attack, and if a stroke attack is suspected, the system prompts the user to seek medical attention immediately and preferably within the 3 hour for receiving TPA.

FIG. 16E shows one exemplary process for determining weakness in the left or right half of the body. The process compares historical left shoulder (LS) strength against current LS strength at step 3200. The process also compares historical right shoulder (RS) strength against current RS strength at step 3202. The process can compare historical left hip (LH) strength against current LH strength at step 3204. The process can also compare historical right hip (RH) strength against current RH strength at step 3206. If the variance between historical and current strength exceeds threshold, the process generates warnings at step 3208. Furthermore, similar comparisons can be made for sensors attached to the left elbow (LE), right elbow (RE), left knee (LK), and right knee (RK) connect the upper and the lower extremities, among others.

The system can ask the patient to squeeze a strength gauge, piezoelectric sensor, or force sensor to determine force applied during squeeze. The user holds the sensor or otherwise engages the sensor. The user then applies and holds a force (e.g., compression, torque, etc.) to the sensor, which starts a timer clock and triggers a sampling start indicator to notify the user to continue to apply (maximum) force to the sensor. Strength measurements are then sampled periodically during the sampling period until the expiration of time. From the sampled strength data, certain strength measurement values are selected, such as the maximum value, average value(s), or values obtained during the sampling period. The user can test both hands at the same time, or alternatively he may test one hand at a time. A similar approach is used to sense leg strength, except that the user is asked to pushed down on a scale to determine the foot force generated by the user.

The system can detect hemiparesis, a very common symptom of stroke, by detecting muscular weakness or partial paralysis to one side of the body. Additionally, the accelerometers can detect ataxia, which is an impaired ability to perform smooth coordinated voluntary movements. Additionally, the system can detect aphasia, including receptive aphasia and expressive aphasia. Aphasia is a cognitive disorder marked by an impaired ability to comprehend (receptive aphasia) or express (expressive aphasia) language. Exemplary embodiments are disclosed for detecting receptive aphasia by displaying text or playing verbal instructions to the user, followed by measuring the correctness and/or time delay of the response from the user. Exemplary embodiments are also disclosed for detecting expressive aphasia by positing sound made by an animal to the user, prompting the user to identify or name the animal, and measuring the correctness and/or time delay of the response from the user. The system can also detect dysarthria, a disorder of speech articulation (e.g., slurred speech), by prompting the user to say a word or phrase that is recorded for subsequent comparison by voice pattern recognition or evaluation by medical personnel.

In the above manner, the system automatically reminds the user to get help if he feels a sudden numbness or weakness of the face, arm or leg, especially on one side of the body, sudden confusion, trouble speaking or understanding, sudden trouble seeing in one or both eyes, or sudden trouble walking, dizziness, loss of balance or coordination.

In one embodiment, the accelerometers distinguish between lying down and each upright position of sitting and standing based on the continuous output of the 3D accelerometer. The system can detect (a) extended time in a single position; (b) extended time sitting in a slouching posture (kyphosis) as opposed to sitting in an erect posture (lordosis); and (c) repetitive stressful movements, such as may be found on some manufacturing lines, while typing for an extended period of time without proper wrist support, or while working all day at a job lifting boxes, among others. In one alternative embodiment, angular position sensors, one on each side of the hip joint, can be used to distinguish lying down, sitting, and standing positions. In another embodiment, the present invention repeatedly records position and/or posture data over time. In one embodiment, magnetometers can be attached to a thigh and the torso to provide absolute rotational position about an axis coincident with Earth's gravity vector (compass heading, or yaw). In another embodiment, the rotational position can be determined through the in-door positioning system as discussed above.

Depending on the severity of the stroke, patients can experience a loss of consciousness, cognitive deficits, speech dysfunction, limb weakness, hemiplegia, vertigo, diplopia, lower cranial nerve dysfunction, gaze deviation, ataxia, hemianopia, and aphasia, among others. Four classic syndromes that are characteristically caused by lacunar-type stroke are: pure motor hemiparesis, pure sensory syndrome, ataxic hemiparesis syndrome, and clumsy-hand dysarthria syndrome. Patients with pure motor hemiparesis present with face, arm, and leg weakness. This condition usually affects the extremities equally, but in some cases it affects one extremity more than the other. The most common stroke location in affected patients is the posterior limb of the internal capsule, which carries the descending corticospinal and corticobulbar fibers. Other stroke locations include the pons, midbrain, and medulla. Pure sensory syndrome is characterized by hemibody sensory symptoms that involve the face, arm, leg, and trunk. It is usually the result of an infarct in the thalamus. Ataxic hemiparesis syndrome features a combination of cerebellar and motor symptoms on the same side of the body. The leg is typically more affected than the arm. This syndrome can occur as a result of a stroke in the pons, the internal capsule, or the midbrain, or in the anterior cerebral artery distribution. Patients with clumsy-hand dysarthria syndrome experience unilateral hand weakness and dysarthria. The dysarthria is often severe, whereas the hand involvement is more subtle, and patients may describe their hand movements as "awkward." This syndrome is usually caused by an infarct in the pons.

Different patterns of signs can provide clues as to both the location and the mechanism of a particular stroke. The system can detect symptoms suggestive of a brainstem stroke include vertigo, diplopia, bilateral abnormalities, lower cranial nerve dysfunction, gaze deviation (toward the side of weakness), and ataxia. Indications of higher cortical dysfunction-such as neglect, hemianopsia, aphasia, and gaze preference (opposite the side of weakness)-suggest hemispheric dysfunction with involvement of a superficial territory from an atherothrombotic or embolic occlusion of a mainstem vessel or peripheral branch.

The system can detect a pattern of motor weakness. Ischemia of the cortex supplied by the middle cerebral artery typically causes weakness that (1) is more prominent in the arm than in the leg and (2) involves the distal muscles more than the proximal muscles. Conversely, involvement of an area supplied by the superficial anterior cerebral artery results in weakness that (1) is more prominent in the leg than the arm and (2) involves proximal upper extremity (shoulder) muscles more than distal upper extremity muscles. Flaccid paralysis of both the arm and leg (unilateral) suggests ischemia of the descending motor tracts in the basal ganglia or brainstem. This is often caused by an occlusion of a penetrating artery as a result of small-vessel disease. Once the stroke is detected, intravenous (IV) tissue plasminogen activator (t-PA) needs to be given within 3 hours of symptom onset. An accurate assessment of the timing of the stroke is also crucial. The system keeps track of the timing off the onset of the stroke for this purpose.

One major symptom of a stroke is unexplained weakness or numbness in the muscle. To detect muscle weakness or numbness, in one embodiment, the system applies a pattern recognizer such as a neural network or a Hidden Markov Model (HMM) to analyze accelerometer output. In another embodiment, electromyography (EMG) is used to detect muscle weakness. In another embodiment, EMG and a pattern analyzer is used to detect muscle weakness. In yet another embodiment, a pattern analyzer analyzes both accelerometer and EMG data to determine muscle weakness. In a further embodiment, historical ambulatory information (time and place) is used to further detect changes in muscle strength. In yet other embodiments, accelerometer data is used to confirm that the patient is at rest so that EMG data can be accurately captured or to compensate for motion artifacts in the EMG data in accordance with a linear or non-linear compensation table. In yet another embodiment, the EMG data is used to detect muscle fatigue and to generate a warning to the patient to get to a resting place or a notification to a nurse or caregiver to render timely assistance.

The amplitude of the EMG signal is stochastic (random) in nature and can be reasonably represented by a Gausian distribution function. The amplitude of the signal can range from 0 to 10 mV (peak-to-peak) or 0 to 1.5 mV (rms). The usable energy of the signal is limited to the 0 to 500 Hz frequency range, with the dominant energy being in the 50-150 Hz range. Usable signals are those with energy above the electrical noise level. The dominant concern for the ambient noise arises from the 60 Hz (or 50 Hz) radiation from power sources. The ambient noise signal may have an amplitude that is one to three orders of magnitude greater than the EMG signal. There are two main sources of motion artifact: one from the interface between the detection surface of the electrode and the skin, the other from movement of the cable connecting the electrode to the amplifier. The electrical signals of both noise sources have most of their energy in the frequency range from 0 to 20 Hz and can be reduced.

As shown in FIG. 17A, to eliminate the potentially much greater noise signal from power line sources, a differential instrumentation amplifier is employed. Any signal that originates far away from the detection sites will appear as a common signal, whereas signals in the immediate vicinity of the detection surfaces will be different and consequently will be amplified. Thus, relatively distant power lines noise signals will be removed and relatively local EMG signals will be amplified. The source impedance at the junction of the skin and detection surface may range from several thousand ohms to several megohms for dry skin. In order to prevent attenuation and distortion of the detected signal due to the effects of input loading, the input impedance of the differential amplifier is as large as possible, without causing ancillary complications to the workings of the differential amplifier. The signal to noise ratio is increased by filtering between 20-500 Hz with a roll-off of 12 dB/octave.

In one embodiment, direct EMG pre-amplification at the skin surface provides the best myoelectric signal quality for accurate, reliable EMG signal detection and eliminates cable motion artifact. The double-differential instrumentation pre-amplifier design attenuates unwanted common-mode bio-electric signals to reduce cross-talk from adjacent muscle groups. Internal RFI and ESD protection prevents radio frequency interference and static damage. The constant low-impedance output of the pre-amplifier completely eliminates cable noise and cable motion artifacts without requiring any additional signal processing within the pre-amplifier. An integral ground reference plane provides immunity to electromagnetic environmental noise. All signal and power conductors in the pre-amplifier cable are enclosed inside an independent, isolated shield to eliminate interference from AC power-lines and other sources. The contacts are corrosion-free, medical grade stainless steel for maximal signal flow. The system uses biocompatible housing and sensor materials to prevent allergic reactions.

In one implementation, MA-311 EMG pre-amplifiers from Motion Lab Systems, Inc., Baton Rouge, La., can be used. The pre-amplifiers incorporate both radio frequency interference (RFI) filters and electrostatic discharge (ESD) protection circuitry resulting in an extraordinarily reliable EMG pre-amplifier that can be used in almost any environment. Featuring a double-differential input, the unique design of the Motion Lab Systems EMG pre-amplifiers enables researchers to produce high-quality, low-noise EMG data from subjects under the most adverse conditions (e.g. on treadmills, using mobile phones etc.) without any skin preparation or subsequent signal processing.

In another implementation, a micro-powered EMG embodiment includes an instrumentation amplifier and an AC coupling that maintains a high CMRR with a gain of about 1000. The electronic circuits are mounted on a flexible circuit board (FPC) with slidable electrode settings that allows differential recording at various distances between the electrodes. The high gain amplifier is placed next to the recording electrodes to achieve high SNR. Battery power provides isolation and low noise at various frequencies that would likely not be fully attenuated by the PSRR and causing alias errors.

The system can detect dominant symptoms of stroke can include weakness or paralysis of the arms and/or legs, incoordination (ataxia), numbness in the arms/legs using accelerometers or EMG sensors. The EMG sensors can detect muscle fatigue and can warn the patient to get to a resting area if necessary to prevent a fall. The system can detect partial/total loss of vision by asking the patient to read a predetermined phrase and detect slur using speech recognizer. The system can detect loss of consciousness/coma by detecting lack of movement. Voice/speech disturbances are not initially the dominant symptoms in stroke, and the disturbances can be detected by a speech recognizer. In one implementation, the system uses PNL (probabilistic networks library) to detect unusual patient movement/ambulatory activities that will lead to a more extensive check for stroke occurrence. PNL supports dynamic Bayes nets, and factor graphs; influence diagrams. For inference, PNL supports exact inference using the junction tree algorithm, and approximate inference using loopy belief propagation or Gibbs sampling. Learning can be divided along many axes: parameter or structure, directed or undirected, fully observed or partially observed, batch or online, discriminative or maximum likelihood, among others. First, the system performs data normalization and filtering for the accelerometers and EMG sensors that detect patient movements and muscle strength. The data can include in-door positioning information, 3D acceleration information, or EMG/EKG/EEG data, for example. The data can be processed using wavelet as discussed above or using any suitable normalization/filtering techniques. Next, the system performs parameterization and discretization. The Bayesian network is adapted in accordance with a predefined network topology. The system also defines conditional probability distributions. The system then generates the probability of event P(y), under various scenarios. Training data is acquired and a training method is built for the Bayesian network engine. Next, the system tunes model parameters and performs testing on the thus formed Bayesian network.

In one embodiment, a housing (such as a strap, a wristband, or a patch) provides a plurality of sensor contacts for EKG and/or EMG. The same contacts can be used for detecting EKG or EMG and can be placed as two parallel contacts (linear or spot shape) on opposite sides of the band, two adjacent parallel contacts on the inner surface of the band, two parallel adjacent contacts on the back of the wrist-watch, or alternatively one contact on the back of the watch and one contact on the wrist-band. The outputs of the differential contacts are filtered to remove motion artifacts. The differential signal is captured, and suitably filtered using high pass/low pass filters to remove noise, and digitized for signal processing. In one embodiment, separate amplifiers are used to detect EKG (between 50 mHz and 200 Hz) and for EMG (between 10 Hz and 500 Hz). In another embodiment, one common amp is used for both EKG/EMG, and software filter is applied to the digitized signal to extract EKG and EMG signals, respectively. The unit can apply Wavelet processing to convert the signal into the frequency domain and apply recognizers such as Bayesian, NN or HMM to pull the EMG or EKG signals from noise. The system uses a plurality of wireless nodes to transmit position and to triangulate with the mobile node to determine position. 3D accelerometer outputs can be integrated to provide movement vectors and positioning information. Both radio triangulation and accelerometer data can confirm the position of the patient. The RF signature of a plurality of nodes with known position can be used to detect proximity to a particular node with a known position and the patient's position can be extrapolated therefrom.

In one embodiment, Analog Device's AD627, a micropower instrumentation amplifier, is used for differential recordings while consuming low power. In dual supply mode, the power rails Vs can be as low as ±1.1 Volt, which is ideal for battery-powered applications. With a maximum quiescent current of 85 µA (60 µA typical), the unit can operate continuously for several hundred hours before requiring battery replacement. The batteries are lithium cells providing 3.0V to be capable of recording signals up to +1 mV to provide sufficient margin to deal with various artifacts such as offsets and temperature drifts. The amplifier's reference is connected to the analog ground to avoid additional power consumption and provide a low impedance connection to maintain the high CMRR. To generate virtual ground while providing low impedance at the amplifier's reference, an additional amplifier can be used. In one implementation, the high-pass filtering does not require additional components since it is achieved by the limits of the gain versus frequency characteristics of the instrumentation amplifier. The amplifier has been selected such that with a gain of 60 dB, a flat response could be observed up to a maximum of 100 Hz with gain attenuation above 100 Hz in one implementation. In another implementation, a high pass filter is used so that the cut-off frequency becomes dependent upon the gain value of the unit. The bootstrap AC-coupling maintains a much higher CMRR so critical in differential measurements. Assuming that the skin-electrode impedance may vary between 5 K- and 10 K-ohms, 1 M-ohm input impedance is used to maintain loading errors below acceptable thresholds between 0.5% and 1%.

When an electrode is placed on the skin, the detection surfaces come in contact with the electrolytes in the skin. A chemical reaction takes place which requires some time to stabilize, typically in the order of a few seconds. The chemical reaction should remain stable during the recording session and should not change significantly if the electrical characteristics of the skin change from sweating or humidity changes. The active electrodes do not require any abrasive skin preparation and removal of hair. The electrode geometry can be circular or can be elongated such as bars. The bar configuration intersects more fibers. The inter detection-surface distance affects the bandwidth and amplitude of the EMG signal; a smaller distance shifts the bandwidth to higher frequencies and lowers the amplitude of the signal. An inter detection-surface of 1.0 cm provides one configuration that detects representative electrical activity of the muscle during a contraction. The electrode can be placed between a motor point and the tendon insertion or between two motor points, and along the longitudinal midline of the muscle. The longitudinal axis of the electrode (which passes through both detection surfaces) should be aligned parallel to the length of the muscle fibers. The electrode location is positioned between the motor point (or innervation zone) and the tendinous insertion, with the detection surfaces arranged so that they intersect as many muscle fibers as possible.

In one embodiment, a multi-functional bio-data acquisition provides programmable multiplexing of the same differential amplifiers for extracting EEG (electroencephalogram), ECG (electrocardiogram), or EMG (electromyogram) waves. The system includes an AC-coupled chopped instrumentation amplifier, a spike filtering stage, a constant gain stage, and a continuous-time variable gain stage, whose gain is defined by the ratio of the capacitors. The system consumes microamps from 3V. The gain of the channel can be digitally set to 400, 800, 1600 or 2600. Additionally, the bandwidth of the circuit can be adjusted via the bandwidth select switches for different biopotentials. The high cut-off frequency of the circuit can be digitally selected for different applications of EEG acquisition.

In another embodiment, a high-resolution, rectangular, surface array electrode-amplifier and associated signal conditioning circuitry captures electromyogram (EMG) signals.

The embodiment has a rectangular array electrode-amplifier followed by a signal conditioning circuit. The signal conditioning circuit is generic, i.e., capable of receiving inputs from a number of different/interchangeable EMG/EKG/EEG electrode-amplifier sources (including from both monopolar and bipolar electrode configurations). The electrode-amplifier is cascaded with a separate signal conditioner minimizes noise and motion artifact by buffering the EMG signal near the source (the amplifier presents a very high impedance input to the EMG source, and a very low output impedance); minimizes noise by amplifying the EMG signal early in the processing chain (assuming the electrode-amplifier includes signal gain) and minimizes the physical size of this embodiment by only including a first amplification stage near the body. The signals are digitized and transmitted over a wireless network such as WiFI, Zigbee, or Bluetooth transceivers and processed by the base station that is remote from the patient. For either high-resolution monopolar arrays or classical bipolar surface electrode-amplifiers, the output of the electrode-amplifier is a single-ended signal (referenced to the isolated reference). The electrode-amplifier transduces and buffers the EMG signal, providing high gain without causing saturation due to either offset potentials or motion artifact. The signal conditioning circuit provides selectable gain (to magnify the signal up to the range of the data recording/monitoring instrumentation, high-pass filtering (to attenuate motion artifact and any offset potentials), electrical isolation (to prevent injurious current from entering the subject) and low-pass filtering (for anti-aliasing and to attenuate noise out of the physiologic frequency range).

FIGS. 17B and 17C shows exemplary sEMG outputs from a differential amplifier to detect muscle strength. FIG. 17B shows the left and right body EMG signals for the patient in a normal state, while FIG. 17C illustrates a patient with degraded muscle capability. In general, muscle fire in a smooth fashion in normal individuals, with little irritability or fasiculation. Muscles fire symmetrically in healthy state when comparing left and right sides in motion. In general, healthy patients show a greater consistency in muscle patterns than injured patients, with the injured showing a greater increase in variability. Such variations are detected by EMG analyzers.

The EMG signal can be rectified, integrated a specified interval of and subsequently forming a time series of the integrated values. The system can calculate the root-mean-squared (rms) and the average rectified (avr) value of the EMG signal. The system can also determine muscle fatigue through the analysis of the frequency spectrum of the signal. The system can also assess neurological diseases which affect the fiber typing or the fiber cross-sectional area of the muscle. Various mathematical techniques and Artificial Intelligence (AI) analyzer can be applied. Mathematical models include wavelet transform, time-frequency approaches, Fourier transform, Wigner-Ville Distribution (WVD), statistical measures, and higher-order statistics. AI approaches towards signal recognition include Artificial Neural Networks (ANN), dynamic recurrent neural networks (DRNN), fuzzy logic system, Genetic Algorithm (GA), and Hidden Markov Model (HMM).

A single-threshold method or alternatively a double threshold method can be used which compares the EMG signal with one or more fixed thresholds. The embodiment is based on the comparison of the rectified raw signals and one or more amplitude thresholds whose value depends on the mean power of the background noise. Alternatively, the system can perform spectrum matching instead of waveform matching techniques when the interference is induced by low frequency baseline drift or by high frequency noise.

EMG signals are the superposition of activities of multiple motor units. The EMG signal can be decomposed to reveal the mechanisms pertaining to muscle and nerve control. Decomposition of EMG signal can be done by wavelet spectrum matching and principle component analysis of wavelet coefficients where the signal is de-noised and then EMG spikes are detected, classified and separated. In another embodiment, principle components analysis (PAC) for wavelet coefficients is used with the following stages: segmentation, wavelet transform, PCA, and clustering. EMG signal decomposition can also be done using non-linear least mean square (LMS) optimization of higher-order cumulants.

Time and frequency domain approaches can be used. The wavelet transform (WT) is an efficient mathematical tool for local analysis of non-stationary and fast transient signals. One of the main properties of WT is that it can be implemented by means of a discrete time filter bank. The Fourier transforms of the wavelets are referred as WT filters. The WT represents a very suitable method for the classification of EMG signals. The system can also apply Cohen class transformation, Wigner-Ville distribution (WVD), and Choi-Williams distribution or other time-frequency approaches for EMG signal processing.

In Cohen class transformation, the class time-frequency representation is particularly suitable to analyze surface myoelectric signals recorded during dynamic contractions, which can be modeled as realizations of nonstationary stochastic process. The WVD is a time-frequency that can display the frequency as a function of time, thus utilizing all available information contained in the EMG signal. Although the EMG signal can often be considered as quasi-stationary there is still important information that is transited and may be distinguished by WVD. Implementing the WVD with digital computer requires a discrete form. This allows the use of fast Fourier transform (FFT), which produces a discrete-time, discrete-frequency representation. The common type of time frequency distribution is the Short-time Fourier Transform (STFT). The Choi-Williams method is a reduced interference distribution. The STFT can be used to show the compression of the spectrum as the muscle fatigue. The WVD has cross-terms and therefore is not a precise representation of the changing of the frequency components with fatigue. When walls appear in the Choi-William distribution, there is a spike in the original signal. It will decide if the walls contain any significant information for the study of muscle fatigue. In another embodiment, the autoregressive (AR) time series model can be used to study EMG signal. In one embodiment, neural networks can process EMG signal where EMG features are first extracted through Fourier analysis and clustered using fuzzy c-means algorithm. Fuzzy c-means (FCM) is a method of clustering which allows data to belong to two or more clusters. The neural network output represents a degree of desired muscle stimulation over a synergic, but enervated muscle. Error-back propagation method is used as a learning procedure for multilayred, feedforward neural network. In one implementation, the network topology can be the feedforward variety with one input layer containing 256 input neurodes, one hidden layer with two neurodes and one output neurode. Fuzzy logic systems are advantageous in biomedical signal processing and classification. Biomedical signals such as EMG signals are not always strictly repeatable and may sometimes even be contradictory. The experience of medical experts can be incorporated. It is possible to integrate this incomplete but valuable knowledge into the fuzzy logic system, due to the system's reasoning style, which is similar to that of a human being. The kernel of a fuzzy system is the fuzzy inference engine. The knowledge of an expert or well-classified examples are expressed as or transferred to a set of "fuzzy production rules" in the form of IF-THEN, leading to algorithms describing what action or selection should be taken based on the currently observed information. In one embodiment, higher-order statistics (HOS) is used for analyzing and interpreting the characteristics and nature of a random process. The subject of HOS is based on the theory of expectation (probability theory).

In addition to stroke detection, EMG can be used to sense isometric muscular activity (type of muscular activity that does not translate into movement). This feature makes it possible to define a class of subtle motionless gestures to control interface without being noticed and without disrupting the surrounding environment. Using EMG, the user can react to the cues in a subtle way, without disrupting their environment and without using their hands on the interface. The EMG controller does not occupy the user's hands, and does not require them to operate it; hence it is "hands free". The system can be used in interactive computer gaming which would have access to heart rate, galvanic skin response, and eye movement signals, so the game could respond to a player's emotional state or guess his or her level of situation awareness by monitoring eye movements. EMG/EEG signal can be used for man-machine interfaces by directly connecting a person to a computer via the human electrical nervous system. Based on EMG and EEG signals, the system applies pattern recognition system to interpret these signals as computer control commands. The system can also be used for Mime Speech Recognition which recognizes speech by observing the muscle associated with speech and is not based on voice signals but EMG. The MSR realizes unvoiced communication and because voice signals are not used, MSR can be applied in noisy environments; it can support people without vocal cords and aphasics. In another embodiment, EMG and/or electroencephalogram (EEG) features are used for predicting behavioral alertness levels. EMG and EEG features were derived from temporal, frequency spectral, and statistical analyses. Behavioral alertness levels were quantified by correct rates of performance on an auditory and a visual vigilance task, separately. A subset of three EEG features, the relative spectral amplitudes in the alpha (alpha %, 8-13 Hz) and theta (theta %, 4-8 Hz) bands, and the mean frequency of the EEG spectrum (MF) can be used for predicting the auditory alertness level.

In yet a further embodiment for performing motor motion analysis, an HMM is used to determine the physical activities of a patient, to monitor overall activity levels and assess compliance with a prescribed exercise regimen and/or efficacy of a treatment program. The HMM may also measure the quality of movement of the monitored activities. For example, the system may be calibrated or trained in the manner previously described, to recognize movements of a prescribed exercise program. Motor function information associated with the recognized movements may be sent to the server for subsequent review. A physician, clinician, or physical therapist with access to patient data may remotely monitor compliance with the prescribed program or a standardized test on motor skill. For example, patients can take the Wolf Motor Function test and acceleration data is captured on the following tasks:

placing the forearm on a table from the side
moving the forearm from the table to a box on the table from the side
extending the elbow to the side
extending the elbow to the side against a light weight
placing the hand on a table from the front
moving the hand from table to box
flexing the elbow to retrieve a light weight
lifting a can of water
lifting a pencil, lifting a paper clip
stacking checkers, flipping cards
turning a key in a lock
folding a towel
lifting a basket from the table to a shelf above the table.

Figure 19:
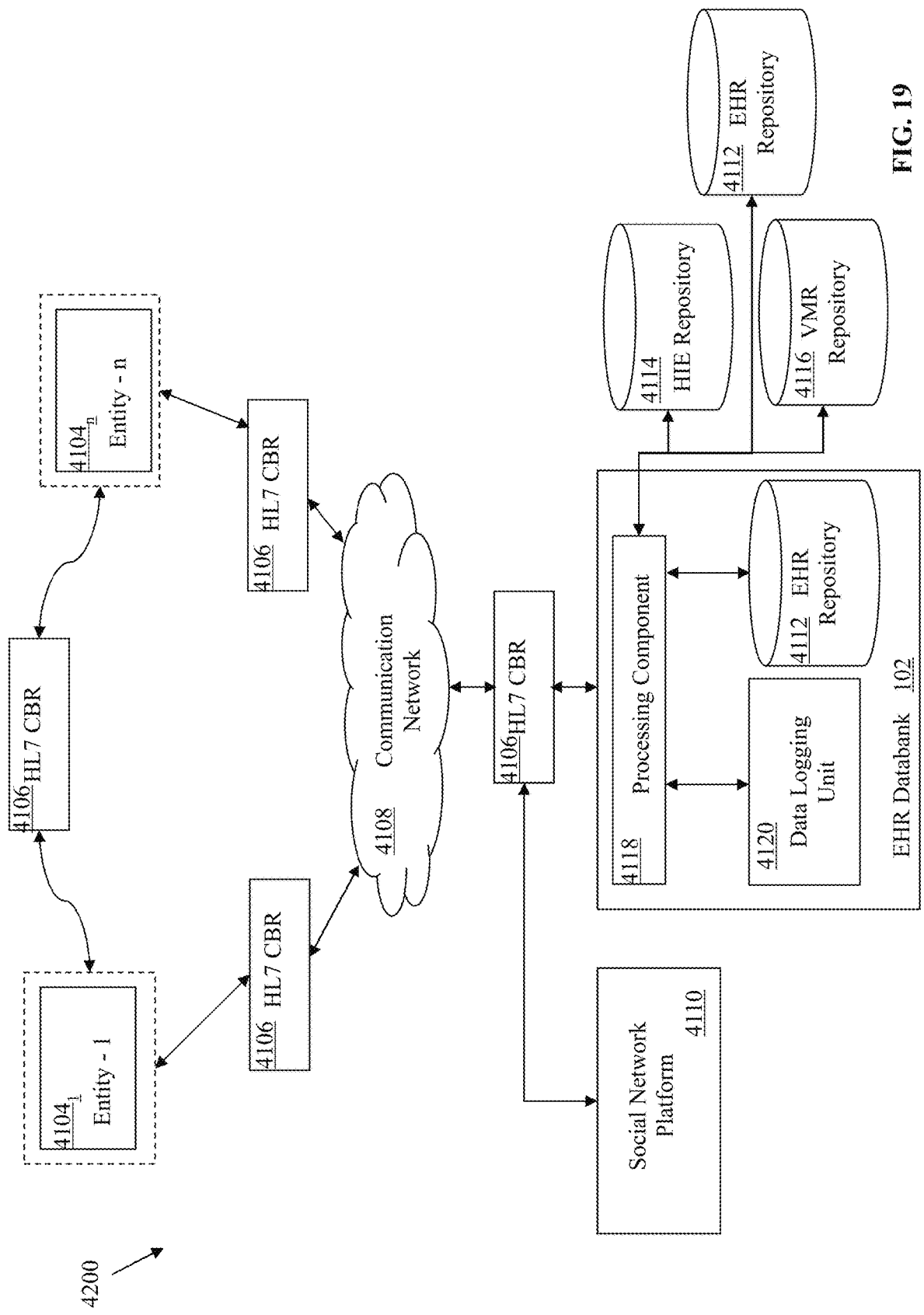
FIG. 19 is a schematic diagram illustrating generally, among other things, an example of portions of a system for implementing a respective HL7 CBR at gateways of organizations, in accordance to embodiments disclosed herein.

In an embodiment, the one or more entities 4104 described herein may be for example, but not limited to, an Implantable Medical Device (IMD), a programming device, a hospital, a clinic, a medical organization, a physician's office, a clinical data provider, or the like. In an embodiment, the HL7 CBR 4106 may be configured to be associated with a database or data storage over the communication network 4108. In an embodiment, the HL7 CBR 4106 may be configured to include a local internal interface to handle direct links to communicate with other nodes. In an embodiment, a respective HL7 CBR 4106 may be configured to be situated at a gateway of the organization such as the one or more entities 4104, a network platform 4110, or the EHRDB 4102 to communicate among each other over the communication network 4108 as shown in FIG. 19. In an embodiment, a common HL7 CBR 4106 may be configured at the endpoint or gateway of the EHRDB 4102, such that the EHRDB 4102 may exchange, integrate, share, receive, or provide data to/from the nodes such as the one or more entities 4104 or the network platform 4110. In an embodiment, the HL7 CBR 4106 may be configured to collect data from the one or more entities 4104 (For example, the IMD and programmers) and convert or normalize the data in a common format such as in accordance with the HL7 standard. The data, within the communication network, between the HL7 CBR 4106 and other devices may comply with the common format. Further, the data may be validated according to a single standard or mechanism (For example, the HL7 standard).

In an embodiment, the HL7 CBR 4106 may be configured to normalize the data received from the one or more entities 4104 to a predetermined standard or a common format. For example, data received or captured by the one or more entities 4104 may be stored as elements linked to the original data of the electronic medical records. In an embodiment, the data received from the entities such as the IMD (which may in machine language) may also be stored as elements linked to the original data of the electronic medical records. In preferred embodiments, the captured elements may be normalized by associating to a standard or a common format. In an embodiment, the HL7 CBR 4106 may be configured to associate the data elements to a predetermined set of medical terms corresponding to the captured data elements. In an embodiment, such normalization may facilitate searching using the natural language queries provided by the one or more entities 4104. For example, if an entity such as medical professional or doctor uses a word or phrase to retrieve the corresponding information then the EHRDB 4102 may be configured to use only a single term or equivalent to the word or phrase, in order to automatically identify the corresponding metadata information. In an embodiment, the EHRDB 4102 may be configured to optionally confirm or verify the normalized data, such as by a physician or clinician.

In an embodiment, the HL7 standard described herein may provide a framework for the exchange, integration, sharing, or retrieval of electronic health information from/to the EHRDB 4102 by using natural language queries. In an embodiment, the HL7 standard may also be used to refer to some of the specific standards such as HL7 v2.x, v3.0, HL7 Reference Information Model (RIM), and the like, created by the organization. Likewise, in an embodiment, the one or more entities 4104 may interact with other entities via the HL7 CBR 4106 to exchange data among each other.

In an embodiment, the communication network 4108 described herein may be configured to provide a communicative interconnection of various nodes (For example, the one or more entities 4104, the EHRDB 4102, the network platform 4110, or any other node) such that the system 4100 may easily create and manage the metadata. In an embodiment, the communication network 4108 may be configured to facilitate the various nodes to exchange, integrate, share, receive, or provide data among each other in accordance with the HL7 standard implemented by the respective HL7 CBR 4106 (which may be configured at the endpoint or at the gateway of the organization).

In an embodiment, the communication network 4108 described herein may include one or more wireless communications network or one or more wire line communications network. The wireless communications network may include for example, but not limited to, a digital cellular network, such as Global System for Mobile Telecommunications (GSM) network, Personal Communication System (PCS) network, or any other wireless communications network. The wire line communications network may include for example, but not limited to, the Public Switched Telephone Network (PSTN), proprietary local and long distance communications network, or any other wire line communications network. In an embodiment, one or more networks may be included in the communication network and may include both public networks and private networks. The communication network may utilize any networking technology and protocol, (for example, Ethernet, Token Ring, Transmission Control Protocol/Internet Protocol (TCP/IP), or the like) to allow interaction among various nodes such as the one or more entities 4104, the EHRDB 4102, the network platform 4110, or any other node in the network 4108.

In an embodiment, where a common HL7 CBR 4106 may be configured at the gateway of the EHRDB 4102, the communication network 4108 may be configured to convert or normalize the data at the common HL7 CBR 4106 such that the system 4100 may exchange, integrate, share, receive, or provide data to or from the various nodes. In an embodiment, the common HL7 CBR 4106 may comply with the common data format and may be validated, such as when the information first enters the EHRDB 4102, according to the single standard or mechanism (for example, the HL7 standard).

In an embodiment, the EHRDB 4102, described herein, may be centralized or decentralized. The EHRDB 4102 may be configured to store the clinical data or information provided by the one or more entities 104 in an EHR repository 4112. The EHRDB 4102 may be configured to communicate with different nodes such as the one or more entities 4104 (for example, clinical data providers, IMDs, programmer devices), the network platform 4110, the EHR repository 4112, Health Information Exchange (HIE) repository 4114, Virtual Medical Records (VMR) repository 4116, or the like to exchange, integrate, share, receive, or provide data via the HL7 CBR 4106. In an embodiment, the EHR repository 4112 may be configured to store the data (for example, an electronic healthcare record). In an embodiment, the data may be organized in a way that facilitates local or remote information management in the communication network 4108 through a processing component 4118. In some embodiments, the processing component 4118 may be, but not limited to, a microprocessor, a microcontroller, or equivalent. The processing component 4118 may be capable of executing instructions to process data over the network 4108. In an embodiment, the data described herein may correspond to the user's (or patient) that may or may not have been derived from medical testing or treatment (e.g., the data may have been derived from a research organization trial in which the individual voluntarily participated or the data may have been derived from insurance services or the real time data derived from the IMD implanted in a patient, or any other sources).

In an embodiment, the EHRDB 4102 may be configured to include data related to different electronic sources such as IMD data, external programmers, patient credentials, doctor's visits, lab tests, hospital stays, clinical trials, patient problems, patients health information, patient habits, patient medical history, patient appointments, patient medical insurance, patient medical bills status, or any other information. In an embodiment, the EHRDB 4102 may also include or couple to other electronic data sources such as the HIE repository 4114 and the VMR repository 4116 to dynamically manage information related to/from the electronic sources. In an embodiment, the HIE repository 4114 may include electronic healthcare information related to a region, community, or hospital system. In an embodiment, the HIE repository 4114 may provide additional storage, retrieval, and manipulation of health information such that the EHRDB 4102 may dynamically mange the EHR data via the HL7 CBR 4106. Some of the advantages of the HIE repository 4114 can include, for example, cross-community clinical summary sharing, cross-community referral management, electronic data access to community wide clinical data, community wide clinical summary viewer, medication history service, image exchange service, vendor-neutral EMR integration, results delivery service, and interoperability profiles and standards.

In an embodiment, the VMR repository 4116 described herein may store data related to the electronic medical information or other sources. The virtual medical records described herein may be a simplified, standardized electronic health record data designed to support interfacing to the EHRDB 4102 such that the present invention may allow the one or more entities 4104 to access the information via the natural language queries.

In an embodiment, the EHRDB 4102 may be configured to include a data logging unit 4120. The data logging unit 4120 may be configured to track a unique network identifier associated with the HL7 CBR 4106. The data or the piece of information received from the respective HL7 CBR 4106 may be uniquely identified via a local identifier associated with the data. In an embodiment, the identifier described herein may be predetermined. In an embodiment, a common metadata configuration may be maintained by the data logging unit 4120 for the data received from the respective HL7 CBR 4106. More detailed information related to the data logging unit 4120 is described in FIG. 3.

FIG. 19 is a schematic diagram illustrating generally, among other things, an example of portions of a system 4200 in which a respective HL7 CBR 4106 may be configured at the gateway of the organization, in accordance to embodiments disclosed herein. In an embodiment, the respective HL7 CBR 4106 may be configured at the gateway of the organization. The respective HL7 CBR 4106 may be situated at the gateways of the one or more entities 4104, a network platform 4110, or the EHRDB 4102 to communicate among each other over the communication network 4108. In an embodiment, the respective HL7 CBR 4106 may be configured to be situated at the one or more entities endpoints, the network platform endpoints, or the EHRDB endpoints to communicate among each other. In an embodiment, the data logging unit 4120 may be configured to maintain a common metadata configuration for the data received from the respective HL7 CBR 4106. In an embodiment, the HL7 CBR 4106 may be configured to support one or more communications, for example, broadcast communications to other content-based routers in the network, directly routed communications to other content based routers, third party routed communications with other content based routers in the network.

Figure 18:
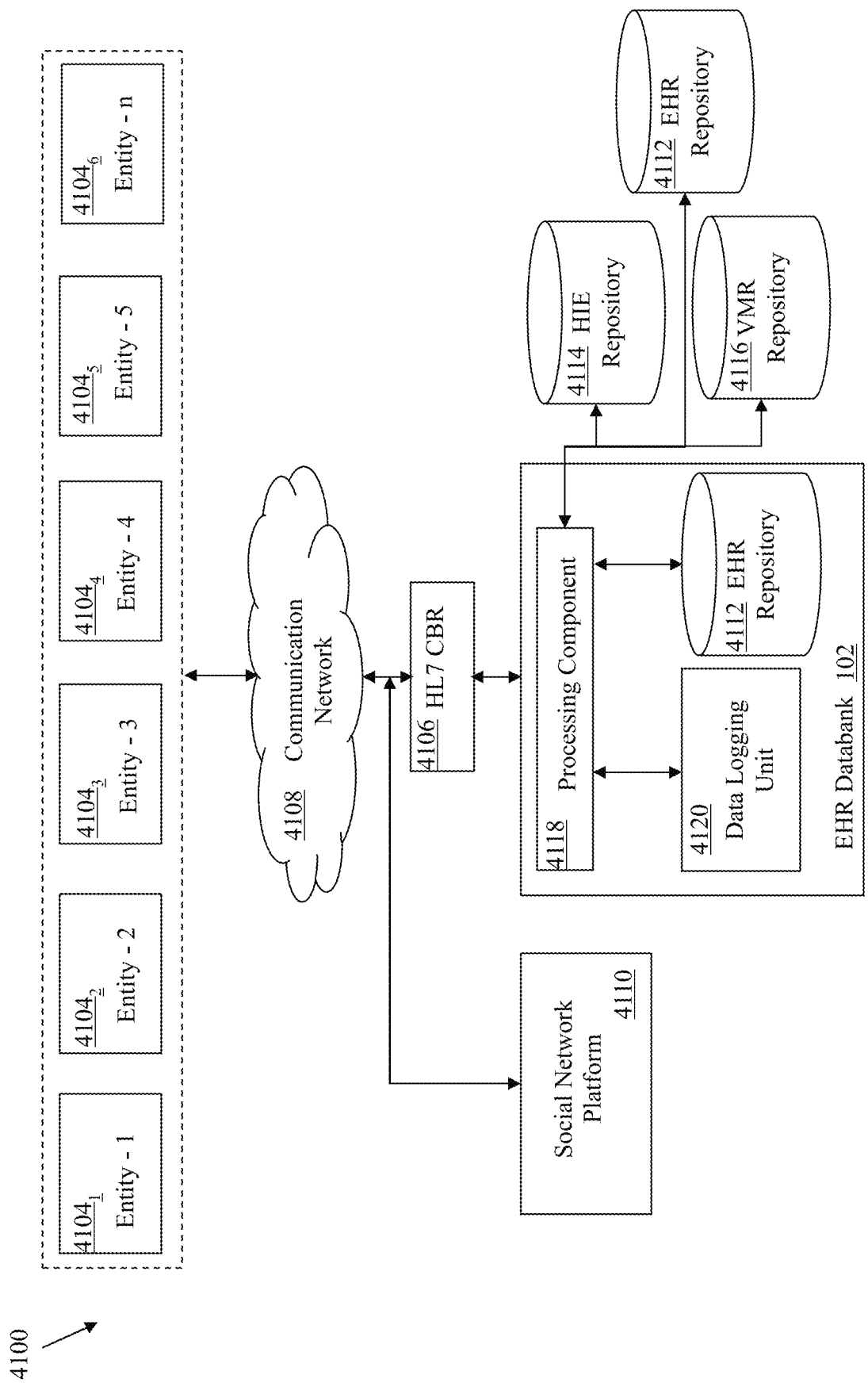
FIG. 18 is a schematic diagram illustrating generally, among other things, an example of portions of a system for implementing natural language or machine data processing capabilities, in accordance to embodiments disclosed herein.
Figure 20:
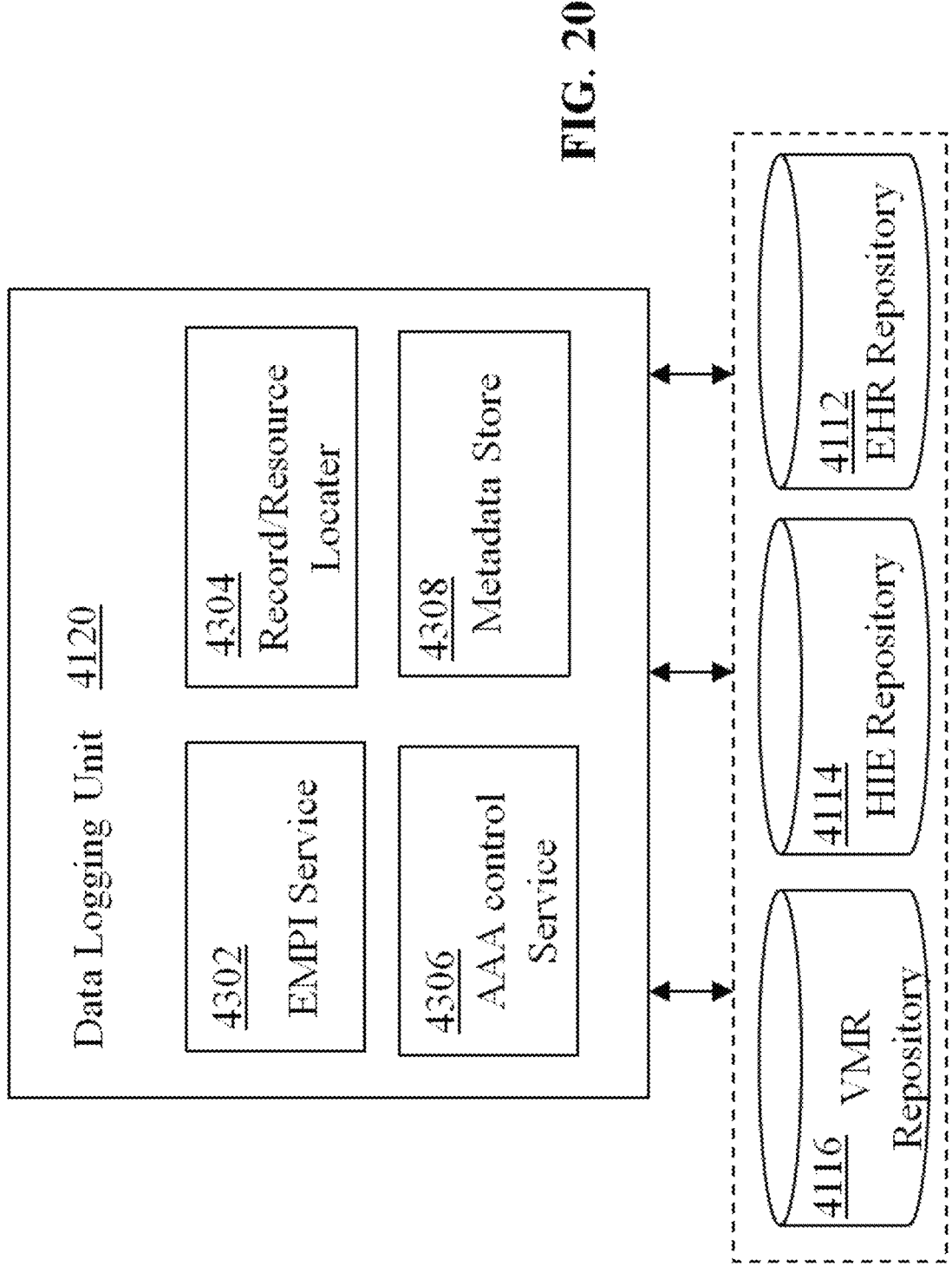
FIG. 20 is a diagram illustrating generally, among other things, a detailed structure of data logging unit, in accordance to embodiments disclosed herein.

FIG. 20 is a diagram illustrating generally, a detailed structure of the data logging unit 4120 as described in the FIG. 18. In an embodiment, the data logging unit 4120 may be configured to maintain an Enterprise Master Patient Index (EMPI) service 4302, a Record or Resource Locater 4304, an AAA (Authentication, Authorization, and Accounting) control service 4306, and a metadata store 4308 to facilitate the NLP capabilities.

In an embodiment, the EMPI service function(s) may be configured to receive the patient's identifier from the respective HL7 CBR 4106, EHR repository 4112, HIE repository 4114, or VMR repository 4116 to help it identify and locate the appropriate records data. In an embodiment, the information about the EMPI is configured to define, use, and interpret the metadata across the system 4100. In an embodiment, the term "metadata" may be composed of the data concerning the one or more entities 4104. For example, the one or more entities identifier data may send the EHRDB 4102 the address where the entity is located, a description data of the one or more entities 4104, and other pertinent data. In an embodiment, a common metadata configuration may be maintained by the data logging unit 4120 for the data received from the respective HL7 CBR 4106. Further, the data logging unit 4120 may be configured to maintain a common way to represent HL7 CBR data in the metadata store 4308. In an embodiment, each of the HL7 CBR 4106 nodes may be configured to describe certain information to define the metadata, which may be configured at deployment time of the HL7 CBR 4106. In an embodiment, the data logging unit 4120 may be configured to populate the metadata store 308 in accordance with each HL7 CBR identifier, name, or any other mechanism, that may uniquely identify the entities through which the data being received by each of the HL7 CBR 4106.

In an embodiment, the data logging unit 4120 may be configured to define the metadata configuration in accordance with the HL7 CBR identifier. An example of such metadata may be, Title: metadata HL7 CBR, Identifier: govthealthcare.com, format: HL7 Standard, Entity: IMD. The EHRDB 4102 may be configured to store the defined metadata in the metadata store 308 to facilitate the NLP capabilities. In an embodiment, the data logging unit 4120 may be configured to define the metadata for the data received from the database of the entities 4104 (for example, clinical data providers). In an embodiment, such clinical data provider may implement a common set of routines (or classes) to connect to the database via the JDBC-ODBC drivers (Java Database Connectivity and Open Database Connectivity Drivers) to provide the clinical data. The JDBC-ODBC database drivers described herein are only for illustrative purpose, in real-time there may be other database drivers such as Structured Query Language (SQL), Oracle, or any other database drivers to connect to the database. An example of such metadata defined from the clinical data providers databases may be, Title: metadata HL7 CBR, Identifier: govthealthcare.com, format: HL7 Standard, Entity: Clinical data provider, Connection: JDBC drivers. In an embodiment, the metadata store 308 may store such metadata learned from the database drivers to facilitate the NLP capabilities.

In an embodiment, the data logging unit 4120 may be configured to define the metadata using the Get( ) method from the HL7 CBR 4106 and provide the data to the HL7 CBR 4106 using the Put( ) method. In an example, the metadata is defined from the one or more entities as shown below as a piece of code.

class JDBCDatabaseMetaDataExample
// Create a connection object on the database
Connection con=JDBCDriver.connect("jdbc:odbc:Database");
// Load the database drivers
Class.forName("sun.jdbc.odbc.JdbcOdbcDriver");
// Get a connection to the database via the database drivers
Connection con=DriverManager.getConnection("jdbc:odbc:Database")
//Metadata configuration data retrieval from the database drivers
DatabaseMetaData metaData=con.getMetaData( )
ResultSet rs=metaData.getTypeInfo( );
//Query statements for metadata information from the database drivers
ResultSet resultSet=st.executeQuery("SELECT*FROM database");
ResultSetMetaData md=resultSet.getMetaData( )

In an embodiment, the data logging unit 4120 may be configured to deploy the metadata configuration as a separate schema into either a directly attached EHRDB 4102 or the shared data repositories such as EHR repository 4112, HIE repository 4114, or the VMR repository 4116, supported by the overall EHRDB deployment. In an embodiment, the EHRDB 4102 may be configured to provide NLP capabilities in accordance with the defined metadata configuration learned from the one or more entities 4104 and the HL7 CBR 4106.

In an embodiment, the data logging unit 4120 may be configured to implement an XML structuring techniques to search the data based on the natural language queries received form the one or more entities 4104. In an embodiment, the system 4100 may be configured to implement XML structures for the information received from the one or more entities 4104 such as to respond to the natural language queries. In preferred embodiments, the XML structures described herein may contain both structural and content constraint of the one or more entities 4104. In an embodiment, the system 4100 may be configured to parse and detect natural language query structural and content constraints and identify the desired entity data. In an embodiment, the system 4100 may be configured to map the structural and content constraint with the corresponding XML tags such as to identify and respond to the desired entity data.

In an embodiment, the data logging unit 4120 may be configured to implement active ontology techniques to actively use the data received from the one or more entities 4104 such as to provide NLP capabilities. In an embodiment, the active ontology described herein may serve as a unifying infrastructure that integrates models, components, or data from other parts of embodiments of the system 4100. In general, in the field of computer and information science, the ontology may provide structures for representation of the data received from the one or more entities 4104. The system 4100 may be configured to represent the data in the form of classes, types, relations, attributes or properties, and their instantiation to process the natural language queries.

In an embodiment, the record or resource locater 4304 may be configured to actively locate the electronic medical records. In an embodiment, the AAA control service 4306 or security technologies may be implemented thereon to store or track currently effective or past data or authorizations provided by, or on behalf of, or relating to different entities. In an embodiment, the EHRDB 4102 may be configured to use the security technologies to validate the information received from the one or more entities 4104. In an embodiment, the EHRDB 4102 may use the security technologies to validate the metadata defined by the one or more entities 4104.

Figure 21:
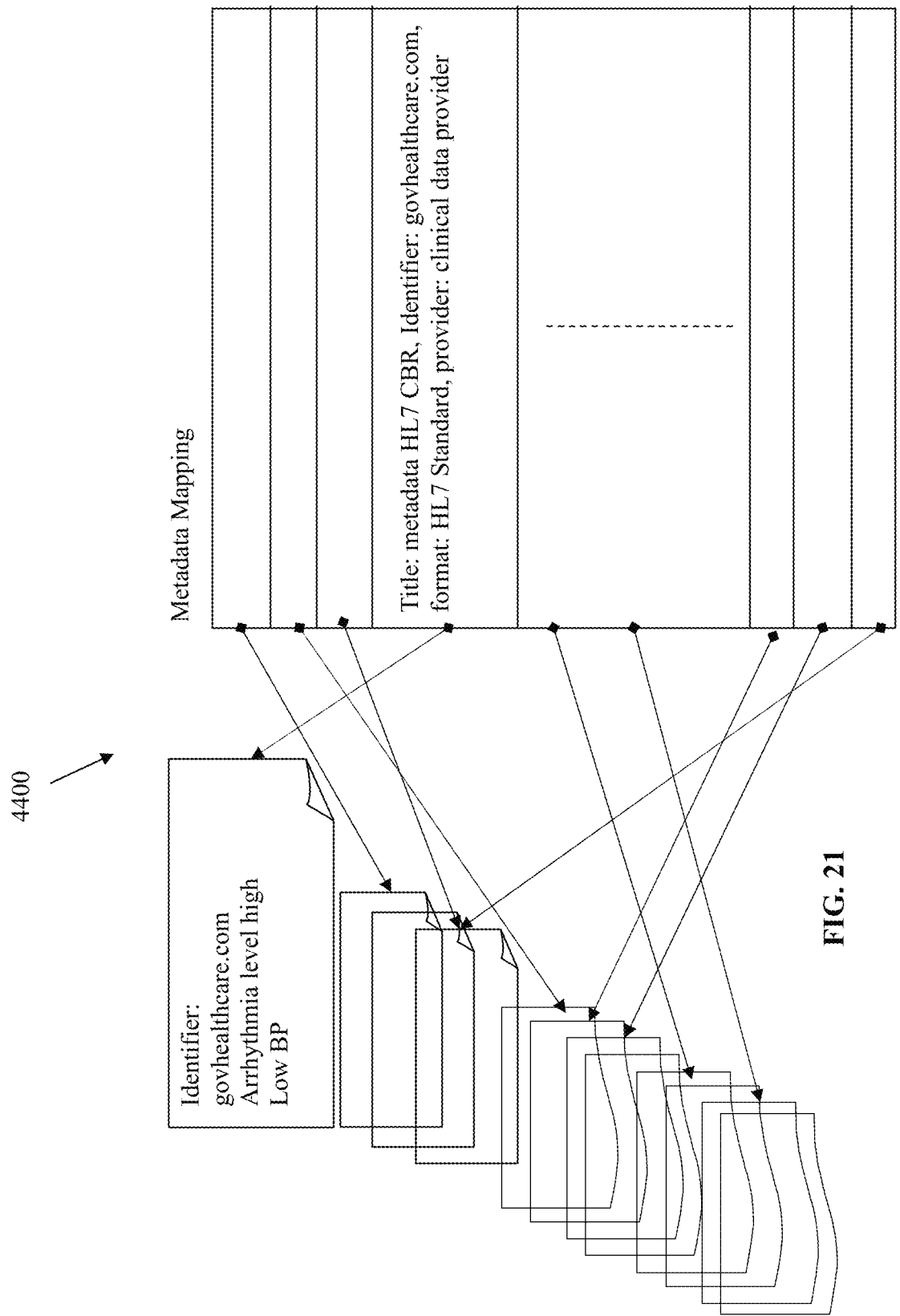
FIG. 21 is a diagram illustrating generally, among other things, an example of portions of a system for defining and mapping a metadata for clinical data received from entities, in accordance to embodiments disclosed herein

FIG. 21 is a diagram illustrating generally, among other things, an example of portions of a system 4400 for defining and mapping a metadata for the clinical data received from the one or more entities 4104 in accordance to an exemplary embodiment of the present invention. The system 4400 may be configured to capture information from the one or more entities 4104. In an embodiment, the EHRDB 4102 may be configured use the entity identifier to define the metadata for the information received from the one or more entities 4104. In an embodiment, upon receiving a natural language query from the one or more entities 4104, the EHRDB 4102 may uses the entity identifier to map the metadata in the metadata store 308 for requesting metadata information for the desired entity. In an embodiment, the natural language query described herein may include one or more keywords for requesting clinical data corresponding to the desired entity from the EHRDB 4102. In an embodiment, the identifier may be cross referenced with the proper information to identify the desired entity clinical data. In an embodiment, the EHRDB 4102 may be configured to address the desired information by using the entity identifier. In an embodiment, the EHRDB 4102 may be configured to provide the desired clinical information by using the desired uniform resource locator of the entity. In an embodiment, the EHRDB 4102 may be configured to store one or more entities 4104 credentials such that the system may easily define the metadata information upon receiving the clinical data from the one or more entities 4104.

Figure 22:
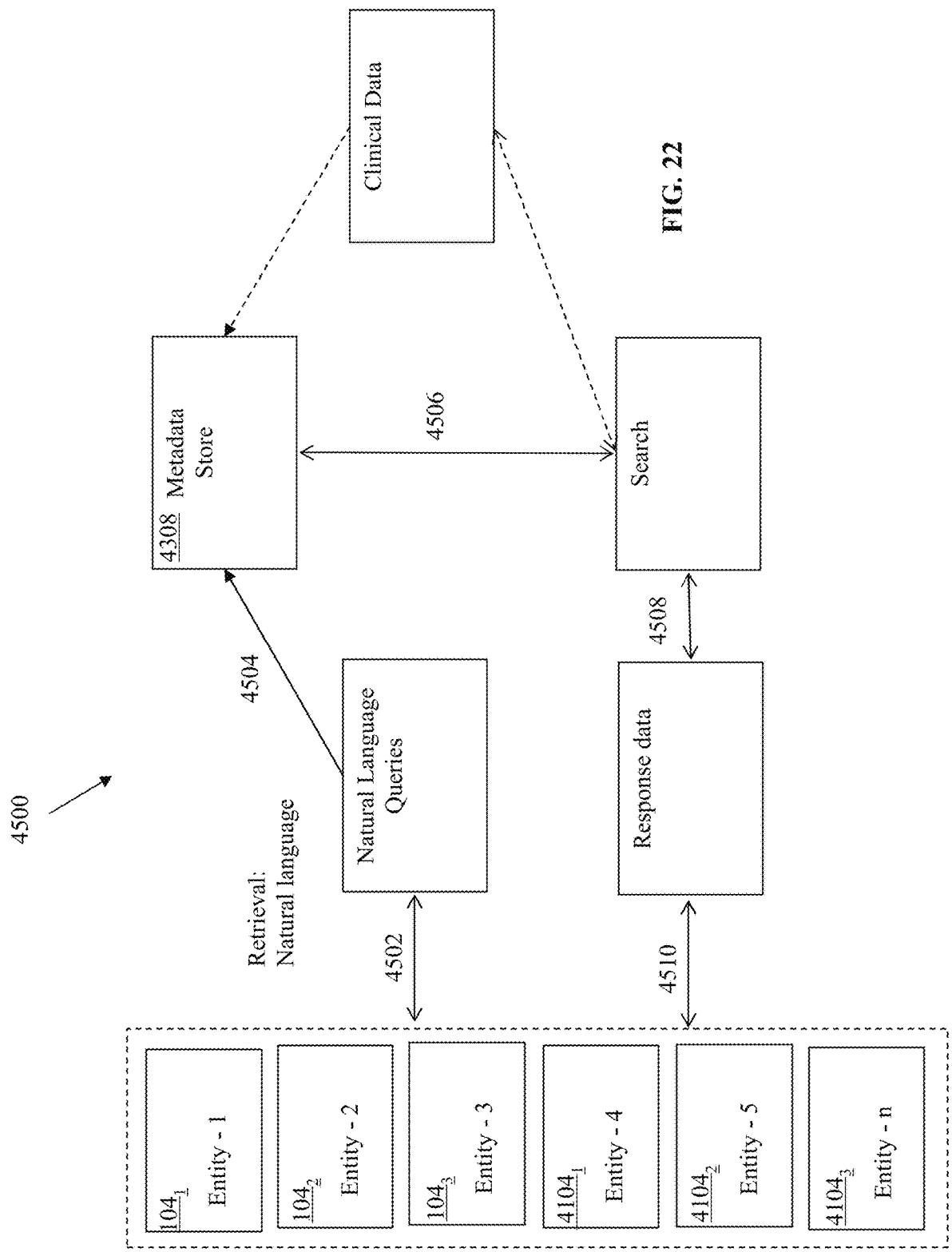
FIG. 22 is a diagram illustrating generally, among other things an example of a method for providing response to natural language queries received from entities, in accordance to embodiments disclosed herein.

FIG. 22 is a diagram illustrating generally, among other things, an example of a method 4500 for providing response to the natural language queries received from the one or more entities 4104, in accordance with the defined metadata information. In an embodiment, at 4502, the method 4500 may include receiving natural language queries from the one or more entities 4104 to access the clinical data associated with the desired entity. In an embodiment, the EHRDB 4102 may receive machine language queries from the one or more entities 4104. In an embodiment, at 4504, the method 4500 may include passing the entity identifier to perform database lookup. In an embodiment, the EHRDB 4102 may perform database lookup to look into the EHRDB 4102 and cross reference the entity identifier to find the corresponding metadata. In an embodiment, at 4506, the method 4500 may include parsing the natural language queries to identify the desired clinical data for the one or more entities 4104. In an embodiment, the EHRDB 4102 may parse the machine language queries to identify the desired clinical data for the one or more entities 4104. In an embodiment, the EHRDB 4102 may use the metadata information to process natural or machine language queries received from the one or more entities 4104. In an embodiment, at 4508, the EHRDB 4102 may generate one or more responses including the desired clinical data for the corresponding entity. In an embodiment, at 4510, the method 4500 may respond to the one or more entities 4104 in accordance with the natural or machine language queries received from the one or more entities 4104. In an embodiment, the query results may simply be reported in the user interface of a computer program of the one or more entities 4104, printed out in a report, or used by the physician on the programmer devices to configure therapy for the patients. In an embodiment, the query results may be exported in various formats such as text, HL7, XML, excel reports, or the like.

In an embodiment, for example, the EHRDB 4102 may capture the information from the entity such as IMD. In an embodiment, the data captured from the IMD may be in the machine language. In an embodiment, the EHRDB 4102, in communication with the HL7 CBR 4106, may normalize the captured data by associating it to a common format. In an embodiment, the EHRDB 4102, in communication with the HL7 CBR 4106, may associate the data elements to a predetermined set of medical terms corresponding to the captured data elements. In an embodiment, the EHRDB 4102 may then define the metadata configuration for the normalized information in accordance with the IMD identifier. An example of such metadata may be Title: metadata HL7 CBR, Identifier: PAT012-IMD21, format: HL7 Standard, Entity: IMD. In an embodiment, the EHRDB 4102 may capture the information from the database of the entities such as clinical data providers. In such cases the EHRDB 4102 may capture the information via the JDBC-ODBC drivers. In an embodiment, the EHRDB 4102, in communication with the HL7 CBR 4106, may then normalize the captured information in accordance to a common format. In an embodiment, the EHRDB 4102 may then define the metadata configuration for the normalized information in accordance with the clinical data provider identifier. An example of such metadata defined from the clinical data provider database may be, Title: metadata HL7 CBR, Identifier: nationalthealthcare.com, format: HL7 Standard, Entity: Clinical data provider, Connection: JDBC drivers.

In an embodiment, for example, the EHRDB 4102 may receive natural or machine language query from the one or more entities (such as doctor using the programmer device or any other clinician) to access the clinical data. The EHRDB 4102 may parse the queries to identify the keywords or data elements and map the identified keywords to the defined metadata. In an embodiment, the EHRDB 4102 may use the metadata configurations to process the natural language queries received from the one or more entities 4104. In an embodiment, the EHRDB 4102 may then generate one or more responses including the desired clinical data for the corresponding entity.

In an embodiment, for example, the EHRDB 4102 may broadcast the clinical data or may constantly send the clinical data, for defined number of intervals, to the one or more entities 4104. The EHRDB 4102, in communication with the HL7 CBR 4106, may convert the clinical data in the respective formats of the one or more entities 4104. In an embodiment, the HL7 CBR 4106 may convert the clinical data in the format as required by the one more entities. For example, if the entity is IMD then the HL7 CBR may convert the data in the machine language and provide to the IMD or if the entity is a computer device then the HL7 CBR may convert the data (such as in the form of an XML format, an excel report, HTML format, or any other format) as desired by the clinician.

Figure 23:
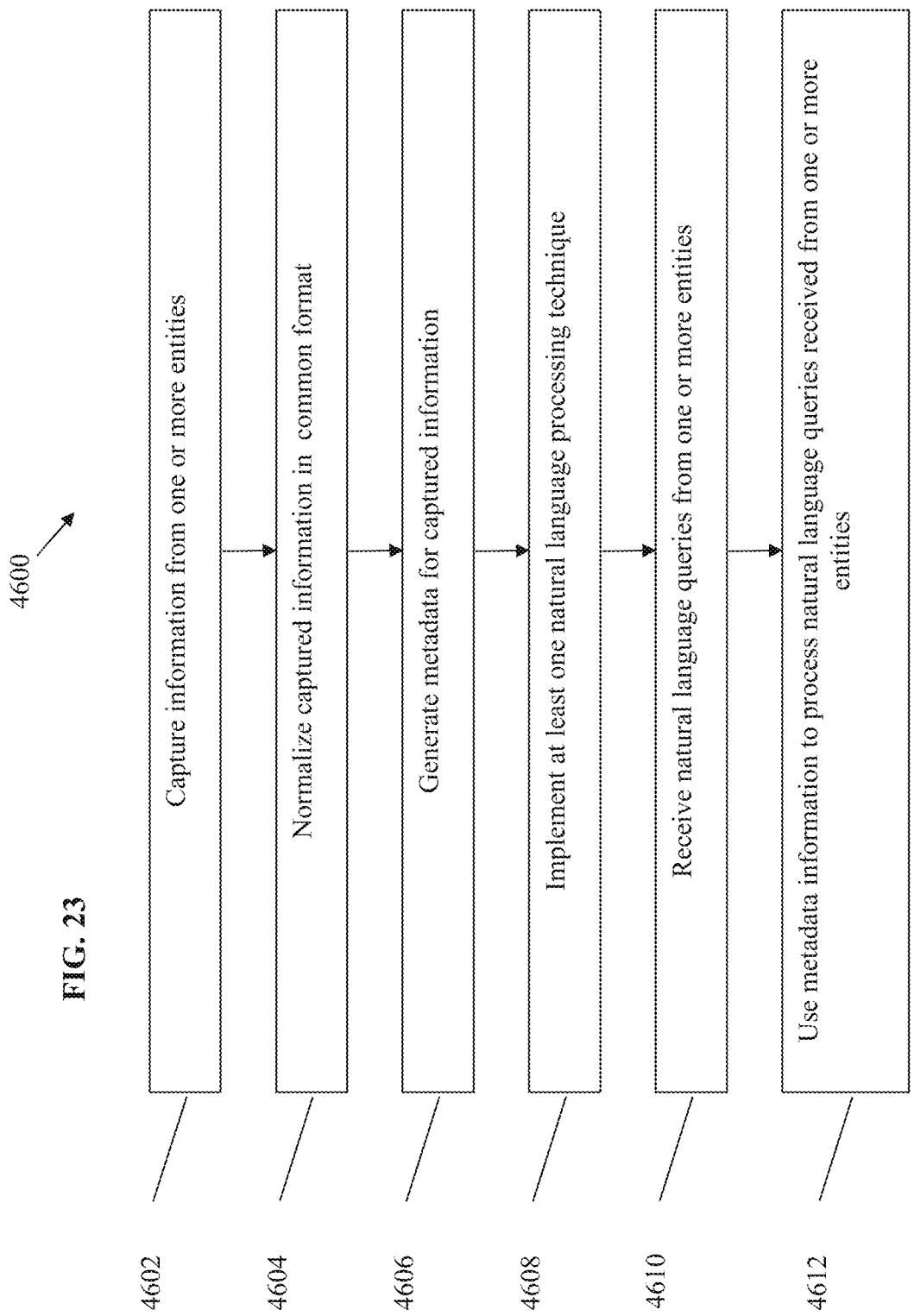
FIG. 23 is a flowchart illustrating generally, among other things an example of a method including natural language data processing capabilities, in accordance to embodiments disclosed herein.

FIG. 23 is a flowchart illustrates generally, among other things, an example of a method 4600 including natural language data processing capabilities, in accordance to embodiments disclosed herein. In an embodiment, at 4602, the method 4600 may include capturing information from the one or more entities 4104. In an embodiment, the information received from the one or more entities 4104 may corresponds to different information standards. At 4604, the method 4600 may include normalizing the captured information in a common format. In an embodiment, the information may be normalized using the one or more HL7 CBRs 4106. In an embodiment, the captured data may be normalized by associating to a standard or a common format. In an embodiment, the method 4600 may allow the HL7 CBR 4106 to associate the captured data to a predetermined set of medical terms corresponding to the captured data. In an embodiment, such normalization may facilitate searching using the natural language queries provided by the one or more entities 4104.

In an embodiment, the method 4600 may include validating information received from the one or more entities 4104. In preferred embodiments, the act of normalizing the information may be performed before the act of validating the information. At 4606, the method 4600 may include generating metadata for the captured information. In an embodiment, the act of generating the metadata information may include extracting an identifier associated with the one or more entities 4104. In an embodiment, the identifier described herein may be predetermined.

At 4608, the method 4600 may include implementing natural language processing technique. In an embodiment, the natural language processing techniques described herein may be a metadata based natural language processing, XML structuring, and active ontology technique. In an embodiment, XML structures may be implemented for the information received from the one or more entities 4104 such as to respond to the natural language queries. In an embodiment, the method 4600 may include parsing and detecting natural language query structural and content constraints to identify the desired entity data. In an embodiment, the method 4600 may include mapping the structural and content constraint to the corresponding XML tags s to identify and respond to the desired entity data. In an embodiment, the active ontology may serve as a unifying infrastructure that integrates models, components, or data of the one or more entities 4104. In an embodiment, the method 4600 may include representing the data received from the one or more entities 4104 in the form of classes or types, relations, attributes or properties using the active oncology to process the natural language queries. In an embodiment, the method 4600 may implement any other natural language processing technique.

At 4610, the method 4600 may include receiving natural language queries from the one or more entities 4104. In an embodiment, the EHRDB 4102 may receive the machine language queries from the one or more entities 4104. In an embodiment, the method 4600 may include parsing the queries to map to the desired metadata information in the metadata store 4308. In an embodiment, at 4612, the method 4600 may include using metadata information to process the natural or machine language queries received from the one or more entities 4104. In an embodiment, the query results may simply be reported in the user interface of a computer program of the one or more entities 4104, printed out in a report, or used by the physician on the programmer devices such as to configure therapy for the patients. In an embodiment, the query results may be exported in various formats such as text, HL7, XML, excel reports, or the like.

Figure 24:
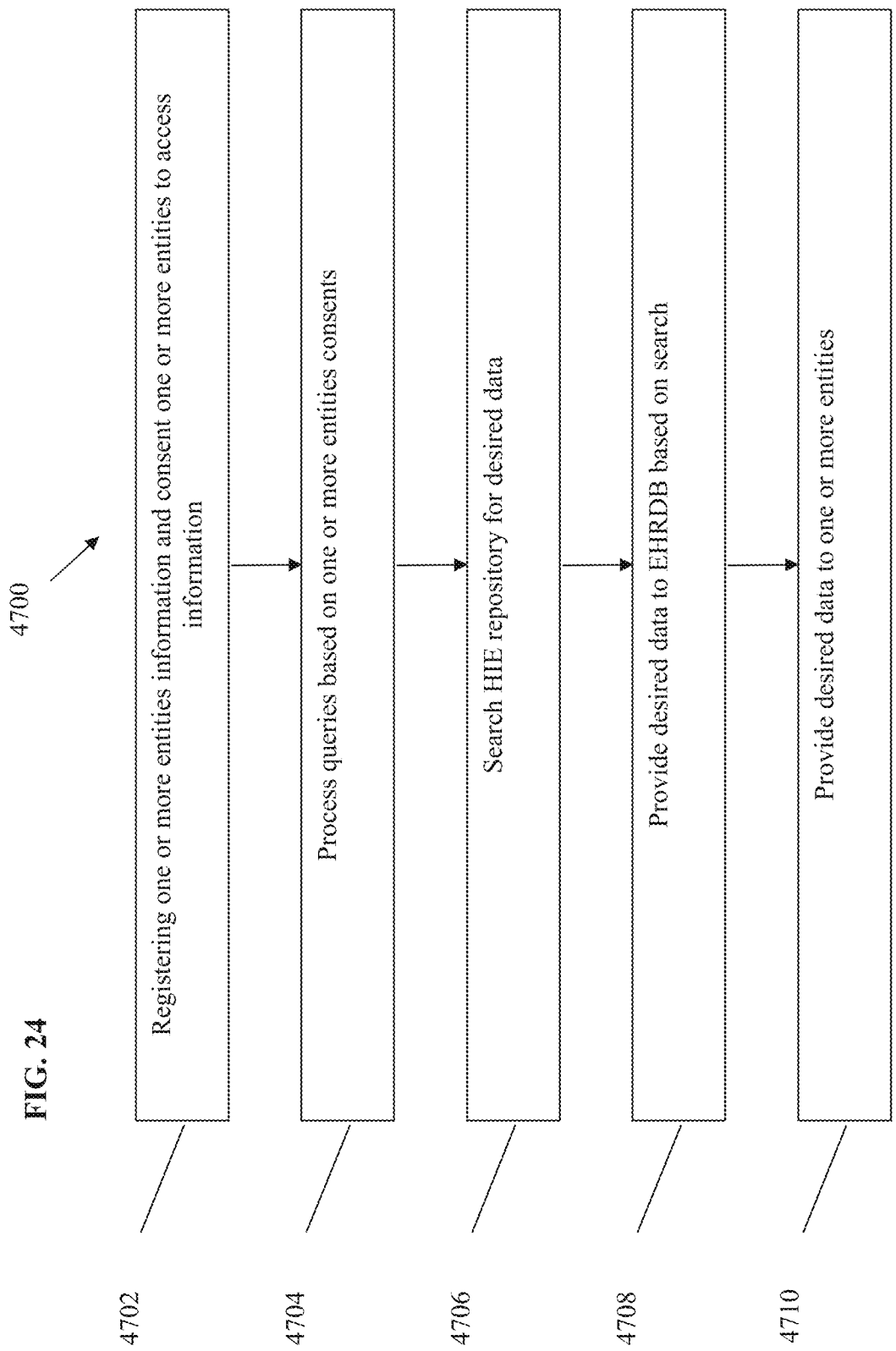
FIG. 24 is a flowchart illustrating operations performed by the system of FIG. 18, in accordance to embodiments disclosed herein.

FIG. 24 is a flowchart 4700 illustrating operations performed by the system 4100, in accordance to embodiments disclosed herein. At 4702, the system 4100 registers the one or more entities information and consent them to access information. The system 4100 can allow the medical practitioners to access the medical records based on the one or more entities consent. In order to consent, each entity may customize the settings of the system 4100 with access record. The entity number and access code may allow the medical practitioners, in communication with the system 4100, to view the medical record of the entity that have been registered, provided that the entity has authorized access. In an embodiment, the information accessed by the medical practitioners may include the entity medication history.

In an embodiment, at 4704, the system 4100 may processes queries based on the one or more entities consents. The system 4100 may prepares queries based on the one or more entities consents for processing. In an example, the system 4100 may checks a flag in the entity electronic chart upon processing the query based on the entity consent. Further, the system 4100 may initiate a command to send a HL7 demographics feed information to the HIE repository 4114 and trigger a search.

In an embodiment, at 4706, the system 4100 searches the HIE repository 4114 for desired data in accordance to the received query. The system 4100 triggers the search on the HIE repository 4114 upon receiving the command including the HL7 demographics feed information. The HIE repository 4114 may processes the desired by communicating with Surescripts network.

In an embodiment, the Surescripts network described herein may be used by the HIE repository 4114 to access prescription benefit, medication history, and prescription routing services of the system 4100. The Surescripts may allow the HIE repository 4114 to retrieve the desired information based on the medications that are preferred by the entity health plan, the medications that meet therapeutic guidelines, medications that are cost effective for the entity, and the entity current and past medications such as to inform the practitioners about the potential medication issues associated with the entity.

In an embodiment, at 4708, the system 4100 provides the desired data to the EHRDB 4102 based on the search. In an example, the HIE repository 4114 may retrieve the desired data including the results matching the search query. The HIE repository 4114 may send the desired data to the EHRDB 4102 based on the entity customized settings of the system 4100. In an embodiment, at 4710, the system 4100 provides the desired data to the one or more entities 4104. In an example, the newly retried data (or the desired data) is unverified data, which may be sent to the medical practitioner for renewal. The practitioner may then review the unverified data to determine weather to add the data on the entity electronic chart. In response to successful verification of the desired data, the medical practitioner may clinks on the flag to provide the desired data to the entity. In an example, the desired may appear in the entity electronic chart, may be outlined in red or highlighted, next to the medications already listed in the chart.

The system or method described herein may increases the accuracy for providing medication information to the entities. The system may provide facilitates the incapacitated entities, older entities, entities with language barrier, or any other entities to educate themselves and use accurate desired medications. The system may help clinicians or medical practitioners to enhance patient safety, for example, by ensuring not to prescribe medications that would react negatively for the first minutes and hours of care. The use of medication histories (or access to the records) of the entities leads to a faster reconciliation thereby enabling the faster, more focused assessment for treatment and medication of the entities.

Further, the present system or method helps to prevent medication transcription/entry errors and workflow interruptions by integrating the data directly into the EHRDB 4102 thereby eliminating the need to log on to another system to view the data. The invention facilitates to achieve a multi-system interoperability by using data from disparate sources for workflow integration into the EHRDB 4102. The standards-based HIE platform of the present invention may enable the semantic interoperability by complying all data formats with IHE (Integrating the Healthcare Enterprise) and Healthcare Information Technology (HITSP) standards. For example, Surescripts medication history service may provide the data in Radio Data System (RDS) format with each drug identified by its National Drug Code (NDC), a unique numeric identifier assigned by the Food and Drug Administration (FDA). Such NDC code is not a Meaningful Use (MU) standard and may be not be easy to integrate into the EHR systems. The present invention system allows the EHRDB 4102 to translate the NDC codes into an RxNorm code and reformats the data into an HL7 Continuity of Care Document (CCD), a format that supports alignment with the MU standards. The system may query the HIE repository 4114 using an IHE XDS profile to retrieve the CCD and map the desired data into local terminology before displaying in the entity electronic chart.

The system or method described herein may be deployed in part or in whole through a machine that executes software programs on a server such as server, domain server, Internet server, intranet server, and other variants such as secondary server, host server, distributed server, or other such computer or networking hardware on a processor. The processor may be a part of a server, client, network infrastructure, mobile computing platform, stationary computing platform, or other computing platform. The processor may be any kind of computational or processing device capable of executing program instructions, codes, binary instructions or the like that may directly or indirectly facilitate execution of program code or program instructions stored thereon. In addition, other devices required for execution of methods as described in this application may be considered as a part of the infrastructure associated with the server.

The system or method described herein may be deployed in part or in whole through network infrastructures. The network infrastructure may include elements such as computing devices, servers, routers, hubs, firewalls, clients, wireless communication devices, personal computers, communication devices, routing devices, and other active and passive devices, modules or components as known in the art. The computing or non-computing device(s) associated with the network infrastructure may include, apart from other components, a storage medium such as flash memory, buffer, stack, RAM, ROM, or the like. The processes, methods, program codes, and instructions described herein and elsewhere may be executed by the one or more network infrastructural elements.

The elements described and depicted herein, including flow charts, sequence diagrams, and other diagrams throughout the figures, imply logical boundaries between the elements. However, according to software or hardware engineering practices, the depicted elements and the functions thereof may be implemented on machines through the computer executable media having a processor capable of executing program instructions stored thereon and all such implementations may be within the scope of this document. Thus, while the foregoing drawings and descriptions set forth functional aspects of the disclosed methods, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this document. As such, the depiction or description of an order for various steps should not be understood to require a particular order of execution for those steps, unless required by a particular application, or explicitly stated or otherwise clear from the context.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device, or other hardware. All such permutations and combinations are intended to fall within the scope of the present disclosure.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A system, comprising:
   a wearable appliance monitoring one or more body parameters, the appliance including a wrist-watch housing, a processor, a transceiver, an accelerometer and one or more heart monitoring sensors coupled to a back of the wrist-watch housing configured to be coupled to a wrist to detect vital sign, wherein the accelerometer detects user movement, and one or more additional sensors that detect body activity;
   a telephone having a positioning system and wirelessly coupled to the wearable appliance, the telephone off-loading at least a portion of speech processing from the processor of the wearable appliance; and
   a remote-server wirelessly coupled to the wearable appliance through the transceiver or the telephone.

2. The system of claim 1, wherein one of the additional sensor detects at least one of: ECG, heart rate, respiration rate, blood pressure, temperature, oxygen saturation, posture, fall, or movement.

3. The system of claim 1, wherein at least one additional sensor determines heart rate, heart pulse, blood pressure, or oxygen level (SpO2).

4. The system of claim 1, comprising a second sensor in the wrist-watch housing coupled to the processor to sense mood or vital sign, wherein text, image, sound, or video is rendered in response to a sensed mood or vital sign.

5. The system of claim 1, wherein the additional sensors in the wrist-watch housing are in communication with the processor to capture vital sign data; and an application executed by the processor to process the vital sign data and movement data detected by the accelerometer and a gyroscope.

6. The system of claim 1, wherein at least one additional sensor detects at least one of: ECG, heart rate, respiration rate, blood pressure, temperature, oxygen saturation, patient posture, patient fall, or patient movement and wherein the wearable appliance communicates voice over a personal area network, a wireless local area network, or a cellular network.

7. The system of claim 1, wherein the telephone or the wearable appliance communicates with a first device configured to provide data in a first protocol or standard from a first manufacturer and a second device configured to provide data in a second protocol or standard from a second manufacturer; and an electronic health record module configured to translate between the protocols or standards.

8. The system of claim 1, comprising a module to communicate wearable user data to a physician database or a hospital database.

9. The system of claim 1, wherein the processor receives calorie, food consumption, exercise activity, or glucose level.

10. The system of claim 1, wherein at least one sensor data is used to select a fitness program targeted at a user.

11. The system of claim 1, wherein the processor executes code to store and analyze information including posture, ambulation habits, medicine taking habits, eating and drinking habits, sleeping habits, or exercise habits.

12. A mobile system, comprising:
a wearable device with a wrist-watch housing;
a cellular, WiFi, and Bluetooth transceiver coupled to a processor;
an accelerometer and a heart sensor coupled to the processor;
wherein the wearable device includes at least one sensor coupled to a back of the wearable device and wherein the wearable device processes a speech command, the cellular transceiver off-loading at least a portion of speech processing to another processor.

13. The system of claim 12, comprising one or more electrodes that contact skin and capture bio-electrical signals; and an amplifier coupled to the electrodes.

14. The system of claim 12, wherein the sensor comprises an ECG sensor, an optical sensor, and a fall detector.

15. The system of claim 12, wherein the wearable device houses the one or more sensors to detect one or more of: ECG, heart rate, brain wave, respiration rate, blood pressure, temperature, oxygen saturation, posture, fall, or movement.

16. The system of claim 12, wherein the wearable device communicates with a first device configured to provide data in a first protocol or standard from a first manufacturer and a second device configured to provide data in a second protocol or standard from a second manufacturer; and an electronic health record module configured to translate between the protocols or standards.

17. The system of claim 12, wherein mood or body vital sign is used to select a fitness program targeted at a user.

18. A wrist-watch device, comprising:
a wrist-watch housing;
a processor;
an accelerometer and a heart sensor coupled to the processor;
a cellular transceiver coupled to the processor, the cellular transceiver off-loading at least a portion of speech processing to a remote processor;
a display screen coupled to the processor; and
a sensor coupled to a back of the wrist-watch housing to detect blood-oxygen level, heart rate or pulse rate, and wherein the processor processes a speech command.

19. The device of claim 18, wherein the processor communicates with a first device configured to provide data in a first protocol or standard from a first manufacturer and a second device configured to provide data in a second protocol or standard from a second manufacturer; and an electronic health record module configured to translate between the protocols or standards.

20. The device of claim 18, wherein the wrist watch housing encloses one or more sensors to detect the one or more of: ECG, heart rate, respiration rate, blood pressure, temperature, oxygen saturation, posture, fall, or movement.

21. The system of claim 1, wherein the processor detects a fall based on sensor data.

22. The system of claim 1, wherein the processor detects one or more sequences of human motion or posture.

* * * * *